US007043486B2

(12) United States Patent
Cope

(10) Patent No.: US 7,043,486 B2
(45) Date of Patent: May 9, 2006

(54) PROCESS AND SYSTEM FOR TRACKING VERSIONS OF FIELD DOCUMENTATION DATA COLLECTION CONFIGURATIONS IN A COMPLEX PROJECT WORKFLOW SYSTEM

(75) Inventor: Warren Scott Cope, Castle Rock, CO (US)

(73) Assignee: Wellogix, Inc., Houston, TX (US)

( * ) Notice: Subject to any disclaimer, the term of this patent is extended or adjusted under 35 U.S.C. 154(b) by 440 days.

(21) Appl. No.: 10/251,560

(22) Filed: Sep. 20, 2002

(65) Prior Publication Data

US 2003/0078874 A1    Apr. 24, 2003

Related U.S. Application Data

(60) Provisional application No. 60/338,228, filed on Dec. 6, 2001, provisional application No. 60/336,390, filed on Nov. 1, 2001, provisional application No. 60/337,445, filed on Oct. 18, 2001, provisional application No. 60/343,565, filed on Oct. 18, 2001, provisional application No. 60/323,928, filed on Sep. 20, 2001.

(51) Int. Cl.
*G06F 17/30* (2006.01)

(52) U.S. Cl. .................. 707/100; 707/10; 707/101; 707/200; 707/202; 707/203; 709/201; 709/203; 709/213; 709/223

(58) Field of Classification Search ............... 707/3–5, 707/10, 100, 101–104.1, 200–203; 705/7, 705/8, 9–11; 709/201–505; 717/101, 105, 717/109; 713/1, 163
See application file for complete search history.

(56) References Cited

U.S. PATENT DOCUMENTS

| 4,799,156 | A |   | 1/1989 | Shavit et al. ............... 364/401 |
|-----------|---|---|--------|--------------------------------------|
| 4,903,201 | A |   | 2/1990 | Wagner ..................... 364/408 |
| 5,155,802 | A |   | 10/1992| Mueller et al. .............. 395/24 |
| 5,381,332 | A | * | 1/1995 | Wood .......................... 705/8 |

(Continued)

OTHER PUBLICATIONS

The Editors, "Turing Machine," Stanford Encyclopedia of Philosophy, http://plato.Stanford.edu/entries/turing-machine/, (1996), 2 pages.

(Continued)

*Primary Examiner*—Jeffrey Gaffin
*Assistant Examiner*—Jacques Veillard
(74) *Attorney, Agent, or Firm*—The Matthews Firm; William E. Johnson, Jr.; Guy E. Matthews

(57) ABSTRACT

A process is provided for capturing a state of a data input interface at a particular time in a complex workflow system. The data input interface provides an interface for entering actual data to populate a field document. The data input interface is modified on a plurality of occasions to accept input of additional or alternate types of actual data. Each modification of the data input interface is considered a version of the data input interface. The process involves saving a first version of the data input interface, which has been used to enter a first set of actual data. Modifications to the first version of the data input interface are then stored to create a second version of the data input interface. The second version of the data input interface is then activated allowing a second set of data to be entered via the second version of the data input interface. The first version of the data input interface is then deactivated to prevent further input of the actual data via the first version of the data input interface.

30 Claims, 84 Drawing Sheets

U.S. PATENT DOCUMENTS

| | | | |
|---|---|---|---|
| 5,446,895 A * | 8/1995 | White et al. | 717/101 |
| 5,592,375 A | 1/1997 | Salmon et al. | 395/207 |
| 5,603,027 A * | 2/1997 | Ohkami | 707/200 |
| 5,715,402 A | 2/1998 | Popolo | 395/237 |
| 5,732,400 A | 3/1998 | Mandler et al. | 705/26 |
| 5,758,327 A | 5/1998 | Gardner et al. | 705/26 |
| 5,758,328 A | 5/1998 | Giovannoli | 705/26 |
| 5,794,207 A | 8/1998 | Walker et al. | 705/23 |
| 5,799,284 A | 8/1998 | Bourquin | 705/26 |
| 5,804,373 A | 9/1998 | Schweitzer et al. | 435/6 |
| 5,806,078 A * | 9/1998 | Hug et al. | 715/511 |
| 5,826,244 A | 10/1998 | Huberman | 705/37 |
| 5,835,896 A | 11/1998 | Fisher et al. | 705/37 |
| 5,842,178 A | 11/1998 | Giovannoli | 705/26 |
| 5,893,904 A | 4/1999 | Harris et al. | 705/27 |
| 5,907,490 A * | 5/1999 | Oliver | 700/90 |
| 5,913,210 A | 6/1999 | Call | 707/4 |
| 5,915,209 A | 6/1999 | Lawrence | 455/31.2 |
| 5,960,196 A * | 9/1999 | Carrier et al. | 717/122 |
| 6,212,549 B1 * | 4/2001 | Page et al. | 709/205 |
| 6,449,624 B1 * | 9/2002 | Hammack et al. | 707/203 |
| 6,578,004 B1 * | 6/2003 | Cimral et al. | 705/7 |
| 6,714,915 B1 * | 3/2004 | Barnard et al. | 705/7 |
| 6,766,334 B1 * | 7/2004 | Kaler et al. | 707/203 |
| RE38,633 E * | 10/2004 | Srinivasan | 707/10 |
| 6,850,952 B1 * | 2/2005 | Tse et al. | 707/102 |
| 6,850,953 B1 * | 2/2005 | Deshpande et al. | 707/103 Y |
| 2002/0138620 A1 | 9/2002 | Brown | 709/227 |
| 2002/0184610 A1* | 12/2002 | Chong et al. | 717/109 |

OTHER PUBLICATIONS

Copeland, B. Jack, "The Church-Turing Thesis," Stanford Encyclopedia of Philosophy, http://plato.Stanford.edu/entries/church-turing/, 14 pages., Jan. 8, 1997.

* cited by examiner

| REQUEST TYPE: | BID | (REQUEST #4136) PRIMARY CEMENTING | 800 |
|---|---|---|---|
| REPLY BY: | 01-SEP-00 | | |

| REQUESTED BY: | ROBERT T DE JONG | OFFICE PHONE: | (303) 3003520-250 |
|---|---|---|---|
| TITLE: | | FAX: | UNKNOWN |
| COMPANY NAME: | COMPANY #1 | E-MAIL: | DEJONG@WELLBID.COM |
| MAILING ADDRESS: | 4155 E JEWELL AV SUITE 300<br>DENVER CO 80222 | REGION & BASIN: | CANADA-ALBERTA<br>CANADA-BRITISH COLUMBIA<br>CANADA-EASTERN CANADIAN OFFSHORE<br>CANADA-FAR NORTH<br>CANADA-SASKATCHEWAN<br>GOM-APALACHICOLA<br>GOM-GULF COAST SALT DOME<br>GOM-RIO GRANDE EMBAYMENT<br>GULF STATES-BLACK WARRIOR<br>GULF STATES-CENTRAL TEXAS<br>GULF STATES-EAST TEXAS<br>GULF STATES-NORTH LOUISIANA<br>GULF STATES-PERMIAN<br>GULF STATES-SOUTH LOUISIANA<br>GULF STATES-SOUTH TEXAS<br>MID-CON-ANADARKO<br>MID-CON-ARDMORE<br>MID-CON-ARKOMA<br>MID-CON-DALHART<br>MID-CON-HUGOTON<br>MID-CON-KANSAS/NEBRASKA<br>NORTHEASTERN-APPALACHIA<br>NORTHEASTERN-ILLINOIS<br>NORTHEASTERN-MICHIGAN<br>PACIFIC-COOK INLET<br>PACIFIC-SACRAMENTO<br>PACIFIC-NORTH SLOPE<br>PACIFIC-SAN JOAQUIN<br>ROCKIES-BIG HORN<br>ROCKIES-DENVER-JULESBURG<br>ROCKIES-GREEN RIVER<br>ROCKIES-PARADOX<br>ROCKIES-PICEANCE<br>ROCKIES-POWDER RIVER<br>ROCKIES-RATON<br>ROCKIES-SAN JUAN<br>ROCKIES-UINTA<br>ROCKIES-WILLISTON |

| PROJECT NAME: | CKH TEST II |
|---|---|
| REGION & BASIN: | ROCKIES-BIG HORN |
| COUNTRY: | USA |

| WELL NAME: | DS18-17 |
|---|---|
| WELL DESCRIPTION: | TEST AS OF 8-13-00 |
| EST SPUD/START DATE: | 01-SEP-2000 |
| WELL API NUMBER: | |
| WELL TYPE: | NEW |
| REGION & BASIN: | ROCKIES-BIG HORN |
| COUNTRY: | UNITED STATES |
| STATE/PROVINCE: | WYOMING |
| COUNTY: | GILLETTE |
| FIELD: | BULL FIELD |
| BLOCK: | |
| SURVEY: | |

| PUMPING REQUIREMENTS FOR THIS STAGE | | |
|---|---|---|
| MAX SLURRY MIXING RATE, BPM | MAX SLURRY PUMPING RATE, BPM | MAX SLURRY DISPLACEMENT RATE, BPM |
| | | |

MISCELLANEOUS EQUIPMENT/SERVICE NEEDS FOR HOLE SECTION

| | | | |
|---|---|---|---|
| BATCH MIXER | ☐ | SIZE | |
| STANDBY PUMPING EQUIPMENT | ☐ | NO. OF UNITS | |
| COMPUTER MONITORING EQUIPMENT | ☐ | | |
| ADDITIVES IN LIQUID FORM | ☐ | | |

— 804

SPECIAL PERSONNEL REQUIREMENTS

COMMENTS FOR THIS HOLE SECTION

CATEGORY ATTACHMENTS:
THERE ARE NO ATTACHMENTS.

FILE ATTACHMENTS:
NO FILE ATTACHED

— 806

| INTERESTED | NOT INTERESTED | SUBMIT BID PROPOSAL | VIEW EFIELD TICKET™ |

SUBMIT BID FEEDBACK

| CLEAR | RESET | SUBMIT |

FIG.8B

| PRIMARY CEMENTING-EFIELD-TICKETS™ | | | |
|---|---|---|---|
| HOLE SECTION | TOTAL COST W/3RD PARTY INCL,$ | VENDOR STATUS | OPERATOR STATUS |
| HOLE SECTION: SURFACE | 16500.00 | SUBMITTED | APPROVED |
| HOLE SECTION: PRODUCTION | 0.00 | | |
| HOLE SECTION: CONDUCTOR | 0.00 | | |

⎬ 808

CREATE EFIELD-TICKET™
⎬ 810

PRIMARY CEMENTING-EFIELD-TICKET™ — 1002

| WELL NAME | DS18-17 | | ACCOUNTING SYSTEM PROJECT#: |
|---|---|---|---|
| FIELD NAME | BULL FIELD | | PROJECT MGT. SYSTEM# |
| PROJECT NAME | CKH TEST II | | GL ACCOUNT # |
| STATE/PROVINCE | WYOMING | | RIG NAME/NO. |
| COUNTY/PARISH | GILLETTE | | FIELD SUPV NAME |
| LEGAL LOCATION | 1000' FNL, 500' FEL, SEC36, T45N, R101E, 8500 FT | | OFFICE REP NAME |

— 1004

| HOLE SECTION | HOLE SECTION/INTERMEDIATE 1 ▽ | CURRENCY TYPE | US DOLLARS |
|---|---|---|---|

JOB SUMMARY

| | DATE (E.G. 01-JAN-2000) | TIME (E.G. 13:31) |
|---|---|---|
| ARRIVE LOCATION | | |
| JOB START | | |
| JOB COMPLETION | | |
| LEAVE LOCATION | | |

— 1006

SERVICE CHARGES — 1008

| ITEM# | DESCRIPTION OF SERVICE | QUANTITY/FOOTAGE | UOM | UNIT PRICE,$ | BOOK PRICE,$ | DISC. % | AMOUNT, $ |
|---|---|---|---|---|---|---|---|
| | | | EA ▷ | | | | |
| | | | EA ▷ | | | | |
| | | | EA ▷ | | | | |
| | | | EA ▷ | | | | |
| | | | EA ▷ | | | | |
| | | | EA ▷ | | | | |

FIG. 10B

PRODUCT CHARGES

| ITEM # | DESCRIPTION OF PRODUCT | QUANTITY/FOOTAGE | UOM | UNIT PRICE, $ | BOOK PRICE, $ | DISC, % | AMOUNT, $ |
|---|---|---|---|---|---|---|---|
| | | | EA ▷ | | | | |
| | | | EA ▷ | | | | |
| | | | EA ▷ | | | | |
| | | | EA ▷ | | | | |
| | | | EA ▷ | | | | |
| | | | EA ▷ | | | | |
| | | | EA ▷ | | | | |
| | | | TOTAL PRODUCTS COST, $ | | | | |

(IF ADDITIONAL LINES ARE NEEDED, SAVE THIS PAGE FIRST)

~1010

EXPECTED ASSOCIATED 3RD PARTY CHARGES

| VENDOR | DESCRIPTION | ESTIMATED COST, $ |
|---|---|---|
| | | |
| | | |

~1012

(Upper table, above PRODUCT CHARGES:)

| | | | EA ▷ | | | | |
|---|---|---|---|---|---|---|---|
| | | | EA ▷ | | | | |
| | | | EA ▷ | | | | |
| | | | EA ▷ | | | | |
| | | | TOTAL SERVICE COST, $ | | | | |

(IF ADDITIONAL LINES ARE NEEDED, SAVE THIS PAGE FIRST)

| Type of Charge | Item # | Description | Qty. | Units of Measure | Unit Price | Book Price | Disc. % | Amount |
|---|---|---|---|---|---|---|---|---|
| Delivery Charge | 445322 | Mileage | 220 | Miles | 2.25 | 450.00 | 0 | 450.00 |
| Setup Charge | 332352 | Flat Charge | 1 | Each | 1500.00 | 1500.00 | 0 | 1500.00 |
| Service Charge | 343222 | Tubing Cutter @ 8323 | 1 | Each | 2200.00 | 2200.00 | 10 | 2000.00 |
| Third Party Charges | 32342-1 | 5-1/2" Riser Rental (G&G Rental) | 1 | Each | 728.00 | 728.00 | 0 | 728.00 |
| Taxes and Fees | 24-3323 | Taxes | 1 | Each | 124.00 | 124.00 | 0 | 124.00 |
| | | | | | | Total Price | | $ 4,802.00 |

Internal Custom Field #1
Internal Custom Field #2
— 1214

Internal Custom Field #3
Internal Custom Field #4
— 1216

Comments - Internal:

Comments to Service Provider:

In order to attach files, please save this page first.

Save | Approve Invoice | Hold For Payment

PROCESS AND SYSTEM FOR TRACKING VERSIONS OF FIELD DOCUMENTATION DATA COLLECTION CONFIGURATIONS IN A COMPLEX PROJECT WORKFLOW SYSTEM

CROSS REFERENCE TO RELATED APPLICATIONS

This application claims priority to the following applications, each of which is incorporated herein by reference in its entirety: U.S. provisional application No. 60/323,928, entitled Process and System for Comparing and Reconciling Estimated Data with Actual Data in a Complex Project Workflow System, filed on 20 Sep. 2001; U.S. provisional application No. 60/336,390, entitled Offline Manager, filed on 01 Nov. 2001; U.S. provisional application No. 60/343,565, entitled Modularization of a Process and System for Comparing and Reconciling Estimated Data with Actual Data in a Complex Project Workflow System, filed on 18 Oct. 2001; U.S. provisional application No. 60/337,445, entitled Customization of Data Collection Methods in a Process for Comparing and Reconciling Estimated Data with Actual Data in a Complex Project Workflow System, filed on 18 Oct. 2001; and U.S. provisional application No. 60/338,228, entitled Customization Manager—Versioning, filed on 06 Dec. 2001.

This application is also related to the following applications, which are also each incorporated herein by reference in their entirety: U.S. patent application Ser. No. 09/801,016 entitled Method and Process for Providing Relevant Data, Comparing Proposal Alternatives and Reconciling Proposals, Invoices, and Purchase Orders with Actual Costs in a Workflow Process, filed 6 Mar. 2001, and U.S. patent application Ser. No. 09/672,938, entitled Process and System for Matching Buyers and Sellers of Goods and/or Services, filed 28 Sep. 2000.

FIELD OF THE INVENTION

The present invention relates in general to the field of automated business processes and systems therefore that match buyers with sellers of goods or services while also targeting marketing to such buyers. More specifically, the present invention relates to automated methods as part of a workflow process that provide for the comparison and reconciliation of estimated data to actual data determined at the conclusion of an event in a multistage project.

BACKGROUND OF THE INVENTION

In today's complex, fast paced economy, many projects exist that require various goods and/or services to be provided by numerous organizations (hereafter, "sellers") while also requiring relationships for providing and monitoring such goods/services to be quickly and efficiently established. Examples of such projects include drilling for oil, commercial and/or residential construction, manufacturing complex objects (for example, aircraft and special use objects), and providing specialized services (for example, brokering excess power and bandwidth, and developing unique software products). When planning such projects, the person(s) responsible for the project (hereinafter, the "buyer") is often faced with the daunting tasks of: (1) designing the project and planning the phases of implementation; (2) determining which goods/services are needed; (3) determining providers (sellers) of such goods/services; (4) establishing a dialogue with such sellers; (5) selecting at least one seller to provide one or more goods/services; (6) starting, managing, and monitoring the project until completion or termination; (7) facilitating post-completion tasks (for example, paying sellers and other back-end processing); (8) analyzing the events of the project to identify areas of improvement for future projects and (9) other related tasks.

Commonly, when faced with such a challenge, many buyers rely upon antiquated systems and processes for accomplishing those tasks necessary implement a project from start to post-completion. Such antiquated systems include, for example: utilizing business listings and other directories to identify sellers; negotiating agreements with the sellers via facsimile, telephone, and other non-real-time responsive systems; and making best-guess judgments as to areas in which future improvements may be realized. As a result, many buyers relying upon such antiquated processes are often left behind in today's fast paced, Internet-driven, information economy. As such, a system is needed that allows buyers to be efficiently matched with sellers, and projects monitored, managed, and coordinated through all phases of the project.

For example, when constructing a building, a general contractor must decide which seller will provide excavation services, what type of materials to use, when the materials will be used, who will supply the materials, who will use the materials (i.e., who will actually construct the building) and other various factors. Currently, when constructing a building, the builder might use a Rolodex® or a personal data assistant (PDA) (for example, a PALMS® device) with contacts to choose preferred sellers to provide the desired goods/services. Upon identifying a seller, the buyer may then engage in a dialogue with the seller about the project parameters, and may solicit proposals for methods to complete specific tasks. Since each seller may identify a unique manner for accomplishing the specified task, the buyer is often left to determine, for example, which seller has identified the best approach, will provide the best value, and can best meet the schedule. Since such determinations can be quite time consuming, buyers generally do not have time to shop for other than a limited number of sellers for any given project. As such, new sellers on the market, and/or new techniques may often be overlooked.

Further compounding the problems faced by buyers in identifying and coordinating goods/services from sellers is that sellers often dictate the purchase processes used to acquire goods/services needed for the project (e.g., auction, fixed price and quantity systems, and other systems well known in the art). For some of these purchase processes, most of the essential terms of the agreement are dictated or controlled by the seller, while the buyer has little input over terms such as price, delivery, location, and quantity. Examples of such seller driven processes include retail, mail order, telephone, and some on-line sales systems. For example, a builder desiring to procure nails might be required by a retail sales process or an on-line sales process to purchase nails only in bundles of 200, for a set price. Since the buyer cannot modify the goods/services or terms or conditions of the procurement process, the buyer's needs are often inadequately, untimely, and inefficiently fulfilled.

Additionally, recent automation of the aforementioned seller-driven processes (for example, via the Internet) has not adequately addressed this problem. While the new, automated processes generally enable a buyer to shop for goods and/or services, for example, without having to travel to the seller's location or obtain a catalog, such processes are commonly characterized by sellers offering items of commerce under seller specified terms and conditions. Such processes do not allow a buyer to identify a project in terms of its specifications, and have the specifications translated into requests for goods/services that are then fulfilled in a timely and efficient manner by a seller providing the requested goods/services or suitable alternatives. Additionally, such processes often do not identify sellers of specialty goods/services and, therefore, are often inadequate for the provisioning of goods and/or services that are not commonly mass marketed. In short, a more efficient process of matching buyers and sellers is needed.

Examples of presently available buyer driven processes include bidding processes and auctions. Regardless of the process (whether bid-based or auction-based), a buyer is generally first required to identify specific goods/services that are needed to complete a project. None of the available processes allow a buyer to specify a project in terms of project details or parameters that are then automatically converted into requests for proposals, requests for specific goods, or other such proposals. Additionally, none of the available processes provide ready access to information to help a buyer, or seller, determine the appropriate details necessary to adequately specify a project or respond to such a request. As is appreciated by those skilled in the art, converting specifications for complex projects into specific requests for goods/services is extremely time consuming, is often incomplete, and is extremely inefficient because the buyers often can not precisely identify and/or specify those goods/services available and needed to fulfill a project. As such, today's buyer driven processes do not provide the degree of flexibility, specificity, and efficiency necessary for many buyers of goods/services. Therefore, a process is needed that enables a buyer to procure those goods/services necessary to undertake and complete a project by providing a project's specifications to an automated process that facilitates the conversion of such specifications into requests for goods/service and matches the buyer with sellers of such goods/services.

Additionally, once an agreement has been entered into to provide goods/services needed to fulfill a project, systems are not available that enable both buyers and sellers to monitor the progress of the project, efficiently implement design changes, provide billing and other back-office functions, and determine areas for improvement by utilizing knowledge based systems. Thus, a process is needed that enables buyers/sellers to enter into agreements for projects and monitor such projects from initialization through post-completion/termination.

Similarly, once goods have been delivered or a service has been performed, processes are not available that enable both buyers and sellers to efficiently compare and reconcile actual costs and project outcomes with the estimated costs and technical specifications provided by a seller in response to a service request, provide for a revision and approval process, and ultimately provide invoices that accurately reflect the goods and services provided. With many complex projects deliveries are made and services are provided in discrete stages over the course of the project. For example, a commercial response for lumber, for a particular project, may detail the various types, sizes, and pricing for the lumber while providing a final total price. However, the delivery may actually be performed in stages over the course of the project. These services are generally documented by delivery tickets or tickets provided at the time deliveries are made and services rendered. In other instances, ongoing services may be recognized by tickets submitted on a regular basis, e.g., weekly or monthly.

Unfortunately, there is great difficulty in reconciling these tickets and allocating them to the appropriate project. Many times tickets are never received by the office accounting departments. For buyers, this means that they have no record of goods or services actually being provided. For sellers, this may mean that they are unable to or fail to invoice a buyer for goods or services rendered. Often it is a nightmare for buyer and seller accounting departments to keep track of tickets because proper routing and coding procedures often are overlooked in the field. As such, much time may be spent on the telephone attempting to contact foremen at job sites to confirm deliveries or services rendered or with the seller to determine to which project the ticket relates. Fraud is also an issue as many times false invoices are presented and paid under the assumption that the ticket was lost because it is too difficult or time consuming to identify the related tickets. Thus a process is needed to enable such reconciliation of proposal prices and project results with actual costs and technical specifications before approval and invoicing.

SUMMARY OF THE INVENTION

At least one embodiment of the present invention is directed to a process and system that matches buyers (in exemplary embodiments herein "operators") and sellers (in exemplary embodiments herein "service providers") of goods/services based upon specifications provided by a buyer for a project. Additionally, various embodiments of the present invention provide a forum for the negotiation of resulting agreements to provide goods/services needed for a project, while also allowing buyers and sellers to monitor the status of the project and/or the provision of the agreed upon goods/services. Systems and/or processes are also provided which enable sellers to directly communicate with a buyer, including providing documents and other information that are readily accessible by the buyer, the sellers, and others (e.g., engineers, subcontractors, project managers, and other project members) from anywhere, at any time, via a suitable communications link. Further, the completion of post-task accomplishment activities, such as back-end accounting and billing operations, reconciliation of proposed costs and other data with actual costs and other actual data, invoicing, resource management, and knowledge management may also be provided by various embodiments of the present invention.

More specifically, a system and/or process is provided that, upon identification of specifications for a project by a buyer, generates one or more requests for goods and/or services needed to fulfill the project and provides the requests to those sellers designated by the buyer and/or those sellers that can provide the requested goods/services. It is to be appreciated that a "project," as used in this description, includes activities involving single operations (for example, procuring casing for a well), as well as activities involving numerous operations (for example, building a house), and is not to be construed as being limited to any specific classes of goods, services, activities, or projects. In response to such requests, the sellers may submit proposals, request additional information, recommend changes to project parameters and/or the goods/services requested, and perform various other activities.

When utilizing the systems and/or processes of the present invention, a buyer may specify one or more parameters that describe a project. Examples of such parameters include the following: physical parameters (e.g., size, weight, height); functional parameters (e.g., able to accelerate from 0 to 60 m.p.h. in less then 6.0 seconds); temporal parameters (e.g., to be delivered by Tuesday); financial parameters (e.g., to cost less than $10.00); transactional parameters (e.g., to be paid by check or money order); and/or geographical parameters (e.g., located in Colorado). The physical, functional, temporal, financial, and/or geographical parameters, or any other parameters that may be appropriate for completion of the project, are hereafter collectively referred to as "parameters." Various embodiments of the present invention also enable users to compare various versions of a given proposal and/or different proposals for various purposes, for example, to manipulate the parameters in such proposals to ascertain different results based upon potential project outcomes. Thus, a process is provided which facilitates the matching of buyers with sellers of goods/services based upon project parameters, and not necessarily upon the specific identification of goods/services by a buyer.

Various embodiments of the present invention further enable buyers and sellers to access industry specific information, for example, to assist them in determining and providing the necessary goods and services for a given project. A knowledge management system may also be included as a component of the invention and may be used, in one respect, as a library of technical information to aid both buyers and sellers in formulating and responding to various kinds of requests. Technical information may include, for example, industry data, articles, general engineering publications, historical or archived data, and data specific to either a buyer's or seller's projects or team (e.g., company specific data). As is commonly appreciated, company specific data may include operational and transaction histories for projects and other data. Access to company specific data may be restricted to protect proprietary information, or it may be shared, for example, as between joint venturers involved in a specific project.

The present invention, in at least one embodiment, facilitates the sharing of such company specific data, as desired and/or permitted by individual companies. In many complex projects, various goods are delivered by a seller for use at various points throughout the project and documented by delivery tickets, even though the entire quantities and related total costs may have been indicated or estimated in a single technical and/or commercial response to the initial service request for the project. Similarly, services provided by a seller over the course of a project may be rendered and documented by what are known in some industries as field tickets. Rather than merely providing an invoice at the completion of the entire project, field tickets may be issued by sellers at various times during the project, for example, weekly, monthly, by hours expended, or by section completed.

In one embodiment of the present invention, a system and/or process is provided for tracking, matching, comparing, reconciling, and/or approving for payment delivery tickets or field tickets for goods/services rendered at the project site. One element of this field approval of delivery tickets process may provide for communications between buyers and sellers that are directly linked to the specific delivery or field document in question. This process may be further enhanced by using an electronic version of a delivery document, one example of which is an eField-Ticket™ provided by WELLOGIX®, Inc. It is to be appreciated, however, that other versions of delivery tickets, in electronic and other forms or methods of communicating field or other conditions may be utilized in conjunction with the various embodiments of the present invention. As such, collectively and individually, delivery tickets, field tickets, electronic tickets, and an eField-Ticket™ are herein considered to be synonymous and are hereinafter referred to as a "Field Document," or on the various WELLOGIX user interface embodiments as an "eFT," in both the singular and plural context, as particular uses require. Further, it is to be appreciated that a Field Document may be generated, provided, accessed and/or utilized in a hardcopy and/or a soft copy embodiment. More specifically, a Field Document may be provided in a hard copy embodiment as a printed page, document, memo, report, invoice, Field Document or the like. Similarly, a Field Document may be provided in a soft copy embodiment as a computer data file, on a screen display of a user or a system device, as an audible text message or via any other known or hereafter discovered method and/or system for communicating information to a person and/or to a computer or similar device.

Further, a historical record of the communications concerning the reconciliation and approval of payment for a specific delivery/Field Document may be provided to document and facilitate the process. In a related manner, actual project data (for example, quantities of lumber actually delivered, quantities of concrete used, time taken to drill a well to a certain depth, and other actual project data) can be compared and reconciled with amounts projected or estimated in technical responses to an original service request.

In one business scenario using a system or process embodiment of the present invention, an operator may award a job with a commercial response or a work order. Once the service provider has completed the designated work or an identifiable portion thereof, a Field Document may be prepared and submitted to the operator for approval. This may be accomplished, for one system embodiment, by logging into an Internet and/or Browser based system, such as the WELLOGIX® system, and communicating a Field Document (or an eField-Ticket™) to an operator.

In another embodiment of the present invention, an offline manager feature may be utilized by which a service provider may submit a Field Document to an operator, or send the Field Document to another employee within his company via an online connection with an Internet or other network connected server/web site, such as one provided by WELLOGIX, or offline using an "Offline Component." An Offline Component is herein defined as a web page that may be accessed even when a connection can not be established with a provider of the web page. An Offline Component has in some literature been called a "sitelet." In short, utilizing the offline manager feature of the present invention, a service provider can prepare a Field Document either online, for example, via the WELLOGIX system, or off-line, for example, via an Offline Component. Further, when an Offline Component is utilized, the Offline Component may be obtained directly, indirectly or even sent to them using, for example, Consilient technology, Microsoft.net™, or other wired or wireless communication technologies. Further, it is to be appreciated that an Offline Component may be provided by other communication mediums including, but not limited to, via computer readable mediums, IR beamed signals, RF signals, fiber optic signals, and other mediums. When the service provider has inputted the desired data into the Field Document, the Field Document may be communicated to the operator, to another member of the service provider company, or to others using wired and/or wireless communication technologies.

In at least one embodiment of the present invention, the offline manager manages Offline Components. Such Offline Components may be stored and/or utilized or created for a given project, for example, in a data array or other computer file data structure. The offline manager may also be configured to: 1) list Offline Components that have been checked out; 2) list who checked out an Offline Component including, for example, a date and time stamp; 3) allow a user to cancel an Offline Component; and 4) list the type of Offline Component checked out. The offline manager may also allow a user, itself or others to cancel an Offline Component. The necessity to cancel an Offline Component may arise as a result of some particular business need. For example, an Offline Component may need to be cancelled when a first employee, who may be scheduled to perform work on a job site and is sent the Offline Component prior to leaving the office, is unable to perform the work and a second employee must perform the work in place of the first. In such a situation, the Offline Component may be cancelled, transferred and used by the second employee, regenerated or otherwise processed. The offline manager may also be configured to manage Offline Components that are currently offline, such that a user may determine whether any Offline Components require their attention.

Depending upon their needs, different companies may use a Field Document differently. For instance, some companies may use a Field Document to capture rental equipment used at the drill site, while others may use a Field Document to capture detailed time information, and yet others may use a Field Document to capture payroll and human resources information. Therefore, flexibility in how a Field Document is designed may be provided so that a Field Document may be configured to display various types of information to meet the needs of different companies and/or users on a dynamic or static basis.

To meet this need, one embodiment of the present invention may include a modularization feature, whereby the format of the Field Document is modular. For example, a modular Field Document may include multiple pages, instead of a single page, multiple sections, and/or other partitions. These partitions/sections/pages in a modular Field Document enable a company to customize Field Documents by using only those modules the company needs instead of having one long form of which most is not utilized. It is to be appreciated that a customizable Field Document may reduce the quantity and time necessary to communicate a Field Document between the field, the front office and otherwise. Further, when modular Field Documents are provided and utilized, the amount of customization that can be done for each company that uses an embodiment of the present invention may be improved. Also, the amount of time that development resources are allocated to build custom features within an application may also be reduced.

Another embodiment of the present invention may include a customization manager that allows for easy customization of various screens to better conform to a company's needs. Further, versioning may be provided, which enables users to retrieve previous versions of Field Documents and/or other information that may be utilized in a system or process implementing a version or embodiment of the present invention.

In one embodiment of the invention, a process is provided for capturing a state of a data input interface at a particular time in a complex workflow system. The data input interface provides an interface for entering actual data to populate a field document. The data input interface is modified on a plurality of occasions to accept input of additional or alternate types of actual data. Each modification of the data input interface is considered a version of the data input interface. The process involves saving a first version of the data input interface, which has been used to enter a first set of actual data. Modifications to the first version of the data input interface are then stored to create a second version of the data input interface. The second version of the data input interface is then activated allowing a second set of data to be entered via the second version of the data input interface. The first version of the data input interface is then deactivated to prevent further input of the actual data via the first version of the data input interface.

These and other features and functions of the various system, process and/or user interface embodiments of the present invention are further described herein with reference to the drawing Figures, the detailed description and the claims.

BRIEF DESCRIPTION OF THE DRAWING FIGURES

Figure 4A:
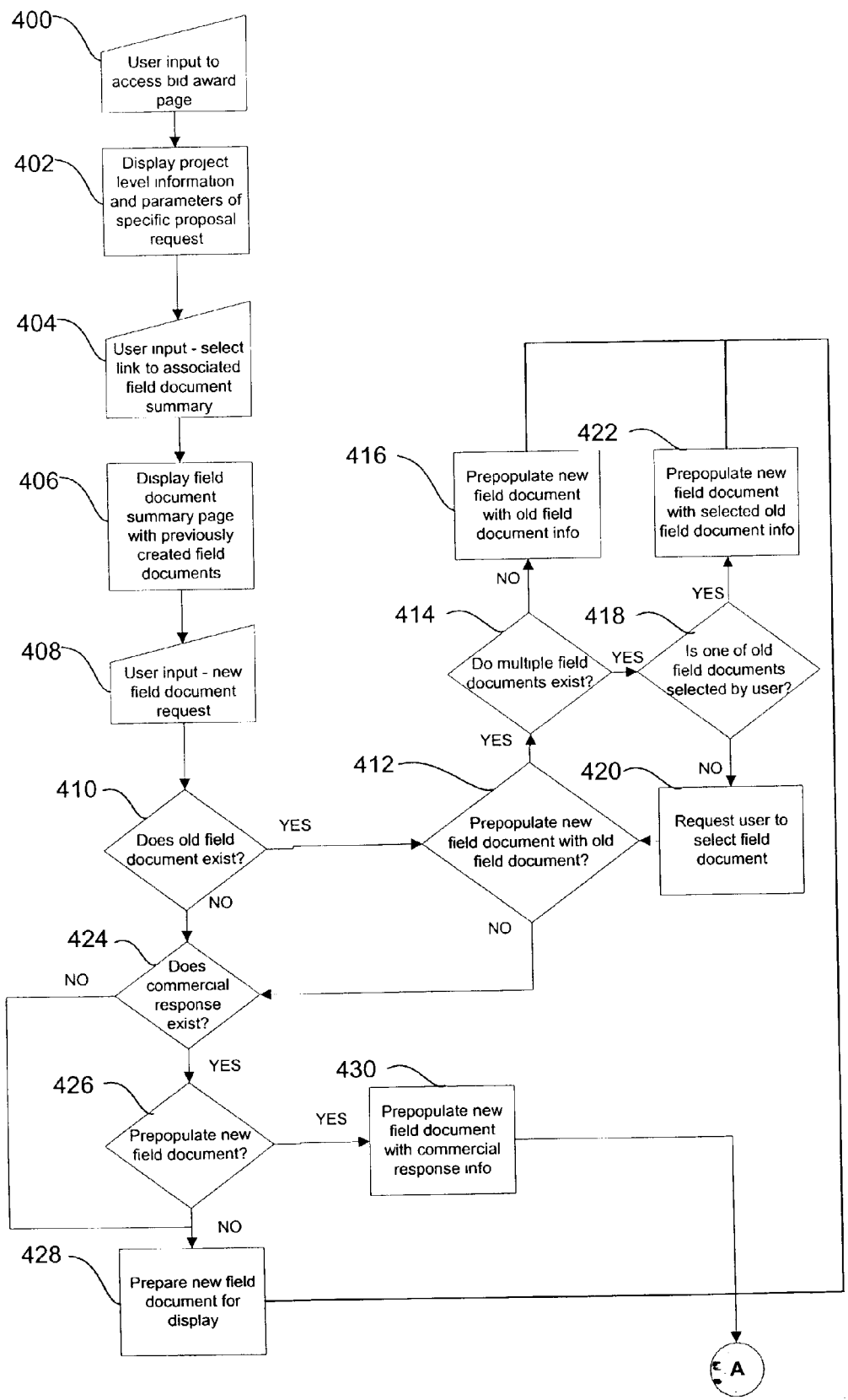
Figure 4B:
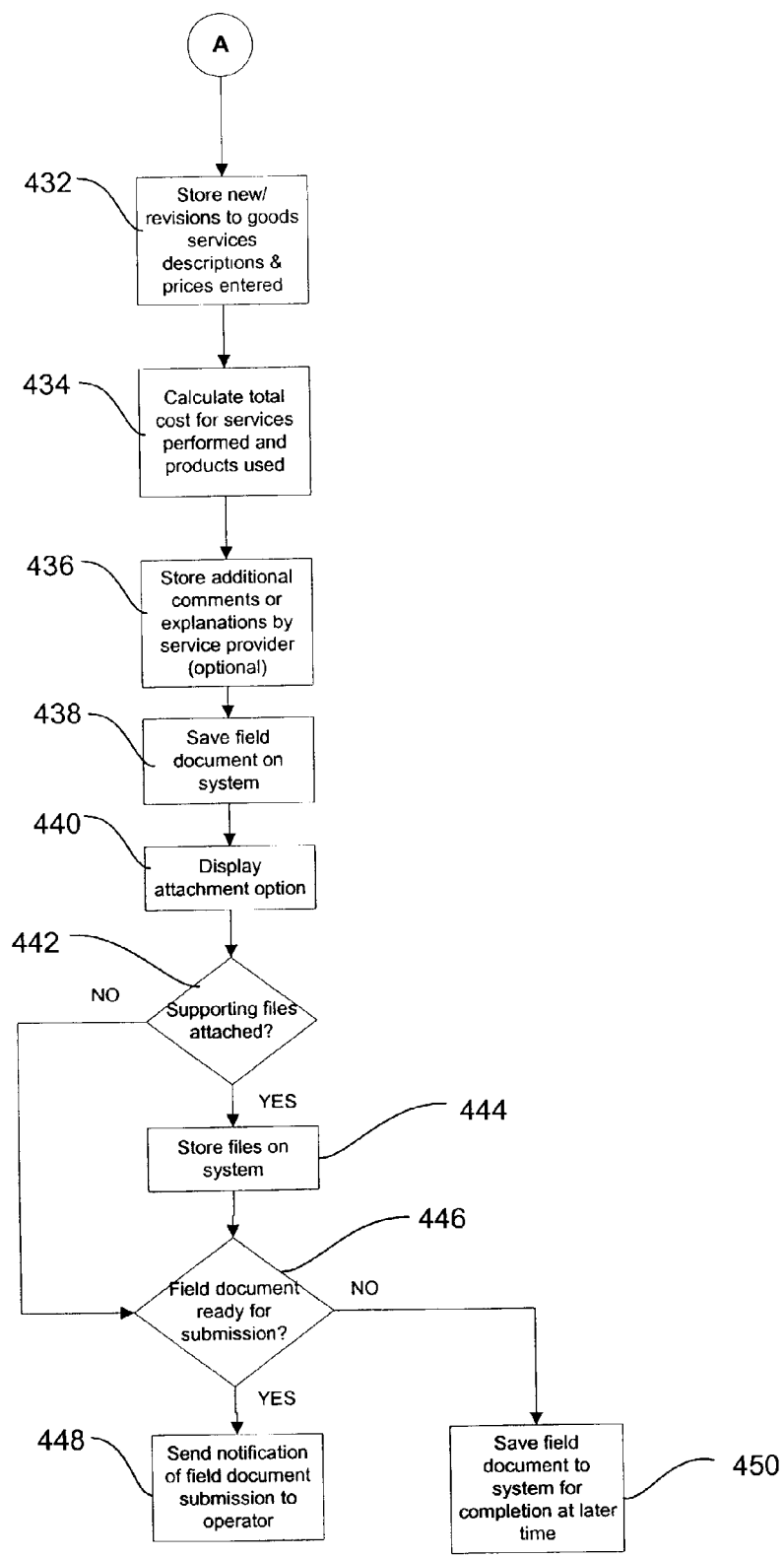

FIGS. 4A–B are flow diagrams depicting one embodiment of a process of preparing and pre-populating Field Documents based upon a commercial response.

Figure 5A:
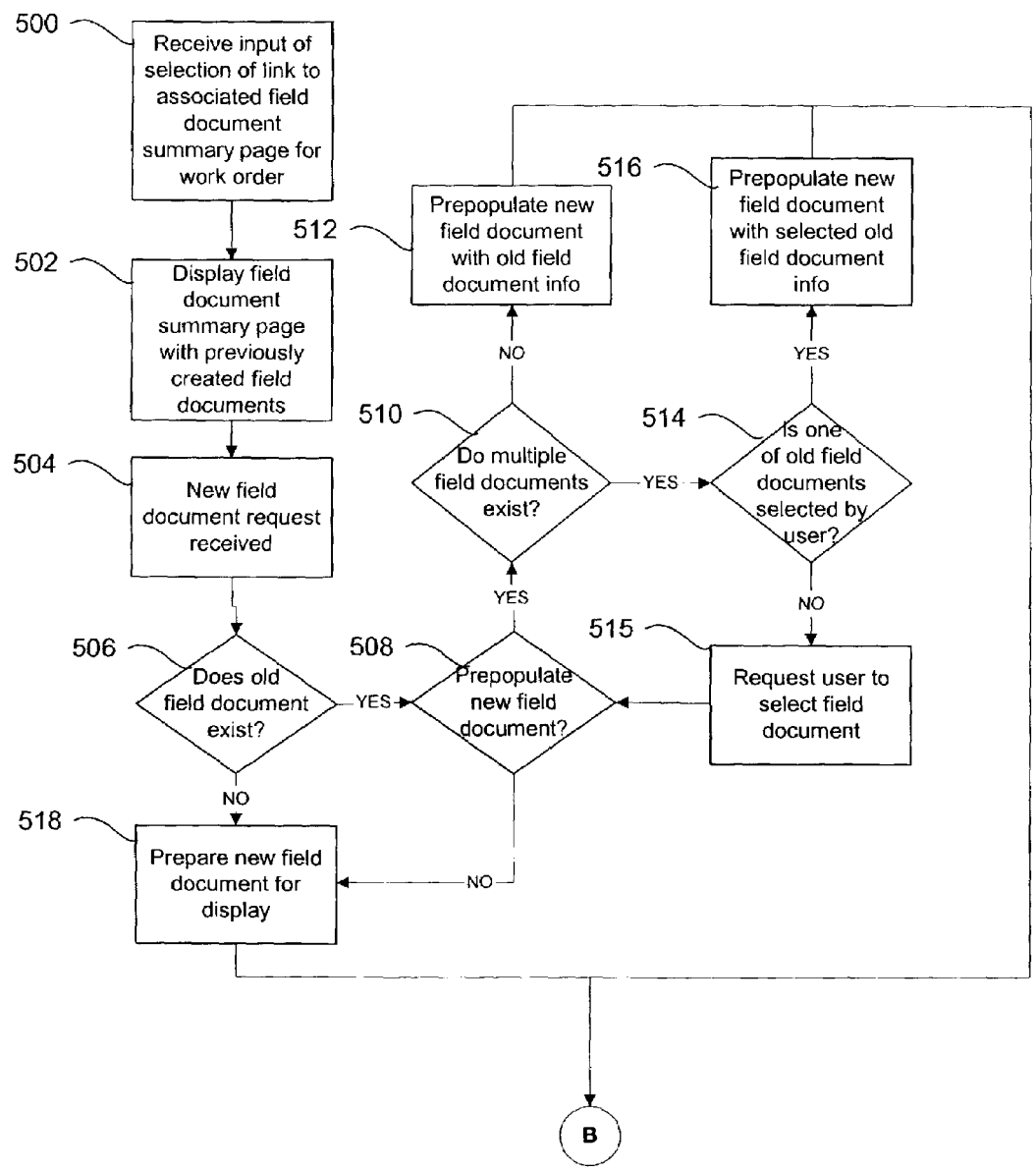
Figure 5B:
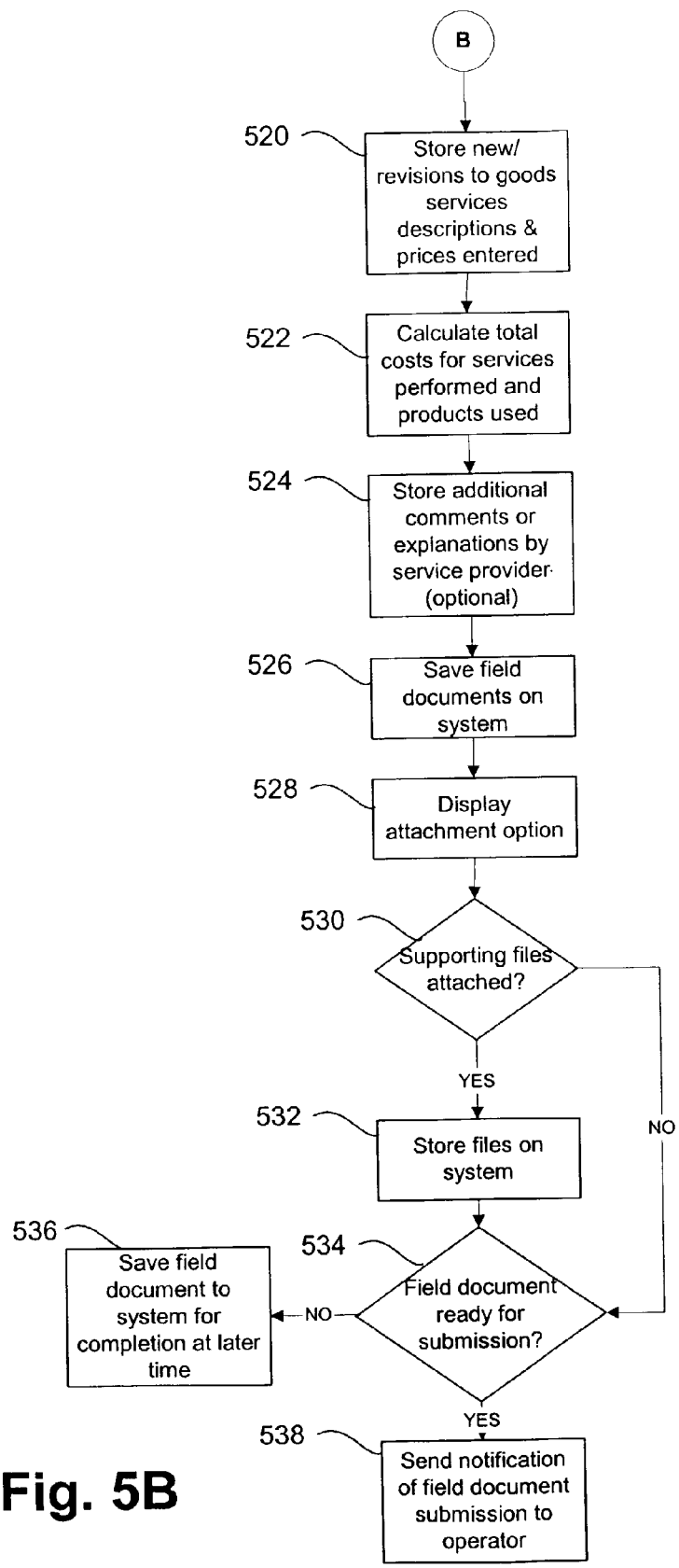

FIGS. 5A–B are flow diagrams depicting one embodiment of a process of preparing and pre-populating Field Documents based upon a work order.

Figure 6:
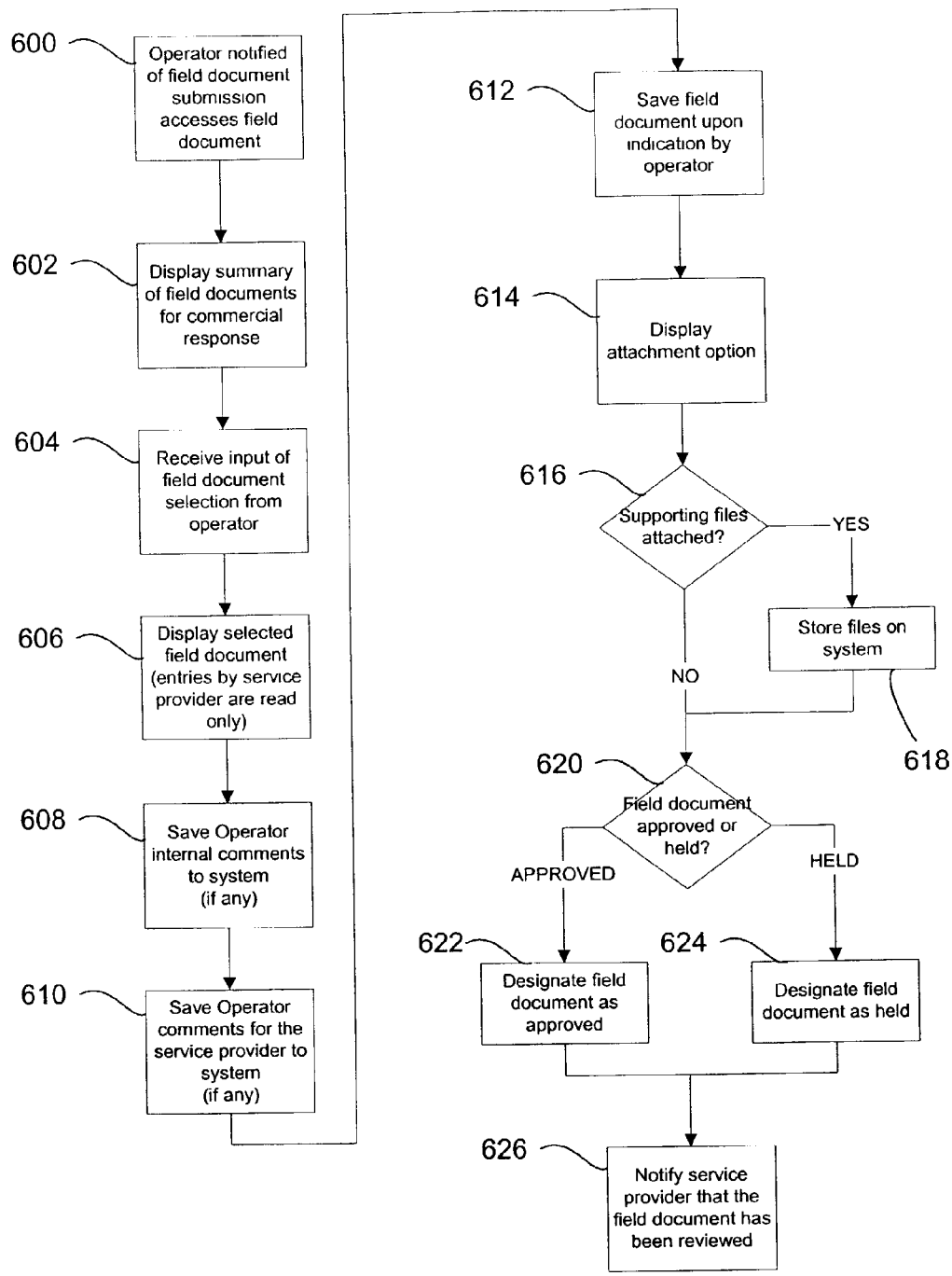

FIG. 6 is a flow diagram depicting one embodiment of a process whereby a Field Document can be reviewed, approved for payment, and/or designated as held.

Figure 7:
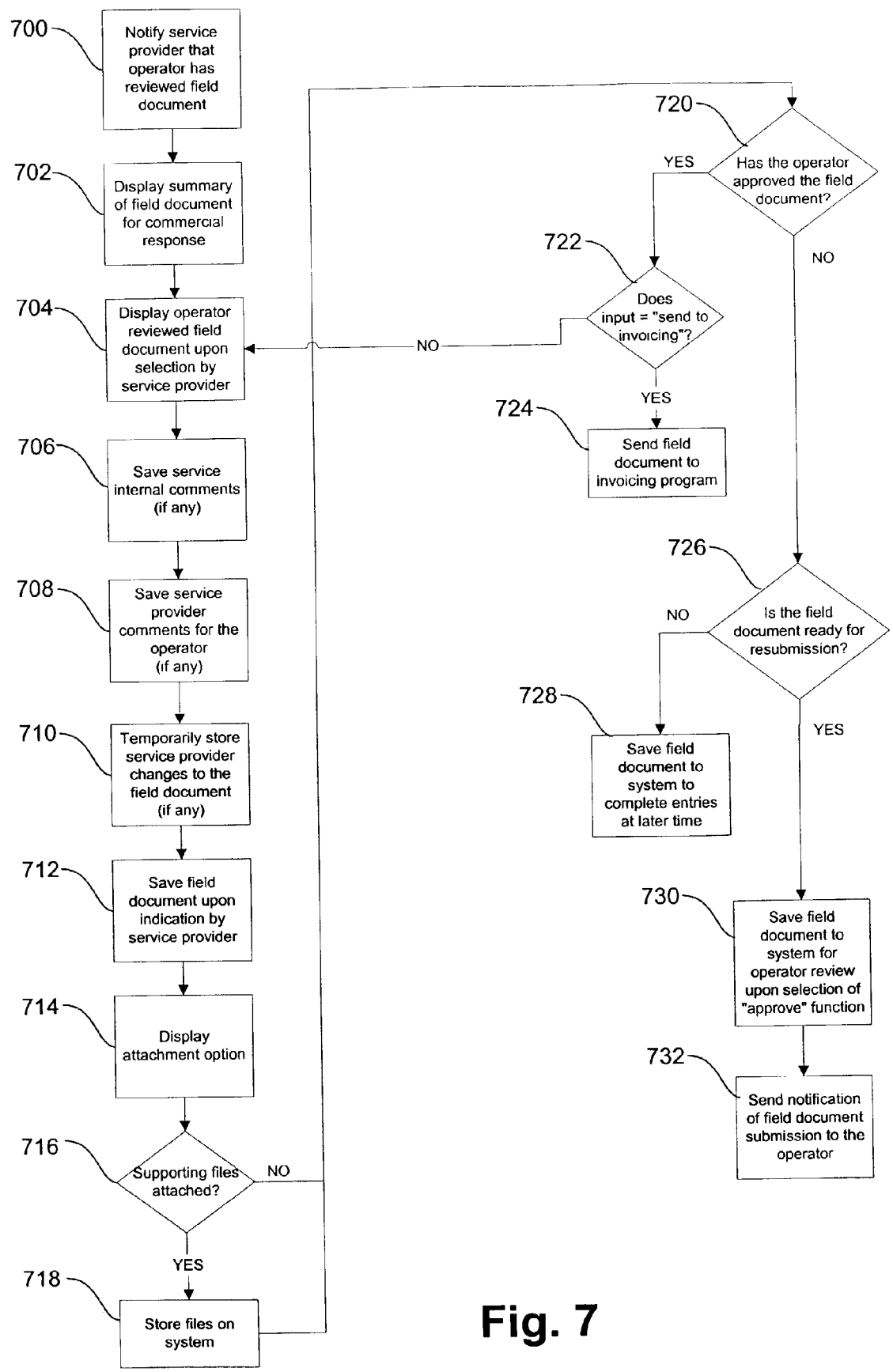

FIG. 7 is a flow diagram depicting one embodiment of a process whereby a service provider can update a Field Document which has been reviewed by an operator, submit a Field Document for invoicing, or designate a Field Document for further review.

FIGS. 8A–B are exemplary screen shots of one embodiment of an award page which may be utilized in an Internet or a Web browser based embodiment of the present invention, wherein a link to enter a Field Document into a reconciliation system is provided.

FIG. 8C is an exemplary screen shot of one embodiment of a Field Document management page for an Internet or Web browser based embodiment of the present invention, wherein a list of submitted Field Documents may be provided for review.

Figure 9A:
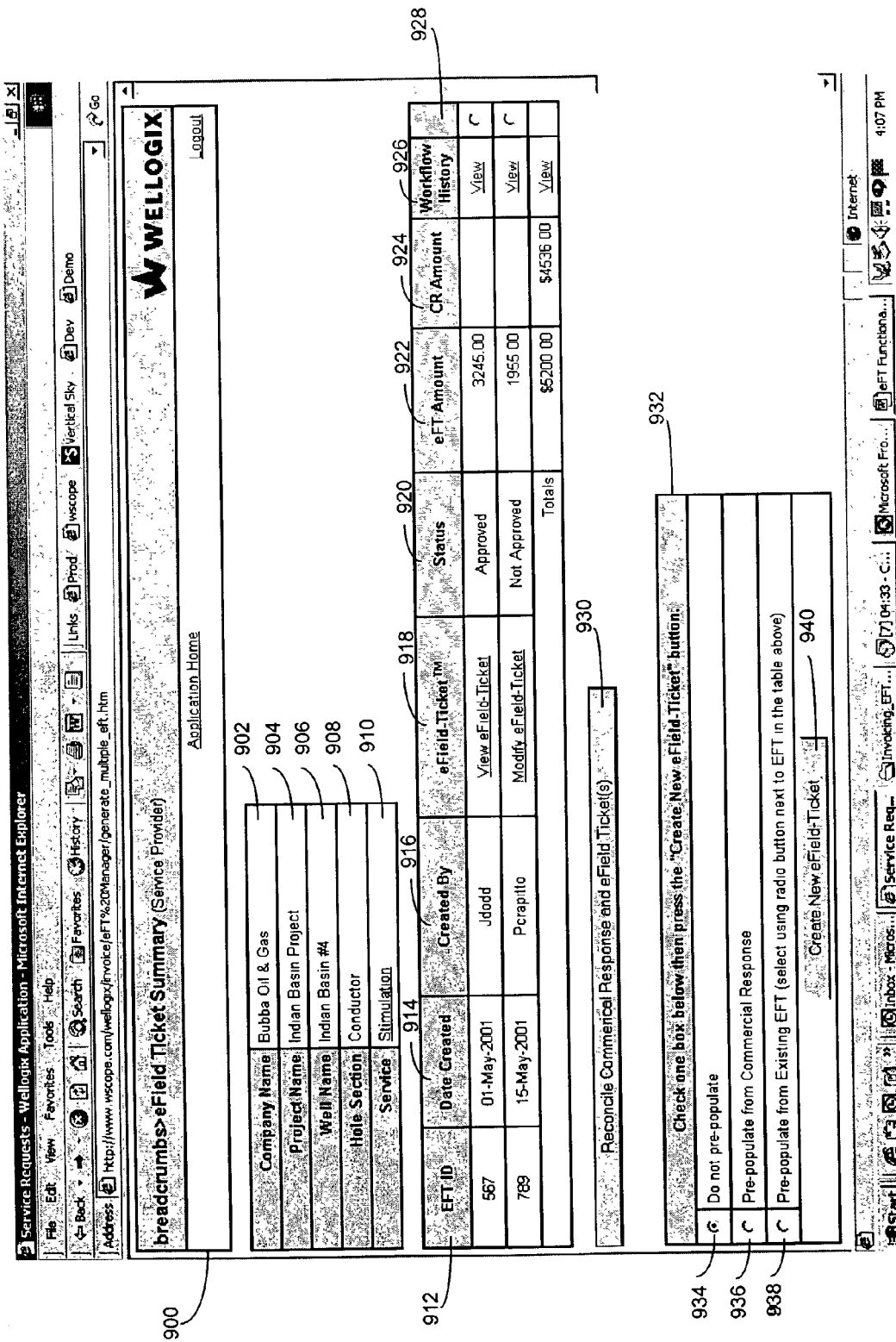
Figure 9B:
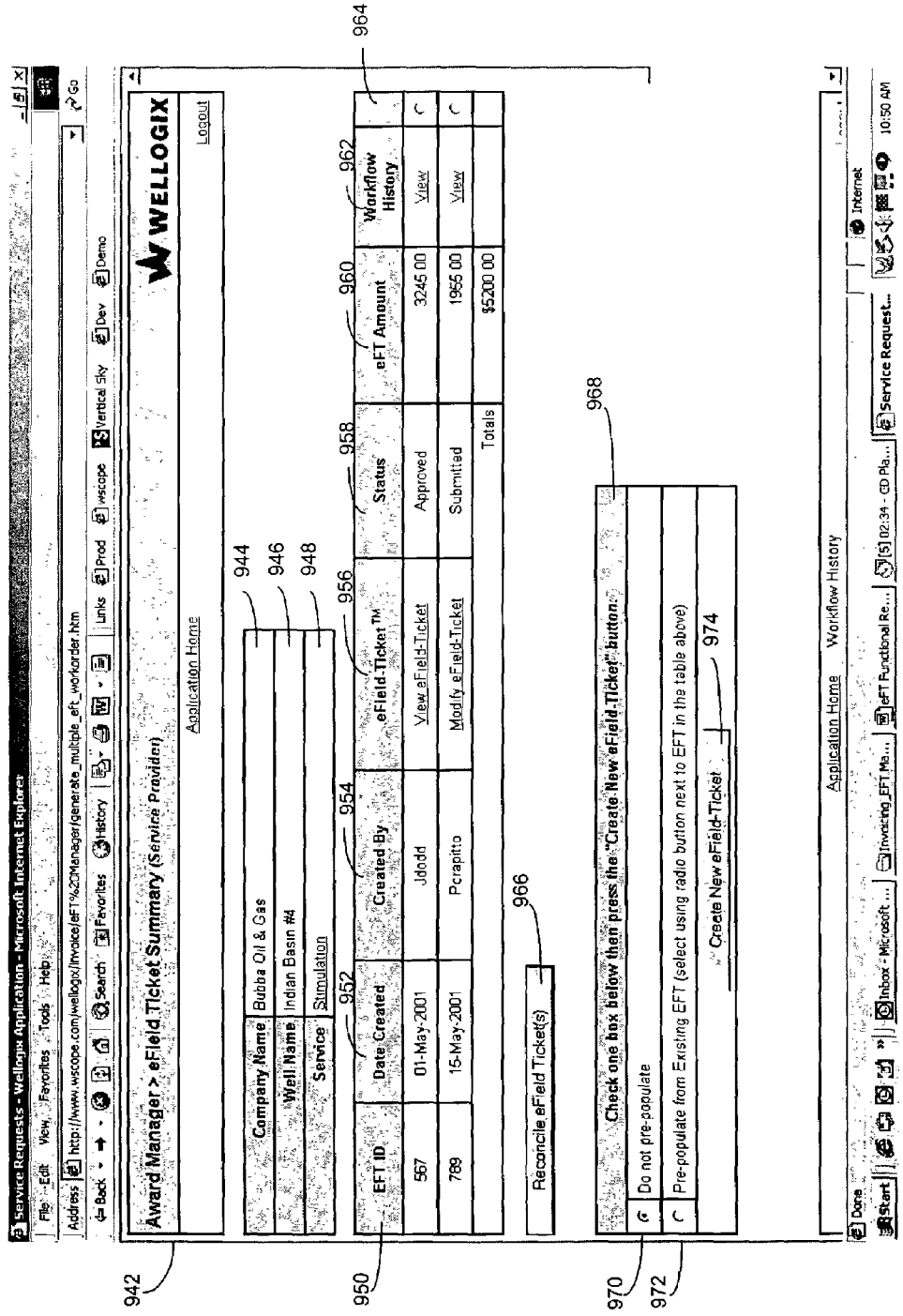

FIGS. 9A–B are exemplary screen shots of two embodiments of Field Document summary pages in which pre-population tools are provided for an Internet or Web browser based embodiment of the present invention.

Figure 10C:
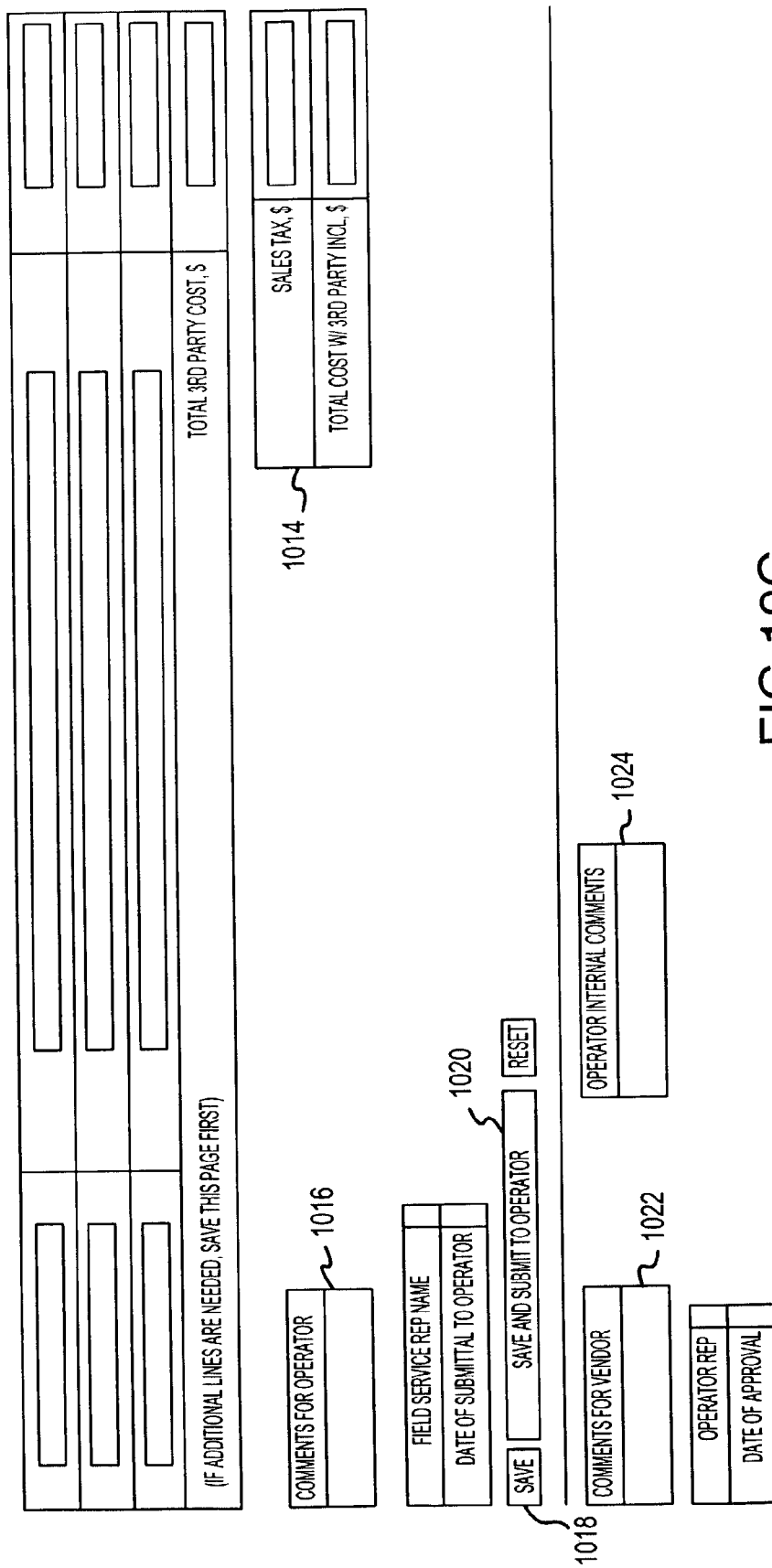

FIGS. 10A–C are exemplary screen shots of one embodiment of a Field Document template page for an Internet or Web browser based embodiment of the present invention in which time, materials, costs and/or fees may be provided.

Figure 11A:
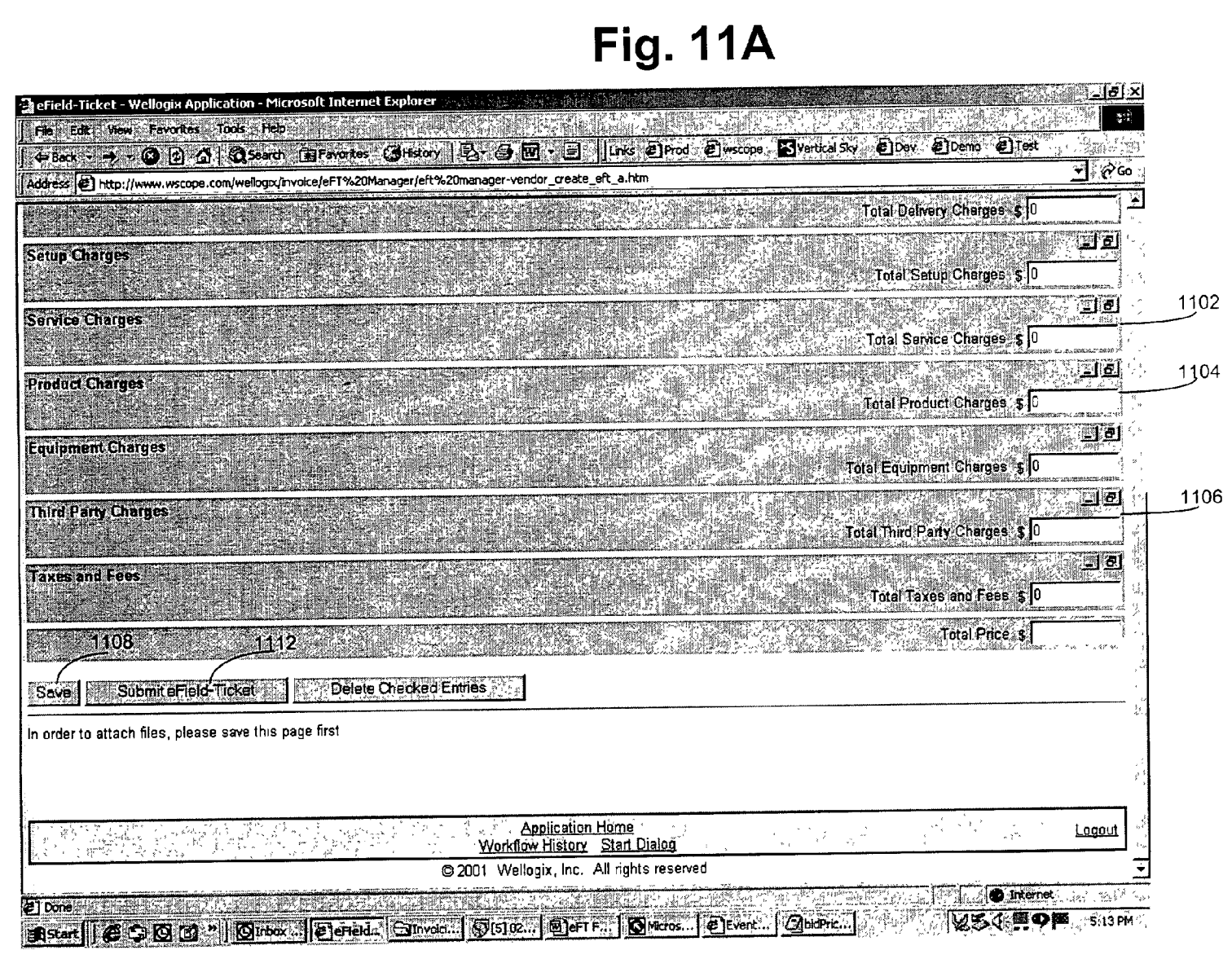

FIG. 11A is an exemplary screen shot of an embodiment of a Field Document template page for an Internet or Web browser based embodiment of the present invention, wherein various line item charge categories have been collapsed into individual windows.

Figure 11B:
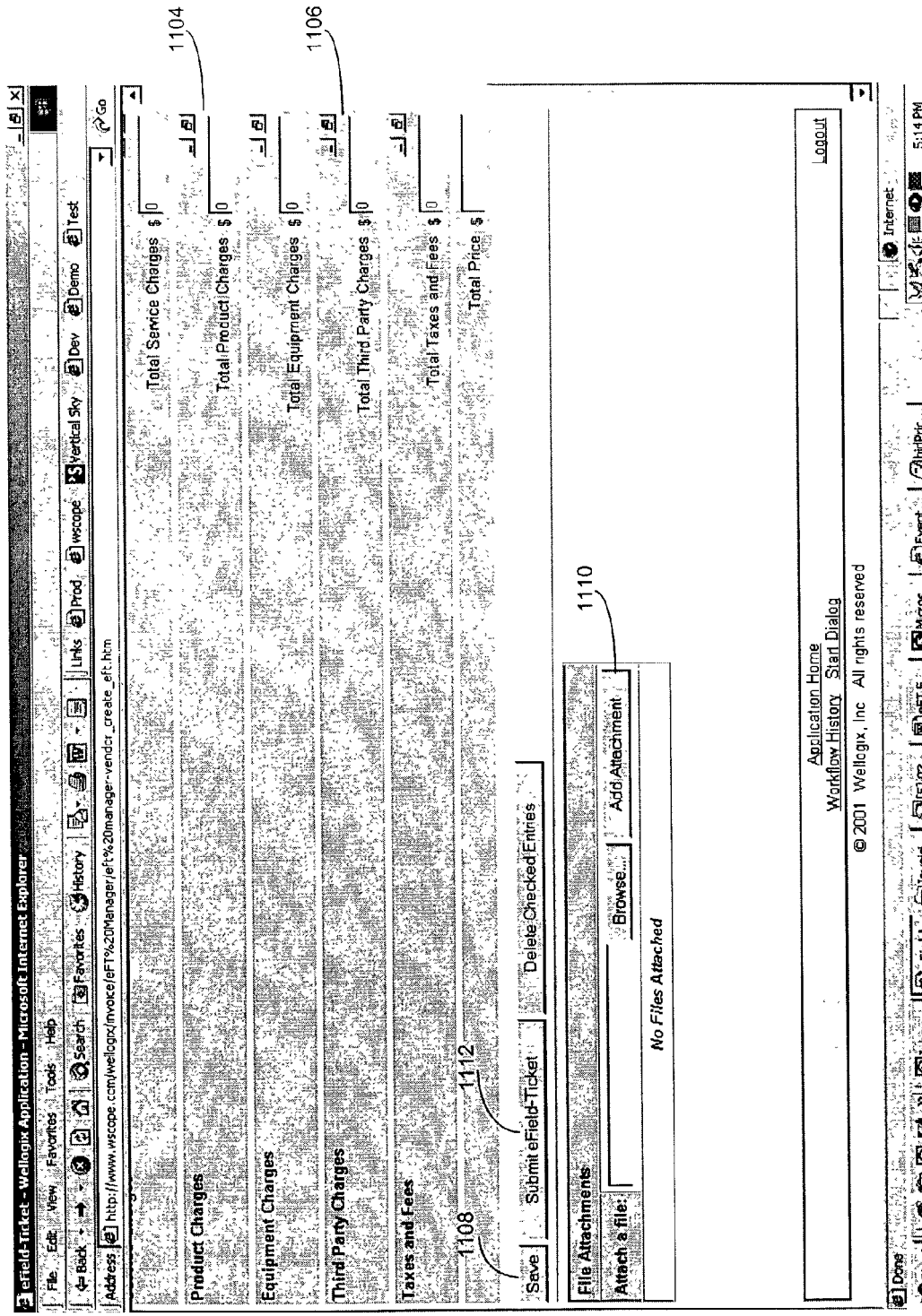

FIG. 11B is an exemplary screen shot of the Field Document template page shown in FIG. 11A after the "save"

button has been selected and further providing an interface with which to attach a file to a Field Document.

Figure 11C:
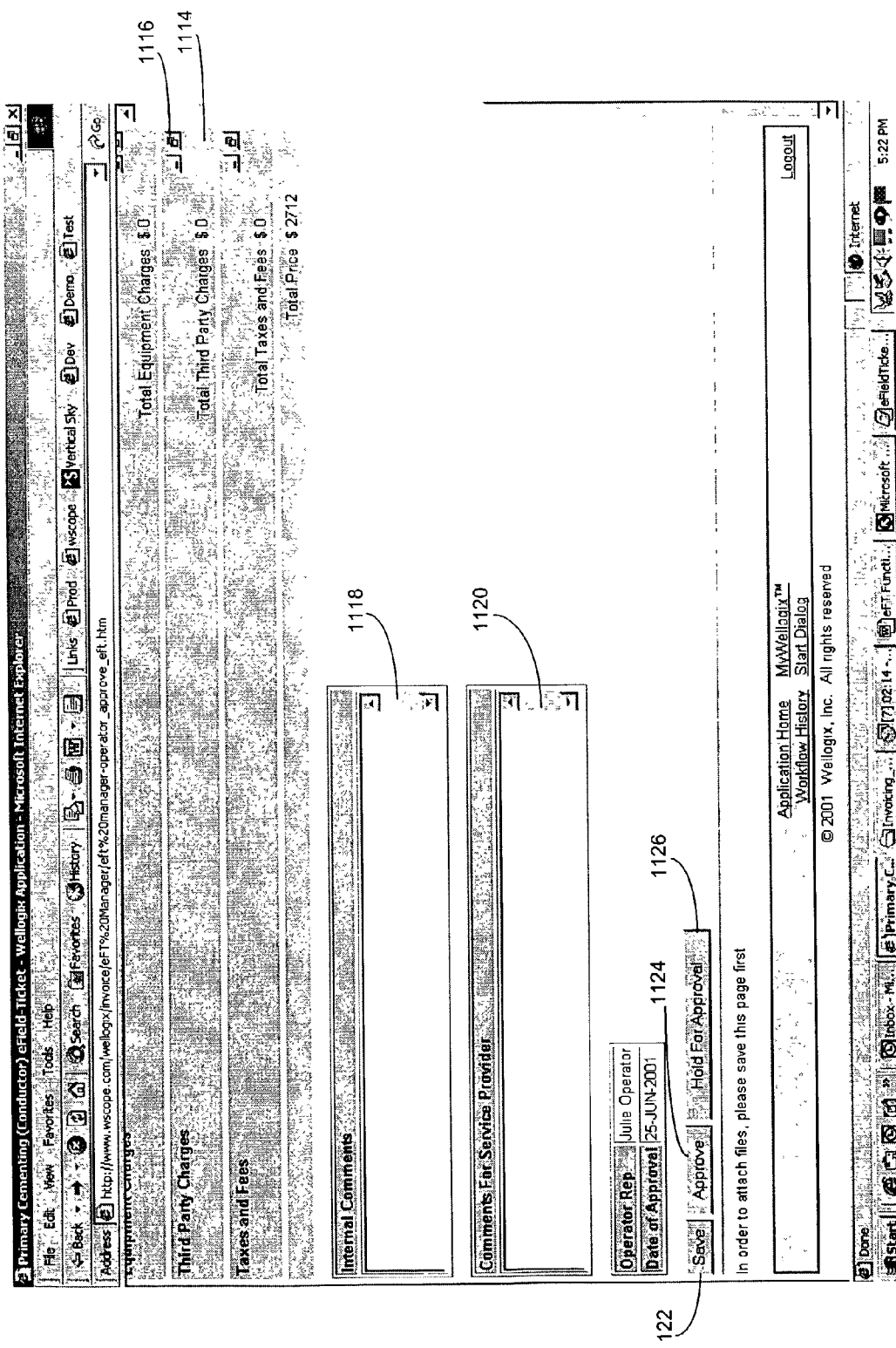

FIG. 11C is an exemplary screen shot of another embodiment of a Field Document template page for an Internet or Web browser based embodiment of the present invention, wherein the various line item charge categories have been collapsed into individual windows and collaboration windows for writing comments are provided.

Figure 11D:
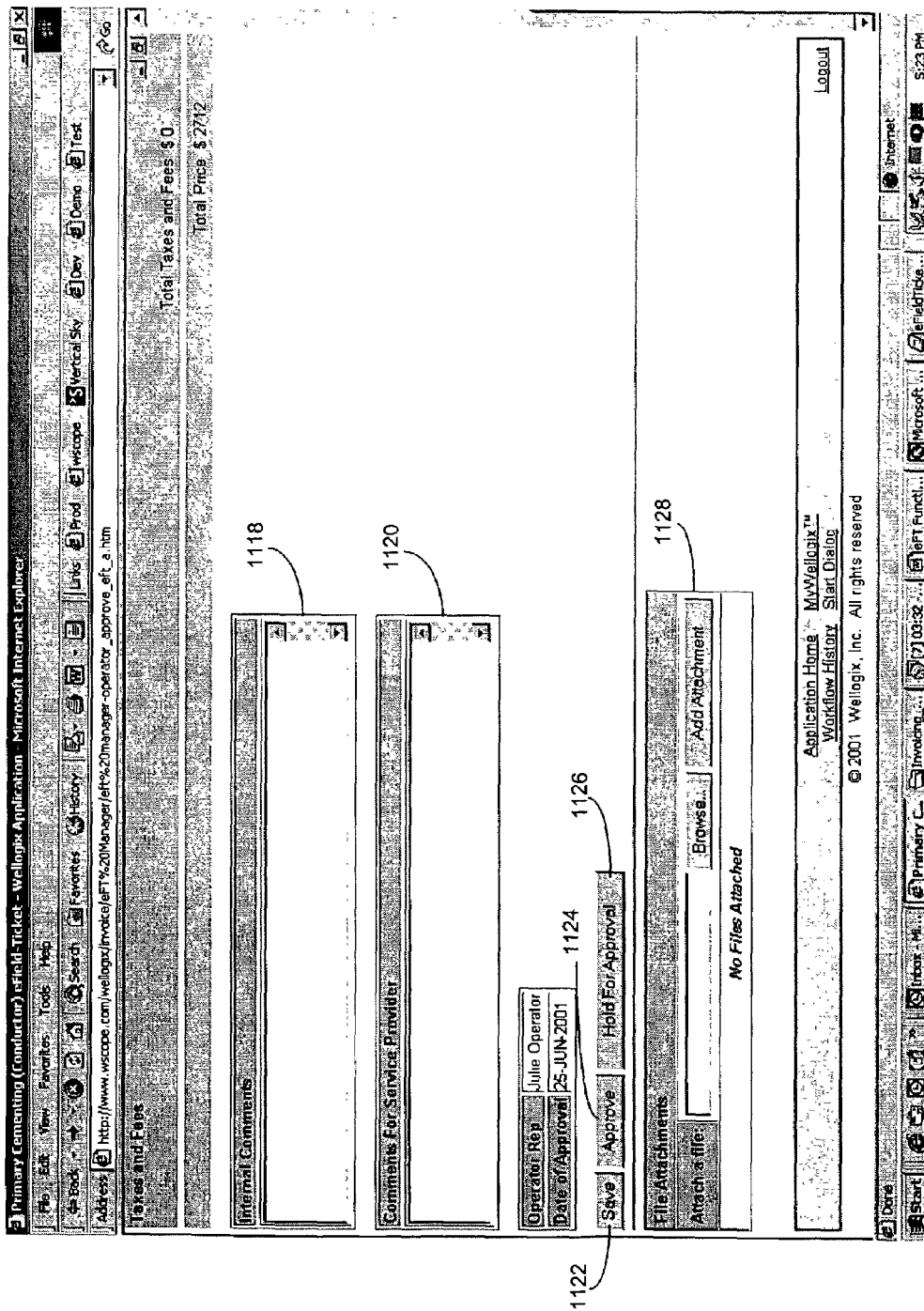

FIG. 11D is an exemplary screen shot of the Field Document template page shown in FIG. 11C after the "save" button has been selected and further providing an interface with which to attach a file to the Field Document.

Figure 11E:
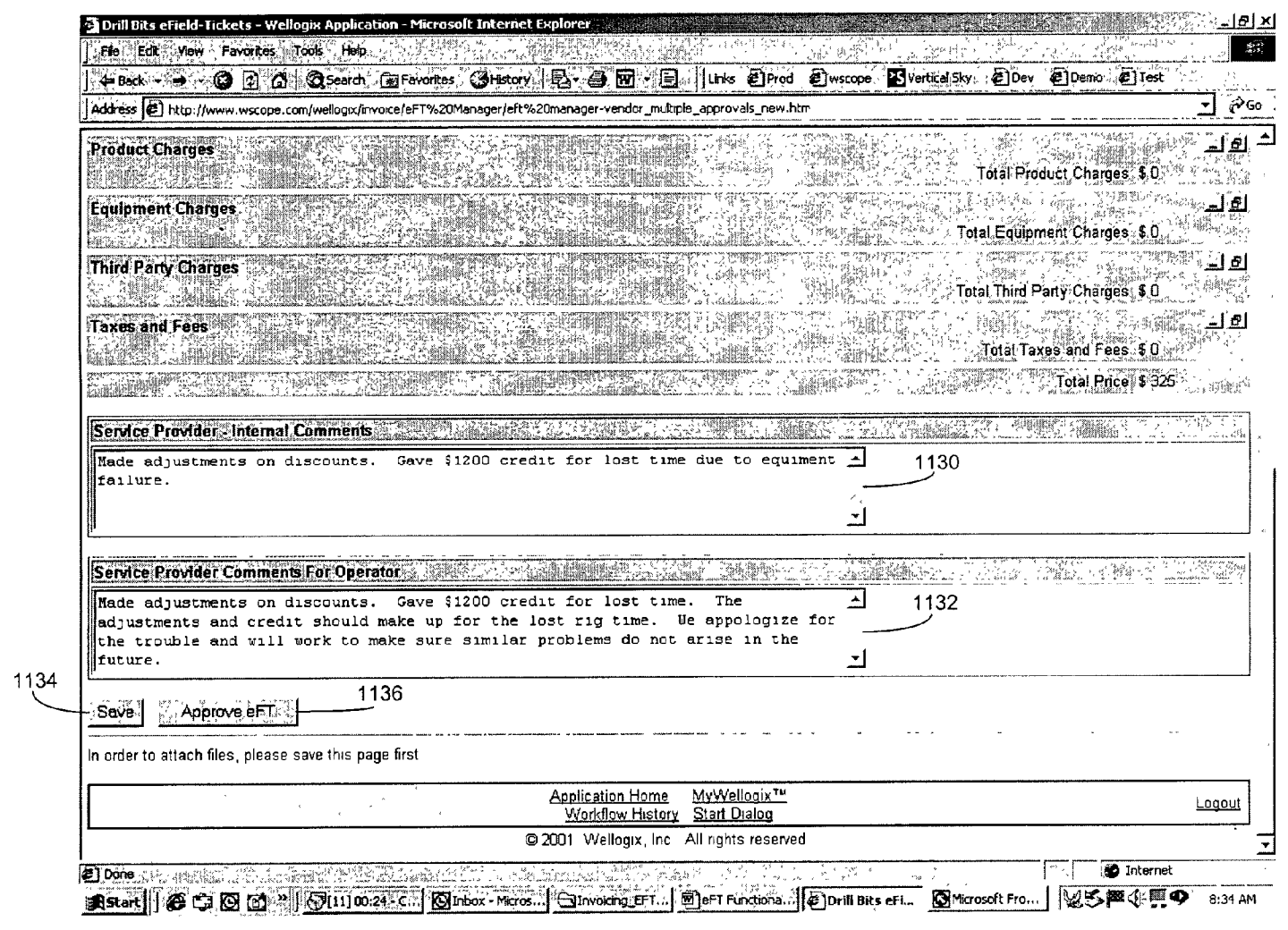

FIG. 11E is an exemplary screen shot of another embodiment of a Field Document template page for an Internet or Web browser based embodiment of the present invention in which an "approve" button is provided for approving a Field Document.

Figure 11F:
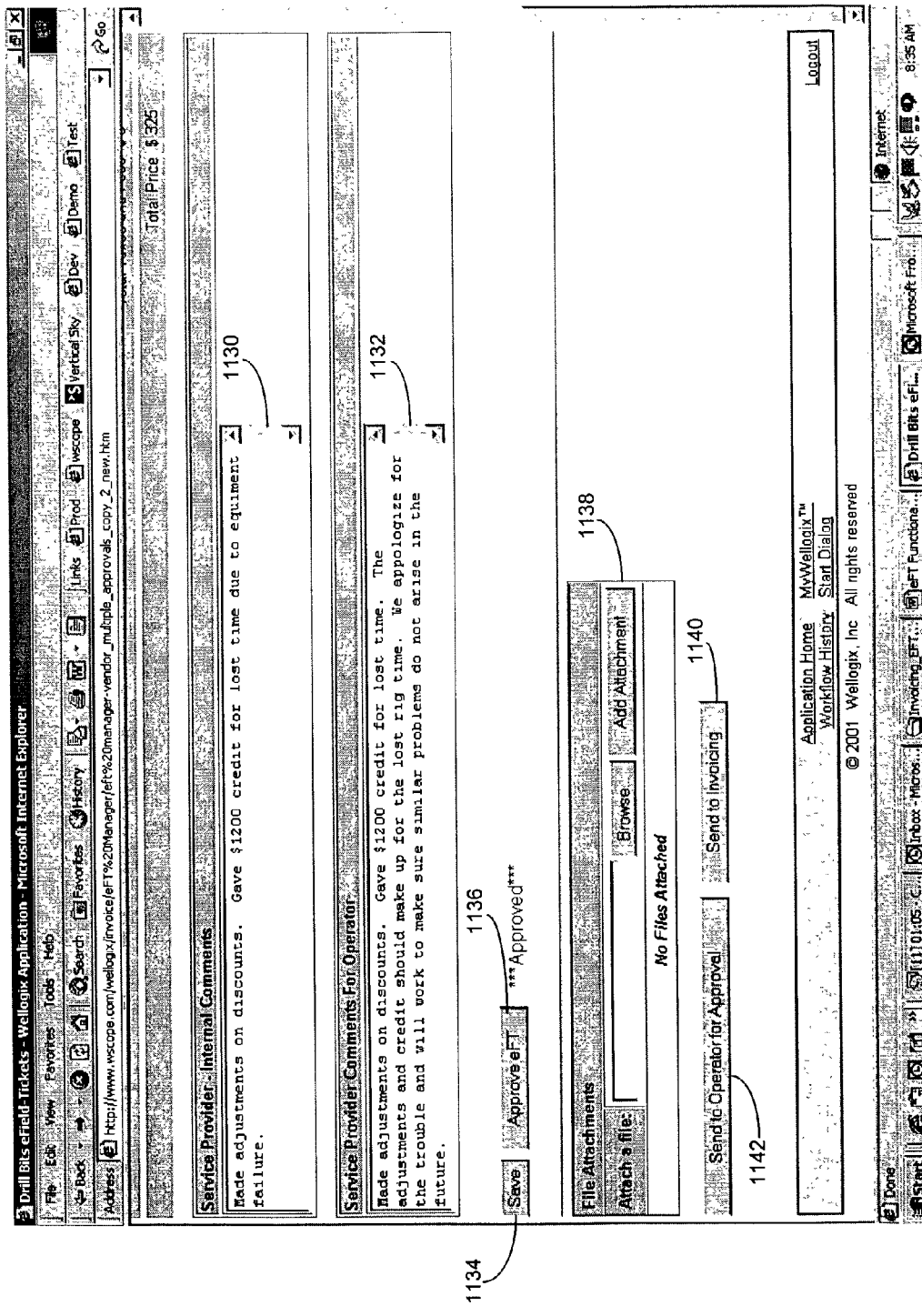

FIG. 11F is an exemplary screen shot of the Field Document template page of FIG. 11E after the "approve" button has been selected and further providing an interface with which to attach a file to a Field Document, send a Field Document for approval, and/or send a Field Document to invoicing.

Figure 12A:
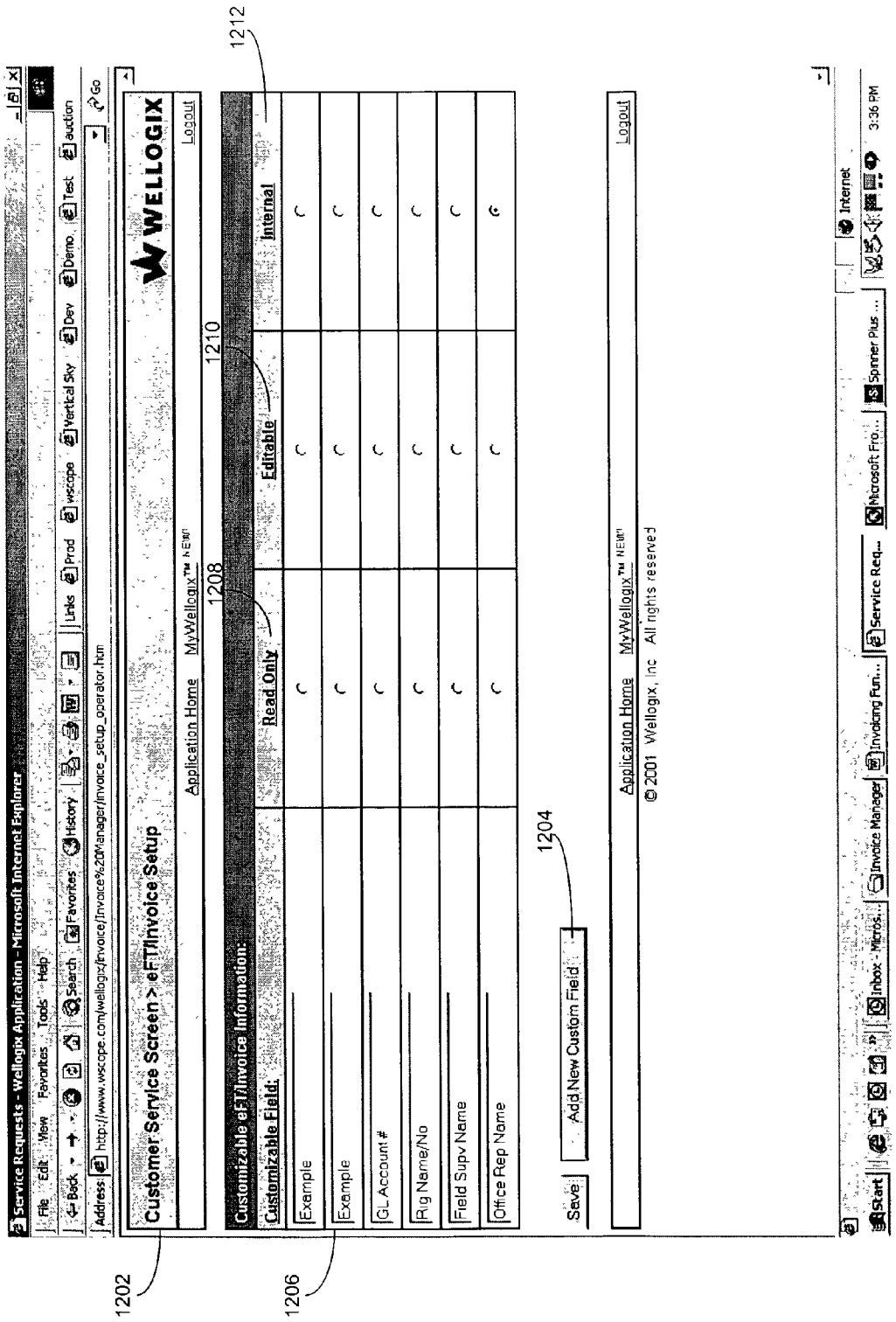

FIG. 12A is an exemplary screen shot of a Field Document template page in another Internet or Web browser based embodiment of the present invention providing for the creation of customized fields within the Field Document.

FIG. 12B is an exemplary screen shot of a Field Document template page in another Internet or Web browser based embodiment of the present invention showing one representation of how customized fields may be displayed on a customized Field Document.

Figure 13A:
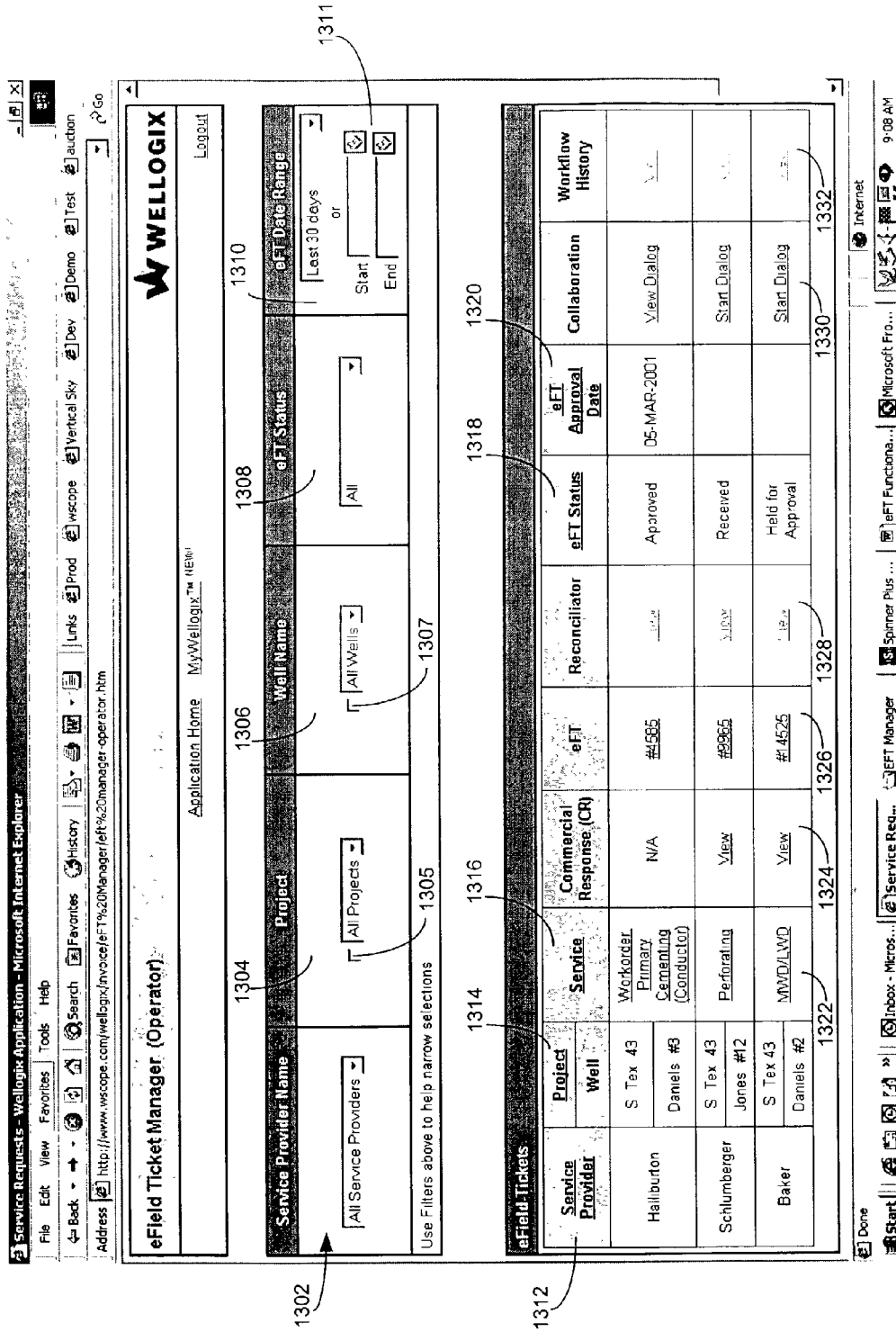
Figure 13B:
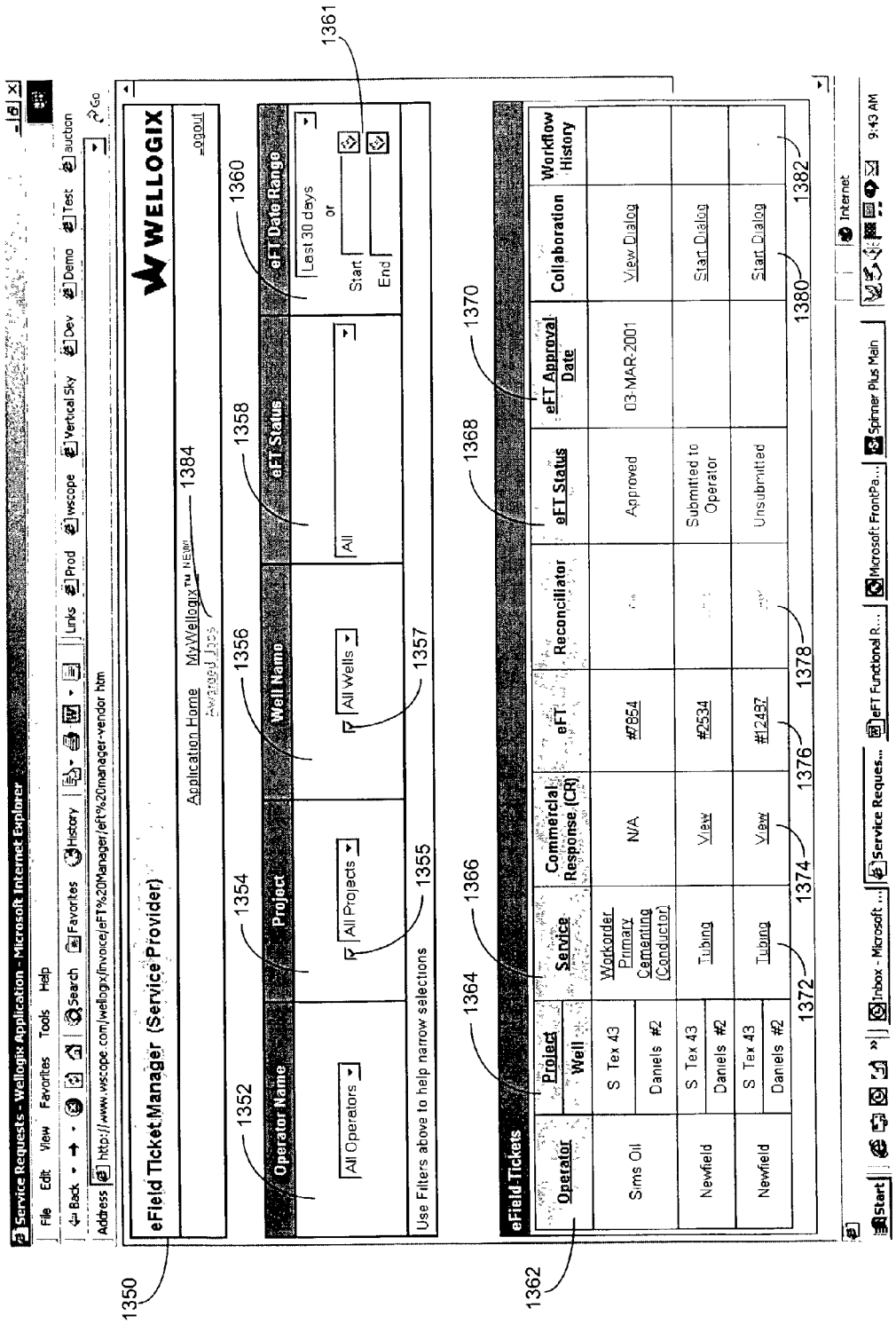

FIGS. 13A–B are exemplary screen shots of a filtering tool for managing Field Documents in an Internet or Web browser based embodiment of the present invention.

Figure 14A:
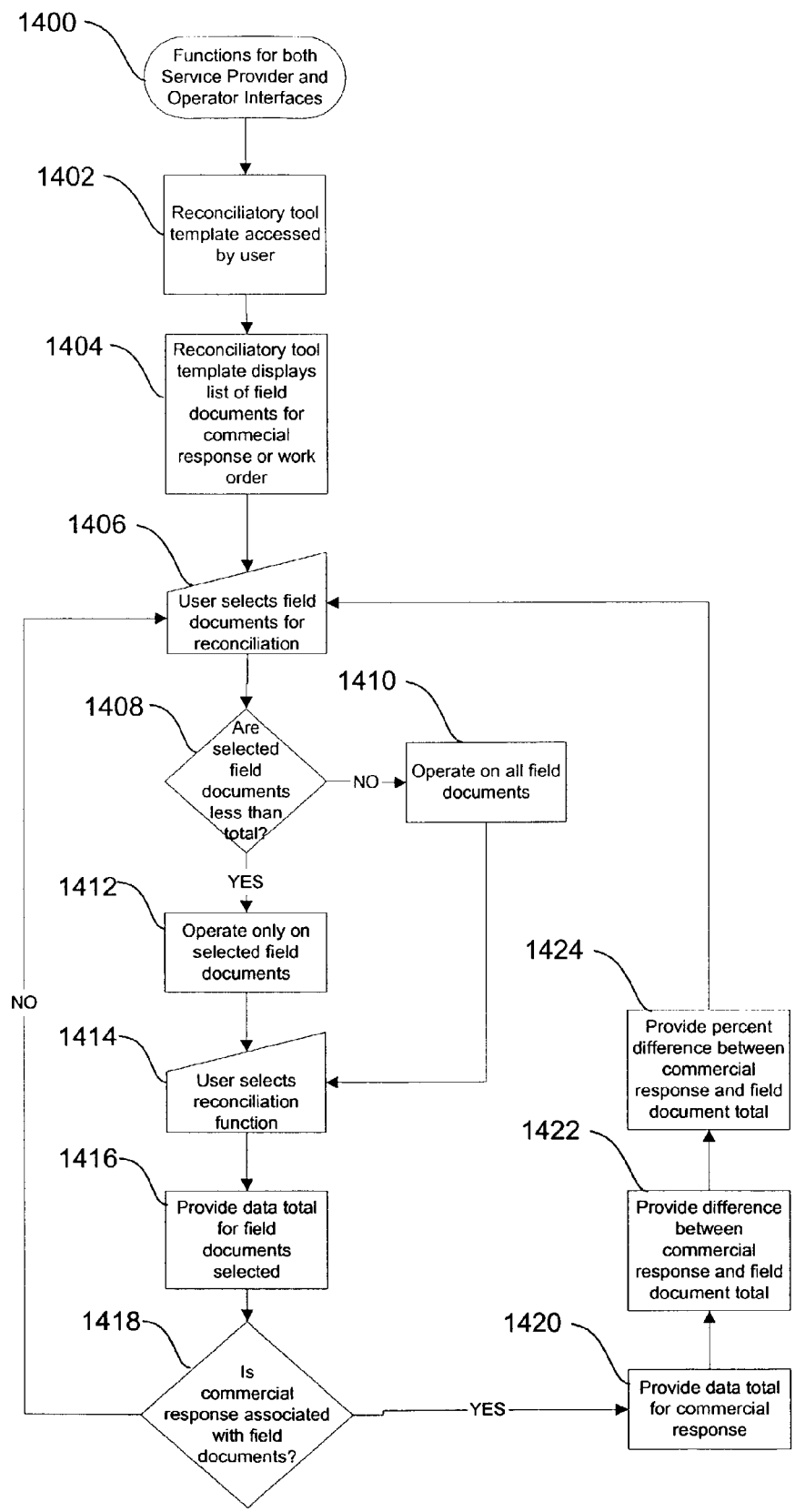
Figure 14B:
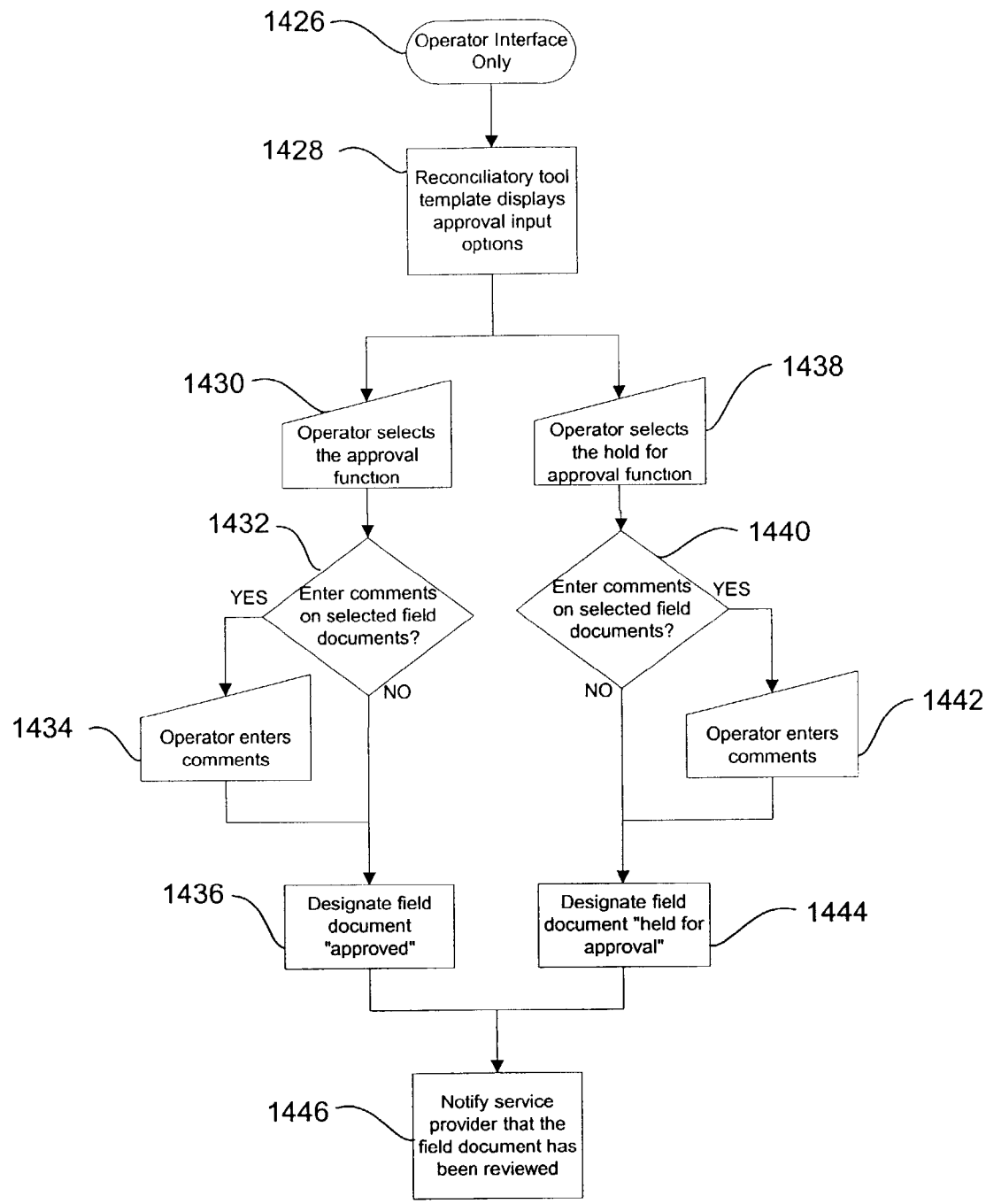

FIGS. 14A–B are flow diagrams of a process whereby a service provider is able to reconcile Field Documents according to one embodiment of the present invention.

FIGS. 15A–D are exemplary screen shots of one embodiment of a Field Document reconciliation tool for an Internet or Web browser based embodiment of the present invention.

Figure 16:
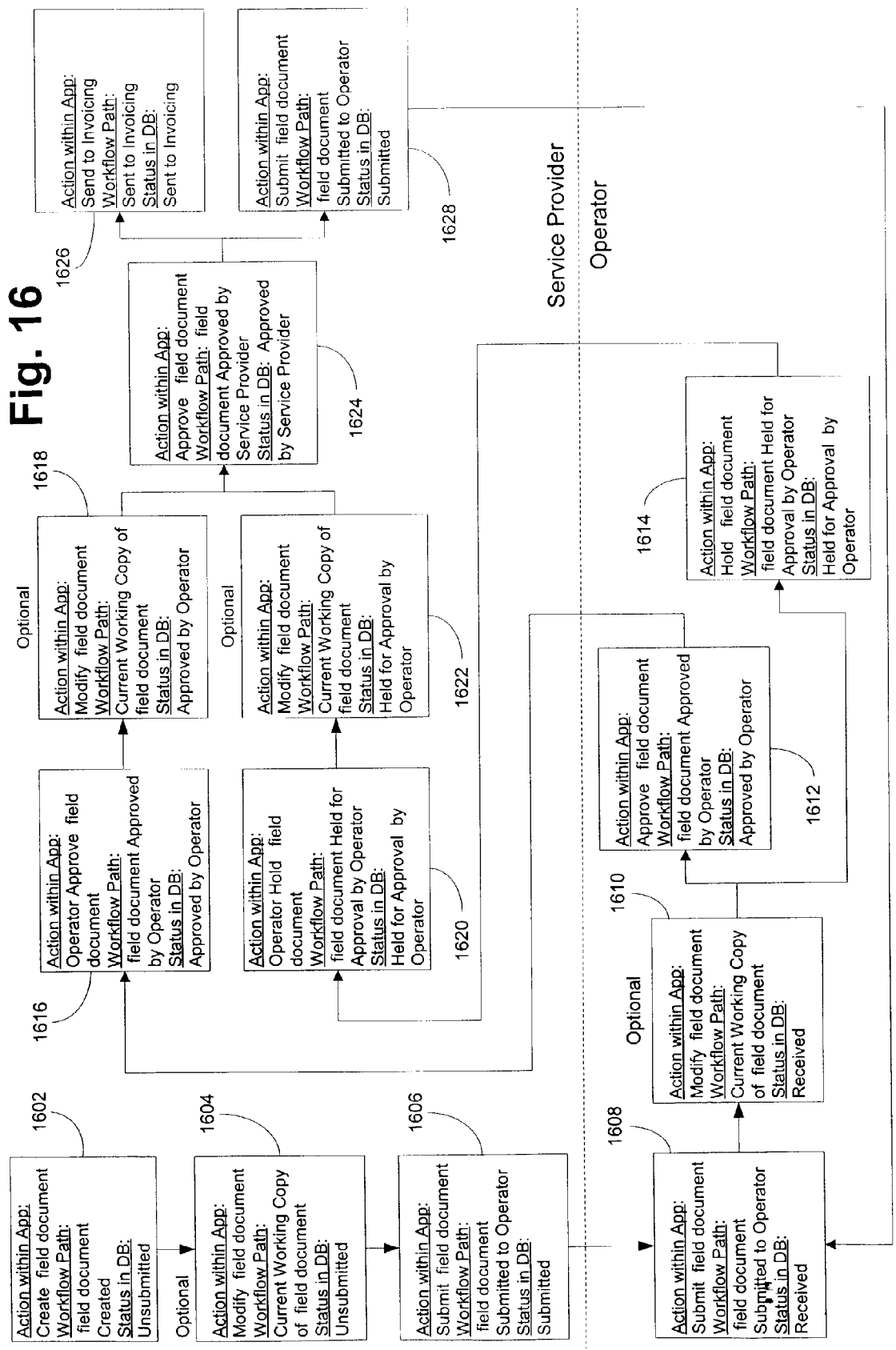

FIGS. 16 is a flow diagram detailing a workflow history process for managing Field Document reconciliation according to one embodiment of the present invention.

FIGS. 17A–H are exemplary screen shots of workflow history template pages for an Internet or Web browser based embodiment of the present invention showing the information tracking entries for a Field Document made by a workflow history tool.

FIGS. 18A–G are exemplary screen shots of workflow history template pages for an Internet or Web browser based embodiment of the present invention showing the information tracking entries for a Field Document made by a workflow history tool.

Figure 19:
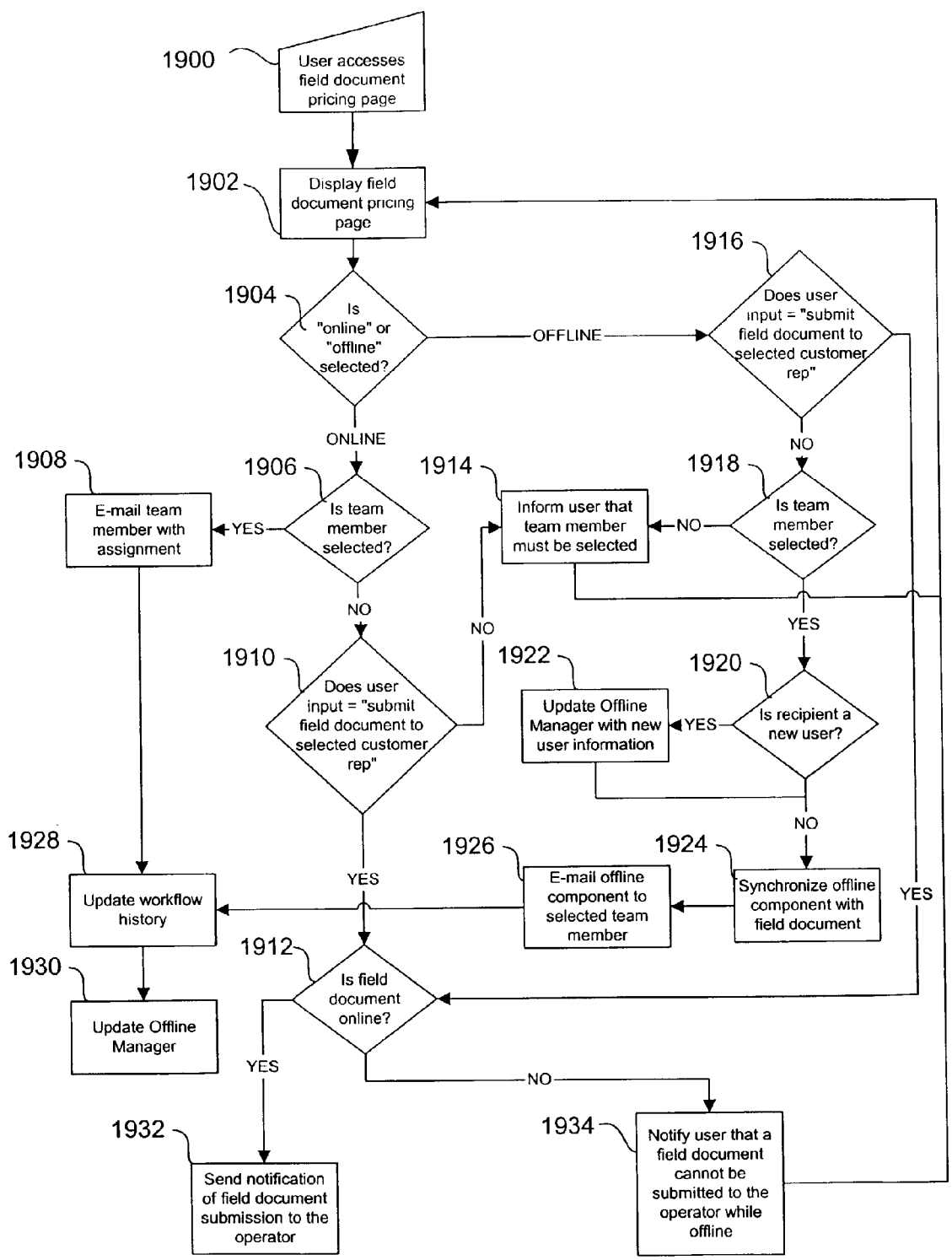

FIG. 19 is an exemplary flow diagram for one embodiment of the present invention depicting a process for assigning, managing, and tracking Field Documents, both online and offline as an Offline Component.

Figure 20:
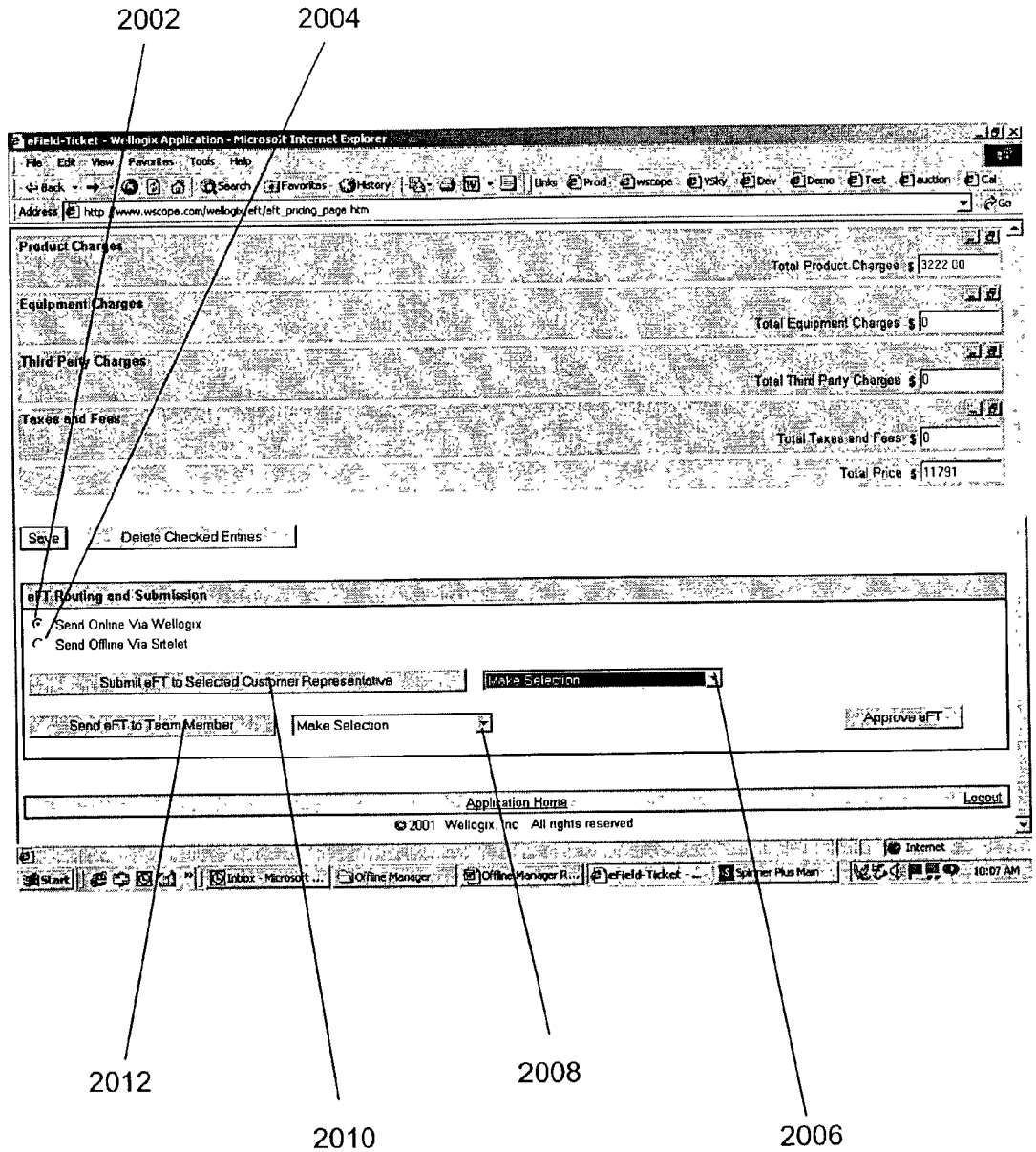

FIG. 20 is an exemplary screen shot of a price list Offline Component.

Figure 21:
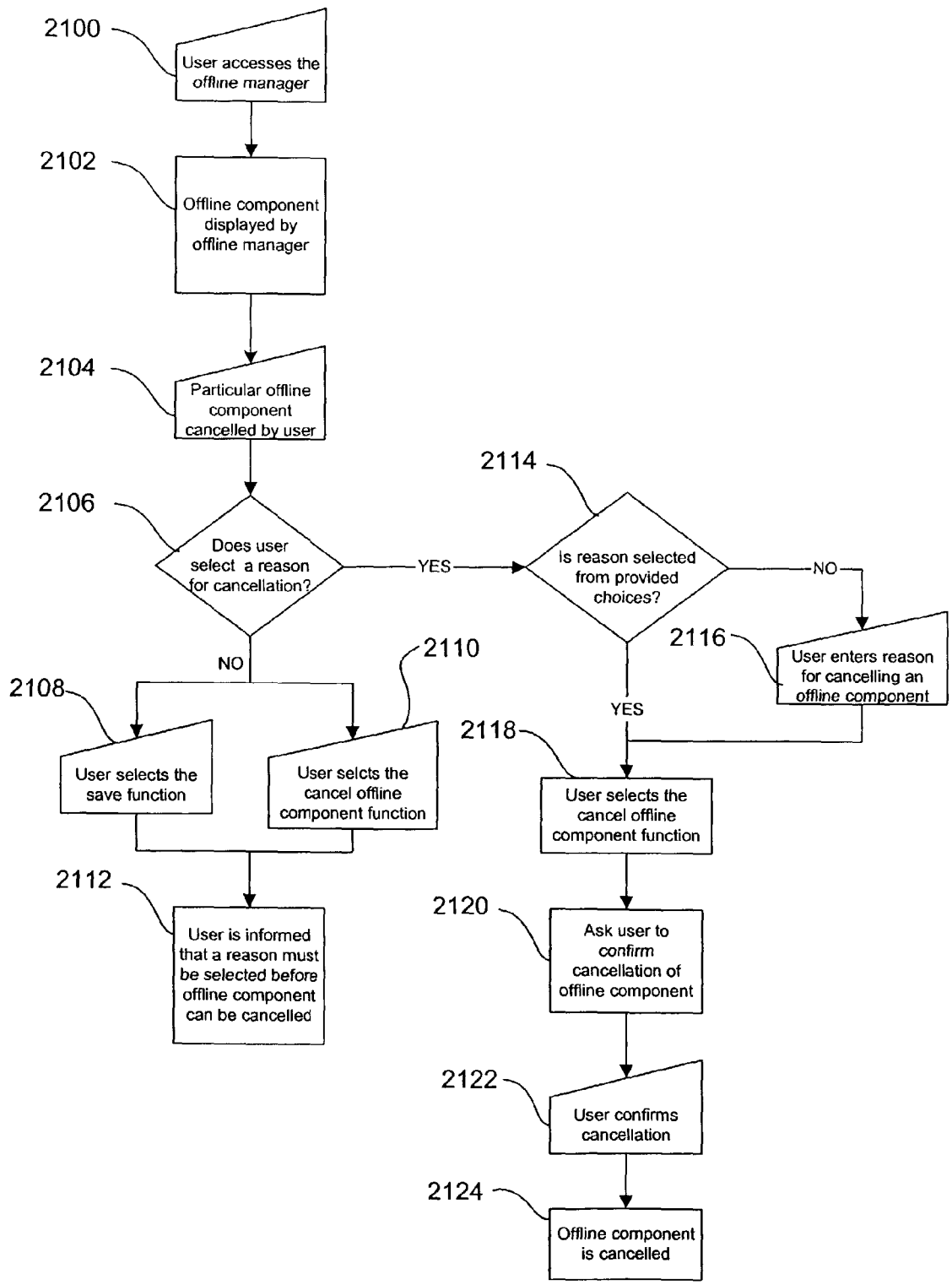

FIG. 21 is a flow diagram for one embodiment of the present invention depicting an exemplary process for canceling Offline Components.

Figure 22A:
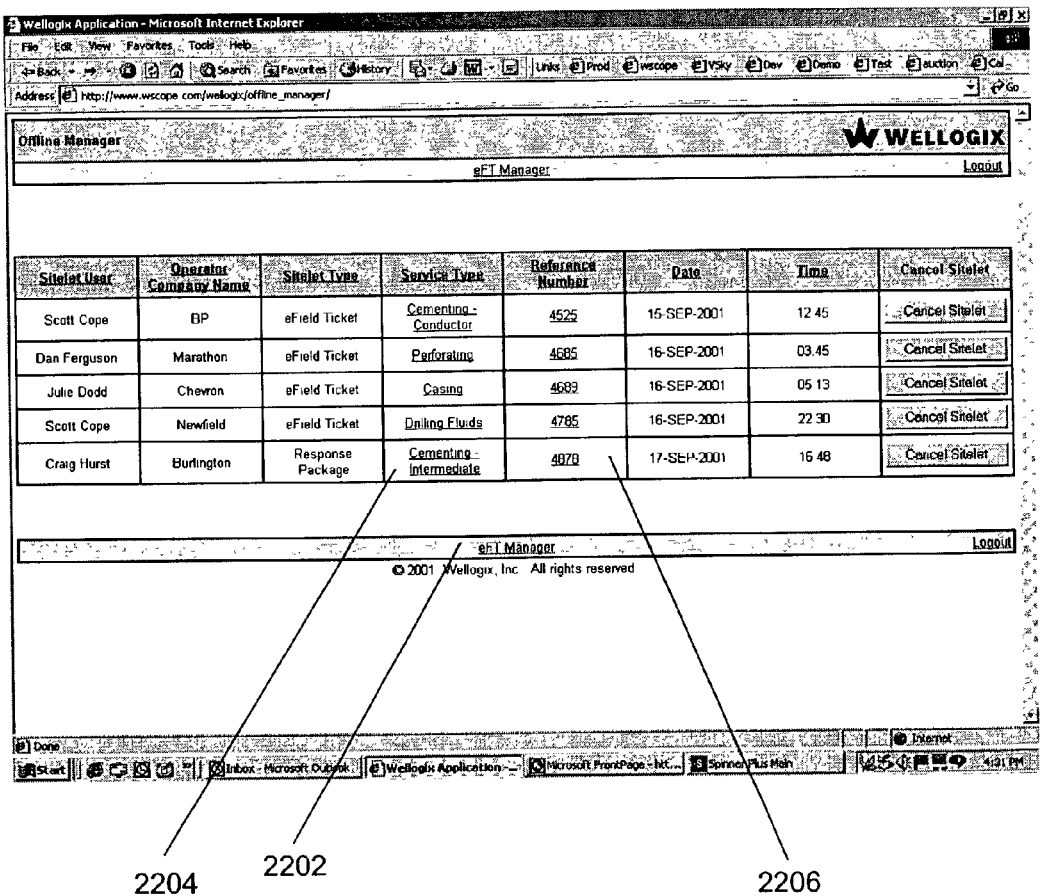
Figure 22B:
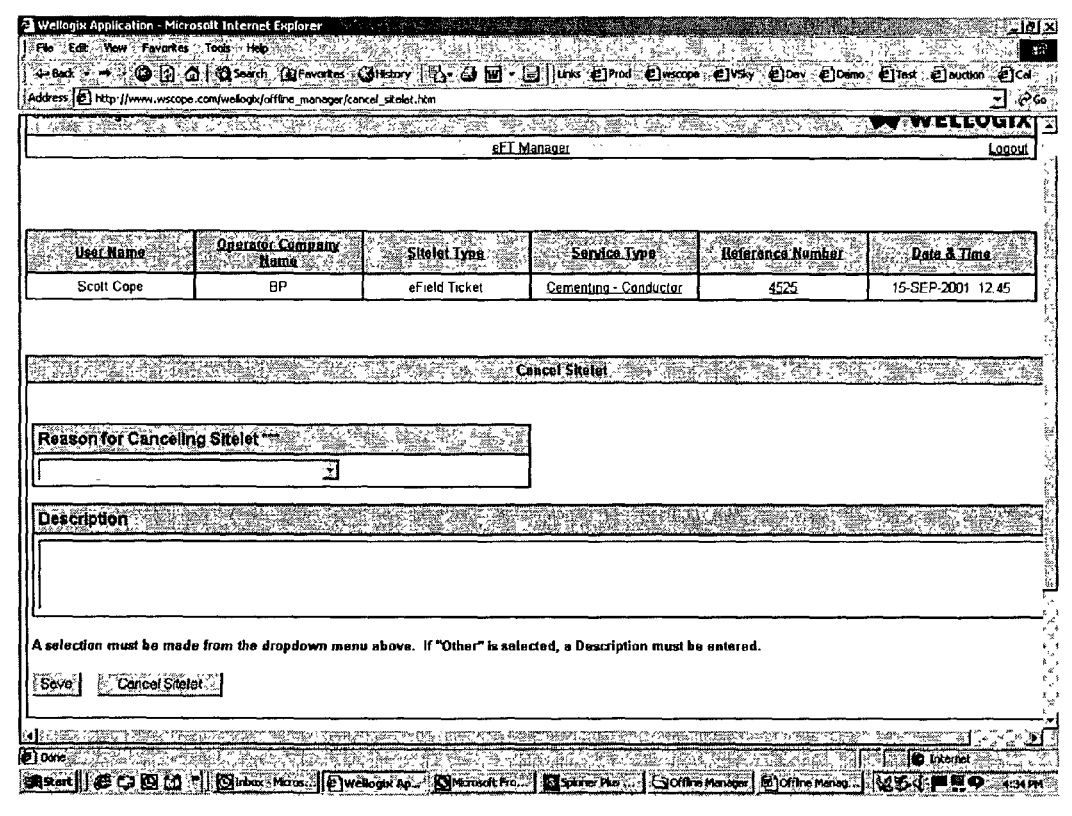
Figure 22C:
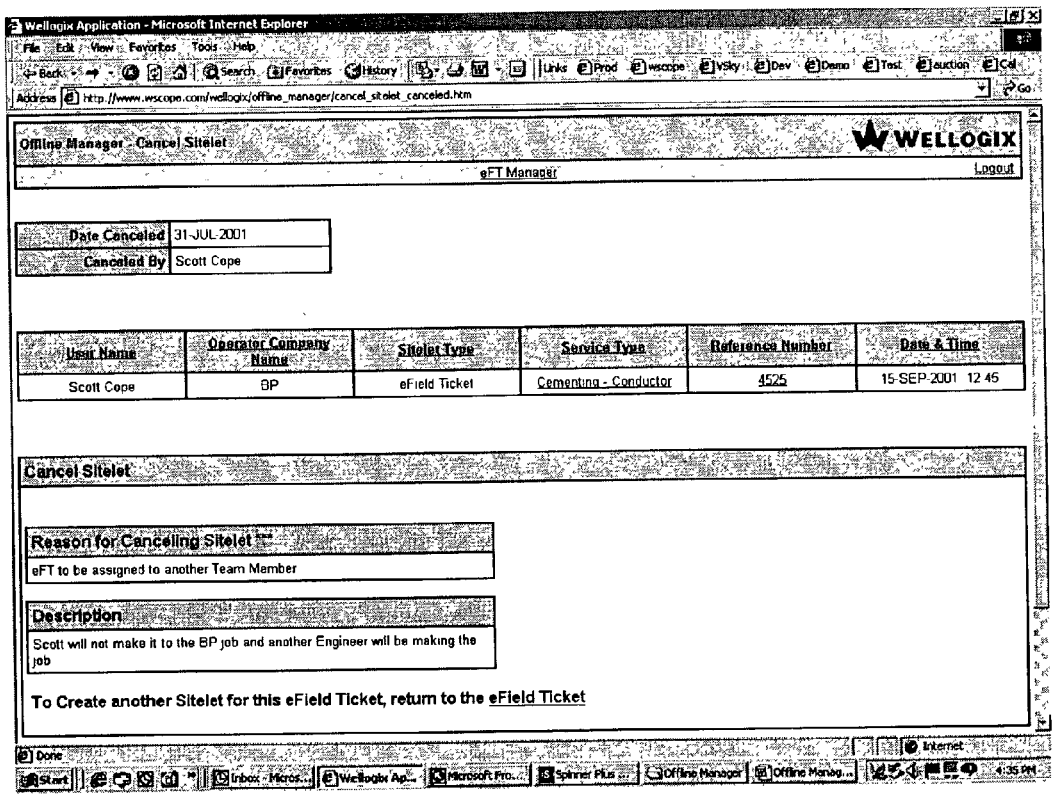

FIGS. 22A–C are exemplary screen shots for one embodiment of the present invention of the offline manager used for canceling Offline Components.

Figure 23:
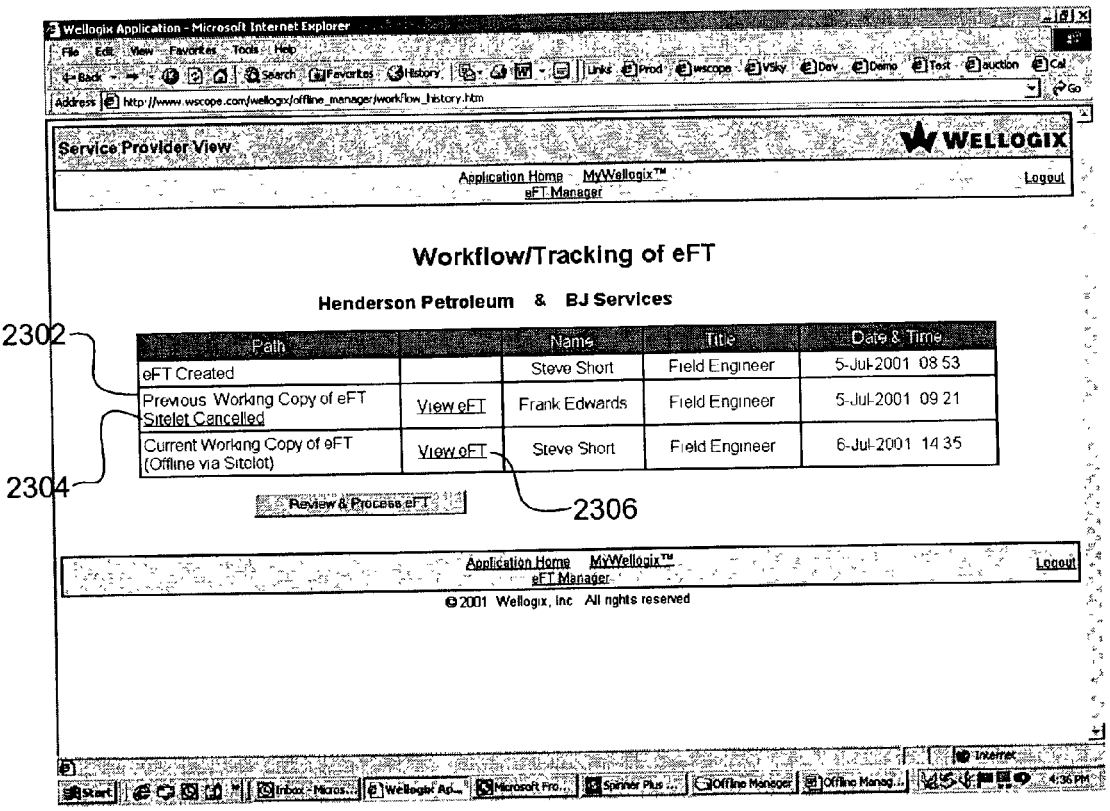

FIG. 23 is an exemplary screen shot for one embodiment of the present invention of a workflow tracking screen showing a cancelled Offline Component.

Figure 24A:
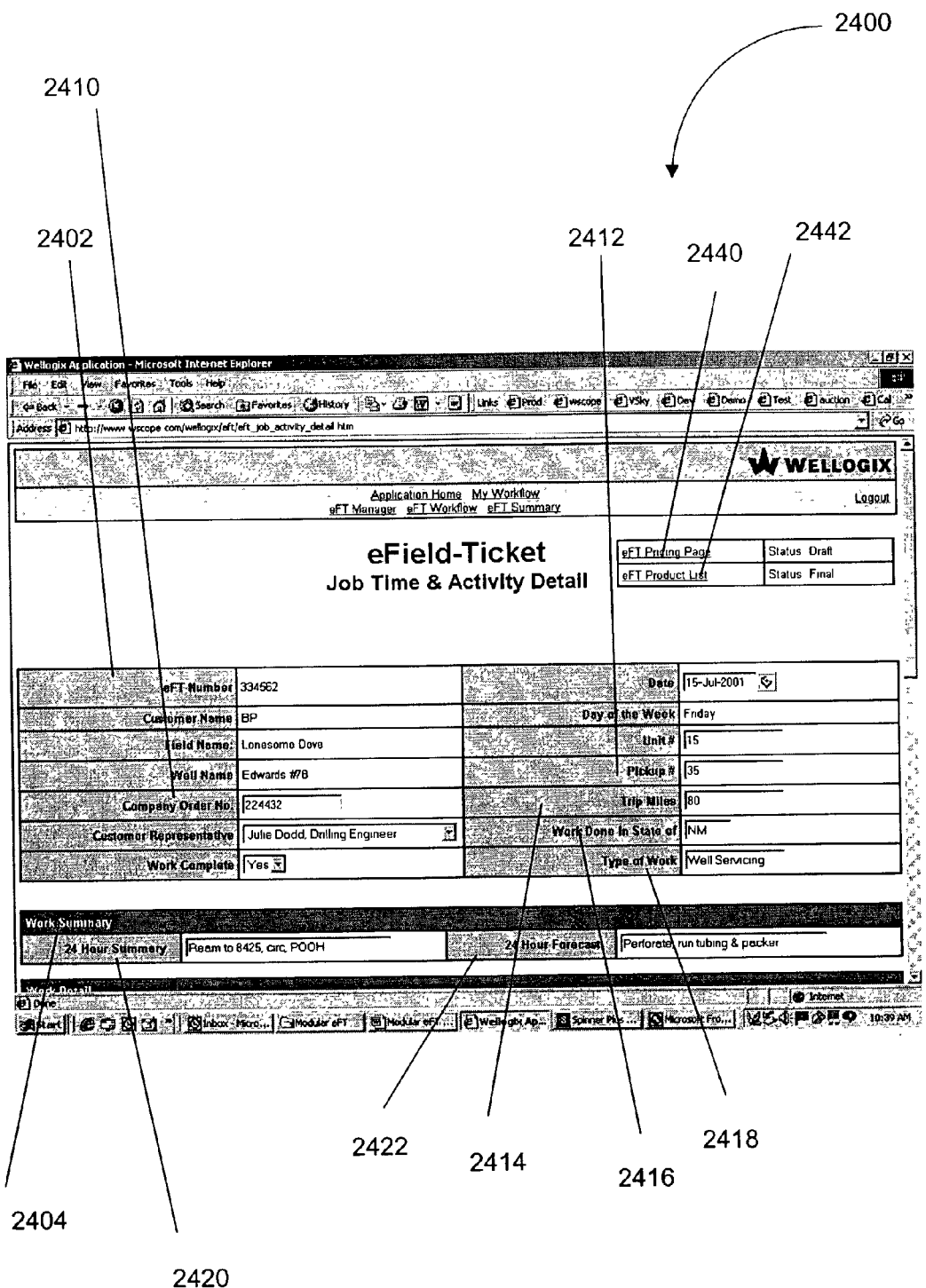
Figure 24B:
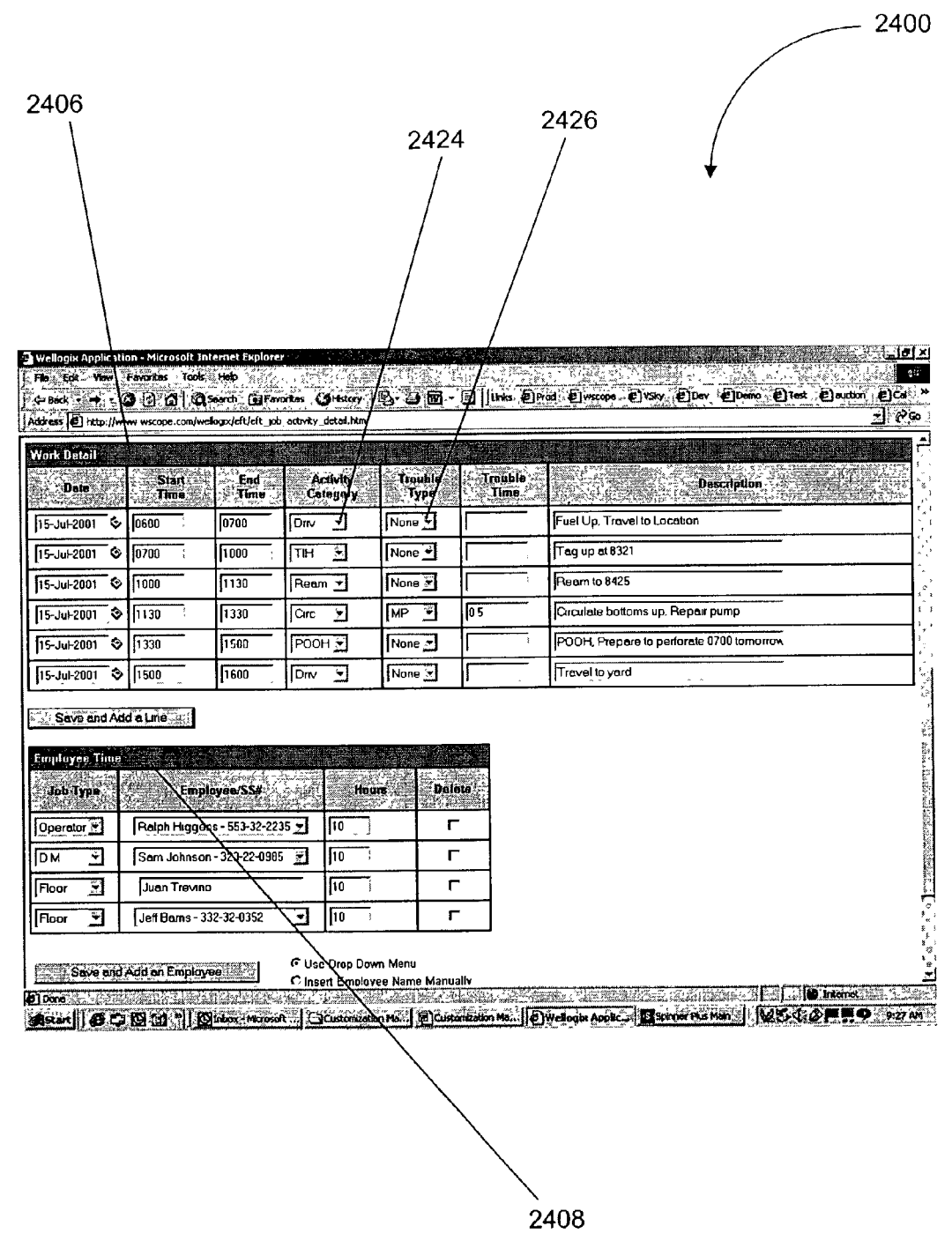
Figure 24C:
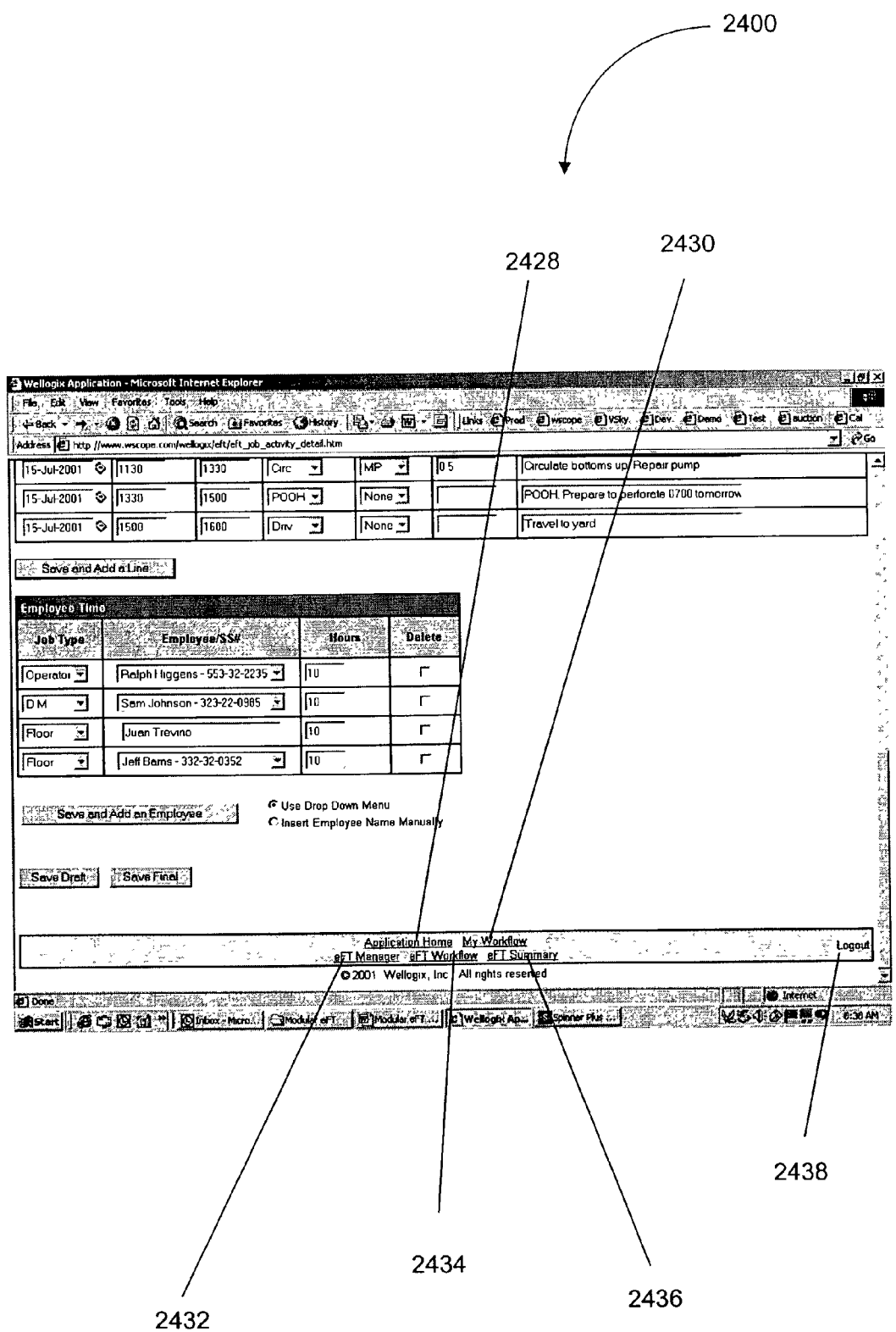

FIGS. 24A–C are exemplary screen shots for one embodiment of the present invention of a job time and activity detail included in a modular Field Document.

Figure 25A:
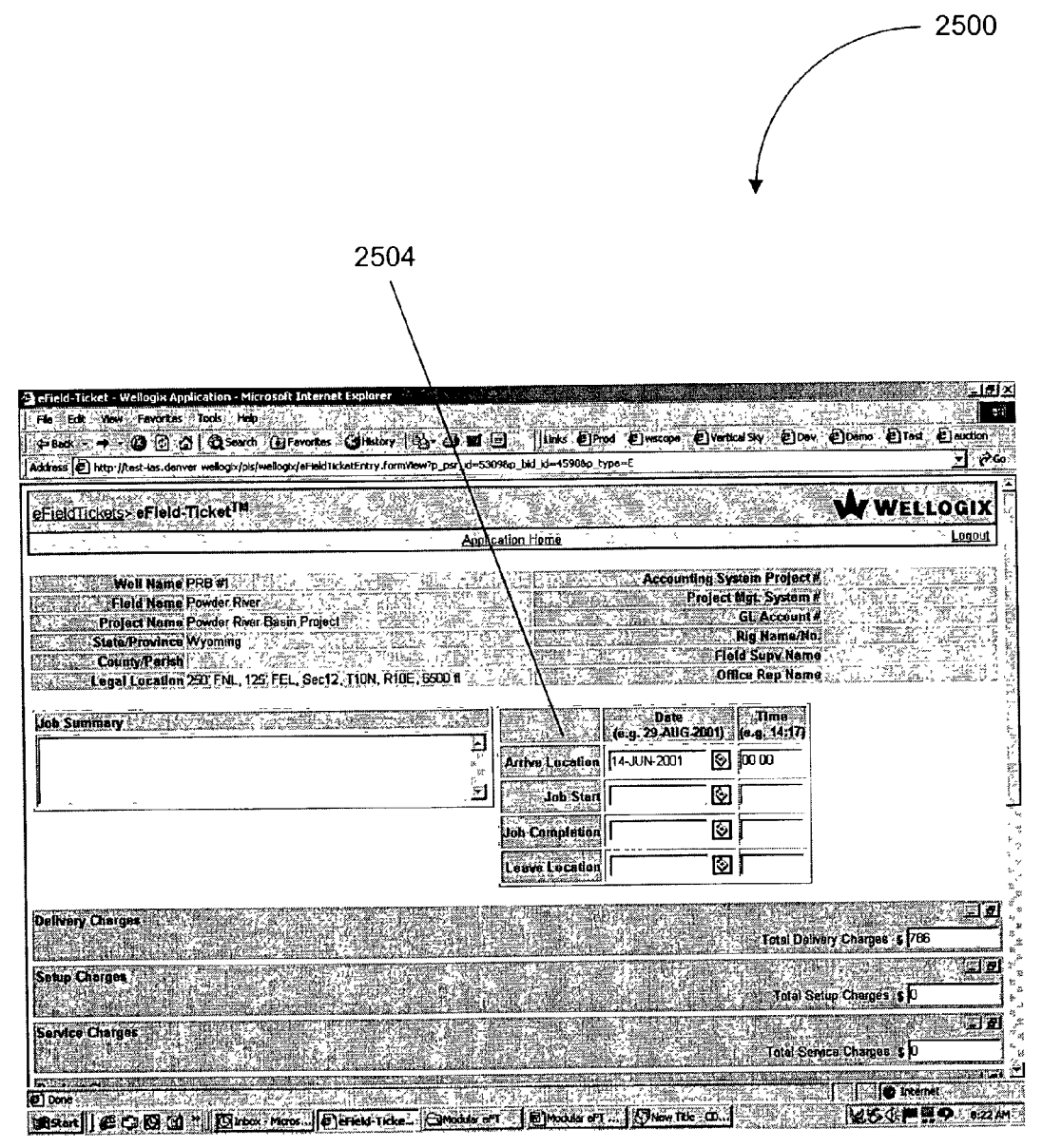
Figure 25B:
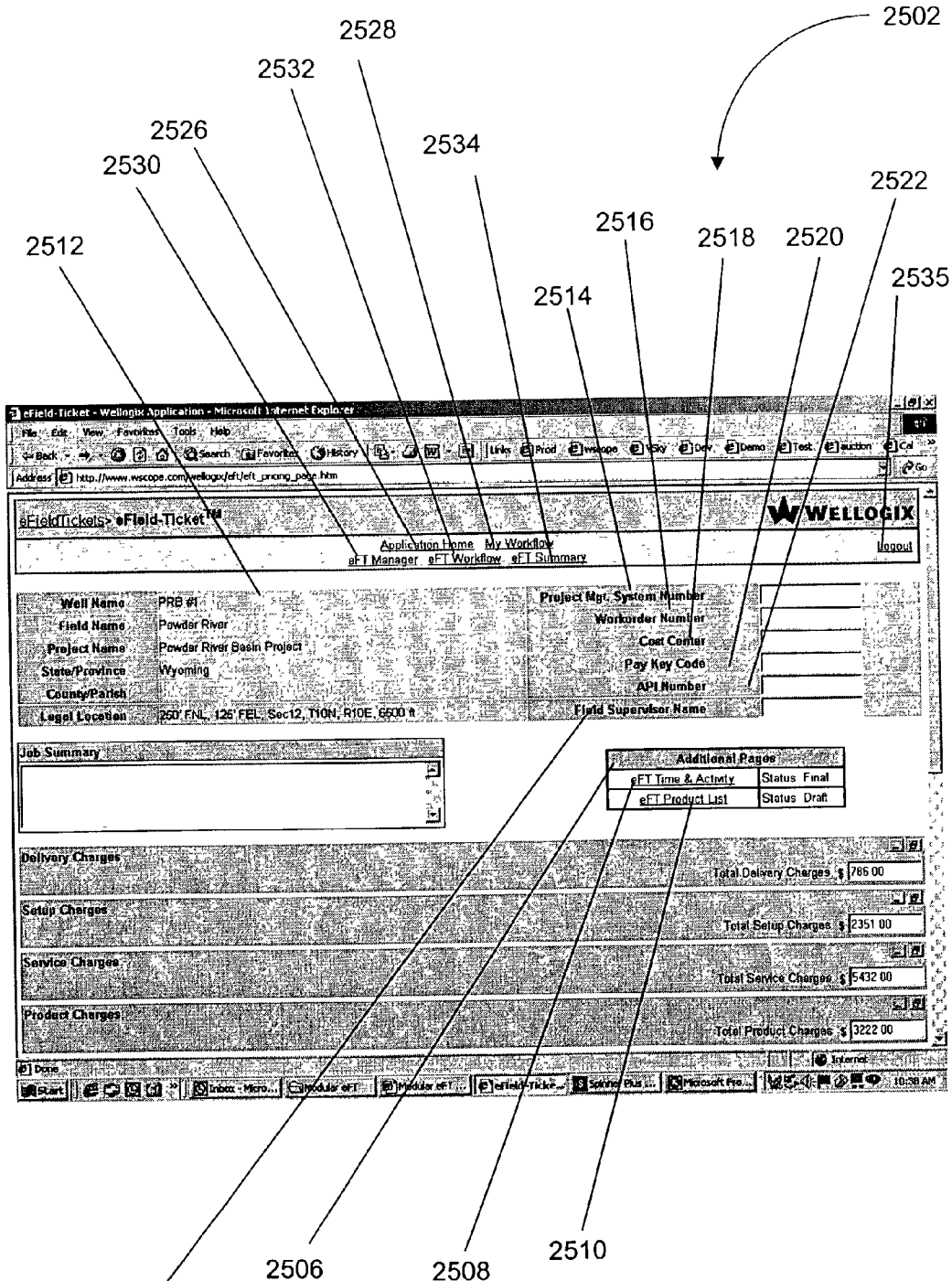
Figure 25C:
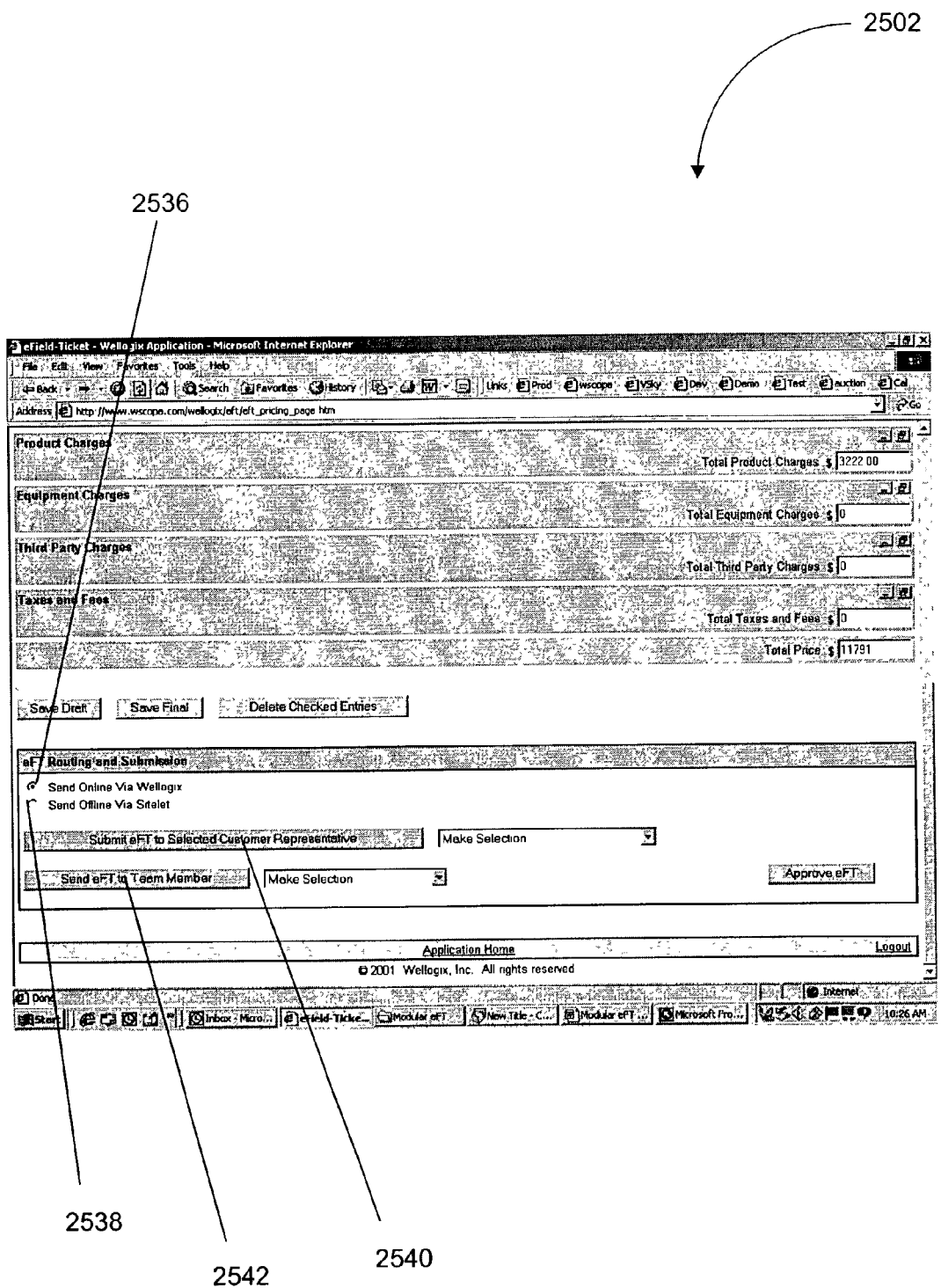

FIGS. 25A–C are exemplary screen shots for one embodiment of the present invention of pricing page included in a modular Field Document.

Figure 26A:
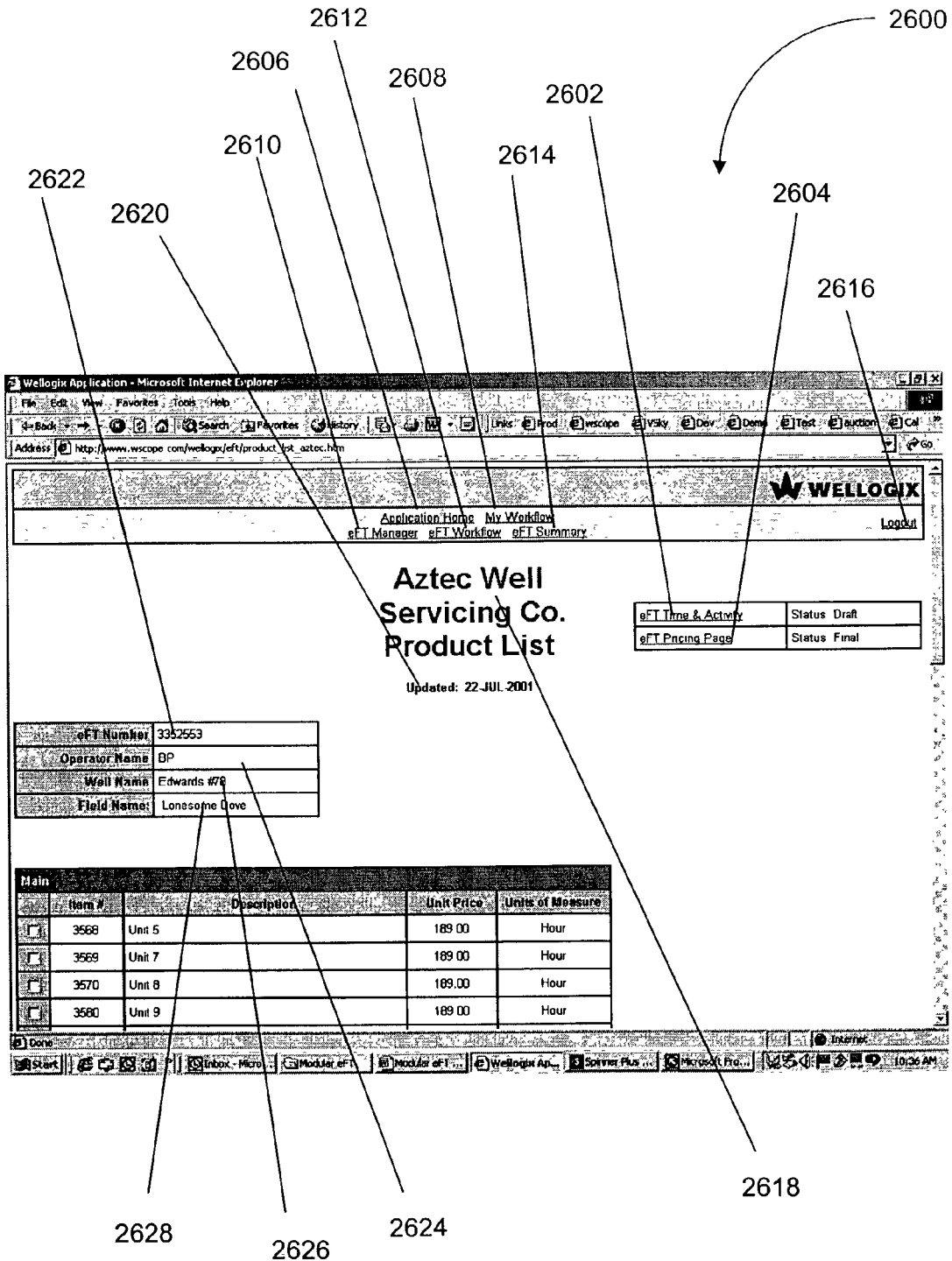
Figure 26B:
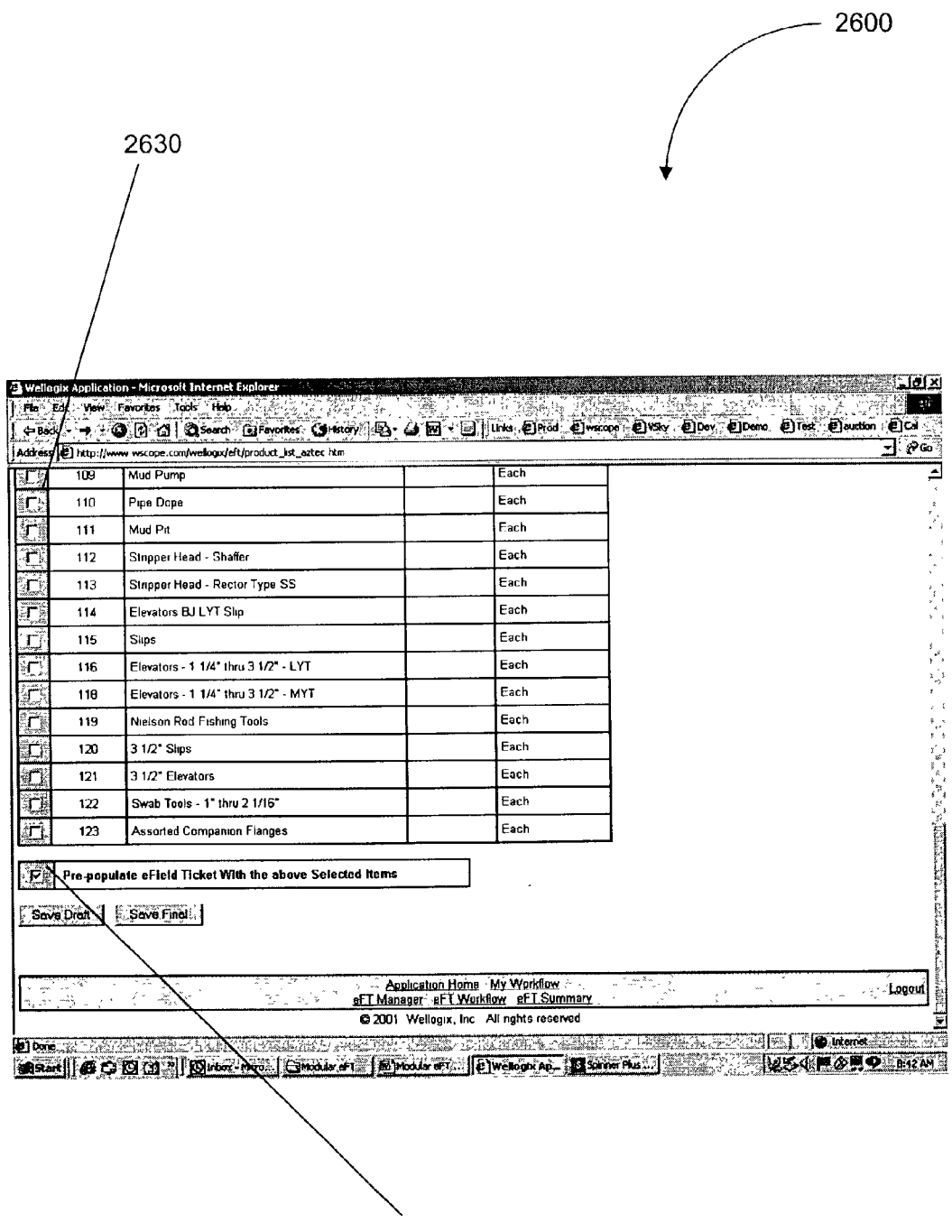

FIGS. 26A–B are exemplary screen shots for one embodiment of the present invention of a product list page included in a modular Field Document.

FIGS. 27A–D provide a flow diagram describing for one embodiment of the present invention a customization manager process.

Figure 28A:
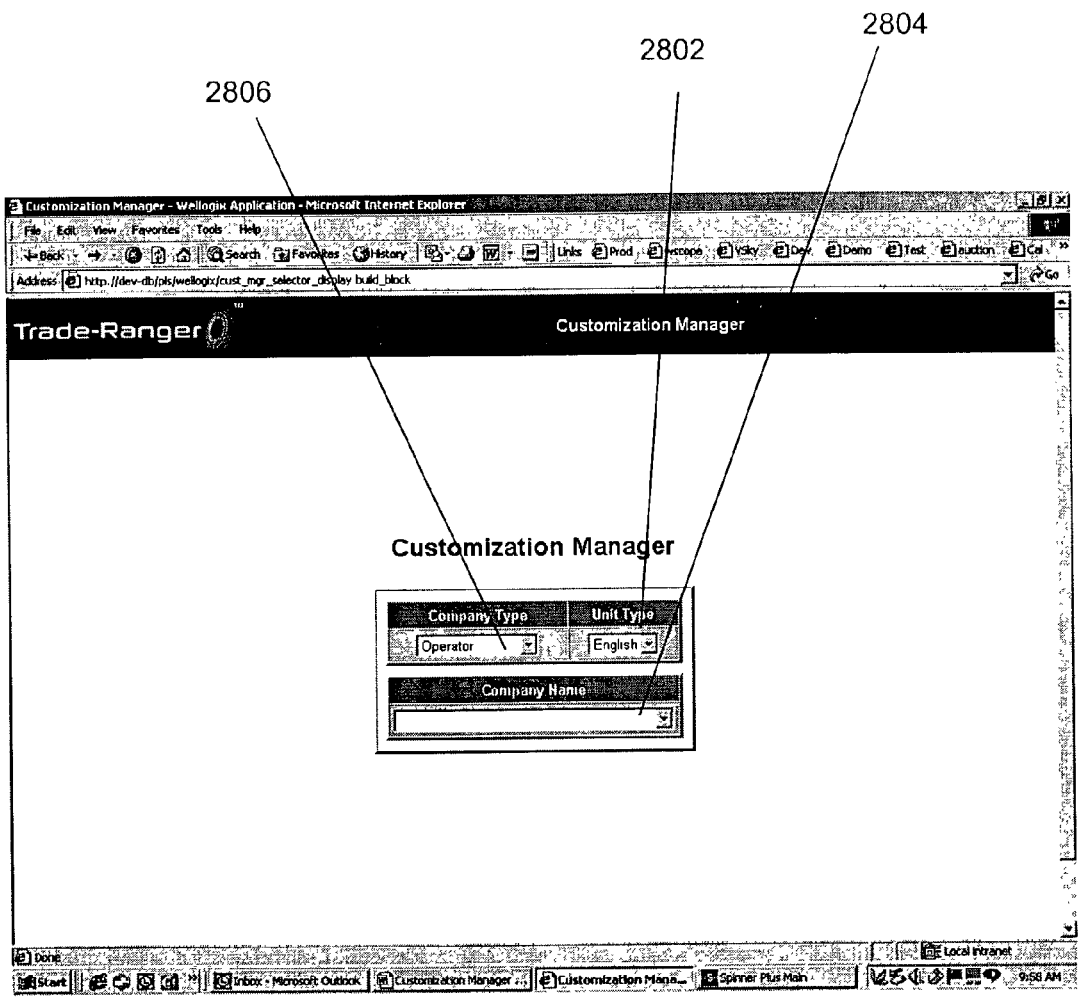
Figure 28B:
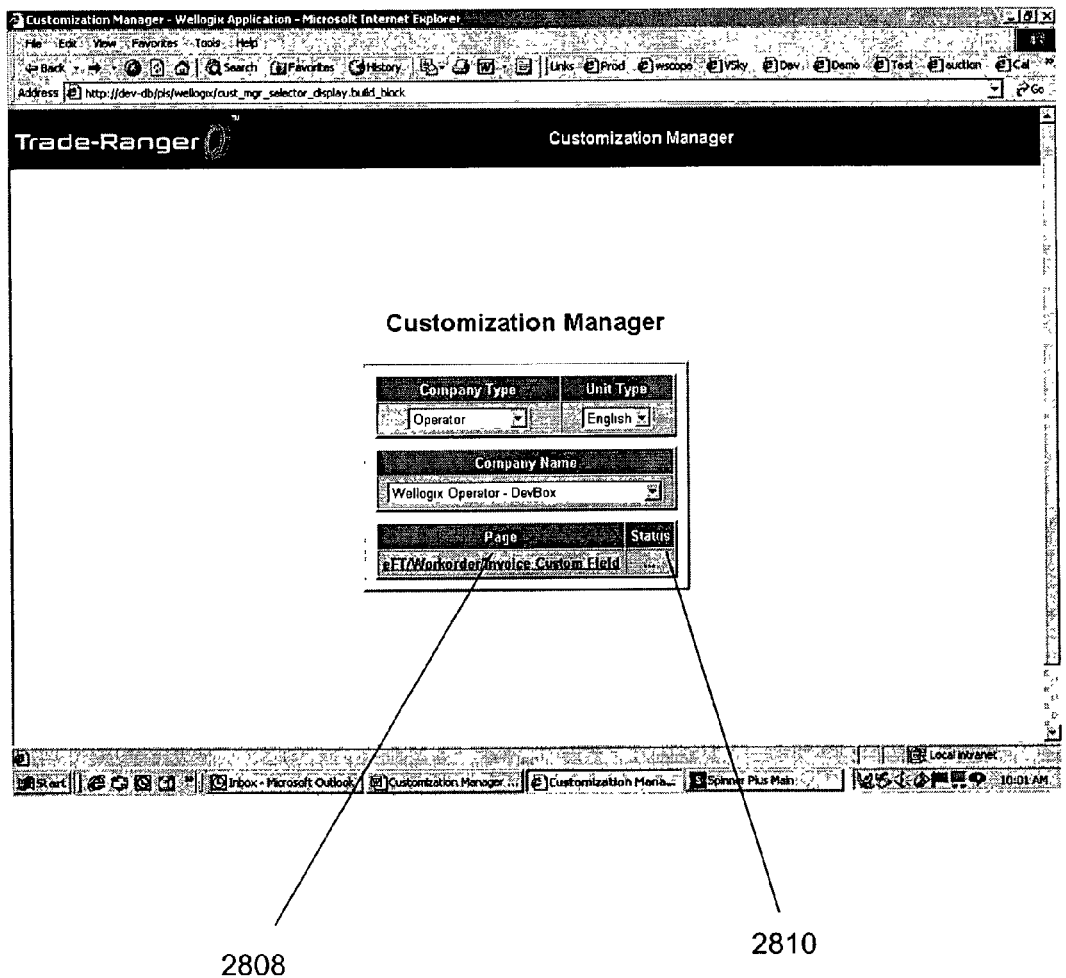
Figure 28C:
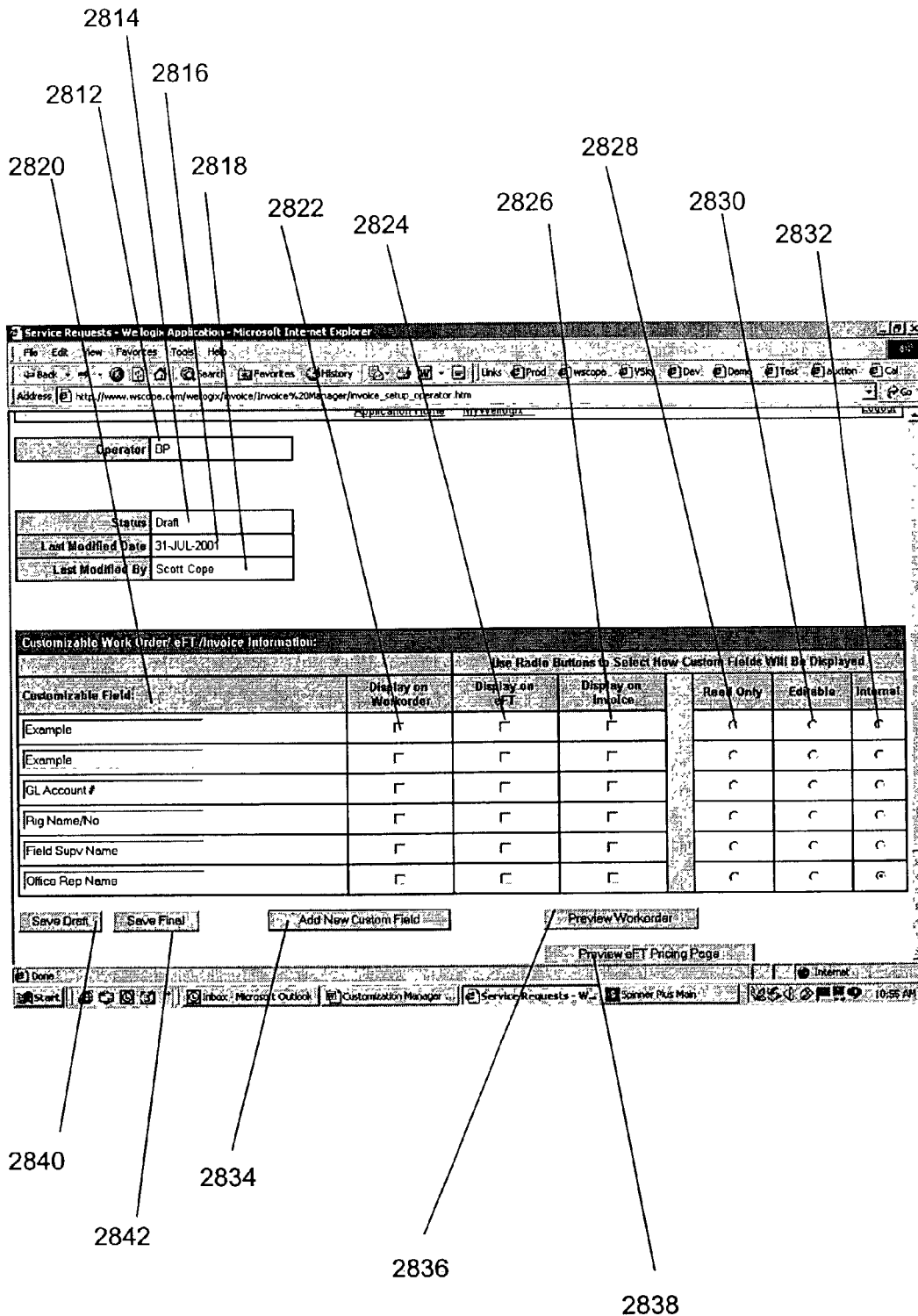

FIGS. 28A–C are exemplary screen shots for one embodiment of the present invention of a user interface which may be used to customize operator screens.

FIGS. 29A–H are exemplary screen shots for one embodiment of the present invention of a user interface which may be used to customize service provider screens.

Figure 30A:
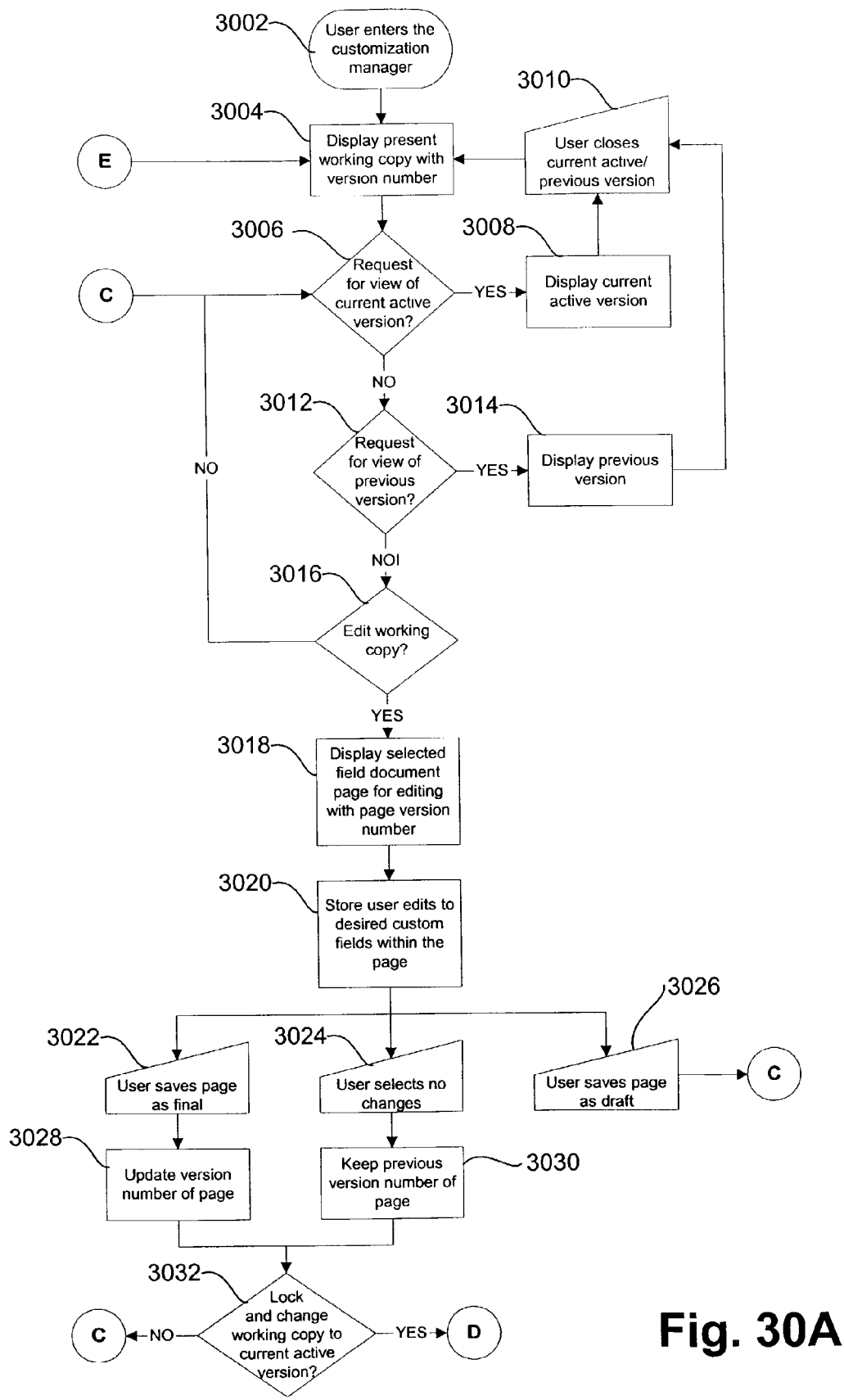
Figure 30B:
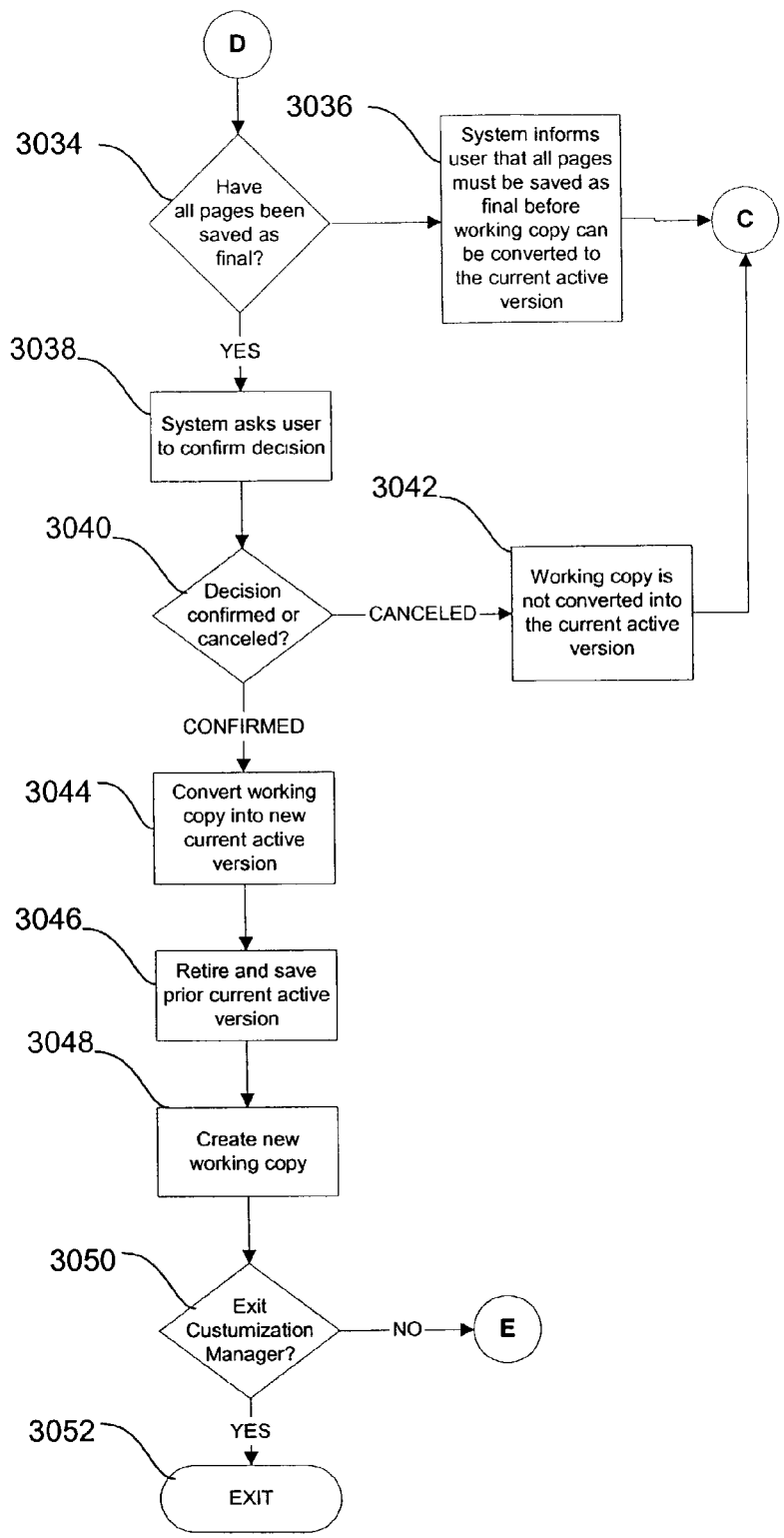

FIGS. 30A–B provide a flow diagram describing for one embodiment of the present invention a process for versioning with the customization manager.

Figure 31A:
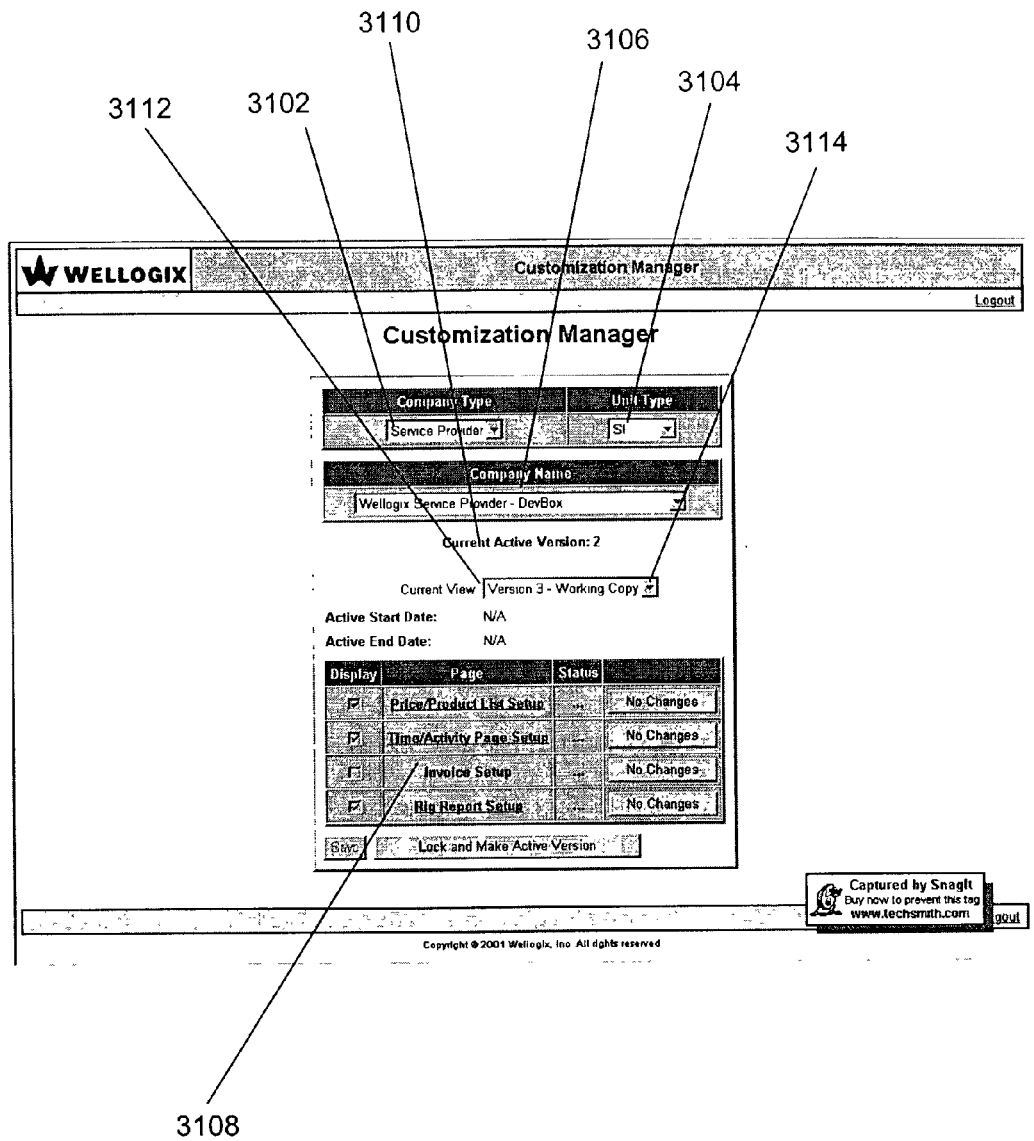
Figure 31B:
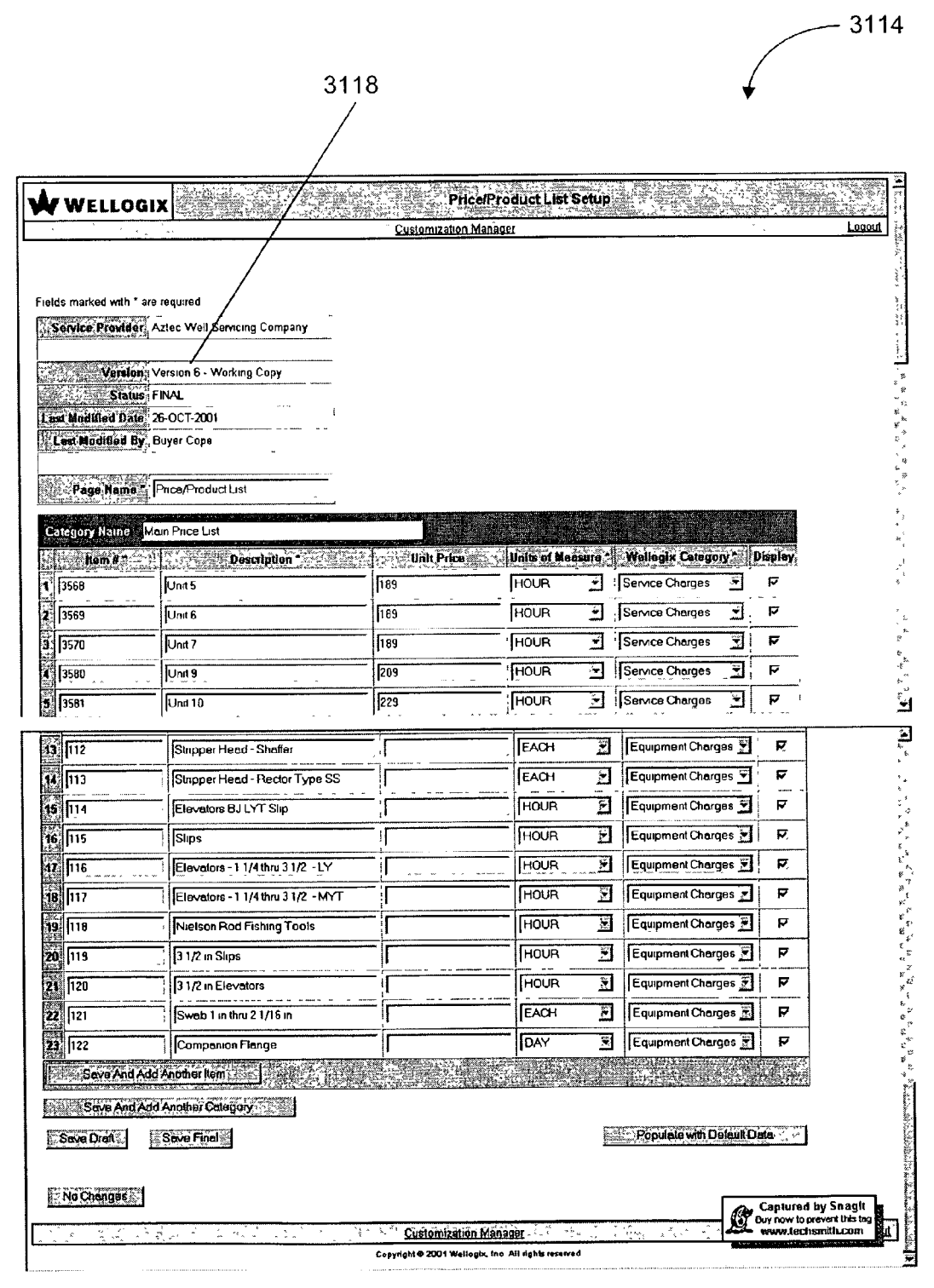

FIGS. 31A–B are exemplary screen shots for one embodiment of the present invention of a customization manager with versioning features.

Figure 32:
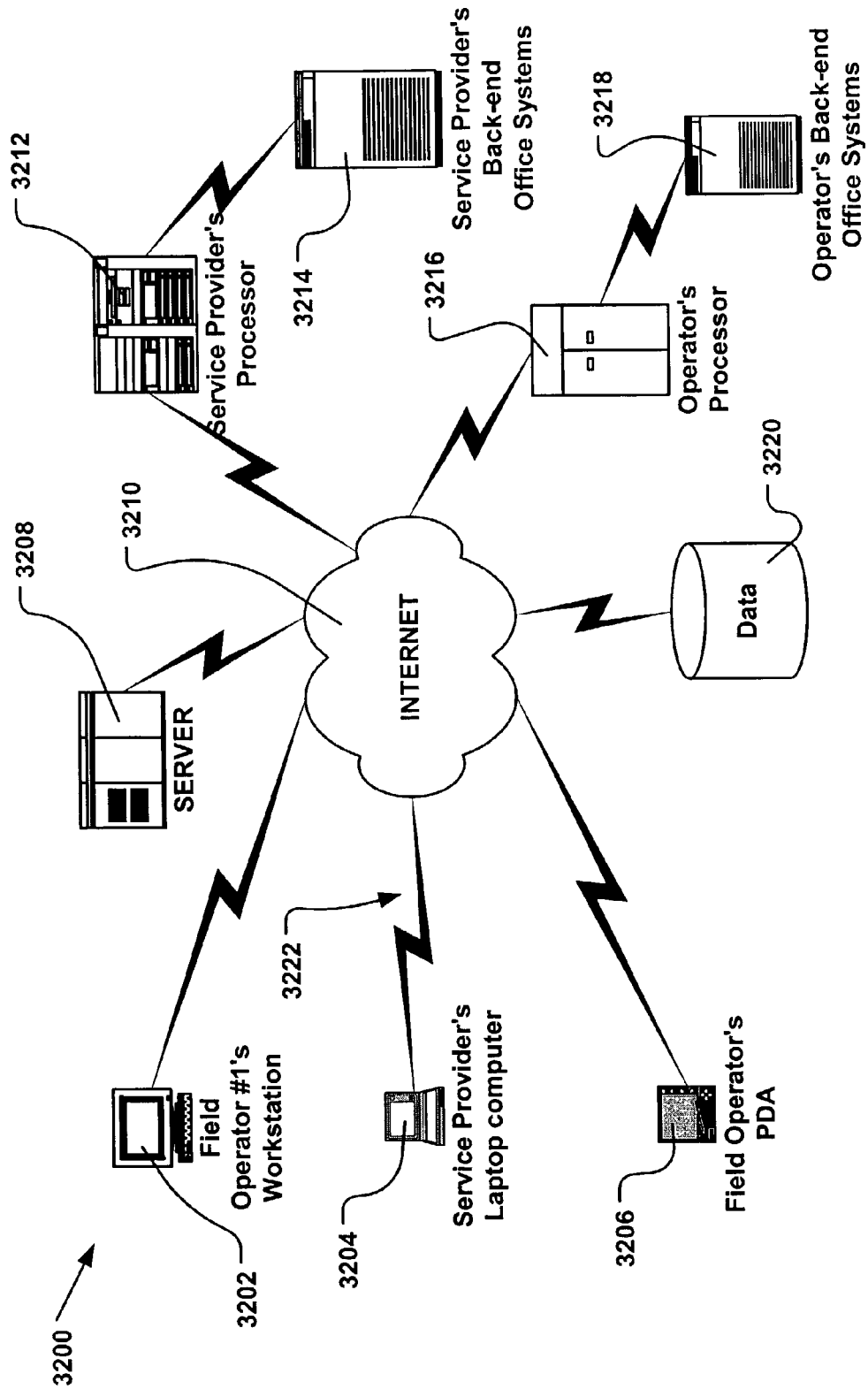

FIG. 32 is an exemplary system for implementing the various process embodiments of the present invention.

DETAILED DESCRIPTION OF THE INVENTION

A representative Internet or Web browser based embodiment of the present invention is depicted through a series of flow diagrams and screen shots of web page templates from an Internet based application provided by WELLOGIX™ and its predecessors WELLBID™ and eNersection.com. Those skilled in the art appreciate, however, that embodiments of the present invention and the WELLOGIX embodiment, in particular, may vary substantially or insubstantially in the features and functions provided by such systems without departing from, modifying, adding to, or deleting from the scope of the present invention as described herein and expressed in the claims.

Figure 1:
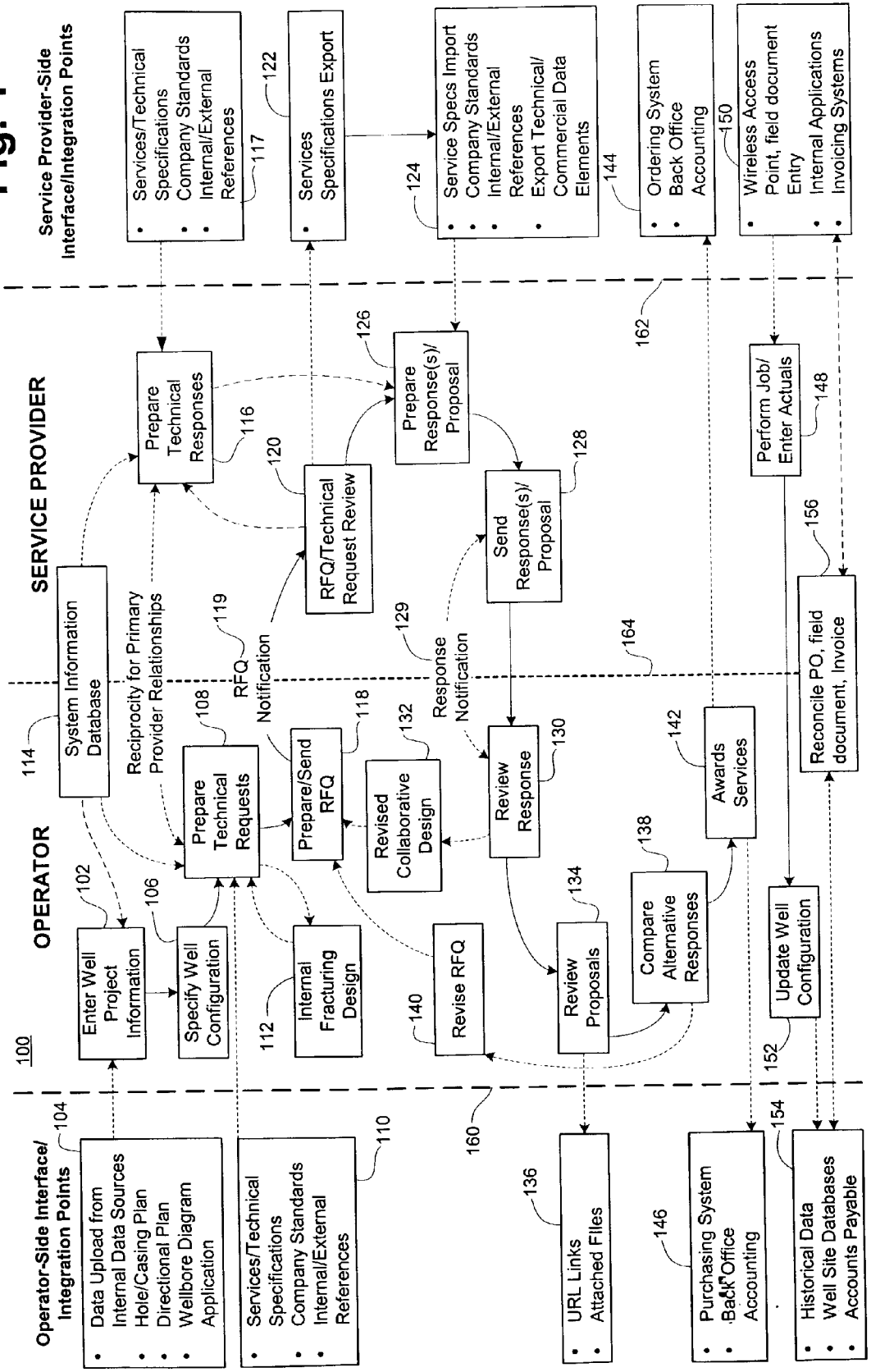
FIG. 1 is an information and interface flow diagram providing an overview of many of the operations supported by at least one embodiment of the present invention.

FIG. 1 provides an information flow diagram depicting the various operations and processes of a WELLOGIX or other Internet or Web browser based embodiment of a system 100, with particular reference to an embodiment designed primarily for the oil and gas industry. It is to be appreciated that this embodiment, and other embodiments discussed herein, may be used in other fields. More specifically, in this embodiment, buyers are generally large "operators" involved in oil and gas exploration and production. These operators procure goods, equipment, and services to drill and operate oil and gas wells from individual sellers, which are the "service providers." For example, goods can include drill bits and concrete; equipment can include drilling rigs and transportation; and services can include drilling and cementing. Dashed line 160 marks the interface/integration boundary between those processes and/or services provided by the system 100 and those provided by an operator's system. Similarly, dashed line 162 marks the interface/integration boundary between those processes and/or services provided by the system 100 and those provided by a service provider's system. Also, dashed line 164 marks the boundary between operator accessible and service provider accessible components in the system 100. It is to be appreciated, however, that these boundaries may vary depending upon the configuration and/or capabilities of actual systems implementing this or other embodiments of the present invention.

One embodiment of the workflow of a project proceeding through the system 100 may proceed as follows. An operator enters well project information 102, preferably via an industry specific template for capturing project parameters, into the system 100. The project parameter information may be entered by the operator manually, semi-manually (for example, by using drop-down menus) or automatically, for example, by uploading the information to populate the template from a system information database 114 (where prior projects may be suitably stored, for example, in a data array or other data structure), from an operator-side information source 104 external to the system 100, and/or from other databases and/or sources of information. The operator-side information source 104 may include internal data created or maintained by the operator, data from any operator or third party application, and/or data from other information sources. Such data may also be stored in data arrays and other data structures. Additionally, such data may be stored as data objects in an object oriented database, such as one provided by Oracle®, and/or in a Structured Query Language format. It is to be appreciated, that these and/or other data structures may also be utilized throughout the various embodiments of the present invention. Further, in an Internet or other networked embodiment, data can be obtained from a variety of local and/or remote sources and that various third party processes and/or systems may be utilized, as necessary, to convert and utilize such data in accordance with particular needs.

In the system 100, additional workflow operations may be undertaken to identify and/or specify those parameters utilized to describe the project. Similarly, various parameters may be used to specify the configuration of particular project related tasks or sub-tasks, such as specifying wells 106 to be drilled for an oil and gas project. Utilizing project level and task/sub-task/well level parameters, the system 100 may be automatically, semi-automatically or manually instructed to transform these and/or other parameters into a technical request for quote 108. In one embodiment, a technical request may be generated by populating appropriate fields for the project in technical request templates. The population of such fields may also be streamlined by utilizing data provided by other systems, such as, Knowledge Management ("KM") systems.

More specifically, information needed, desired and/or helpful to the preparation of technical requests may be available from several sources. Applications for modeling different aspects of a project may be made available for use within the system 100. For example, in an oil and gas industry embodiment, an internal fracture design module 112 may be used by an operator to model how a formation can be fractured to enhance the oil or gas flow into the well. Further, parameters may be imported into such a modeling application module 112, and modeling information may be exported and/or used to populate a technical request template 108.

Further, the system information database 114 may also have a repository of industry specific parameters, information, references, links and/or addresses to providers of such information. The system information database 114 may also be part of a KM system, for example, one that automatically seeks out, stores, and catalogs relevant information, and further identifies particular information collected with particular operations, templates, or fields used to define parameters within the system 100.

A third source of information for constructing technical requests 108 in the system 100 may be an operator-side information source 110. This information source 110 may provide, for example, historical data captured by the operator, common project specifications and standards developed by the operator, and/or other internal or external information references. Information source 110 may also be a part of a single operator-side information source, such as one that includes information source 104.

A fourth source of technical information support may be solicited from, or provided by, a service provider. A service provider may also use a technical response creation component 116 or a comparable component, for example, one provided by the system 100. The service provider's technical response creation component 116 may access data and other relevant industry information from the internal information database 114 in the system 100, from a service provider-side information and data source 117, and/or from other sources of information. For example, in this embodiment, a service provider with particular experience or expertise could provide parameter information to help the operator develop a technical request 108. In other instances, service providers familiar with the operator's projects may convince the operator to initiate a request for quote ("RFQ") 118 by providing a technical response 116 to the operator indicating an alternative method of managing a project. Other types of complex projects, i.e., other than the oil and gas industry example, may have different components with greater or fewer operations or templates to adequately and accurately capture and describe the parameters of any particular project and convert those parameters into RFQs.

Ideally, the RFQ is eventually communicated to appropriate or chosen service providers who may be notified 119 by the system 100 that such an RFQ has been made. The RFQ may or may not include any additional information or data attachments. In certain embodiments, all service providers or a selection of service providers may be designated to receive the RFQ. The RFQ, including any technical request 108 and attachments, if any, may be reviewed 120, upon receipt thereof, by the service provider and/or other recipients and a response (i.e., a proposal) or an alternate proposal may be provided to the operator. For one embodiment, the service providers/recipients may prepare the response by exporting the data from the technical request 108 and any attachments to a service provider-side system 122. . The service provider may analyze and manipulate the data as needed using the service provider's own applications and/or other applications in order to determine and generate, if desired, an appropriate response. The service provider may also import data provided in the RFQ into the system 122 for integration into a response or proposal 126. The service provider may also import other information 124 into the system 124, for example, industry or company standards, internal or external references, or other technical or commercial data. Similar to the operator-side, the system 124 may be configured to translate data, as necessary, to populate those templates utilized and/or necessary to respond to an RFQ. Additional information may also be provided as attachments to the response, or provided as reference links, for example, hyperlinks, which enable an operator to access information directly from the service provider or from a third party source via an Internet or other network connection.

The service provider may submit a completed response or proposal 128 to the system 100. The response 128 may include a commercial response (i.e., one providing quantities, pricing, and similar transactional information), a technical response 116 (i.e., one detailing the service provider's rationale for the goods selected and/or a proposed method for providing the services requested), a request for more information and other responses. The system 100 notifies 129 the operator when a response from the service provider has been lodged. The operator can review the response 130 immediately upon notification or at a later time.

At this point in the process, the operator has several options. If a service provider provides a suggestion within the response 128 that the operator finds particularly helpful, the operator may want to revise the RFQ 132 with the service provider's suggestion and re-bid 118 the project to all of the service providers. In another instance, the proposals may have additional attachments of data, information, or references. In this case, the operator may want to review 134 this additional information by accessing it from remote sources or processing the data on operator-side applications 136.

Within the service providers' response(s), alternate solutions for completing the project may be offered by different service providers or by a single service provider. The operator may wish to compare these alternate responses 138, if any, to determine the best method for completing the project. Alternatively, the operator may determine the best price between multiple service providers of the same goods or services. If an alternate response is particularly desirable, the operator may wish to revise the RFQ 140 with the suggestion and resubmit a revised RFQ 118 to the service providers. Once the operator has compared a desired portion or all of the possible proposals and alternatives, the project, or portions thereof, may be awarded 142 to one or more service providers. Financial information detailing the project award is preferably transmitted to accounting, sales, and other financial management systems of both the operator 146 and the service provider 144.

As the service provider completes performance on the project, it provides actual performance data 148 to the system 100. This actual performance data preferably includes both costs for the goods and services provided, and information about the conditions encountered that the parameters attempted to define. Actual performance data may be provided by service provider-side systems 150 such as accounting programs, and in the case of oil and gas projects, by entry into Field Document(s) (as described herein below in greater detail). More specifically, a Field Document attempts to capture and/or describe many of the actual results of a project, in terms of financial, functional and/or other types of parameters. In general, a Field Document provides actual data, measurements or observations taken during the performance of the project. Such actual data observed may be provided to the system 100 using wired and/or wireless processing and communications technologies. The actual performance data may be used to update configuration parameters 152 with the actual information to aid in the request process for future projects involving the same or similar parameters. This actual information or data may further be stored by the operator system 154 for historical reference purposes or otherwise. Actual cost information may also be used by the system 100 to reconcile 156 purchase orders, field actuals, and final invoices in order to facilitate the expeditious and appropriate payment of service providers by operators.

In many industries, contracts for complex projects are often negotiated and entered into on a time and materials basis. Proposals from service providers generally indicate the time involved in providing necessary services and the quantity of materials they believe will be necessary to complete a given task for a given project. But, pricing is often based upon a per unit basis of time and materials. Therefore, the actual costs and fees incurred for a project may be higher or lower than the bid or contracted for price.

For example, in the construction industry, a shortage of construction materials or skilled labor in a certain region can drive project costs beyond the proposal because of higher priced substitute materials or the ability of labor to demand higher wages. Similarly, in the oil and gas industry, a drilling team may encounter an unforeseen-operational problem that increases the time necessary to reach a desired well level, thereby increasing the cost of the project. In time and materials projects such as these, the operator typically continues to manage the project through its completion despite time and cost overruns. Through ongoing management of the parameters, however, the operator is able to make decisions concerning any available options to reduce the time and cost.

Returning to the embodiment of the present invention shown in FIG. 1, the system 100 enables a user to immediately begin the invoicing process for time, services, and materials actually used in a job or event of the project. In many industries, a "delivery Field Document" provides evidence of the delivery of a certain quantity of goods to a project site. In the oil and gas industry, discrete quantities of services render are documented by Field Documents. In other industries, immediate documentation of goods/services may be called an "actual." For the purposes of the function of the processes described herein, the terms "delivery Field Document," Field Document, and "actuals" are synonymous. Usually a representative of the operator either visits or oversees the project site to ensure that the work is progressing and Field Documents are documented accordingly.

At the conclusion of the job or a discrete event, the service provider's representative may prepare a Field Document detailing the actual work performed, time taken, and materials and equipment used, with the related costs and fees for the job. The operator's representative may approve payment directly from the Field Document or hold for payment until receipt of the official invoice. In many instances the Field Document merely operates as a verification that services have been performed, but not as a payment authorization. In the regular course of matters, there may be times when there is a discrepancy between the actuals reflected in the Field Document, the purchase order based upon the service provider's proposal, and the final invoice for the job. These discrepancies ultimately require reconciliation.

The Field Document process is similar to the project management control process in the construction industry. Before submitting invoices to the operator for work performed on a construction project, the service provider's work must usually first be approved by the field project manager, or perhaps a government certification officer, to give the operator assurance that the work was performed according to specifications. Many other industries use similar controls for ensuring appropriate performance from service providers, and various embodiments of the present invention provide an environment for the management and transfer of such approval information and invoicing.

Processing of a Field Document

Figure 2:
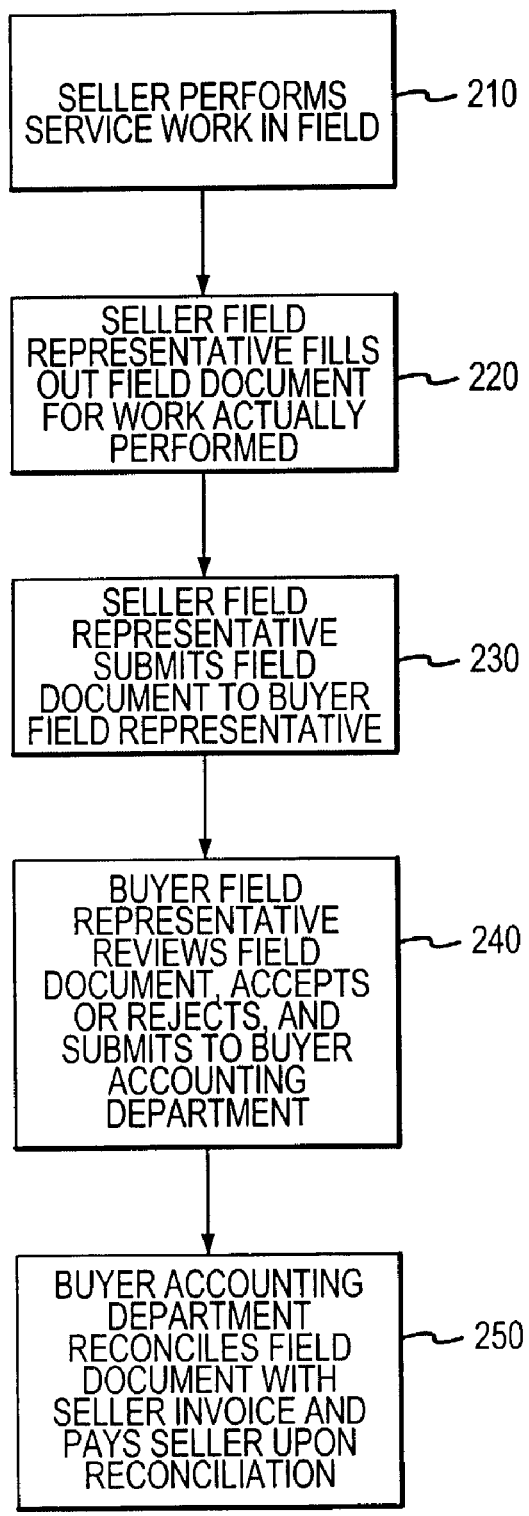
FIG. 2 is an exemplary flow diagram of a process which may be used to process a Field Document according to one embodiment of the present invention.

For the system and process embodiment shown in FIG. 1, once a service provider completes a project, operation 210 of FIG. 2, a Field Document reflecting the actual work performed, goods and equipment used, and costs thereof may be prepared. Desirably the Field Document is prepared using a system and devices which facilitate communications over local and/or remote networks, such as the Internet, a private network, a public network, a local area network (LAN), a wireless local area network (WLAN), a wide area network (WAN), or any other type of network, operation 220. When the service provider's representative confirms the entries, notification that the Field Document is ready for review is communicated to the operator's representative, operation 230. In one embodiment, the service provider accesses the Field Document via a wireless network connection from the field. In the alternative, if the project site is so remote that it may be impractical or impossible to connect with a wired or wireless network, the invoicing environment may be provided locally on the service provider's equipment and later interfaced with the system 100 when access to a network connection is available. The operator's representative, if present at the project site can approve the Field Document or negotiate changes before confirming the Field Document on the system. If the operator's representative is not at the project site, the operator's field and/or office representative may access the Field Document from the network once the Field Document is entered into the system. The system 100 facilitates the interchange between operator and service provider to reconcile any variances between the Field Document, purchase order, and the actual invoice(s) submitted by respective service providers.

Once a Field Document is issued and approved, the system 100 may pass the invoice information from the Field Document to the operator's accounting or "back office" system for payment processing, operation 240. If the Field Document is not approved by the operator's representative, the Field Document actuals may still be passed to the operator's accounting system. In either case, payment processing may then include reconciliation of the Field Document with the service provider's final invoice before payment is made, operation 250.

Integration of Field Documents with Accounting and Office Systems

Figure 3:
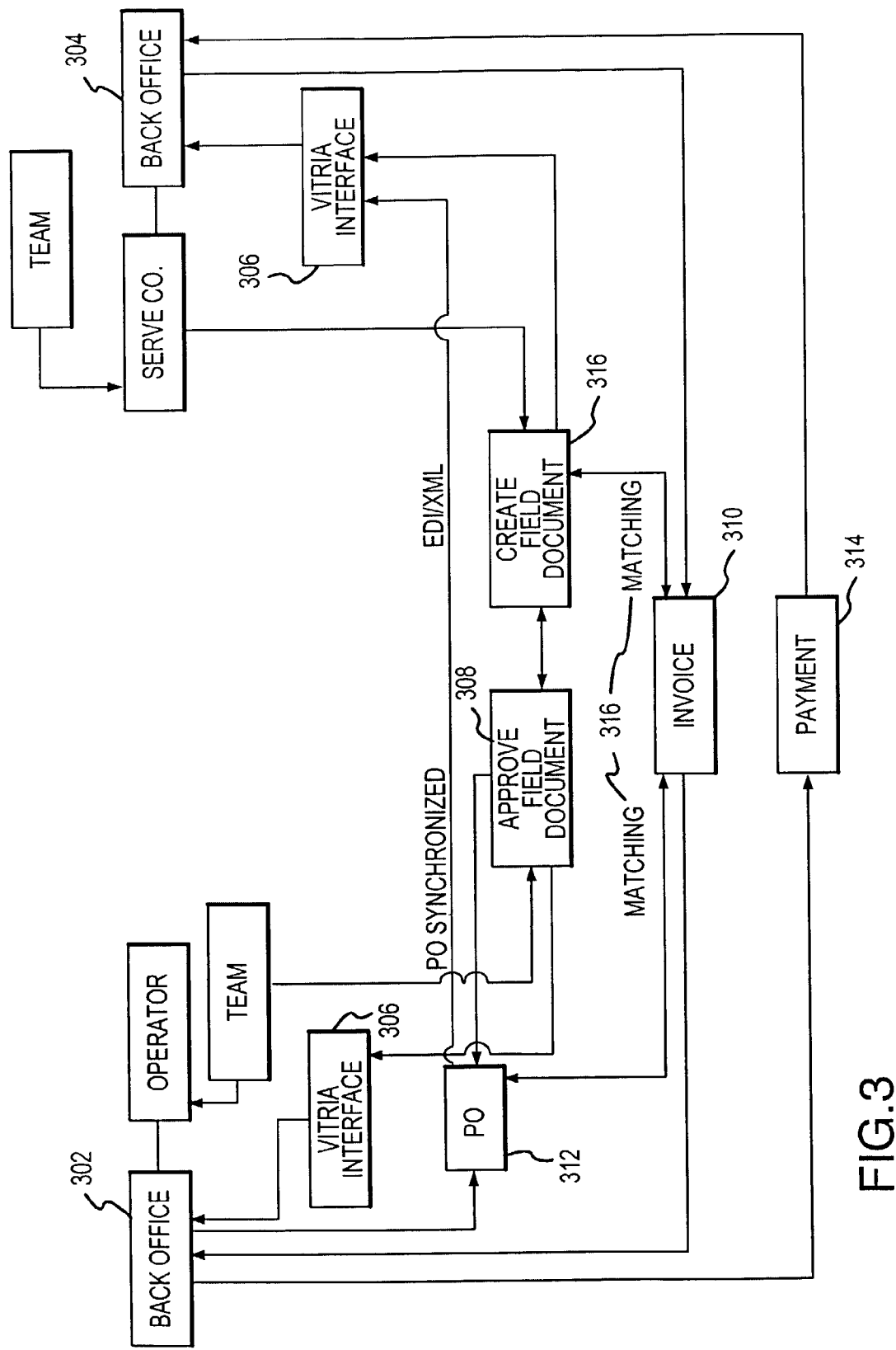
FIG. 3 is an information and interface flow diagram depicting one embodiment of the present invention for processing a Field Document and providing payment thereof.

Additionally, the system may be configured to integrate the operator and service providers' accounting systems. As shown in FIG. 3, for another embodiment of the present invention, information transfers may occur automatically or upon command, for example, via a computer-to-computer electronic transfer, between the system 300, the operator's accounting system 302, and/or the service provider's accounting system 304. Such information transfers may occur over any suitable communications network. Further, for one embodiment, the information transfer may be accomplished by implementing interface integration tools 306, for example, Vitria®, Inc. software, in both the operator's accounting system and the service provider's accounting system. It is commonly appreciated that Vitria® software is designed to interface between large-scale enterprise resource planning software systems such as those provided by SAP®, J D Edwards®, and others. The system may also interface with such typical accounting software systems as QuickBooks® or Peach Tree®. However, the various embodiments of the present invention are not limited to the use of Vitria or any other software applications or systems and may be configured, as desired, to utilize any software applications which enable back-end accounting and business systems to interface and communicate data between operator and service provider systems.

Referring again to FIG. 3, the system may also be configured to reconcile 316 a Field Document against a proposal award 312 or other form of a purchase order. Further, the system may be configured to provide for manual, semi-automatic or automatic payment authorizations 314. Additionally, the system may be configured to utilize interface integration tools 306 to match and reconcile 316 an invoice 310 against either approved or held Field Documents 318 and coordinate payment 314 from the operator's accounting system 302. If the system is unable to reconcile a Field Document with an invoice or purchase order, the system may also be configured to flag the Field Document for review and approvals before payment is made and/or other project related tasks are accomplished. As such, this embodiment facilitates the early and often reconciling and approval of Field Documents such that work discrepancies can be timely addressed and delays in the project minimized.

Pre-population of Field Documents

A method by which one embodiment of a workflow system may pre-populate a Field Document and submit a Field Document to an operator is detailed in the flow diagrams of FIGS. 4A and 4B. As shown, the method preferably begins when a user accesses a bid award page for a particular commercial response (operation 400). The bid award page generally includes project level information, parameters associated with a specific bid proposal, commercial response information, and links, if any, to submitted Field Documents (operation 402). When a user selects a link to a specific Field Document summary page for the commercial response (operation 404), the system displays a summary page listing those Field Documents previously created for that commercial response (operation 406), if any. If the user selects an option for creating a new Field Document (operation 408), the system queries whether any old/existing Field Documents exist(operation 410). If there are any old Field Documents, the system queries the user as to whether to pre-populate the new Field Document with data from an old Field Document (operation 412). Depending upon the user response, the system may take several actions.

If the user would like to pre-populate the new Field Document with data from a previous Field Document, the system determines whether multiple old Field Documents exist (operation 414). If there is only one previous Field Document, the system automatically populates the new Field Document with data from the old Field Document (operation 416). If there are multiple old Field Documents, the system determines whether the user has selected a particular old Field Document to use for the population data (operation 418). If the user has not selected one of the old Field Documents, the system requests the user to select a Field Document (operation 420). The system then queries the user as to whether the user wants to pre-populate the new Field Document with the identified old Field Document (operation 412). If the user has already selected a particular old Field Document, the system automatically pre-populates the new Field Document with data from the selected old Field Document (operation 422).

If the user does not wish to pre-populate the new Field Document with data from an old Field Document, the system determines whether data from a commercial response can be used to populate the new Field Document (operation 424). If data exists, the system queries the user as to whether to populate the new Field Document with the data provided in the commercial response. (operation 426). If pre-population is not desired, the system generates and displays a blank Field Document for manual population by the user (operation 428). On the other hand, if the user does want to populate the new Field Document with data obtained from the commercial response, the system will automatically populate the new Field Document(operation 430).

Once the new Field Document has been pre-populated with previously collected data or newly populated, the user may make changes to such data, as desired. After any additions or changes have been made by the user, if any, the system stores the data (operation 432). The system calculates a total cost for the services performed and any goods/products used and enters a total on the new Field Document (operation 434). If the service provider adds any comments or additional information to the Field Document, such information may also be stored with the Field Document (operation 436). The system saves the new Field Document on a workflow system, such as a system embodiment shown in FIG. 1 or FIG. 2. The new Field Document, generally, may be accessed through the system by others (operation 438). The system may also be configured to notify the user of the ability to attach files and other information to the new Field Document. Such attachments may provide, for example, supporting documentation or data for review by the operator (operation 440). At this point or at other times, the system may be configured to perform a query to determine whether any files have been attached (operation 442). If so, the system may store the files to the workflow platform or other systems and provide links between the files and the new Field Document (operation 444).

The system also queries whether the new Field Document is ready for submission to the operator (operation 446). If so, the system notifies the operator that a new Field Document is available for review (operation 448). If the service provider is not ready for the new Field Document to be submitted to the operator for review, the system may be configured to not notify the operator or otherwise make the new Field Document available for review and to indicate that the Field Document is still a draft (operation 450).

Generation of New Field Documents

In a similar manner, one embodiment of the present invention may provide a system which facilitates the generation of a new Field Document based upon a work order. Generally, pre-population of Field Document is not possible when a work order is the basis for the Field Document. This condition generally exists because work orders usually relate to needs that arise in the field and are only partially, if at all, addressed in the terms of a commercial response. As depicted in FIGS. 5A and 5B, upon a user selecting a link to a Field Document summary page for a work order (operation 500), the system may be configured to present a summary page providing a listing of those Field Documents, if any, previously created for a specific work order (operation 502). Upon the user selecting an option for creating a new Field Document (operation 504), the system determines whether an old Field Document exists(operation 506). If an old Field Document exists, the system queries the user as to whether the user desires to pre-populate the new Field Document (operation 508). Depending upon the user response, the system may take several actions.

If the user desires to pre-populate the new Field Document, the system determines whether multiple old Field Documents exist (operation 510). If only one old Field Document exists, the system populates the new Field Document with data from the old Field Document (operation 512). If multiple old Field Documents exist, the system queries the user as to whether to use data in a particular old Field Document to populate the new Field Document (operation 514). If the user does not select one of the old Field Documents, the system prompts the user to make a selection (operation 515). The system then queries the user as to whether the user wants to pre-populate the new Field Document with data from an old Field Document (operation 508). Referring again to operation 514, if the user has selected an old Field Document, the system automatically pre-populates the new Field Document with data from the selected old Field Document (operation 516). If the user does not wish to pre-populate the new Field Document with data from an old Field Document, or there are no old Field Documents associated with the work order, the system generates and displays a blank Field Document for population by the user (operation 518).

Once the new Field Document has been pre-populated or a blank Field Document provided with new data provided by the user, and after any additions or changes have been made by the user, the system stores the data (operation 520). The system then calculates the total costs of services performed and products used as specified in the new Field Document or as otherwise specified (operation 522). The service provider may also add any comments and/or additional information to the new Field Document, such comments and/or additional information may also be saved and/or stored with the new Field Document (operation 524). The system saves the new Field Document preferably such that it is accessible, via the workflow system, by authorized users (operation 526). The system next notifies the user of the ability to add file attachments to the Field Document to provide any supporting documentation or data for review by the operator (operation 528). The system performs a query to determine whether any such files have been attached (operation 530). If so, the system stores the files, desirably with the workflow platform, and provides links them to the via the new Field Document (operation 532). The system then queries whether the new Field Document is ready for submission to the operator (operation 534). If the user indicates yes, the system notifies the operator that a new Field Document is available for review (operation 536). If the service provider is not ready for the new Field Document to be submitted to the operator for review, the system does not send notification to the operator or otherwise make the new Field Document available for review and designates the new Field Document as being a draft Field Document (operation 538).

Reviewing Field Documents

As shown in FIG. 6, one embodiment is provided of a process for reviewing a Field Document by an operator after the Field Document has been submitted by a service provider. As shown, this process preferably begins with the operator receiving a notification that a Field Document has been submitted and is available to access and review (operation 600). When the operator accesses a particular commercial response, at least one Field Document related to the commercial response is presented to the operator for review (operation 602). Upon the operator selecting a particular Field Document, for example, from a summary list, (operation 604), a read only version of the Field Document may be displayed for review by the operator (operation 606). However, a writable versions of the Field Document may also be provided in alternative embodiments. If any comments are provided by the operator, these are suitably saved. Such comment may be inputted into a field specifically provided for such comments (operation 608). Similarly, comments made by the service provider relating to the Field Document or otherwise may also be saved. Comments by a service provider may, for example, be inputted into a second input field (operation 610).

Upon receiving an indication from the operator, the Field Document may be saved in a workflow system which provides to authorized users (operation 612). While the save operation is depicted as occurring in operation 612, it is to be appreciated that a Field Document may be saved at any time. Also, notifications may be provided to the operator that files may be attached to the Field Document. Such attachments may include, for example, supporting documentation or data for review by the service provider or other authorized users (operation 614). Further, a query may be issued in order to determine whether any files have been attached to the Field Document (operation 616). This query may also be repeated throughout the process as desired. If a file has been attached to a Field Document, the file may be suitably stored with links being provided, as desired, to the Field Document and/or from the Field Document to the file (operation 618).

At this point, a determination may then be made as to whether the saved Field Document has been approved for invoicing (operation 620). If the Field Document has been approved, the Field Document may be suitably designated as approved (operation 622) and the service provider may be notified that the Field Document has been reviewed and approved by the operator (operation 626). If the Field Document has not been approved, the Field Document may be designated as held for approval and the service provider suitably notified that the Field Document has been reviewed by the operator but has not been approved and that the Field Document is available for review, revision and/or resubmission by the operator (operation 626).

Invoicing Field Documents

As shown in FIG. 7, one embodiment of a process for revising and/or submitting for payment a Field Document that has already been reviewed by an operator is provided. This process generally begins when a service provider is notified that the operator has reviewed a Field Document and the operator again accesses the related commercial response (operation 700). When a user selects a link to the Field Document summary page for the commercial response, a summary page providing a listing of all Field Documents related to the commercial response may be provided (operation 702). When the service provider selects a Field Document previously reviewed by the operator, the selected Field Document is suitably presented (operation 704). If any internal comments are made by the service provider, for example, in a field specifically provided for such comments, these comments may be suitably stored (operation 706). Similarly, comments by the service provider for the operator may also be suitably entered, for example, in a second input field provided for that purpose, and/or suitably stored (operation 708). Further, changes, if any, by the service provider to the Field Document may also be temporarily or permanently stored (operations 710). Once any desired changes have been made to the Field Document, the Field Document may be suitably saved to a platform, server or other system implementing this process. The saving of the Field Document may be accomplished automatically, on a periodic basis, and/or upon input from the service provider(operation 712).

Further, the process also enables a service provider to add file attachments to the Field Document. Such file attachments may provide any supporting documentation or data for review by the operator. Such attachments may also, for example, be provided for invoicing purposes when the Field Document has been approved (operation 714). Queries may also be accomplished, as necessary, to determine whether any files have been attached to a Field Document (operation 716) and to save such attachments to a suitable system or workflow platform. Links between such attachments, if any, and the Field Document may also be provided (operation 718).

At this point in the process, a determination may be made as to whether the Field Document has been approved for payment by the operator (operation 720). If approved, a determination may be made as to whether the Field Document has been designated as ready for invoicing (operation 722). If so, the data necessary to pay an invoice may be extracted from the Field Document and suitably communicated to a designated accounting and invoicing system (operation 724). In certain embodiments, the process of communicating data to an accounting system may be accomplished via a network. In other cases, the accounting systems may be provided with a system implementing this process. As such, it is to be appreciated that local and/or remote systems may be used and interconnected in order to facilitate the before mentioned processes.

Further, when the Field Document has been approved by the operator, but has not been designated for invoicing by the service provider, service providers may display and edit the Field Document, as desired(operation 704).

Additionally, when the Field Document has not been approved by the operator, a determination may be made as to whether the Field Document has been or should be designated for resubmission to the operator (operation 726). If not, the Field Document, and/or any changes thereto, may be suitably saved for later review and revision by the service provider (operation 728). If the Field Document has been designated for resubmission, the updated Field Document may be saved for future access and review by the operator (operation 730). Appropriate notification may also be provided to the operator regarding the availability of the revised and saved Field Document for further review (operation 732).

User Interface for Generating a Field Document

As mentioned previously hereinabove, various embodiments of the present invention provide systems and processes for generating a Field Document. It is to be appreciated that such systems and/or processes may generate various user interfaces or series thereof, including those provided audibly and/or visually, which users may utilize to generate, edit, review, revise and/or approve Field Documents. One such embodiment of an user interface is shown in FIGS. 8A–8C. As shown, in FIG. 8A, an user interface may be provided as a Web page which can be displayed on a Web browser, such as Microsoft' Internet Explorer® or Netscape's Navigator®.

More specifically, one particular instantiation of an user interface, provided by a system implementing at least one embodiment of the present invention, that may be utilized to initiate the Field Document preparation process is depicted. In order to initiate the Field Document process in this embodiment, a service provider preferably accesses a Bid Award page 800 which may be configured to present Project Level information 802 as well as those parameters which relate to a specific request for which the proposal was awarded 804 (as shown in FIG. 8B).

Further, this embodiment of a the Bid Award page 800 includes a View Field Document button 806, which provides a hyperlink or other link to a Field Document. Upon selection of such button 806, a user desirably is presented with a Field Document process page, at least one embodiment of which is shown in FIG. 8C. As shown, this page includes a list of previously created Field Documents 808 for a given project. Upon selecting a link to a Field Document item from the list, a previously saved and/or submitted Field Document, that has been prepared for a specific request, may be reviewed. Additionally, a link or button 810 may be provided which enables one to create a new Field Document.

In another embodiment of the present invention, multiple Field Documents may be associated with a single commercial response. In this embodiment, multiple, discrete aspects of an ongoing, complex project may be accounted for at the time the service is performed, rather than having to wait until the end of the entire project. Further, by providing for the linking and reconciling of multiple Field Document(s) with associated commercial response(s), performance and budget issues may be reviewed as the project progresses. Additionally, since multiple Field Documents for a single commercial response may be very similar, this embodiment provides for the pre-population of Field Documents from several sources of data.

User Interface for Reviewing a Field Document

When a Field Document already exists for a particular project, a system implementing an embodiment of the present invention may be configure to present a service provider with a user interface which enables the service provider to review summary information relating to one or more Field Documents. An example of such a user interface is shown in FIG. 9A as a Field Document summary template 900. More specifically and as shown, the Field Document summary template 900 may include a header which identifies a particular project for which one or more Field Documents have been submitted. In an oil and gas embodiment, as shown in FIG. 9A, the header may include the identity of the operator 902, the project name 904, the well name 906, the hole section 908, and the service type 910. Further, the service type 910 may include a link which enables a service provider or other user to access additional and/or more detailed information about a parameter(s) of a given project. These fields may also be customized, as needed. For example, when well or hole section information for a discrete project is not available, the well name 906 and hole section 908 fields may not be shown in the header information.

The Field Document summary template 900 may additionally provide summary information for existing Field Documents previously populated. This summary information may include, for example, a Field Document reference number (i.e., an EFT ID) 912, the date the Field Document was created 914, the name of the person who created the Field Document 916, a functional link to access and review the most recent version of the Field Document 918, the status of the Field Document 920 (e.g., whether or not the Field Document has been approved ), the amount of charges detailed in the Field Document 922, the estimated charges as originally specified in a commercial response, if at all, 924, and a link to the workflow history of the Field Document 926.

When creating a new Field Document, for example, when one or more Field Documents already exist, the Field Document summary template 900 may also be configured to provide the service provider/user with choices for pre-populating the Field Document. For example, in the embodiment shown in FIG. 9A, the service provider is provided the choose of whether to: not pre-populate the Field Document 934 and instead manually enter new information; pre-populate from a commercial response 936 (wherein the Field Document is populated with information obtained from the commercial response 936 using a process similar to that previously described hereinabove with reference to when a user initially generates a Field Document); and pre-populate the Field Document from an existing Field Document/EFT 938. As shown, the service provider/user suitably selects one of these options (or other options, when available), for example, by clicking a radio button associated with the particular choice. Additionally, if the new Field Document is to be populated by data from a previous Field Document, a radio button 928 associated with the particular previous Field Document may be selected to indicate the desired data.

Further, by selecting a "Create New Field Document" button 940, a new Field Document may be populated by the system. Also, when the "Reconcile Commercial Response and Field Document(s)" button 930 is selected, a system implementing this embodiment may be configured to generate a reconciliation tool template, one example of which is described in further detail herein below.

The system may also allow one or more new Field Documents to be pre-populated when the Field Documents are based upon a work order. In contrast to a commercial response, a work order is generally a document issued in the field requesting a discrete project be performed that was not considered in an original bid request or commercial response. For example, it may be necessary to construct a fence around a project site to keep out unanticipated trespassers (perhaps cattle on range land). When a work order template is provided for a particular project, the service provider may choose a function to create Field Documents for the work order. Further, when no previous Field Documents have been created for the work order, a system, implementing an embodiment of the present invention, may be configured to create an initial blank Field Document, for completion by the service provider or others. For such an embodiment, generally, it is not desirable to pre-populate a Field Document(s) with information obtained from a work order because a work order is commonly a request by an operator to have services performed rather than an estimate by a service provider to provide such services. Or in other words, a work order generally provides actual costs rather than estimates of such costs, and thus, there is commonly no value obtained by reconciling a work order against a Field Document However, in those rare cases where a work order does provide an estimate, the various embodiments of the present invention may be suitably configured to reconcile Field Documents against work orders.

Referring now to FIG. 9B, when a Field Document already exists for a particular work order, at least one embodiment of a system of the present invention may be configured to present the service provider or others, via a suitable user interface, a Field Document summary template 942 which may be specifically tailored to a specific work order. The Field Document summary template 942 may include header information to identify the particular project associated with the work order for which the Field Documents have been submitted. As discussed previously with reference to FIG. 9A, in an oil and gas embodiment, such header information may include an identity of the operator 944, a project name 946, a well name (if applicable), a hole section (if applicable), and/or a service type 948. The service type 948 may also include a link to the work order entered by the operator which enables the service provider to access more detailed information about the parameters of the project.

As shown in FIG. 9B, this embodiment of a user interface of a Field Document summary template 942 may additionally include summary information for existing Field Documents previously populated. This summary information may include, for example, a Field Document reference number 950, the date the Field Document was created 952, the name of the person who created the Field Document 954, a functional link to access and review the most recent version of the Field Document 956, the status of the Field Document 958 (i.e., whether or not it has been approved by the operator), the actual charges detailed in the Field Document 960, and a link to the workflow history of the Field Document 962, to be described in greater detail below. It is to be appreciated that additional or less information may also be provided, as particular implementations require.

When one or more Field Documents already exist for a given project, the Field Document summary template 942 may also be configured to provide the service provider/user with various options for pre-populating a Field Document. These options include: not pre-populating the Field Document 970 and instead manually entering new information, and an option to pre-populate the Field Document from an existing Field Document/EFT 972. A selection of either of these options may be suitably made, for example, by clicking a radio button associated with a particular choice.

Additionally, when the new Field Document is to be populated by data from a previous Field Document, a radio button 964 associated with the previous Field Document may be selected by the service provider/user to indicate the desired data to be used in the new Field Document. When the create new Field Document function 974 is selected, the system proceeds with generating a new Field Document which has been populated by the system as desired by the service provider. A service provider may further select the reconcile Field Documents function 930 from the Field Document summary template 942 to connect with reconciliation tool template, which is described in further detail herein below.

User Interface for Inputting Actual Costs in a Field Document

Referring again to FIGS. 8C, 9A and/or 9B, once a service provider/user selects a "Create New Field Document" button 810, 940, or 974 at least one embodiment of a system implementing the present invention may be configured to present a Field Document template page 1002 (as shown in FIGS. 10A–10C). As shown, the Field Document template page 1002 provides an user interface via which a service provider/user may enter the costs of goods and services and/or other information related to a specific project request. More specifically, in the embodiment shown in FIGS. 10A–10C, project level information 1004 may be prepopulated into the template as may information obtained from previous proposals or purchase orders if any. Such information may be pre-populated automatically or upon request by a service provider or other users.

Further, the template 1002 may be used to enter other information including, but not limited to, temporal information about the work performed on the project 1006, descriptions and prices of services performed 1008, descriptions and prices of products and materials used 1010, and descriptions and costs of third party services utilized by the service provider in completing the project 1012. The system may also be configured to total costs for the services performed and products used and to provide such totals in at least one field 1014. The system and template may also be configured such that the service provider/user may enter any comments or explanations about entries and charges in the Field Document in a comment dialogue box 1016.

Information entered into the Field Document template page 1002 may also be saved as desired, for example, the service provider may complete tasks and then record such tasks on the Field Document over a period of time by suitably entering such information and periodically selecting the save button 1018. Further, when entries to the Field Document are final, the service provider may save such entries and simultaneously submit them to the system for review by the operator by selecting, for example, the "save and Submit to Operator" button 1020.

Upon selection of button 1020, for this embodiment, the operator may timely receive a message that a new Field Document has been prepared, which the Operator may access at any time. When the operator selects a given Field Document from the list on a summary page, the system may be further configured such that the operator may, for example, review the service provider's cost entries for the project and compare them to the original Bid Award amounts and any actual invoices received from the service provider. Further, the system and user interface shown in FIGS. 10A–10C (or other user interfaces) may be configured such that when an issue or subject matter arises that the operator desires to share with the service provider, the operator may submit comments to the service provider/vendor in a field, such as the "Comments for Vendor" field 1022. Further, this embodiment may also be configured such that the operator's portion of the Field Document includes an additional comment section 1024 in which an operator may provide internal comments, for example, comments directed to the operator's accounting department.

As such it is to be appreciated that the system embodiment illustrated by the user interfaces shown in FIGS. 9A, 9B, and 10A to 10C facilitate communications between an operator and at least one service provider. Such communications may be further enhanced by providing comment fields 1022 and 1016. This and other information may be utilized, for example, to negotiate and agree upon a final cost figure or the like. Further, FIGS. 10A to 10C illustrate one embodiment of a user interface compatible with a system implementing the present invention. It is to be appreciated, however, that the operator's page may include additional buttons, for example, buttons, fields or other interfaces (all of which are well known in the art) which enable the operator/user to save any comments and submit them to the service provider.

Further, this system embodiment provides that during any negotiation, a Field Document is "alive" and changes may be made to such Field Document by the service provider, the operator or other authorized users.

When the operator and service provider reach agreement, buttons may be provided by which the operator may approve a Field Document while also submitting information on the Field Document to other interested parties, for example, an operator's accounting department. If the operator and service provider are unable to come to an agreement, the system/user interface may also be configured so that the operator may submit an unapproved Field Document which may include a hold for payment request designation or some other designation which indicates to an accounting department and/or others that a Field Document is not ready for payment. Further, once the operator submits an approved and/or an unapproved Field Document to an accounting department, the cost fields may also be locked by the system, while the operator and service provider may still be able to exchange communications with each other via the comment fields or other fields. Further, the system may be configured such that the operator may change any project level information and accommodate any other changes, if any, to the operator's internal project designations and record keeping.

Thus, it is to be appreciated that the system embodiment as reflected by the user interfaces shown in FIGS. 9A, 9B, and 10A to 10C may include many other additional features and functions and that buttons and other user interface devices (such as text entry fields, drop-down menus, and the like) may be provided.

User Configurable Field Documents

Another embodiment of a system for implementing at least one aspect of the present invention is illustrated through the user interfaces, screen displays, and/or templates shown in FIGS. 11A–F, 12A and 12B. As shown in FIG. 11A, the presentation of a Field Document may be modified to provide greater navigability and organization for the user. Each of the potential service and charge categories may be provided in a separate collapsible window or combinations thereof. For example, the service charges 1008 (in FIG. 10A) may be collapsed into closed window 1102 (as shown in FIG. 11A) with only the total cost shown. Similarly, product charges 1010 (in FIG. 10B) may be collapsed into closed window 1104 and third party charges 1012 (in FIG. 10B) may be collapsed into closed window 1106. Each of these windows can be opened to display a full itemized list of entries, as desired. Further, the system or software processes implementing this embodiment, may be configured such that each time a window is closed, the entries in the Field Document are saved.

If a service provider desires to attach any supporting documentation to the Field Document, supporting documents may be attached after the entries to a particular Field Document have been saved by executing the "save" function 1108. It is to be appreciated, however, for other embodiments, that supporting documents may be attached to a Field Document before or after the Field Document has been saved.

Referring again to the system embodiment shown in FIG. 11A, once the Field Document has been saved, the system suitably presents an "Add Attachment" dialog box 1110, on the service provider's template, as shown in FIG. 11B. The system is preferably configured so that the attachment box 1110 function enables a service provider to attach any desired documentation (e.g., summary reports, core sample charting, and project designs), in any format (e.g., word processing files, spread sheet files, and computer aided design files) to the Field Document for subsequent review by the operator. When the Field Document is complete and any desired files are attached, the service provider may submit the Field Document to the system for review and/or approval by the operator, for this embodiment, by choosing the "submit" function 1112. Upon submission of the Field Document, the system may automatically send notification to the operator that the Field Document is available for review.

When the operator accesses the Field Document, the system desirably presents an operator's user interface such as the one shown in FIG. 11C. As shown for this embodiment, the user interface includes collapsible windows, for example, the collapsed third party charges window 1114. The interface also enables the operator to view a detailed enumeration of third party charges, by selecting the expand button 1116 which, as is commonly known in the art, expands a given window to occupy the entire viewable area of a given display. Further, the system may be configured such that the operator can view the entries and charges in a read only format. Read only formatting is preferably utilized so that the operator can not alter the information previously entered by the service provider. However, the system does provide the operator with the capability to enter internal comments about a given Field Document or an element thereof by including an internal comments box 1118. Similarly, comments may also be directed to the service provider by making entries in the service provider comments box 1120. Such comments to the service provider may be, for example, an indication of changes to the Field Document requested by the operator before payment will be approved. It is to be appreciated, that while the various embodiments of systems and user interfaces described herein generally provide for the entry of textual comments, the system and process embodiments of the present invention may also be configured to attach audio and/or video files, including audio commentary, to any Field Document, commercial response, work order and/or any other aspect of the present invention by which information is communicated between various parties.

When an operator desires to approve a Field Document for payment, the operator may select the "approve" function 1124, which function is illustrated in FIG. 11C as being implemented by selecting an approve button. If the operator wants the service provider to make changes to the Field Document, for example, in response to comments entered in the service provider comments box 1120, the operator so directs the system by choosing the "hold for approval" function 1126. The operator may also save the Field Document template at any time by selecting the "save" function 1122. Additionally, if the operator wishes to attach a document to the Field Document (for example, for review by the service provider), this action generally may be performed after the save function 1122 is selected, as shown in FIG. 11D. When the save function 1122 is selected, a file attachment box 1128, similar to that provided to the service provider in FIG. 11B, may be provided to the operator with the same functionality of the service provider's attachment box 1110. The operator may wish to provide updated, edited, and/or corrected versions of the attachments submitted by the service provider, or the operator may wish to provide entirely new attachments.

When the operator selects either the approve function 1124 or the hold for approval function 1126, the Field Document is suitably saved by the system and the service provider may be notified that the Field Document has been reviewed by the operator. It is to be appreciated, that a Field Document and other data or information utilized in conjunction with the various embodiments of the present invention may be saved in local and/or remote databases in data arrays, as objects in a SQL structure or otherwise.

Desirably, the service provider may view the operator's comments when the Field Document is accessed. If the Field Document has been held for approval by the operator, the system desirably enables the service provider to adjust the Field Document and make any internal notes by providing an internal comment box 1130, as shown in FIG. 11E. The service provider may further indicate the changes made, or provide any other communication to the operator, in the operator comment box 1132. Again, the service provider may save the Field Document at any time and return to it to complete the entries at a later time by selecting the save function 1134. Selecting the save function 1134, as before, also allows the service provider to attach other files to the Field Document (see file attachment box 1138 in FIG. 11F). If the Field Document is ready for resubmission for review by the operator, the "approve" function 1136 may be selected.

When the service provider selects the approve function 1136, for this embodiment, the system may be configured to present the user interface shown in FIG. 11F. If the Field Document was previously approved by the operator, and no further corrections have been entered by the service provider, the system enables the service provider to send the Field Document directly to an invoicing program by providing an invoicing function which may be activated via the "Send to Invoicing" button 1140. Further, if the service provider made any changes to the Field Document, after initial approval by the operator, the system enables the service provider to send such changes to the operator for approval before sending the Field Document to invoicing by providing the "Send to Operator for Approval" button 1142.

In addition to the fields provided by the system for the Field Document, operators and services providers may also be provided user interfaces by which they may add their own, customizable fields to a Field Document. One example of a user interface for this customization process is the Field Document setup interface 1202, as shown in FIG. 12A. By selecting the "add new custom field function," 1204 an operator or service provider may insert a new field 1206 into the table, as shown. The custom fields may be labeled in any way desired, for example to keep track of particular account numbers or personnel responsible for a given Field Document. The custom fields may be designated as "read only," "editable" by any party, or limited to "internal" presentation to agents of the customizing party by selecting either the read only function 1208, the editable function 1210, or the internal function 1212, respectively. Once created, each customized field may be displayed as part of the Field Document template. For example, as shown in FIG. 12B, operator designated custom fields 1214 designated as "internal," and therefore viewable desirably by the operator only, may be provided below the internal operator comment box 1216.

Field Document Management Tool(s)

In order to manage a multiplicity of Field Documents associated with a multiplicity of projects, operators and service providers, another embodiment of the system may be configured to provide at least one Field Document management tool. An exemplary embodiment of a Field Document management tool is illustrated by the user interface templates shown in FIGS. 13A–B.

More specifically, a Field Document manager template 1300 provided for an operator is shown in FIG. 13A. This template 1300 enables an operator to sort and/or search Field Documents by various categories. Filters may be provided in the Field Document manager template 1300 and may be used by operators to select the Field Documents to be displayed. Possible filtering criteria may include, for example:

a) by service provider name 1302, wherein the list of service providers may include all service providers that have submitted Field Documents;
  b) by project 1304, wherein the selection list may include each project name for which Field Documents have been submitted;
  c) by well name 1306, for example, when used in an oil and gas embodiment, wherein the list may include each well name for which a Field Document has been submitted;
  d) by Field Document status 1308, whereby the Field Documents may be filtered by whether they have been received by the operator, approved, held for approval or have any other status; and
  e) by Field Document date range 1310, wherein the filter may offer commonly used date ranges for selection, or allow the operator to enter a specific date range 1311 for Field Documents to review.

It is to be appreciated that other categories may also be utilized to filter Field Documents. Additionally, rather than showing only Field Documents related to a selected project, added functionality may be provided by allowing an operator to hide all Field Documents related to a specific project, for example, by selecting a check box 1305. A similar option may also be provided with respect to well names, as depicted in the Field Document manager template 1300 by check box 1307. Additionally, a particular system embodiment may be configured such that each filter may provide the option of displaying all Field Documents. If the operator selects "all" as the filter for the Field Document status filter 1308, the date range filter 1310 will not be able to accept a specific date range 1311. Further, the date range filter 1310 will show only Field Documents that have been modified to hold the selected Field Document status 1308 within the given time frame.

The Field Document manager template 1300 for a particular system embodiment, may also be configured to provide a listing of all Field Documents meeting the filter criteria. Preferably, such a listing is generated once the filtering criteria are established. But, the listing may also be generated as each filtering option is selected, it is anticipated that such "on-the-fly" filtering may enable users to detect subtle nuances between various Field Documents. The system also provides for the sorting of Field Documents based upon at least one of a plurality of data attributes, which may or may not be selectable by a user. For example, Field Documents may be sorted by service provider 1312, project name 1314, service type 1316, Field Document status 1318 (e.g., whether or not the Field Document has been submitted, or perhaps has been approved or held by the operator), and Field Document approval date 1320. Other data fields may likewise be used for sorting purposes as desired by particular system embodiments. The Field Document listing may also provide links to additional information associated with particular Field Document data, for example:

a) a service type link 1322 may provide access to the service request or work order;
  b) a commercial response link 1324 may provide access to a commercial response, for example, when the project was initiated by a service request and the service provider completed a commercial response; likewise, if the project was initiated with a work order a link may not be provided;
  c) a Field Document link 1326 may provide access to the most recent version of the Field Document and thereby enable the operator to approve, provide comment, or hold for approval a given Field Document;
  d) a reconciliation tool link 1328 may provide access to a reconciling process, which may or may not be an element of the system (one example of such a reconciling process is described in greater detail herein below);
  e) a collaboration link 1330 may provide access to a dialog interface where the operator may review existing messages or create new messages for the service provider regarding the particular Field Document or other aspects of the project; and/or
  f) a workflow link 1332 may provide access to a workflow history manager process (one embodiment of which is describe in greater detail herein below) which enables an operator to review significant changes that have been made to a given Field Document, by whom such changes were made and when such changes were made.

Additionally, the present system embodiment also provides a Field Document manager template 1350, as shown in FIG. 13B, for a service provider. This template 1350 similarly enables a service provider to sort and/or search Field Documents based upon various categories. Filters may be provided in the template 1350 and suitably utilized to select Field Documents to be displayed. Possible filtering criteria may include, for example:

a) by operator's name 1352, wherein the list of operators may include all operators that have submitted Field Documents;

b) by project 1354, wherein the selection list may include each project name for which Field Documents have been submitted;

c) by well name 1356, wherein the list may include each well name for which a Field Document has been submitted;

d) by Field Document status 1358, whereby the Field Documents may be filtered by whether they have or have not been submitted to the system, approved by the operator, held for approval by the operator, approved by the service provider, sent to invoicing, or otherwise designated; and/or e) by Field Document date range 1360, wherein the filter may offer commonly used date ranges for selection, or allow the service provider to enter a specific date range 1361.

It is to be appreciated that other categories may also be utilized to filter Field Documents.

Rather than showing only Field Documents related to a selected project, the system may be configured to provide additional functionality, for example by enabling a service provider to hide all Field Documents related to a specific project, for example, by selecting a check box 1355. A similar option may be provided with respect to well names and/or other fields, as depicted on the template 1350 by check box 1357. Additionally, each filter may be configured (depending upon particular system embodiments utilized) to provide the option of displaying all Field Documents. For example, if the service provider selects "all" as the filter for Field Document status filter 1358, the date range filter 1360 is desirably configured to not accept a specific date range 1361. However, in other system embodiments, the Template 1350 could be configured so that an "all" selection may relate to certain sub-fields, such as "all" Field Documents generated within a particular time period, regardless of other filter selections such as the Operator Name, the Project, or the Well Name. Further, the date range filter 1360 may also be configured to list only those Field Documents that have been modified and/or to hold the selected Field Document status 1358 within the given time frame.

The template 1350, for a particular system embodiment, may also be configured to provide a listing of all Field Documents meeting the filter criteria. Preferably, such a listing is generated once the filtering criteria are established. But, the listing may also be generated as each filtering option is selected, it is anticipated that such "on-the-fly" filtering may enable users to detect subtle nuances between various Field Documents. The system may also be configured such that a Field Document listing may further be sorted by a selection of data attributes, for example, by operator 1362, project name 1364, service type 1366, Field Document status 1368 (e.g., whether or not the Field Document has been submitted, or perhaps has been approved or held by the operator), and/or Field Document approval date 1370. Other data fields may likewise be used for sorting purposes as desired by particular system embodiments. The Field Document listing may also provide links to additional information associated with particular Field Document data, for example:

a) a service type link 1372 may provide access to a service request or work order;

b) a commercial response link 1374 may provide access to a commercial response, when the project was initiated by a service request and the service provider completed a commercial response; likewise, if the process was initiated with a work order, a link may not be provided;

c) a Field Document link 1376 may provide access to the most recent version of the Field Document and thereby enable the service provider to submit, edit, provide comment, or take other possible action with regard to a given Field Document;

d) a reconciliation tool link 1378 may provide access to a reconciling process, which may or may not be an element of the system (one example of such a reconciling process is described in greater detail herein below);

e) a collaboration link 1380 may provide access to a dialog interface where the service provider may review existing messages or create new messages for the operator regarding the particular Field Document or other aspects of the project; and f) a workflow link 1382 may provide access to a workflow history manager process (one embodiment of which is describe in greater detail herein below) which enables a service provider to review significant changes that have been made to a given Field Document, by whom such changes were made, and when such changes were made.

Reconciliation of Field Documents

Another embodiment of the present invention provides a process for reconciling a Field Document and a commercial response. This process may be accomplished by utilizing a reconciliation tool (which ideally is provided in software that has been loaded into a system implementing an embodiment of the present invention). The processes performed by an embodiment of such a reconciliation tool are depicted in the flow diagrams of FIGS. 14A and 14B. It is to be appreciated, that for this and other embodiments, certain common processes may be made available to both the operator and service provider, such common processes are identified by operation 1400 and are further described in greater detail herein below.

Initially, this process begins when a reconciliation tool template, which may be provided in an user interface or otherwise, is accessed by a user (operation 1402). Once the tool is accessed, the user identifies at least one commercial response or work order in which they are interested in reconciling and a list of Field Documents associated with the selected commercial response(s) or work order(s) is presented to the user (operation 1404).

Next, the process may be configured to present an interface from which the user may select which, if any, of the Field Documents on the list to reconcile (operation 1406). Once a user's selection has been made, a query may then be initiated in order to determine whether the user has selected less than all of the Field Documents listed for the selected commercial response(s) and/or work order(s)(operation 1408). If all of the Field Documents have been selected by the user, the process continues the reconciliation functions using all the filed Field Documents (operation 1410). However, if the number of Field Documents selected is less than the total number of Field Documents, the process continues with performing the reconciliation functions with respect to only the selected Field Documents (operation 1412).

When the user selects the reconciliation function (operation 1414), the process provides, for the selected Field Documents, data totals that are generally provided in reference to the discrete categories or fields of data collected in the Field Document(s) (operation 1416). Next, it is determined whether a commercial response or work order is associated with each of the selected Field Document(s) (operation 1418). If there is a commercial response, a system implementing this process suitably retrieves data totals for the fields of data in the commercial response which relate to fields specified in a given related Field Document (operation 1420). It is to be appreciated that such data may be obtained from local and/or remote databases.

Next, a comparison is made between the estimated data in the commercial response and the actual data provided in a given Field Document, or a sum total when data is accessed from a plurality of Field Documents. The result of this comparison may be provided as the difference between the values (operation 1422). Additionally, a percentage difference between the values of the commercial response and the Field Document(s) may be calculated and provided to the user (operation 1424). The process may then end or may continue with the user reviewing the comparison data, and/or selecting other Field Document(s) to reconcile (operation 1406). Thus, it is to be appreciated that FIG. 14A provides one embodiment by which a user may select at least one commercial response and/or work order, identify Field Documents to be reconciled against the selected commercial response(s) or work order(s), and obtain value and percentage differences between estimates and actual work performed for a given project.

FIG. 14B depicts another embodiment of a process for reconciling Field Documents. This process may be directed towards an operator, however, comparable processes may also be provided for a service provider. More specifically, this process begins when a user accesses an operator user interface provided by a system or device implementing an embodiment of this process of the present invention (operation 1426). For the operator's benefit, this process may be configured to enable an operator to approve at least one Field Document for payment directly via a user interface which includes a reconciliation tool (operation 1428). The user interface and this process may be configured to provide the operator with a template which enables the operator to choose between at least two input options. It is to be appreciated, that providing the option of to pay or not to pay via a reconciliation tool may be highly desirable because a result of such a decision will likely be based upon the results of the reconciliation of at least one Field Document.

As shown, this process may also be configured to provide two function: an approval function, and a hold for approval function. When the operator selects the approval function (operation 1430), the operator may be provided an input field (for example, on a user interface), by which the user may add comments or information to the Field Document (operation 1432). Once any comments have been added (operation 1434), or if no comments were added, the Field Document is designated as approved and is saved (operation 1436). Ideally, the approved Field Document is saved to a workflow platform provided by a system implementing the present invention. Such workflow platform generally may be accessed by other authorized users at any time. Alternatively, the approved Field Document may be saved in other systems, as desired, and accessed via Internet connections or other connections.

Once a Field Document has been approved and/or saved, a notification may be communicated to the service provider (s) associated with the Field Document (operation 1446). This notification may be communicated via any suitable communications medium including, but not limited to, paging systems, e-mail, instant messaging, telephone messaging, teletype, facsimile, or the like.

Referring again to operation 1428, should the operator select the hold for approval function (operation 1438), the operator may be provided the opportunity to add any comments or information to the Field Document before submitting the Field Document to the service provider for revision (operation 1440). Once any comments have been entered (operation 1442), or if no comments were added, the Field Document may be designated as "held for approval" and saved (operation 1444). A notification may then be communicated to the service provider that the Field Document has been reviewed by the operator, designated as "held for approval" and is available for revision (operation 1446).

User Interfaces for Reconciling

Figure 15A:
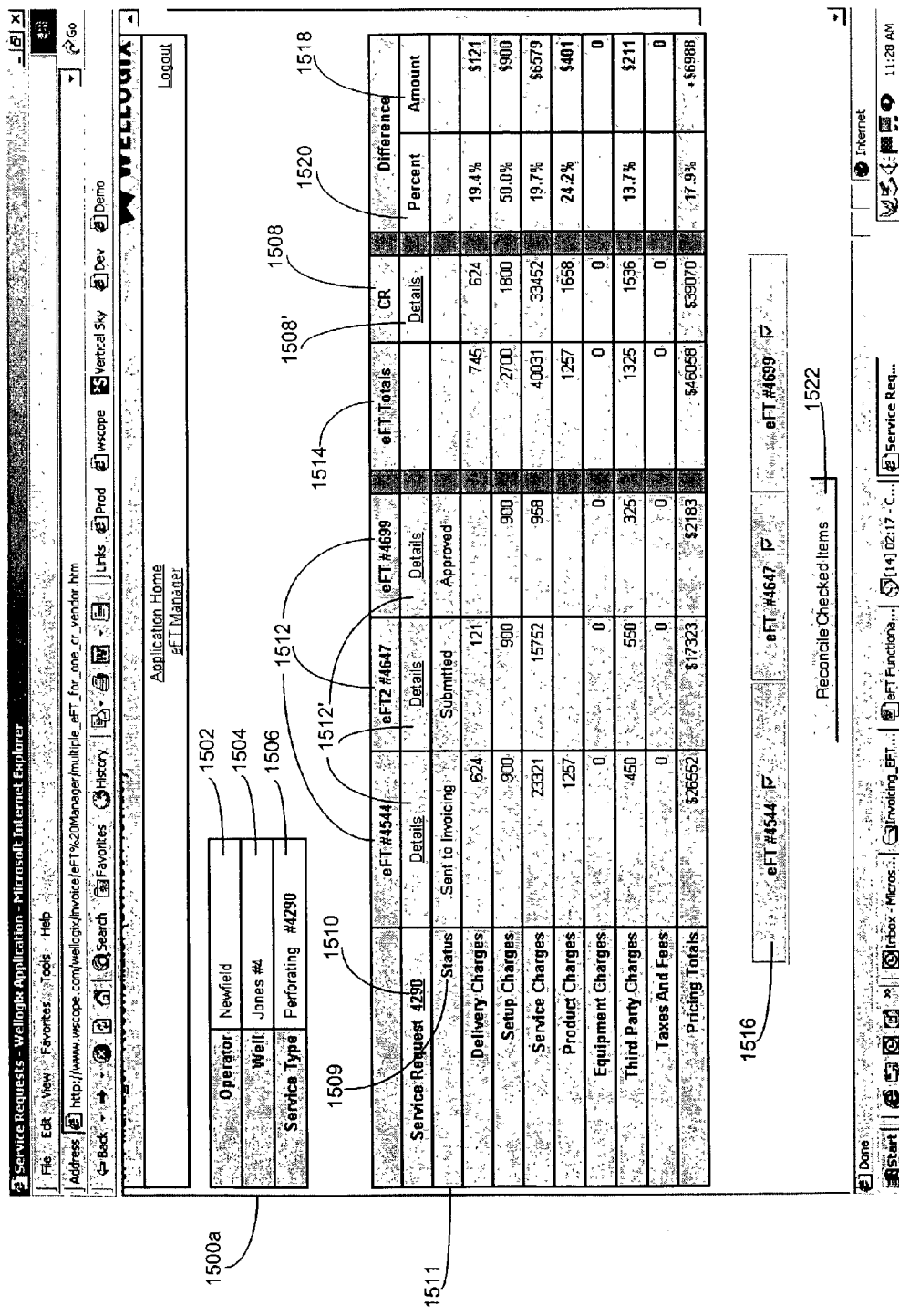
Figure 15B:
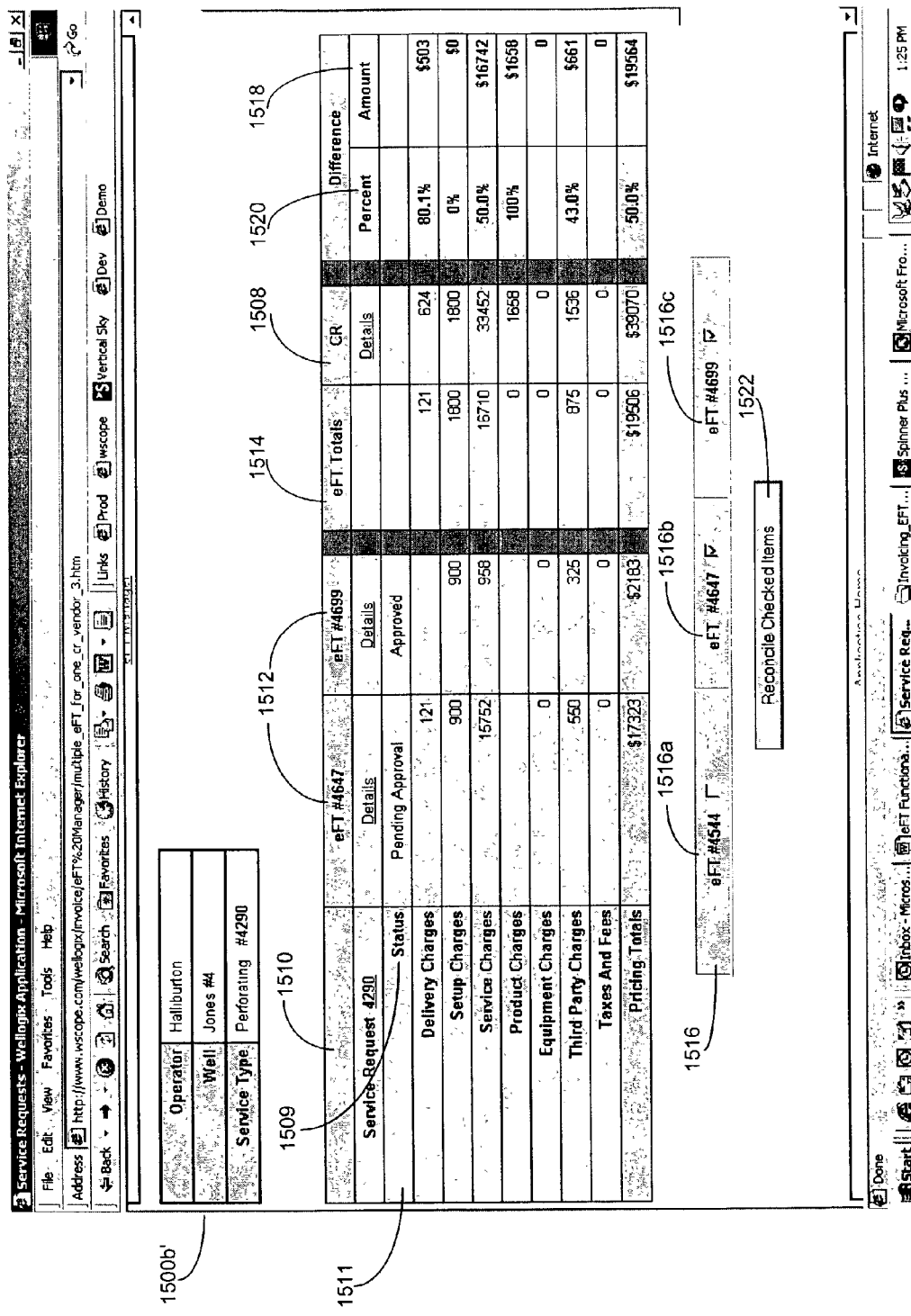
Figure 15C:
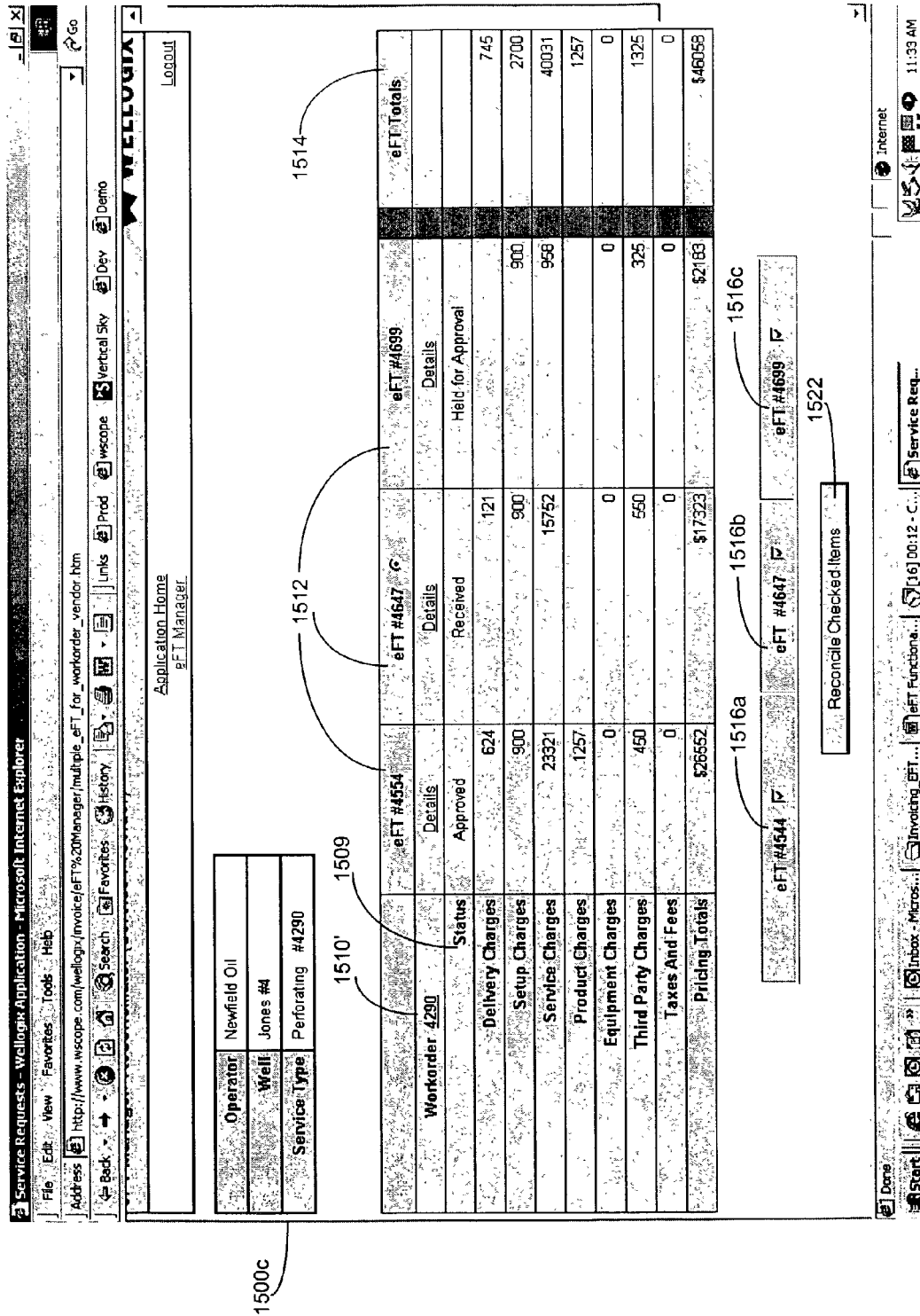

FIGS. 15A–C provide an exemplary series of user interfaces/templates by which a service provider may utilize at least one embodiment of the before mentioned reconciliation process. Generally, the user interfaces shown in FIGS. 15A–15C provide a reconciliation tool which contains substantially the same fields and functions for both the operator and the service provider, since all but a few f the available functions of the reconciliation tool are provided to both parties. However, other embodiments may utilize user interfaces and reconciliation tools which may substantially vary from an operator's perspective to a service provider's perspective. All such variations are considered to be within the scope of the present invention.

In the embodiment shown in FIG. 15A, Field Documents may be linked to a particular commercial response. The reconciliatory tool template 1500a suitably includes a header section in which project specific information may be provided, for example, the operator (or service provider) name 1502, the well name 1504, and a service type description 1506. Further, a table 1511 may be provided in which comparisons between the totals of various fields of Field Documents 1512, for example, the different categories of charges incurred, to the related commercial response 1508 may be displayed. Another data field in the table 1511 may also include an indication of the status 1509 of the Field Documents 1512, i.e., whether the Field Document has been submitted for approval, approved, held, or has been transferred for invoicing. Hyperlinks and other types of links may also provide a user with access to the most recent version of each actual Field Document 1512 via links 1512' and similarly to the commercial response 1508 via link 1508'. Similarly, links to the original service request 1510 may also be provided to allow for review and comparison of all the project documents.

Further, it is to be appreciated that access to Field Documents, commercial responses, original service requests and/or other information may be provided immediately or on a delayed basis, in accordance with particular system and/or user device configurations and/or limitations. For example, a user in the field may not have immediate access when communications links are inoperable between a user device and a system or database at which a given Field Document or commercial response is saved.

The table 1511 shown in FIG. 15A may further include a Field Document total calculation column 1514 in which combined total amounts for each discrete data field of the Field Documents 1512 may be presented. These totals may be obtained using, for example, known in the art column adding formulas. The user interface may also provide a comparison between the Field Document total amounts 1514 and the commercial response estimates 1508 as both an actual comparison 1518 (the difference) and a percentage comparison 1520 (the difference divided by the commercial response amount 1508). Again, such totals and percentages may be calculated utilizing well known in the art processes.

In essence, via the user interface provided in FIG. 15A, Field Documents related to a particular service request can be presented to a user via one reconciliation tool such as the table 1511. This feature of the present invention may be especially advantageous when Field Document submissions or receipts may never reach a service provider or operator's accounting department, the service may never be billed, or an invoice may be received for which there is provided no evidence showing that the work was ever performed. Further, not only does this and other embodiments of the present system keep track of all Field Documents issued, it ensures that they are tied to the particular service request. Further, via a reconciliation tool, such as the embodiment shown in FIG. 15A, when multiple Field Documents are issued for the same service request, the Field Documents can be viewed together, along with the commercial response, to determine whether the Field Documents track the commercial response and/or whether there are discrepancies that require further investigation.

Further, the present invention suitably supports reconciliation tools which enable a user to select which Field Document(s) to include for comparisons and calculations. Such functionality may be provided in various manners, for example, by a Field Document selection bar 1516, as shown in FIG. 15A. As shown in FIG. 15A, each of the Field Documents 1512 associated with the particular service request 1510 may be selected for display in the table 1511. Similarly, FIG. 15B depicts a reconciliation tool template 1500b for the same service request 1510 wherein a user has selected only two, 1516b and 1516c, out of the three Field Documents possible via the Field Document selection bar 1516. In order to update the table 1511 to reflect the selected Field Documents 1516a and 1516b, a "reconcile" function 1522 may be provided whereby, upon selection, the table 1511 is recalculated with only the selected Field Documents 1512.

For example, when the first Field Document 1516a on the Field Document selection bar 1516 is not selected, the data associated with such Field Document may be excluded from the Field Documents 1512 displayed in the table 1511. Further, in this example, because only two Field Documents 1512 are provided in the table 1511, the actual comparison 1518 and percentage comparison 1520 figures are different in this template 1500b than in the previous template 1500a. Such comparison information between estimates and actuals, between all Field Documents, or only a subset thereof, may be used to manage a project by facilitating determinations as to whether there are cost overruns or savings, or additional work is yet to be performed because the Field Document totals 1514 do not reflect the totals in the commercial response 1508.

It is to be appreciated that numerous variations may be made to the reconciliation tool and how such tool may be presented to a user. One such variation is shown in FIG. 15C. In this variation, a table 1511 may be provided wherein the Field Documents 1512 are related to a work order 1510' rather than a commercial response 1510 (as shown in FIG. 15A). The reconciliation tool, for this embodiment, may be configured to merely calculate the totals 1514 of the selected Field Documents 1512. Since there generally is no underlying commercial response, there are no differences or percentages to calculate. Also, the user may be provided with the option of choosing which Field Documents 1512 to reconcile by using the Field Document selection bar 1516 and selecting the reconcile checked items function 1522.

Figure 15D:
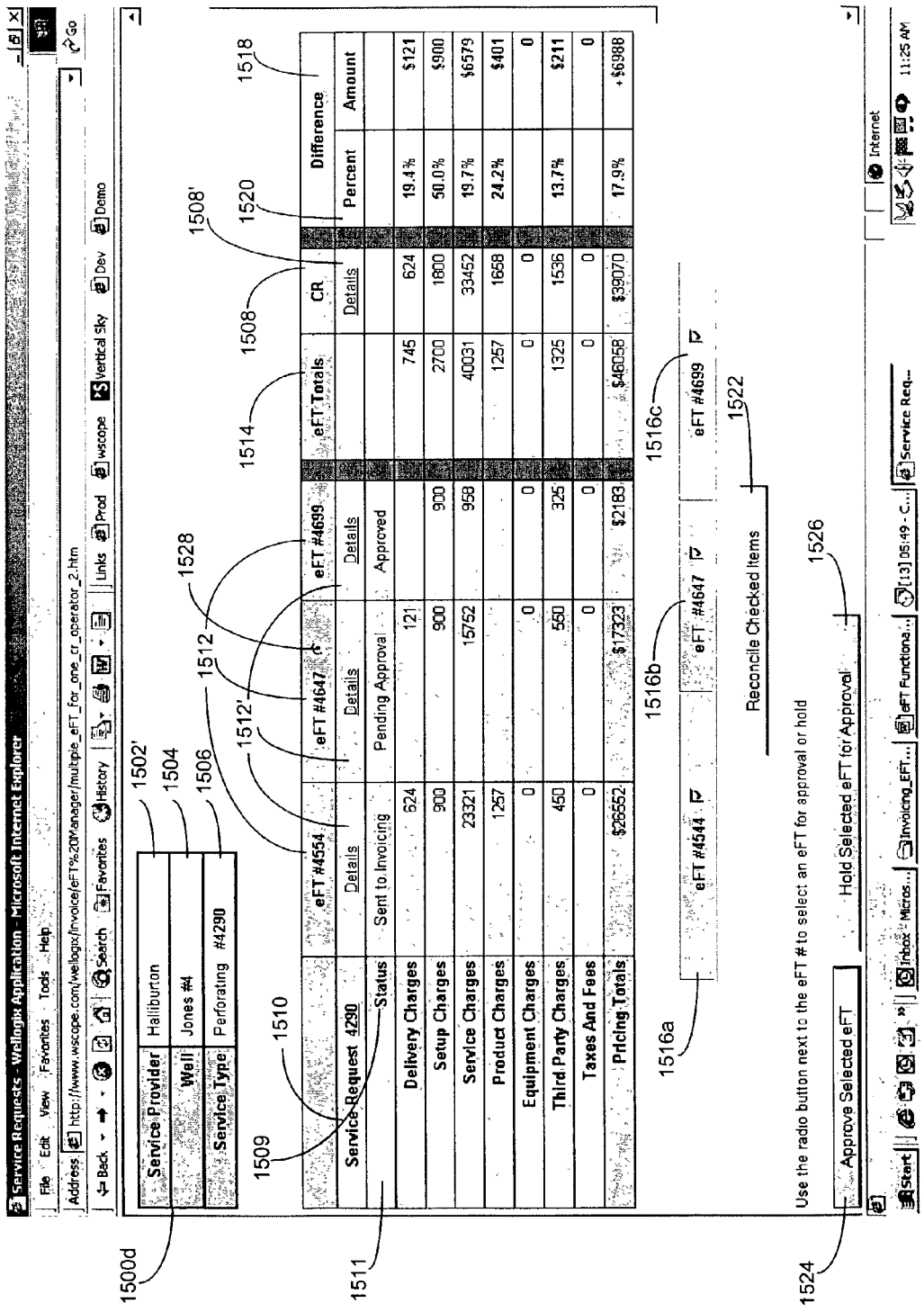

An embodiment of a user interface providing access to reconciliation tool by an operator is generally shown in FIG. 15D. As shown, this embodiment provides for additional functionality in the reconciliation tool template 1500d FIG. In this operator embodiment, generally, most of the header information will be the same as that provided in the embodiment shown in FIGS. 15A to 15C. However, the service provider information 1502' for the project may be provided instead of operator information 1502. In addition to the before mentioned comparison capabilities, this embodiment may also be configured to enable an operator to approve Field Documents for invoicing by the service provider, or if there is some discrepancy, hold the Field Document for approval pending resolution of the discrepancy. These Field Document review capabilities may be provided by the approve selected Field Document function 1524 and the hold selected Field Document function 1526, respectively. Further, designation of particular Field Documents 1512 for approval or holding may be provided by the selection of one or more radio buttons 1528 on the template table 1511 next to the Field Document number 1512. Additionally, in at least one embodiment, the availability of radio buttons 1528 is related to the status 1509 of the particular Field Document. For example, if a particular Field Document has already been approved by an operator, then a radio button 1528 may not be provided for selection of that particular Field Document for approval or holding. Such selecting may be accomplished by selecting the approve selected Field Document function 1524 or the hold selected Field Document function 1526. In short, this and other system embodiments may be configured, as desired, to operate with other process embodiments described herein in order to provide an integrated system.

If an operator does select either the approve selected Field Document function 1524 or the hold selected Field Document function 1526, a message may be generated inquiring whether the operator would like to enter internal comments or comments for the service provider. If the operator responds affirmatively, the particular Field Document may be accessed for entry of the comments or other information, thereby associating the information directly with the Field Document. If the operator chooses not to enter comments, the Field Document may be approved or held for later approval.

In another aspect of the invention, a workflow history tracking software application (i.e., a tool) may be provided to document the workflow of at least one of the various embodiments of the Field Document reconciliation and approval processes. This workflow history tracking tool may be configured to create a record providing various information relating to Field Documents and a project in general. For example, the tool may record an identification of a user (for example, an gent of the operator or service provider's team), the action(s) taken by the user, and the date and time of such action(s) while also providing an indication of the Field Document, project, commercial response, work order or other information accessed and/or modified by the user. It is to be appreciated that by creating a recorded history, uncertainty facing many projects can be reduced and/or eliminated. For example, the issue of whether a Field Document was ever submitted, by whom it was authorized, and by whom payment was authorized may be quickly resolved when a workflow history tracking tool is utilized. Similarly, a workflow tracking tool may also eliminate or at least significantly reduce the incidence of time consuming searches for paper and/or computerized documents, reconciliation of such documents against other documents, and the verification of, for example, payment approvals and authorization for write-offs. In general, the workflow history tracking tool may be configured to utilize a relational database to provide the before mentioned and other features and functions.

Workflow History Tracking Tool

One embodiment of a process which may be utilized to provide a workflow history tracking tool is shown in FIG. 16. This embodiment is shown with respect to a Field Document approval process. It is to be appreciated, however, that other embodiments of a workflow tracking tool may be utilized for processes utilized in conjunction with the various embodiments of the present invention.

More specifically, for the embodiment shown in FIG. 16, the workflow path status at each particular operation generally corresponds with an action taken in relation to a Field Document or other document and may correspond to the state of such a document in a system database wherein at least one version of a particular Field Document may be stored. For example, in operation 1602, when a new Field Document is created by a service provider, the workflow path may be configured to record the action as "Field Document created" while a system database may indicate the status of Field Document as being unsubmitted.

Further, if the Field Document is modified before submission to the system, the workflow path may be configured to identify the actions taken as "current working copy of Field Document," while a system database might continue to indicate the Field Document as being unsubmitted, operation 1604. When the service provider submits a Field Document for approval, the database might recognize the status of a Field Document as being "submitted" while the workflow path may indicate to the service provider that the Field Document was "submitted to the operator," operation 1606.

Similarly, when observed from an operator's point of view, once the Field Document is submitted to the system by the service provider, the database may be configured to identify to the operator the Field Document as being "received," while the workflow manager may indicate that no actions were taken and that the status of the Field Document was still "Submitted to the operator," operation 1608. Further, when the operator reviews, modifies, or comments upon the Field Document, the workflow path may be configured to indicate that the Field Document is a "current working copy," while the database may indicate the status of the Field Document as being "received," operation 1610.

As mentioned previously with reference to other process embodiments, at this point, the operator may be provided with two choices: the Field Document can either be approved or held for later approval. If the Field Document is approved by the operator, the workflow path may be configured to record this action as "approved by the operator," while the database suitably stores the status of the Field Document as being "approved by operator," operation 1612. Instead, if the Field Document is held for approval by the operator, the database suitably stores the status of the Field Document as being "held for approval by the operator" while the workflow path might be configured to record the actions as "held for approval by operator," operation 1614.

In either event and as discussed previously, future action is generally required by the service provider. In the case of an approved Field Document, the workflow path on the service provider side may be configured to indicate the approved status of the Field Document for example by designating the Field Document's workflow as "Field Document approved by operator" and designating the status of the Field Document in the database as being "approved by operator," while also providing the service provider access to the approved version of the Field Document in the database, operation 1616. If the service provider optionally decides to additionally modify the approved Field Document, a working copy may be saved in the database, and the workflow path may be configured to indicate the working status of the Field Document as "current working copy of Field Document," operation 1618. If the service provider approves of the modifications, or if optional modifications were not made, the service provider will normally approve the Field Document, either for invoicing or resubmission to the operator, the database may be configured to store the approved Field Document as being "approved by service provider," and the workflow path may be configured to reflect the last action as "approved by service provider," operation 1624. Further, if the Field Document was not modified by the service provider after approval by the operator, the Field Document may be transferred to an invoicing process. In such event, the database may be configured to record the status of the Field Document as "sent to invoicing," while the workflow path may be configured to indicate the last action for the Field Document as being "sent to invoicing," operation 1626.

Referring again to operation 1614, in the case of a Field Document being held for approval by the operator, the service provider will generally be notified of such status by an indication of "held for approval by operator" while the workflow path may indicate that the last action on the Field Document was "held for approval by operator," operation 1620. If the service provider makes any modifications to the held Field Document, the workflow path may be configured to indicate the last action on the Field Document as being "current working copy," while the database might be configured to continue to represent the status of the Field Document as being "held for approval by operator," operation 1622. Once any modifications are made, the service provider will generally approve the Field Document, either for invoicing or resubmission to the operator. The database may be configured to store the status of the approved Field Document as being "approved by service provider," and the workflow path may be configured to reflect the last action as being "approved by service provider," operation 1624. At this point, the Field Document may then proceed with operations 1626, as discussed hereinabove. More likely, however, because the Field Document was not approved by the operator originally, the service provider may desire to resubmit the Field Document to the operator for approval, whereby the database may be configured to indicate the status of the Field Document as being "submitted," while the workflow path may indicated the last action taken as being "submitted to operator," operation 1628. Once resubmitted, the workflow path cycle returns to operation 1608 on the operator side for approval of the Field Document.

Therefore, as illustrated by the foregoing discussion and the process flow shown in FIG. 16, the workflow history tracking tool essentially provides a process for tracking actions taken with respect to a given document or item of information. The foregoing example was provided with respect to a Field Document, it is to be appreciated, however, that various embodiments of the workflow tracking tool may also be utilized to track actions taken with respect to bids, commercial responses, work orders, invoices and any other identifiable piece of information.

User Interfaces for Providing Workflow History Tracking

Figure 17A:
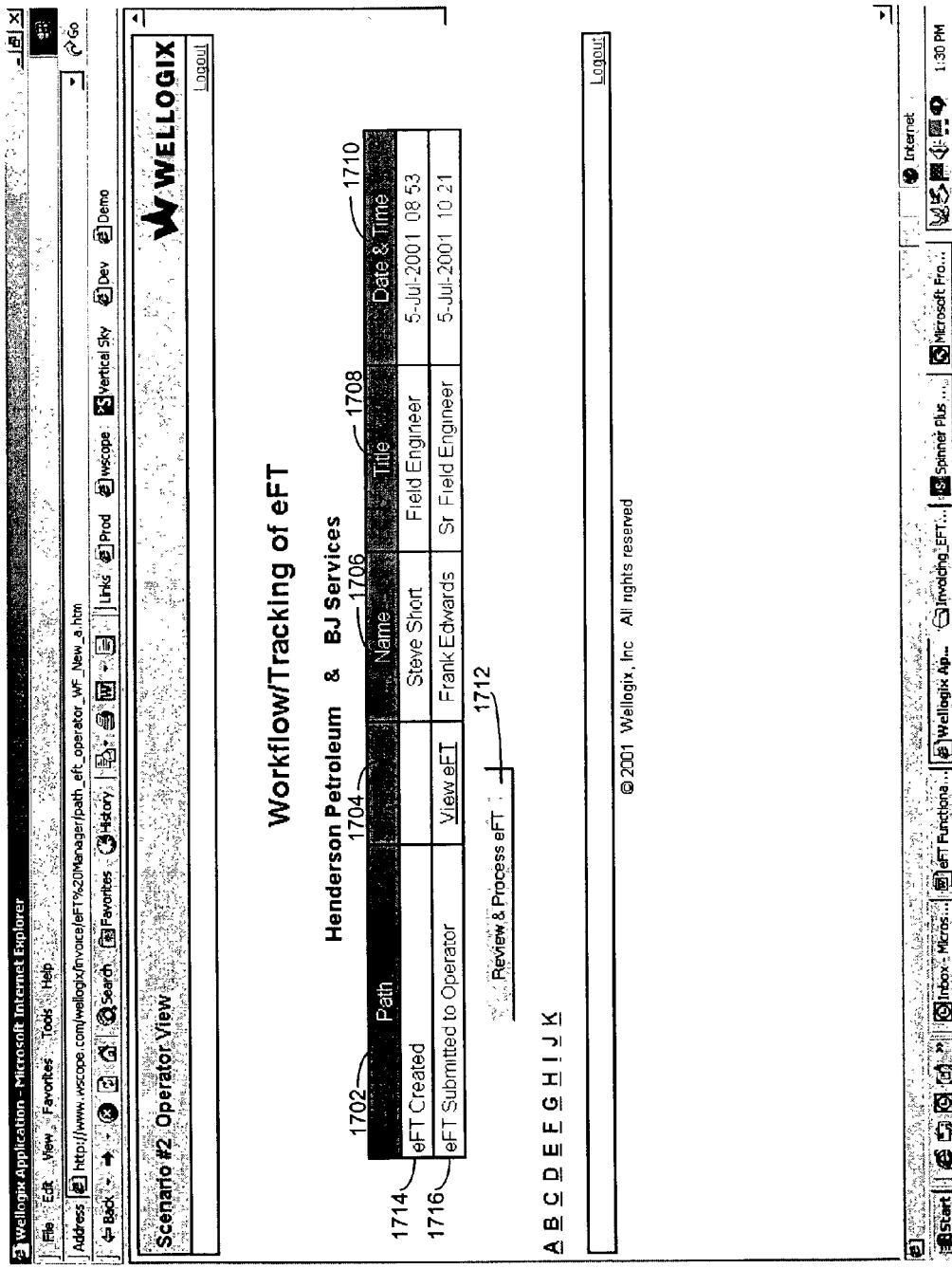

One embodiment of a user interface for providing workflow history tracking is shown in FIGS. 17A–H. More specifically, FIG. 17A provides one embodiment of a user interface which includes a workflow tracking template that may be utilized to provide the point of view of an operator. As shown, the workflow history may be suitably presented via a table containing various columns, such as: a column 1702 indicating a path taken by a given Field Document; a view column 1704 providing link options by which an operator may view a specific version of a Field Document; a column 1706 identifying persons who have taken some action with respect to the Field Document; a column 1708 indicating such person's titles; and a column 1710 indicating the date and time a particular action occurred. As shown, for this first template, the operator may be advised, by corresponding entries in the table, that a Field Document has been created 1714, and that the Field Document has been submitted to the operator for review 1716. In this instance, if the operator wishes to review and modify the Field Document, this may be accomplished by selection of either the related links in the "view" column 1704, or by selection of the "review and process" function 1712. However, this functionality may not always be provided, because a given "view" link may not include or may only include a link which provides only access to historical copies of the Field Document. In contrast, for this embodiment, the review and process function 1712 is generally configured to provide access to the current working version of the Field Document.

Figure 17B:
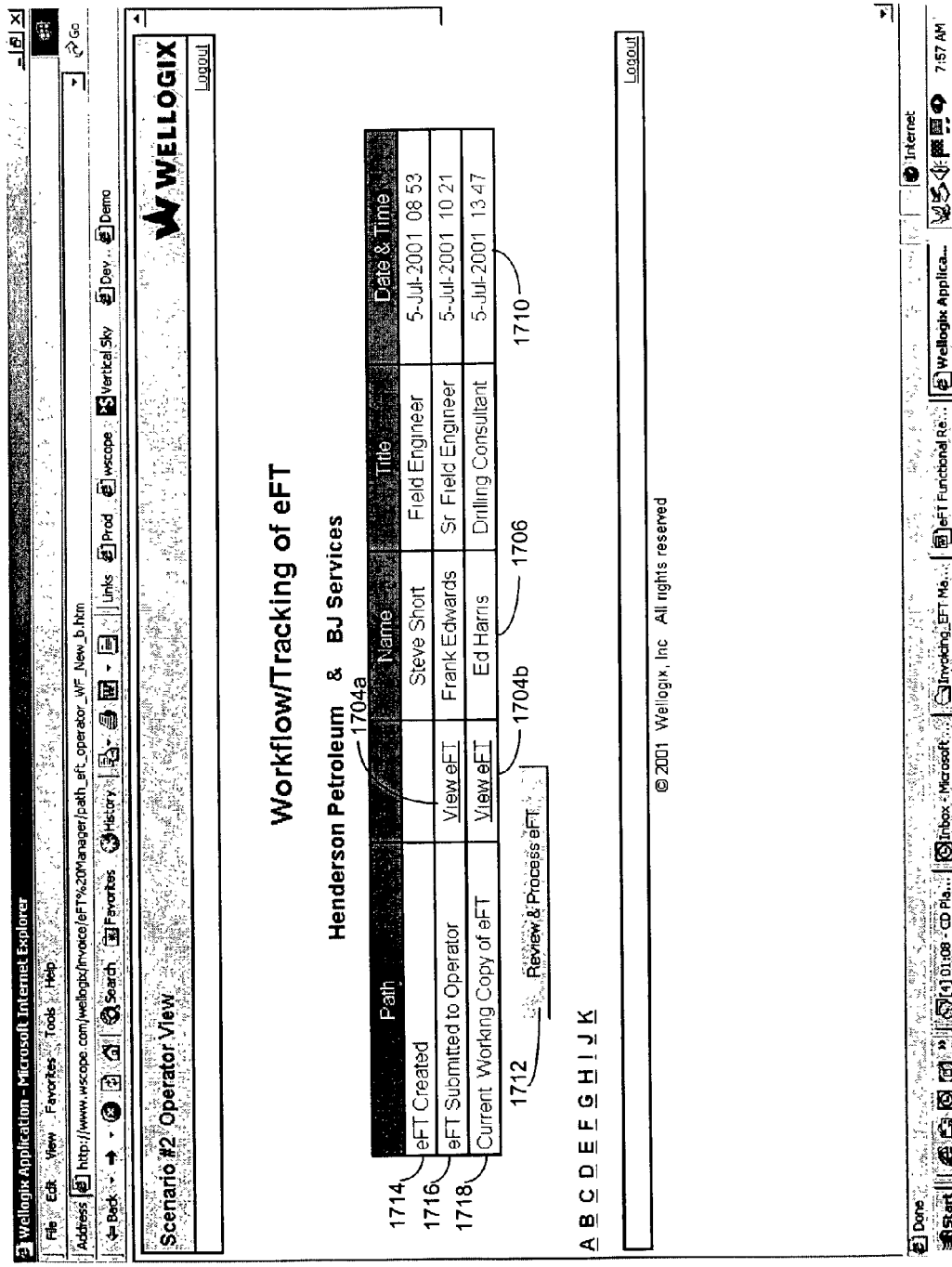

FIG. 17B depicts the next operation in the workflow process after the operator has chosen to review the submitted Field Document. In this embodiment, the current working copy of the Field Document 1718 is listed as the next entry in the table. Generally, this version of the Field Document is only visible to the operator. The view link 1704a may be configured to retrieve and present to the operator the original Field Document submitted by the service provider. Similarly, the view link 1704b may be configured to retrieve and present the current working version of the Field Document. Upon selection of the review and process function 1712 the process may be configured to then access the current version of the Field Document with any changes to the submitted version 1716.

Figure 17C:
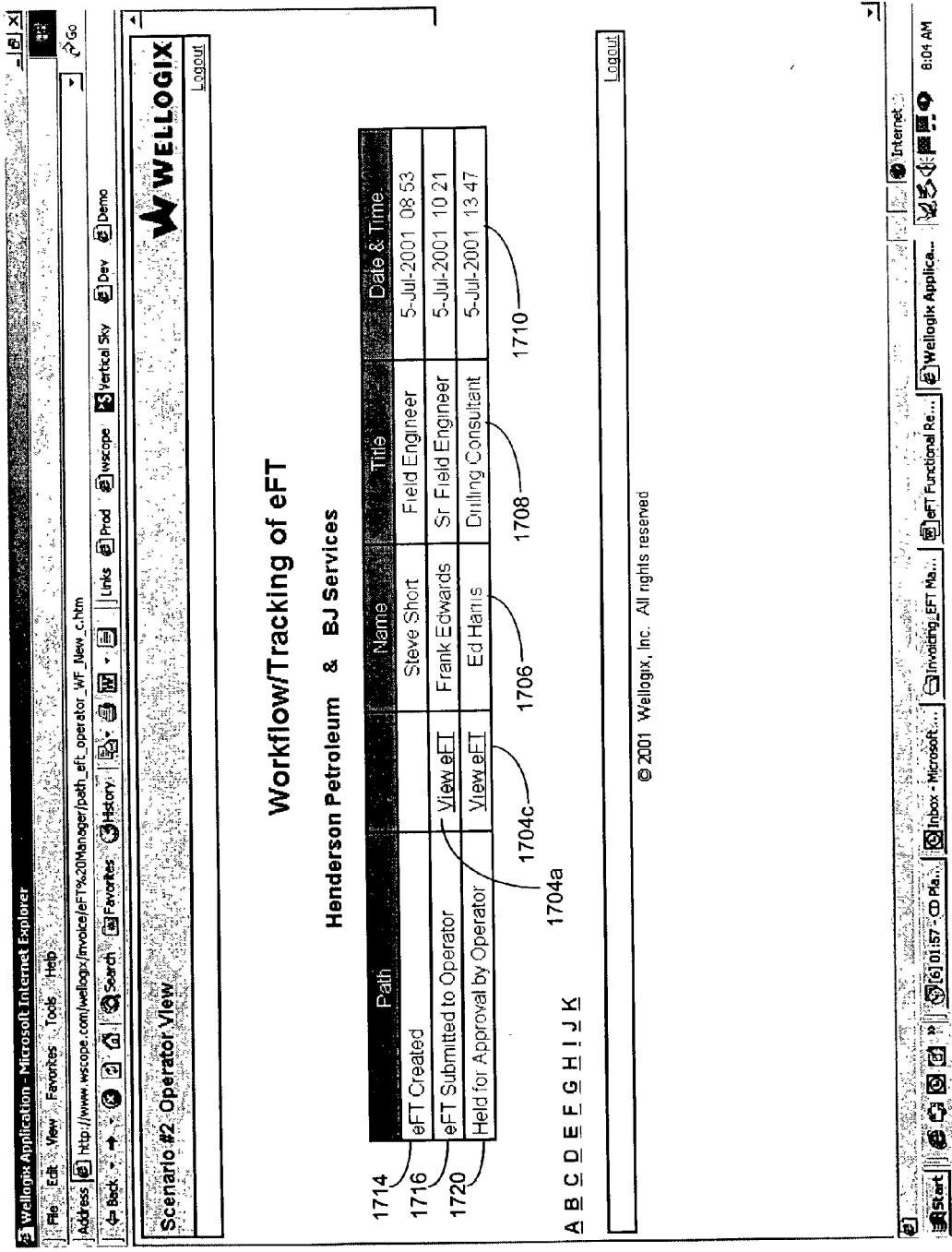

FIG. 17C shows a next possible operation in the workflow process wherein the operator has previously chosen to hold the Field Document for approval 1720. When the operator approves or holds a Field Document for approval, the process may be configured to remove the working copy of the Field Document 1718 (in FIG. 17B), changes the approval status to held for approval 1720, identify the name 1706 and title 1708 of the person who made the decision to hold the Field Document, and specify the date and time 1710 the decision to hold was entered or logged into a system implementing this embodiment. In this instance the review and process function 1712 (in FIG. 17B) generally is not accessible by an operator because the service provider needs to take the next operation in the Field Document process. The view link 1704a may be configured continue to access the original Field Document submitted by the service provider. Also, the view link 1704c may be configured to access the Field Document in which the operator changes, which resulted in the held for approval by Operator workflow condition, have been recorded.

Figure 17D:
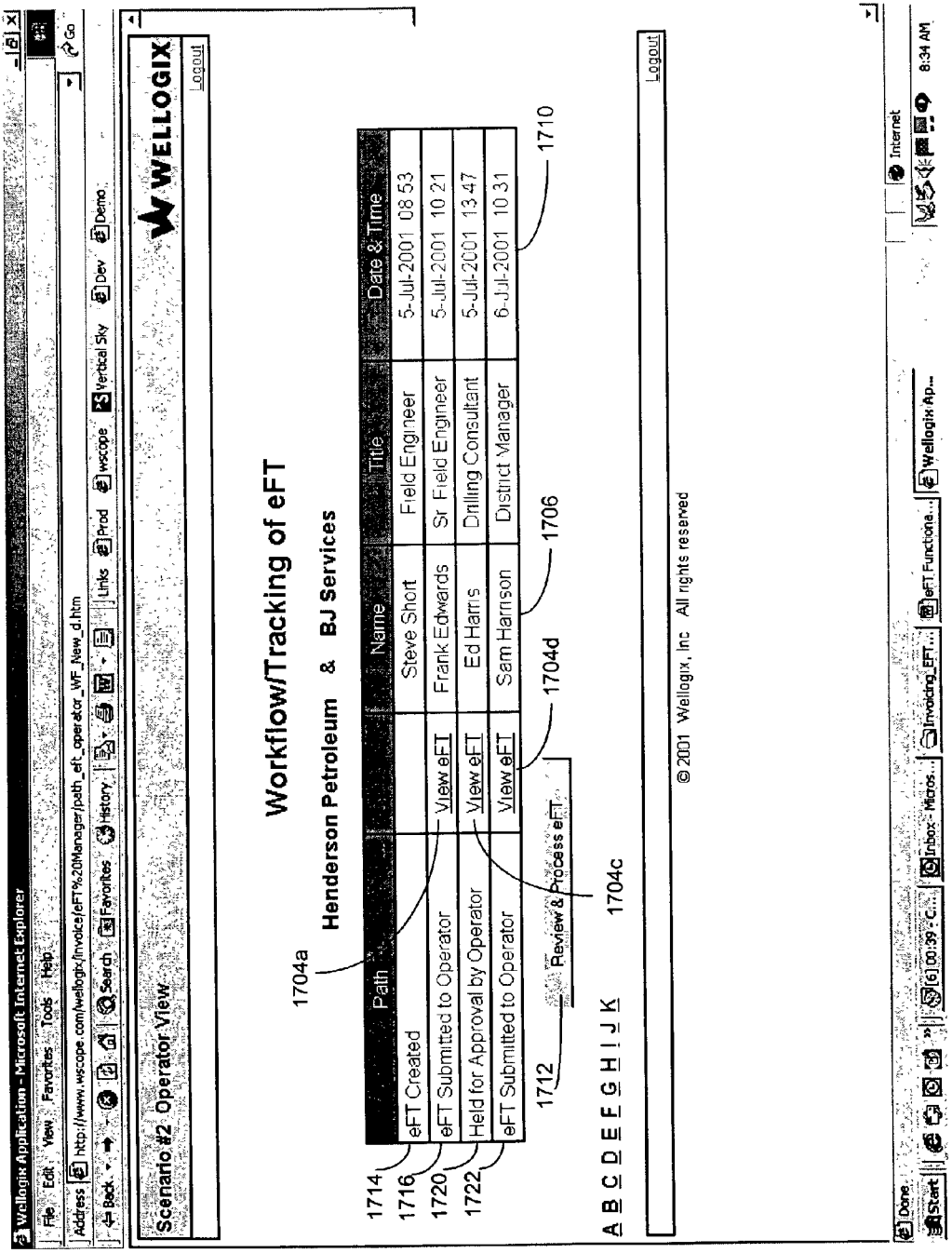

FIG. 17D shows a possible next operation in the workflow process. Once the operator has held the Field Document for approval, the service provider may resubmit 1722 the Field Document to the operator, perhaps with modifications to enhance the likelihood of approval. In this instance, the approval and hold options available to the operator may generally be the same as those described with reference to FIG. 17B. The operator may view and modify the resubmitted Field Document with the service provider's modifications, for example, by selecting the review and process function 1712, or by selecting the view link 1704d. Older versions of the Field Document may also be accessed by the selection of corresponding view links 1704a and 1704c, while information about previous reviewers 1706 and the dates and times 1710 of those reviews may also be provided.

Figure 17E:
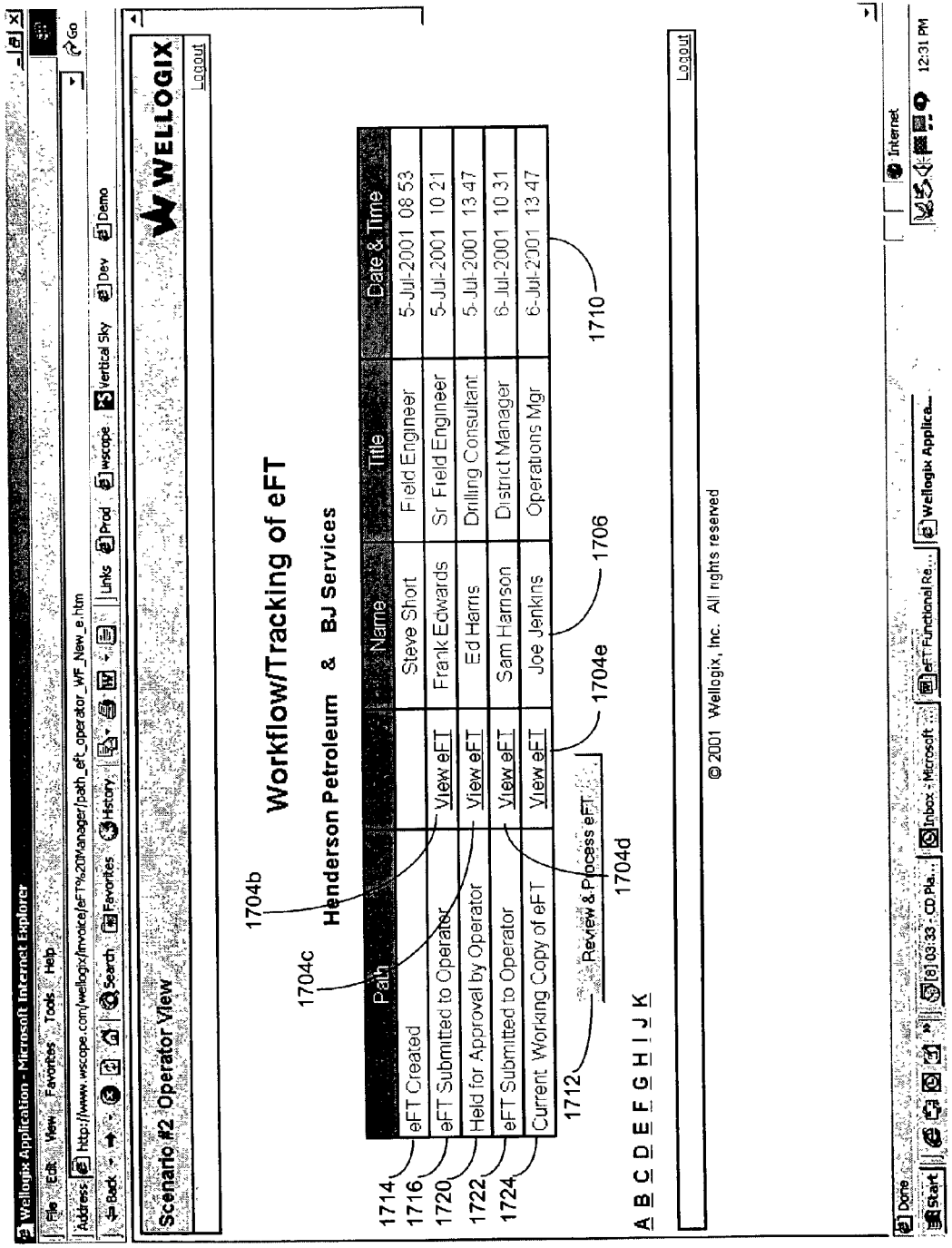

FIG. 17E shows a next possible operation in the workflow process, the operator's review of the resubmitted Field Document 1722. Preferably, the current working copy of the Field Document 1724 will only be visible to the operator. The corresponding name 1706 and date 1710 shown are presented as of the date and time of the last revision. The view link 1704b may be configured to take the operator to the original version of the Field Document submitted by the service provider. This version should be different from the second submitted Field Document 1722, which may be accessed through a separate view link 1704d. Selection of the view link 1704c similarly may be configured to provide access to the held version of the Field Document returned to the service provider. View link 1704e and the review and process function 1712 may each be configured to provide access to the current version of the Field Document as modified by the operator from the resubmitted Field Document 1722.

Figure 17F:
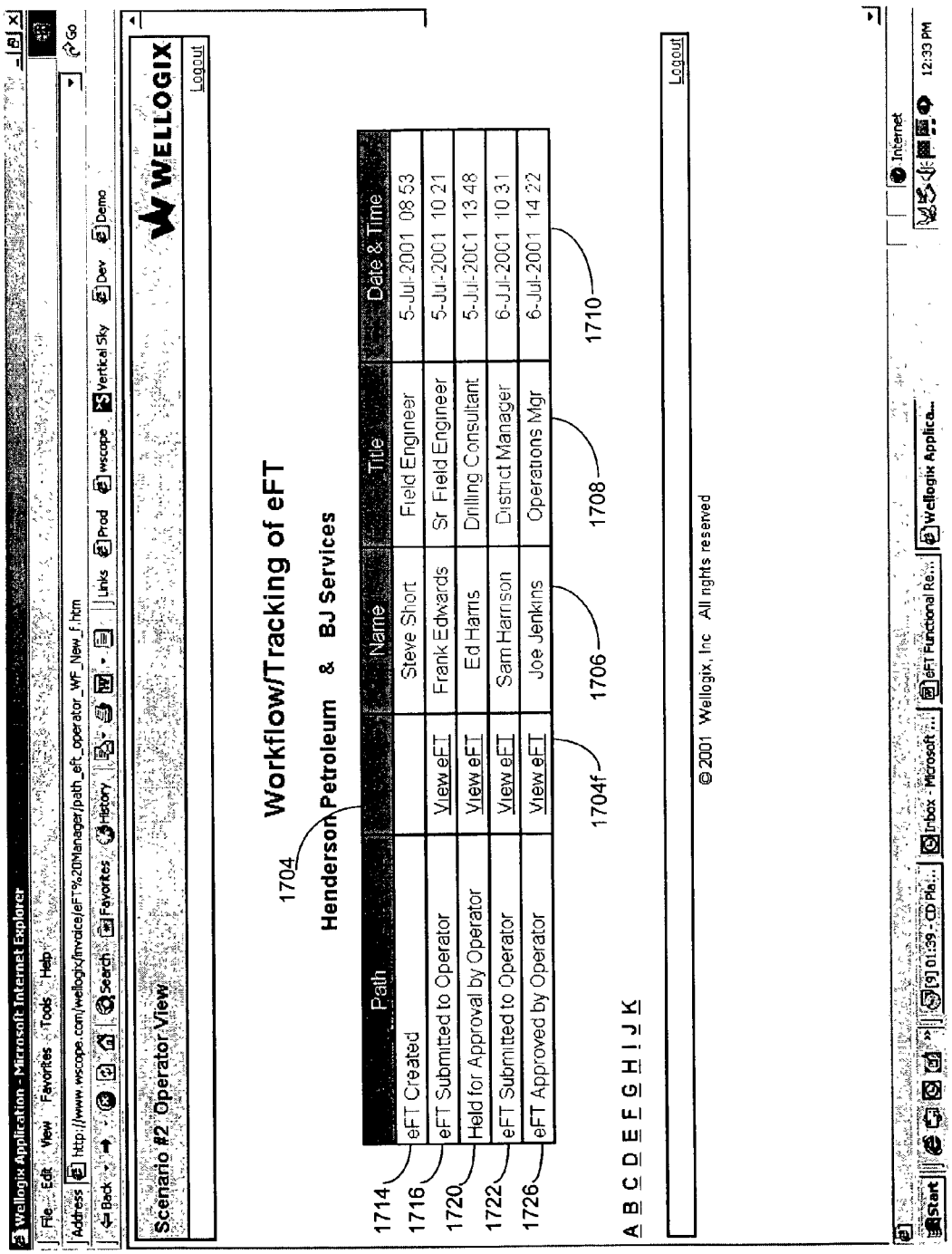

FIG. 17F shows the next operation in the workflow process, approval of the Field Document by the operator. Once the operator approves the Field Document, the working copy entry 1724 (in FIG. 17E) may be replaced by an approved entry 1726. The review and process function 1712 (in FIG. 17E) is not active because the next process operation should be undertaken by the service provider. The view link 1704f may be configured to provide access to the latest changes to the Field Document made by the operator. The other view links 1704 generally provide access to their respective Field Document versions, as previously described hereinabove.

Figure 17G:
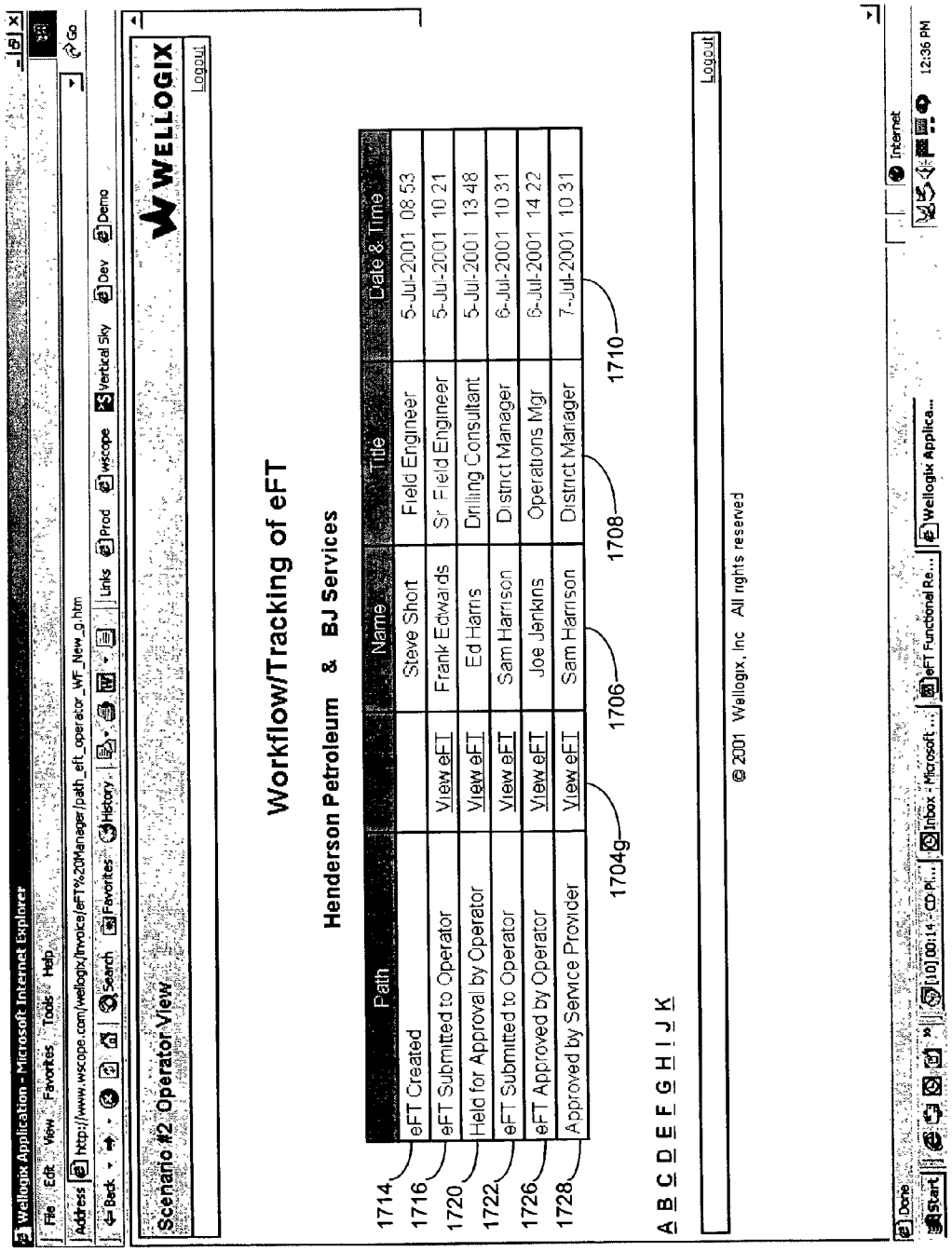

FIG. 17G depicts a possible next operation in the workflow process, approval of the Field Document by the service provider. The workflow history process documents the service provider's approval and enables an operator to access an approved by service provider Field Document entry 1728 through a related view link 1704g.

Figure 17H:
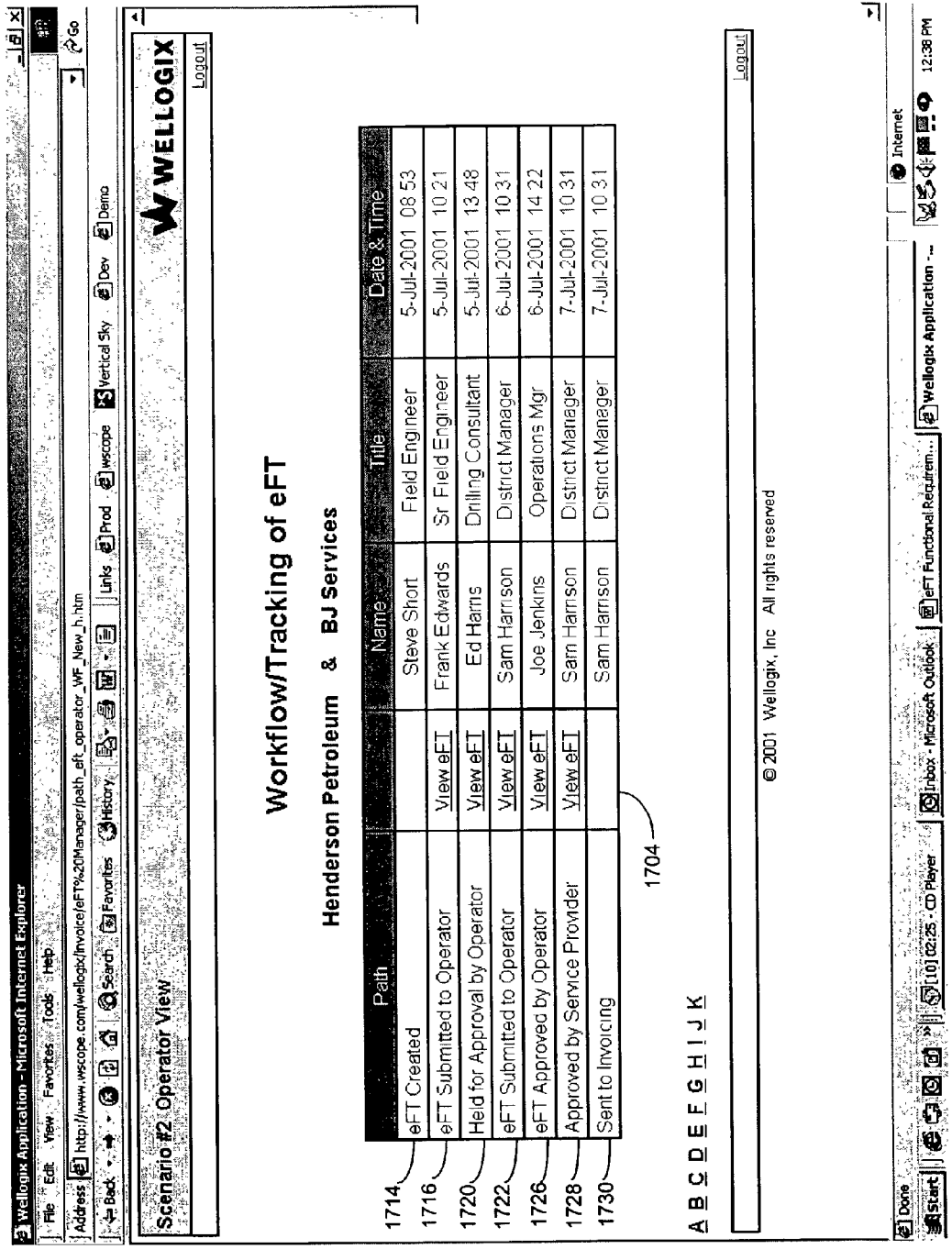

FIG. 17H shows another operation in a workflow history process for a particular Field Document. As shown, the template indicates, in a new entry, that the Field Document has been sent to invoicing 1730. It should be noted, that this same workflow tracking tool may also be used to track the operations in an invoicing process while providing the same features and functions. Further, it is to be appreciated that other, less and/or additional workflow actions may also be displayed by this and/or other embodiments of a workflow tracking tool.

Figure 18A:
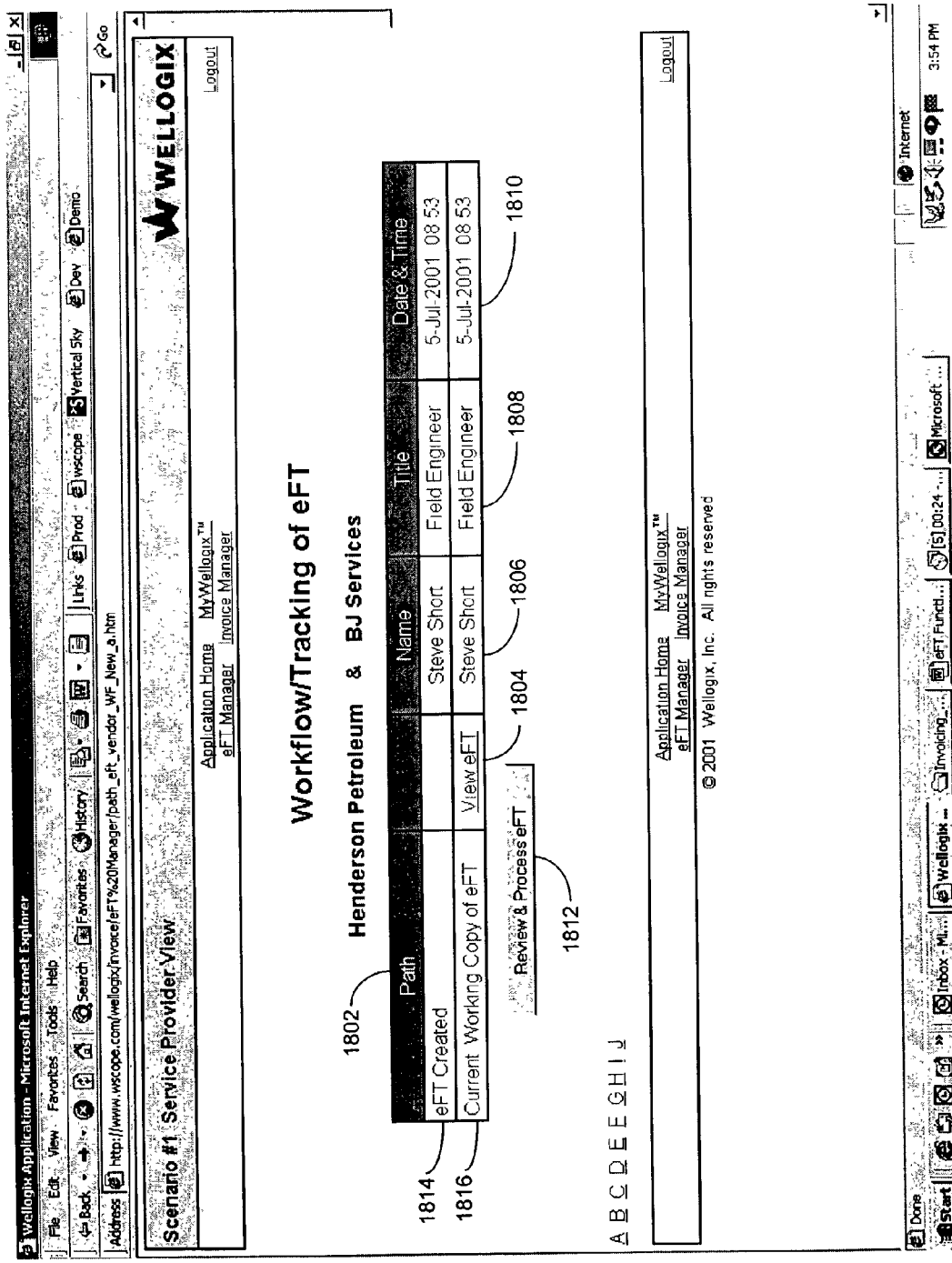

FIG. 18A depicts an initial workflow history user interface/template for managing a Field Document from the point of view of the service provider. As may be provided for an operator template, the workflow history may be represented via a table containing various columns, such as: a column 1802 indicating a path taken by a given Field Document; a view column 1804 providing link options by which a service provider may view a specific version of a Field Document; a column 1806 identifying persons who have taken some action with respect to the Field Document; a column 1808 indicating such person's titles; and a column 1810 indicating the date and time a particular action occurred. As shown, for this first template, the service provider may be advised, by corresponding entries in the table, that a Field Document has been created 1814, and that a current working copy of the Field Document 1816 is available for review. In this instance, if the service provider wishes to review and modify the Field Document, this may be accomplished by selection of either the related links in the "view" column 1804, or by selection of the "review and process" function 1812. However, this functionality may not always be provided, because a given row on the table may not include a "view" link or may include a link which only provides access to historical copies of the Field Document. Further, for this embodiment, the review and process function 1812 is generally configured to provide access to the current working version of the Field Document.

Figure 18B:
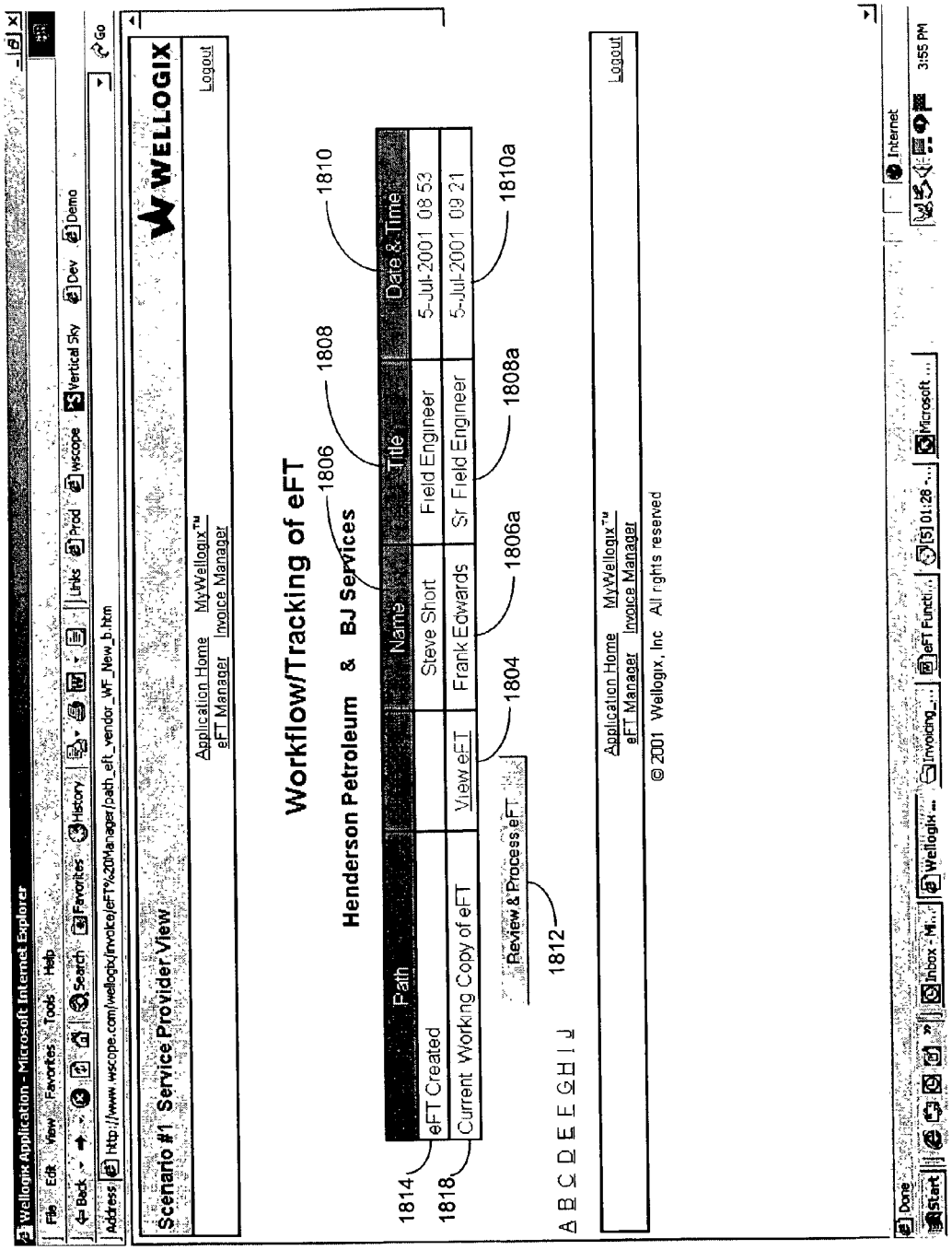
Figure 18C:
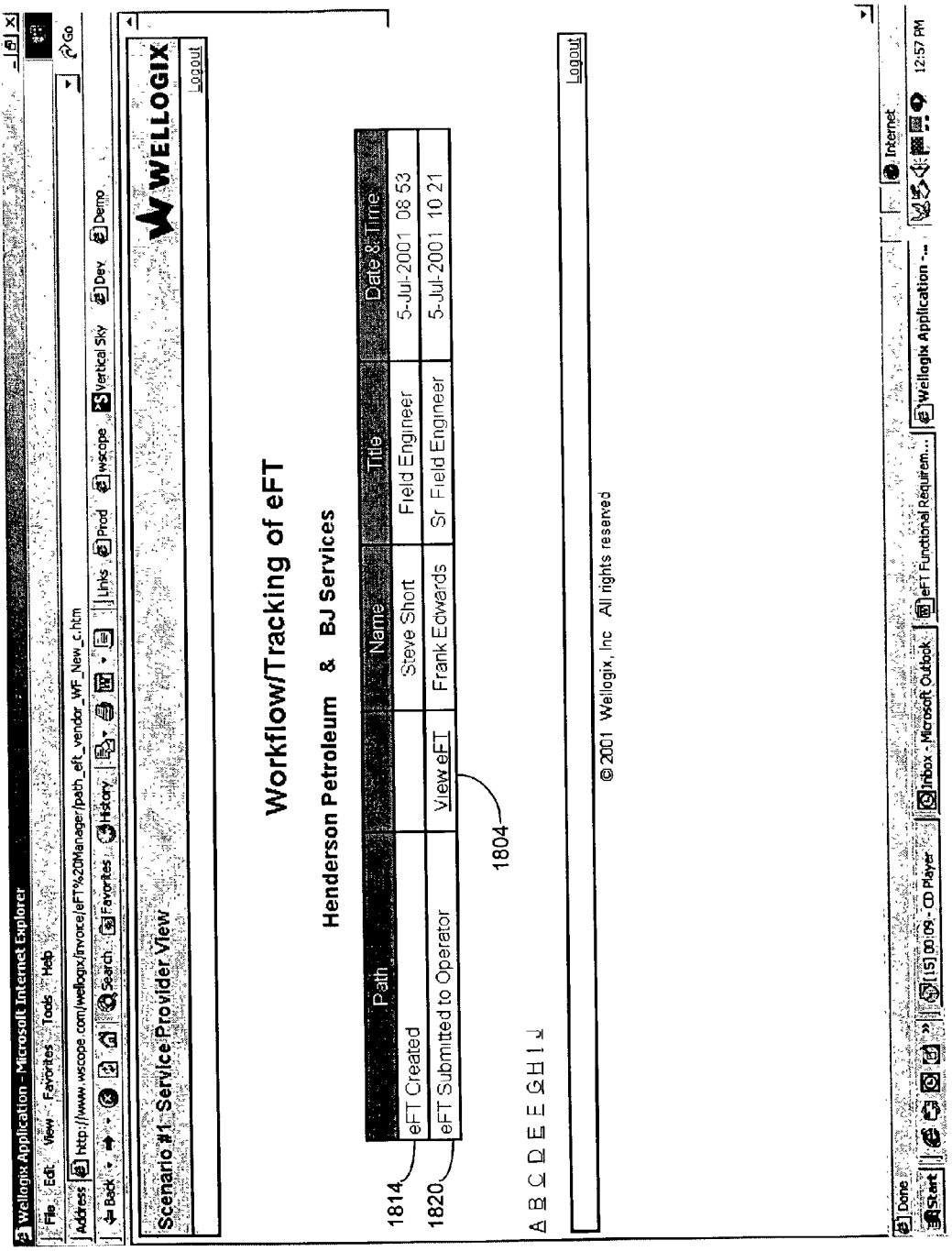
Figure 18D:
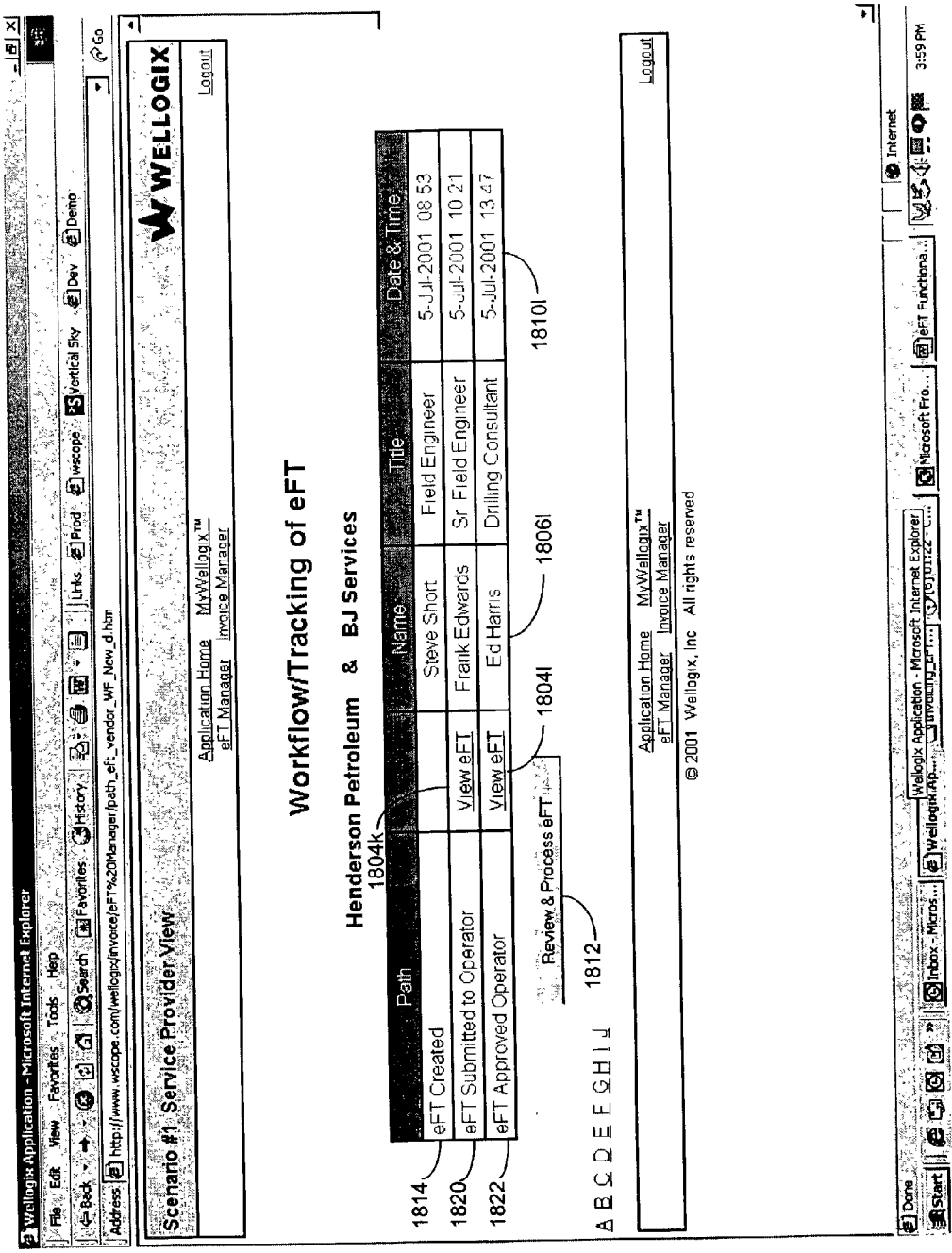
Figure 18E:
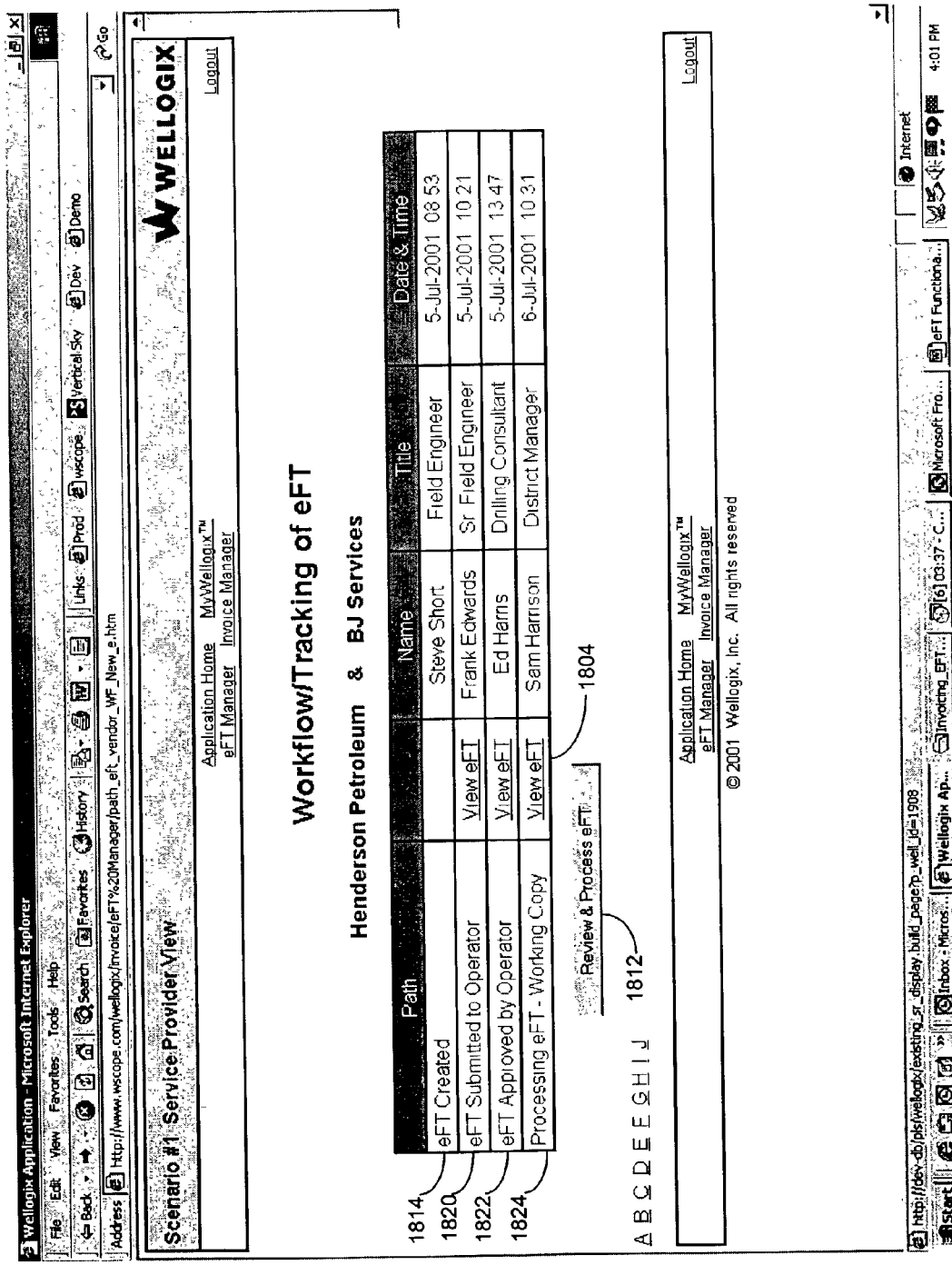
Figure 18F:
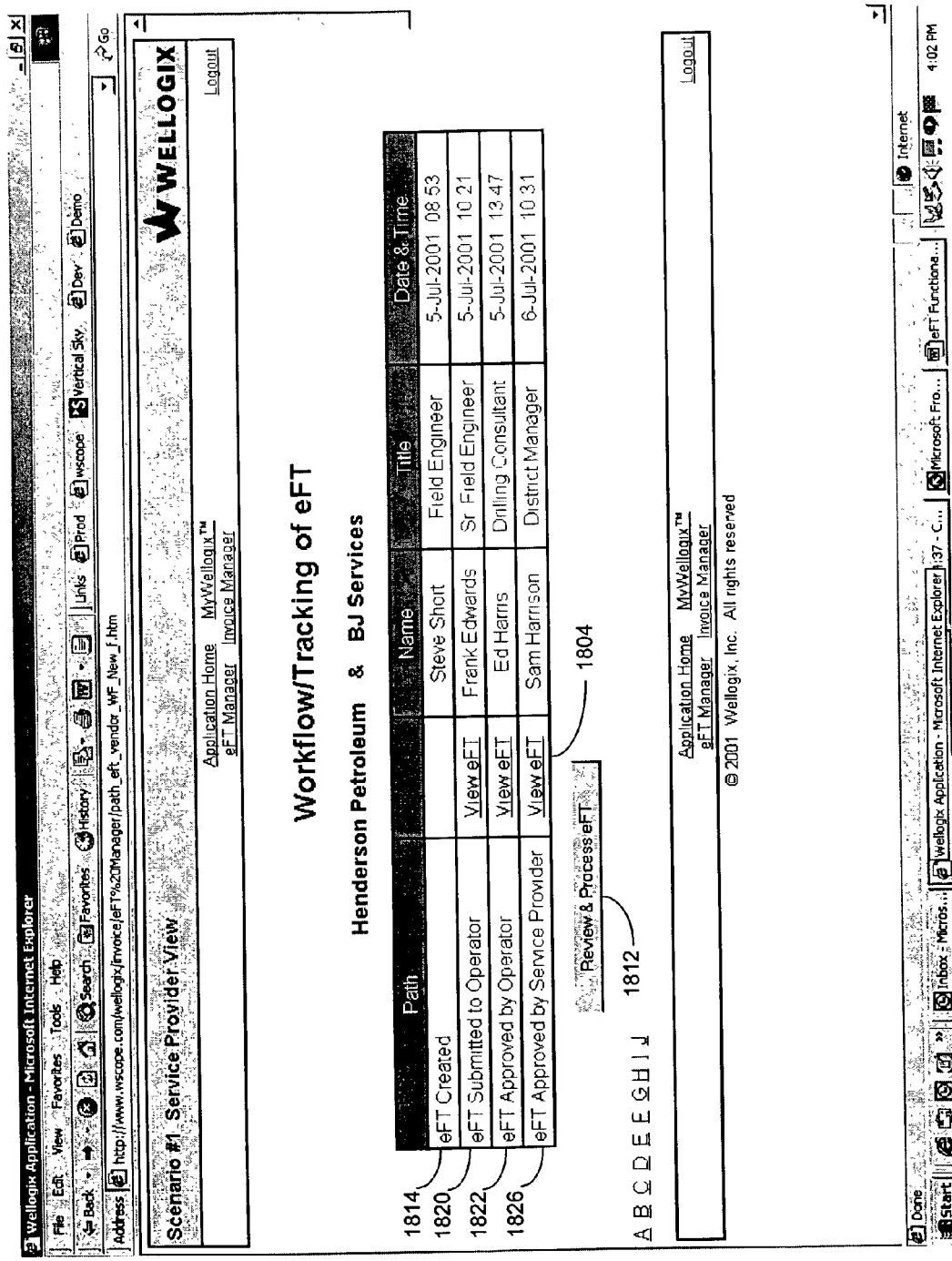
Figure 18G:
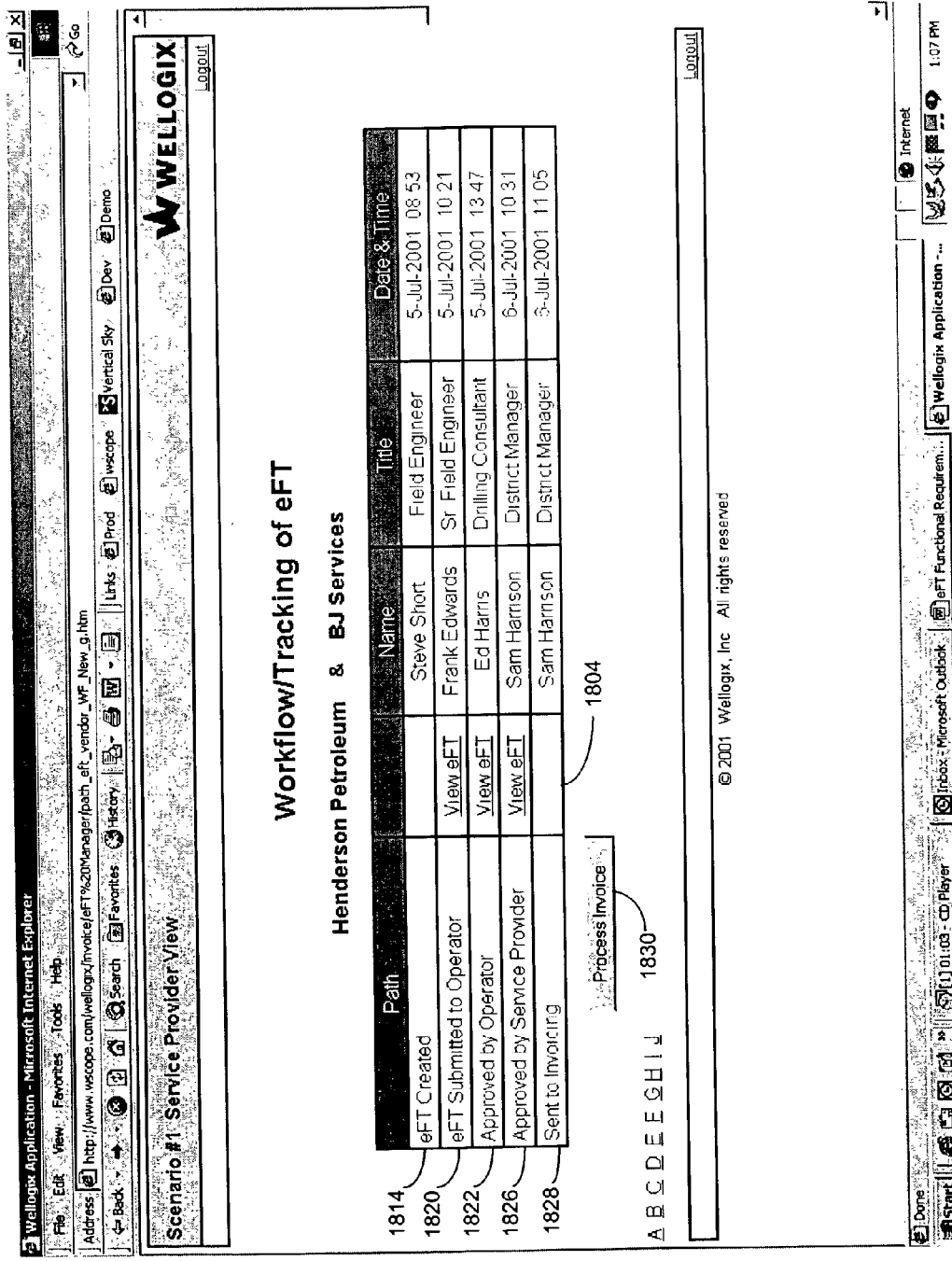

If any changes are made to the Field Document after it is first created, the current working copy entry may be updated to show who made the most recent changes, by name 1806a and title 1808a, and when the changes were made, by date and time 1808a, as shown in FIG. 18B. When the Field Document is submitted to the operator the working copy entry 1818 (as shown in FIG. 18B) is replaced by a submitted entry 1820 as shown in FIG. 18C and the associated personnel and date information is updated.

After the Field Document is submitted, desirably no changes can be made to it. The ability to view the Field Document by selection of view link 1804 is generally provided as a read only link and the review and process function 1812 (in FIG. 18B) is not active because the operator must perform the next operation in the process. Once the Field Document is approved by the operator, the workflow history may indicate such status in an entry 1822 and the service provider may be able to see who 18061 approved the Field Document and when 18101. The view link 1804k may be configured to access the originally prepared Field Document. Similarly, the view link 18041 may be configured to enable to provide the service provider with read only access to the approved Field Document. To make changes to the Field Document or process a final approval, the service provider may select the review and process function 1812. Further, if the service provider saves changes to the Field Document, a current working copy entry 1824 may be created in the workflow path (see FIG. 18E).

The service provider may give final approval of the Field Document or resubmit a modified Field Document to the operator. A Field Document with final service provider approval may be listed as an entry in the workflow path 1826 in FIG. 18F. The service provider may then transfer the Field Document to an invoicing function for further processing. In this event, the workflow history tool may be configured to record the transfer of the Field Document to invoicing also as an entry 1828 in the table (see FIG. 18G).

Field Document Management Tools

Various embodiments of the present invention may also include an offline manager that allows a user to work with a Field Document offline using, for example, an Offline Component. While in the field, a user can enter information into or make selections within the Offline Component, and once reconnected to the network, the information added or changes made to the Offline Component may be uploaded to the actual web site through a communications network.

One embodiment of a process for assigning, managing and tracking Field Documents, both online and offline as an Offline Component, is shown in FIG. 19. As shown, this process may be suitably implemented when a user accesses a Field Document Pricing Page (operation 1900). Once the page is accessed, the process, and/or a system implementing the process, may be configured to display the pricing page with an input alternative which enables a user to assign a Field Document either online or offline (operation 1902). A query may be communicated to the user as to whether the user desires to select online or offline processing (operation 1904). If the online option is selected, the process continues with querying whether a team member has been selected by the user to receive the Offline Component (operation 1906). If a team member has been selected, a notification may be communicated to the designated team member, for example via an e-mail, that the team member is now responsible for some further action with respect to the Field Document (operation 1908). The workflow history, if any, may then be suitably updated to indicate that the assignment (operation 1928) has been given to a team member. Further updates the offline manager module may also be provided, as necessary, to indicate an additional activity with respect to the Field Document (operation 1930).

If a team member is not selected, a query may be generated as to whether the user has indicated that the Field Document is to be submitted to a customer representative of the operator (operation 1910). If so, another query may be issued as to whether the Field Document is in fact online or is offline (operation 1912). If the Field Document is online, notification of submission of the Field Document for review and approval may be sent to the operator (operation 1932). If the Field Document is offline, a notification may be sent to the user that a Field Document cannot be submitted to the operator while the Field Document is offline (operation 1934). The display or other presentation medium may then be reset to the Field Document Pricing Page to allow the user to make any desired inputs (operation 1904). If there is no user input directing submission of the Field Document to the operator, the user may be suitably informed that a team member must be selected in order to proceed with assigning a Field Document (operation 1914). This notification may also include resetting the display to the Field Document Pricing Page in order to enable the user to make any desired inputs (operation 1904).

Returning to the query of whether online or offline action is requested by the user (operation 1904), in the instance where the user has indicated an offline transmittal of the Field Document, a query may be generated as to whether the user has indicated that the Field Document is to be submitted to a customer representative of the operator (operation 1916). If this selection is affirmative, a check may be performed to determine whether the Field Document is online (operation 1912). If the Field Document is online, notification of submission of the Field Document for review and approval may be sent to the operator (operation 1932). If the Field Document is offline, a notification may be sent to the user that a Field Document cannot be submitted to the operator while the Field Document is offline (operation 1934). Again, the display may then be reset to the Field Document Pricing Page in order to enable the user to make any desired inputs (operation 1904). If there are no user inputs directing submission of the Field Document to the operator, then a notification may be sent informing the user that a team member must be selected in order to proceed with assigning a Field Document (operation 1914). Again, the display may be reset to the display to the Field Document Pricing Page in order to enable the user to make any desired inputs (operation 1904).

If the Field Document is not to be presently submitted to the operator, another query may be issued as to whether a team member has been selected by the user to receive the Offline Component (operation 1918). If a team member has been selected, a query may be issued to determine whether the team member is new to the workflow process platform (operation 1920). If so, information about team member may be obtained and the offline manager updated to include the additional information (operation 1922). After the team member information has been updated, or if the team member is not new, an Offline Component holding the Field Document may be created and the Offline Component may be synchronized to the workflow platform (operation 1924). The designated Offline Component may be communicated to the team member via a communications network. At this point in the process, the team member is now responsible for some further action with respect to the Field Document (operation 1926). The process then provides for the updating of the workflow history to indicate the assignment (operation 1928) and further updates of the offline manager module to indicate an additional activity with respect to the Field Document (operation 1930).

On-line and Off-line Field Document Management using Offline Components

One embodiment of a user interface, which may be utilized in conjunction with the previously described above process is a Field Document Pricing Page and which includes the necessary functionality to enable a user to assign a Field Document online or offline, is shown in FIG. 20. As shown, generally an user can choose whether the Field Document is to be sent offline or online using radio buttons 2002 and 2004. Further, this particular embodiment enables the user to access an existing database of customer representatives using a drop down menu 2006. Similarly, the user may access the existing database of team members by accessing a second drop down menu 2008. The pricing page shown in FIG. 20 may also be equipped with button 2010 which enables the user to submit the Field Document to the selected operator and a second button 2012 which enables the user to send the Field Document to the selected team member.

Once assigned by the offline manager, Offline Components may further be canceled before they are resynchronized with the system. FIG. 21 provides one embodiment of a flow diagram depicting an exemplary process for canceling Offline Components. When a user first accesses the offline manager (operation 2100), a user device, for example, a lap top computer or a personal data assistant, which is configured to implement the process, suitably displays a list of Offline Components previously assigned and not yet synchronized with the system (operation 2102). A user may select to cancel a particular Offline Component (operation 2104). In this event, the device may query as to whether the user has entered a reason for canceling the Offline Component (operation 2106). If the user has not indicated a reason for cancellation and selects the save function (operation 2108), the device will then notify the user that a reason for cancellation must be entered before the Offline Component will in fact be cancelled (operation 2112). Likewise, if the user has not indicated a reason for cancellation and selects the cancel Offline Component function (operation 2110), he device will notify the user that a reason for cancellation must be entered before the Offline Component will in fact be cancelled (operation 2112).

The device or system implementing this process may further provide a selection of reasons for cancellation of an Offline Component. If the user did provide a reason for cancellation (in operation 2106), the device may further inquire as to whether any of the choices for cancellation provided by the device were used (operation 2114). If not, the user may be requested and/or required, in certain embodiments, to input a reason for cancellation in a field provided (operation 2116). Once a reason for cancellation has been secured, the user may then select the cancel Offline Component function (operation 2118). The device may be further configured to interject an interrogatory to confirm that the user indeed wants to cancel the Offline Component (operation 2120). If the user confirms cancellation (operation 2122), the device cancels the Offline Component and restores as active on the device and/or the system the Field Document version before the Offline Component was assigned (operation 2124). It is to be appreciated that when a user device does not have access to a system, the foregoing actions may be accomplished remotely and then updates provided, as necessary to the system. Similarly, when a user device is connected via a communications network or directly to a system, the foregoing actions may be suitably accomplished on either the user device and/or the system, with the necessary data and information passing therebetween to implement the desired changes.

Additional embodiments of an offline manager are shown in FIGS. 22A–22C. More specifically, as shown in FIG. 22A, for at least one embodiment, an offline manager may be configured to provide at least one of four major functions: a listing of all Offline Components that have been checked out, a listing of who checked out a particular Offline Component along with a date and time stamp, a listing of the type of Offline Component, and the ability to cancel an Offline Component. This embodiment (and other embodiments) of the offline manage may also include links to other pages provided by the various embodiments of the present invention discussed herein and/or to other pages. For example, the embodiment may include a link 2202 to an eFT Manager, a link 2204 to the service request or work order submitted by the operator, and a link 2206 to the eFT or Response Package.

When utilizing the offline manager feature, the current functionality of the workflow history may also be changed so that each time a new user modifies a current working copy of a Field Document, a new version of the Field Document may be created and listed in the workflow history. One embodiment of a system implementing such functionality is depicted by the user interface shown in FIG. 23. As shown a "Previous Working copy of the eFT" 2302 may be created every time a user sends a Field Document to a different user either online or offline via an Offline Component. If an Offline Component is cancelled, such cancellation may also be shown in the workflow history. The Offline Component cancelled link 2304 may be configured to present to the user a screen display or user interface on which comments may be entered and/or presented as to why the Offline Component was cancelled. Such screen may also shows who cancelled the Offline Component and when the Offline Component was cancelled by providing a date and time stamp. If the Offline Component is offline, a View eFT link 2306 may be provided which enables the user to access generally a read only version of the Field Document before it was provided offline. This link 2306 may be further configured to present the given Field Document to the user and also to present a pop-up message stating something to the effect that "The Field Document is read only because it is currently offline."

Another embodiment of system and/or process for processing Field Documents which operates separately or in conformance with the other embodiments of the present invention, may include a modularization feature whereby multiple pages may be provided within a modular Field Document. It is to be appreciated that a modularization function consistent with the present invention preferably enables a service provider to select the particular pages desired, and further to modify each page, as desired. As such, generally, a single long form containing multiple parts or pages that are not used for a particular embodiment may be avoided. Further, custom fields may also be created and/or designated by the service provider to appear on each modular page as desired, for example, tracking numbers and other similar data may be included on custom forms, while not being included on other, non-custom forms. Additionally, the modularization processes of the present invention generally make it more easy to add or subtract pages to a Field Document and to create Field Documents which are tailored to individual operators, as desired by a service provider.

In another embodiment of the present invention, which may be utilized in the oil and gas industry and/or other industries, a modularization feature may be utilized in which a user is encouraged and/or required to utilize a Job Time & Activity Detail page, for example, one as shown in FIG. 24A. The embodiment may also be configured to require a user to utilize a Field Document Pricing Page, such as one shown in FIG. 25A. Similarly, a user may be encouraged or required to utilize a Product List page, such as one shown in FIG. 26A. In other embodiments of the invention, additional optional pages may also be utilized, required, added to or subtracted from a modular Field Document as desired. Further, when utilizing these and other customization features, custom fields for the operator are generally located on the Pricing page while and custom fields for the service provider are generally located on the Job Time & Activity Detail page.

When viewing any one page of a modular Field Document, it is to be further appreciated that links to the other pages in the modular Field Document may be provided. Further, the status of each page may also be displayed next to each link. A page may also have a status associated with it, such as Final or Draft. However, generally, before a modular Field Document may be submitted to an operator, all of the pages in the Field Document should be saved and their status designated as Final. Modular Field Documents may also be configured to work with an Offline Manager in order to enable such modular Field Documents to be sent to other team members either offline or online.

User Interface for Job Time and Activity Monitoring

In another embodiment of the present invention, a user interface may be provided by a system via which a first user may enter and other users may verify job time and job activity details. As shown in FIG. 24A, a Job Time & Activity Detail page 2400 may be provided. This page may be designated, as desired, as the main modular Field Document page. When this page (or any other page) is designated as the main modular page, whenever a user clicks on a link to a particular Field Document, the system present page 2400 to the user instead of another page, such as, the Field Document Pricing Page. As depicted in FIGS. 24A to 24C, the Job Time & Activity page 2400 may be configured to include a header table 2402, a work summary table 2404, a work detail table 2406, and an employee time table 2408. Other fields may also be provided as specific implementations require.

Additionally, various fields may be made available for customization on this page 2400. For example, custom fields may be provided in the header table 2402. Currently, six custom fields are provided and include the following: company order no. 2410, pick up # 2412, trip miles 2414, work done in state of 2416, and type of work 2418. These and/or other custom fields may be configured to utilize text entry boxes, drop down menus, or other data entry techniques (such as voice memos).

Similarly, customizable options may be provided for the work summary table 2404. For example, it may be possible to rename the work summary 2404, the 24 hour summary 2420, and the 24 hour forecast 2422 fields, or to not include such fields at all, while including additional or other fields. The user may also be provided with the capability of hiding, minimizing, maximizing or otherwise displaying the work summary table 2404.

Referring now to FIG. 24B, activity category 2424 and trouble type 2426 drop down menus may be also be provided and customizable within the work detail table 2406. In addition, the user may choose to display or hide the employee time table 2408. Further, as shown on FIG. 24C, links 2428, 2430, 2432, 2434 and 2436 may be included on the Job Time & Activity page 2400 as desired. The links depicted are: application home 2428, my workflow 2430, eFT manager 2432, eFT workflow 2434 eFT summary 2436, and logout 2438. Additional links to the eFT pricing page 2440 and eFT product list 2442 are shown on FIG. 24C along with their respective statuses (i.e. draft or final). Thus, it is to be appreciated that the job time and activity detail page may be customized as particular implementations of the present invention specify.

User Interface for Field Document Pricing

Referring now to FIG. 25A, one embodiment of a Field Document Pricing Page 2500 is shown. This embodiment may be provided for an implementation of the present invention similar to that which was described in reference to FIGS. 8A–C. Further, FIGS. 25B and 25C provide depictions of a Field Document Pricing Page 2502 which may be utilized, for example, as part of a modular Field Document. As shown in FIGS. 25A and 25B, a table 2504 containing an arrive location, job start, and job completion fields, as shown in FIG. 25A, may be replaced or augmented, for example, with an additional pages table 2506 containing a link 2508 to a Job Time & Activity page and or a second link 2510 to the a product list page.

Various custom fields may also be made available to the operator on the Field Document Pricing Page. For example and as shown in FIG. 25B, exemplary custom fields may be located on a header table 2512, and may be described as follows: project mgt. system number 2514, work order number 2516, cost center 2518, pay key code 2510, API number 2522 and field supervisor name 2524. Similar to the Job Time & Activity page, links to other locations may be provided including links to an application home 2526, my workflow 2528, eFT manager 2530, eFT workflow 2532, eFT summary 2534, and logout 2535.

Further, as shown in FIG. 25C, the bottom of the Field Document Pricing Page of the modular Field Document may also be modified to include radio buttons which enable a user to select, for example, whether to assign the modular Field Document online 2536, or to send the Field Document offline 2538, e.g., via an Offline Component. Additionally, the Field Document Pricing Page may include a button 2540 that enables a user to send the modular Field Document offline or online to a selected team member and a button 2542 that enables the user to submit the modular Field Document online to a customer representative of the operator.

User Interface for Product Listing

FIGS. 26A and 26B depict another embodiment of a user interface for the present invention in which a Field Document Product List page 2600 is included in a modular Field Document. As with other pages previously described hereinabove or to be described herein below, which may be included in a given modular Field Document page, a link to the Job Time & Activity page 2602 and a link to the Field Document Pricing Page 2604 may be provided and/or displayed along with their respective statuses. In addition, and similar to the before mentioned Job Time & Activity and the Field Document Pricing Pages, links may also be provided to the following locations: application home 2606, my workflow 2608, eFT manager 2610, eFT workflow 2612, eFT summary 2614, and logout 2616. The service provider name 2618 may also be displayed on the product list page 2600. The date shown in the update field 2620 may also be the same date entered in, for example, a pricing current as field on a Field Document Pricing Page. The eFT number 2622 shown may also be provided as a system generated eFT ID. As further shown in FIG. 26A, some fields may also be pre-populated from the Field Document Pricing Page and/or other pages or information, for example, the operator name 2624, well name 2626, and field name 2628 may be pre-populated.

Referring now to FIG. 26B, the product list page may be configured such that the user can check radio boxes 2630 next to the items in the product list to specify what items were used on a job site. The user may also choose check a pre-populate radio button 2632 in order to have the checked items pre-populated onto the Field Document Pricing Page. It is to be appreciated that pre-populating the Field Document Pricing Page with frequently used items reduces the need to duplicate information across entries as new Field Documents are created. Further, this function enables users to only enter quantities used and other task specific information while not having to repeatedly reenter commonly utilized categories on the Field Document Pricing Page and/or other pages.

Customization Manager

In another embodiment of the present invention, a customization manager may be provided. The customization manager enables a user to customize various aspects of systems, user interfaces, and/or process implementing the present invention. For example, the customization manager may provide for customization of the Job Time & Activity page, the price list page, and the product list page within a modular Field Document. Similarly, custom fields, which may also require custom processing, may also be provided on work orders and invoices.

Figure 27A:
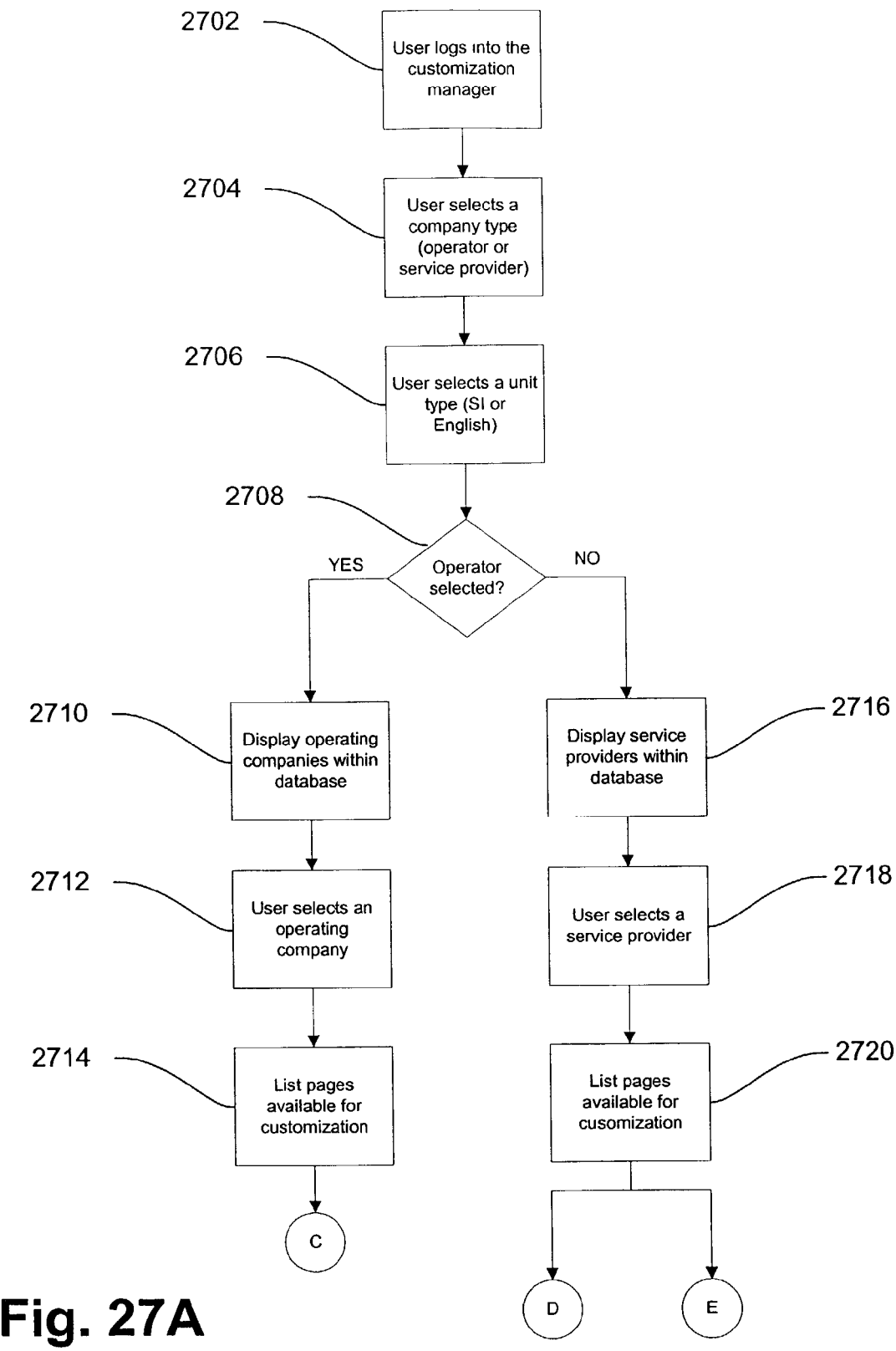
Figure 27B:
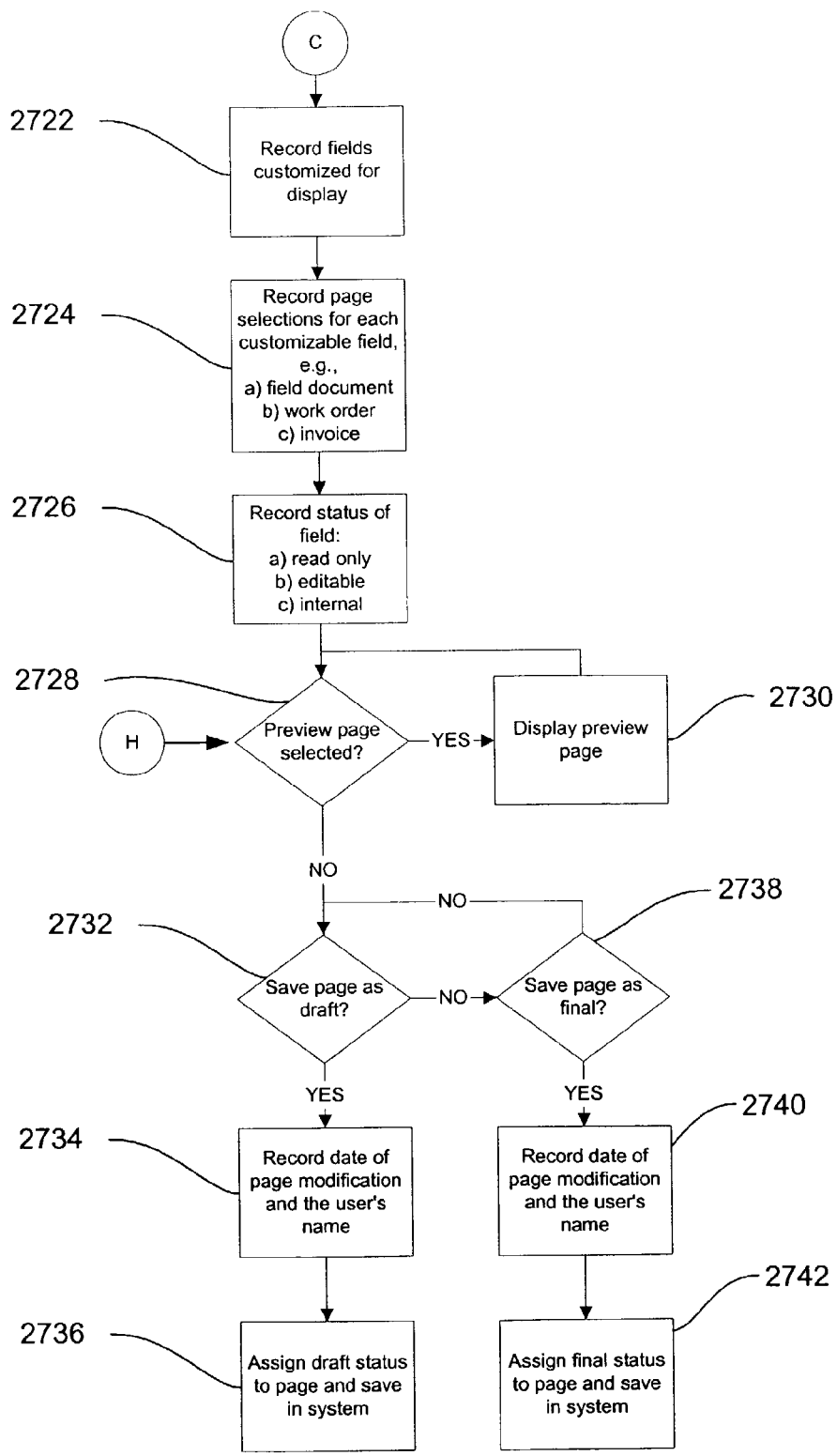

One embodiment of a process illustrating how the customization manager feature may be utilized is provided with reference to the flow charts shown in FIGS. 27A–F. Although not necessary, it may be desirable to limit access to the customization manager in order to prevent the creation of duplicate custom fields. Limiting access the customization manager may be achieved by utilizing a login routine, for example, one requiring a username and password. Referring now to FIG. 27A, this process begins when a user first logs into the customization manager (operation 2702). Once logged into the customization manager, which may be suitably provided by a system or device configured commonly via software or via hardcoding to provide such features, the user may select a company type (operation 2704) and a unit type (operation 2706). Examples of company types are operator and service provider, and examples of unit type are SI and English. In this embodiment, the system then determines whether an operator or service provider has been selected as the company type (operation 2708).

If the system determines that an operator has been selected (operation 2708), the system displays the list of operating company names within a database (operation 2710). The user may then select a company name (operation 2712). The system then refreshes the page to display a list of pages available for customization (operation 2714) for the particular company selected. The system may also be configured to then record the user's customizations to various fields for display (operation 2722, FIG. 27B) and record the user's selections of pages where the customized fields will be displayed (operation 2724). In one embodiment of the present invention, the system may provide a user with a choice of displaying customized fields on the work order page, the Field Document, and/or the invoice page. In other embodiments, other customizable pages may be provided.

Once the user has completed any customizations to a selected page, the system determines if the user wishes to preview a particular page (operation 2728). If so, the system displays the particular page (operation 2730). If not, (the system determines if the user has requested to save the customizations as a draft version (operation 2732) and, if so, the system records the date of modification and the user's name (operation 2734). The system may then assign the customized page a status of "draft" and save the customized page in a database accessible by the system (operation 2736).

However, if the system determines that the user did not request to save a draft version of the page (operation 2732), the system determines if the user requested to save a final version of the page (operation 2738). If so, the system records the date of modification and the user's name (operation 2740), assigns the customized page a status of "final" and saves the customized page in a database accessible by the system (operation 2742).

Referring back to operation 2708 in FIG. 27A, if the system determines that an operator was not selected (i.e. a service provider was selected), the system displays the list of service provider company names obtained from a database accessible by the system (operation 2716). Upon the user selecting a company name (operation 2718), the system refreshes the page to display a list of pages available for customization (operation 2720) for the selected company. The system then displays the page chosen by the user for customization. In one embodiment of the present invention, the user may choose from among four pages for customization. The available customizable pages for a service provider may be the product/price, the Job Time & Activity page, the custom invoice setup page, and a rig report. However, in other embodiments additional and/or other pages may be available for modification, as particular needs require.

Figure 27C:
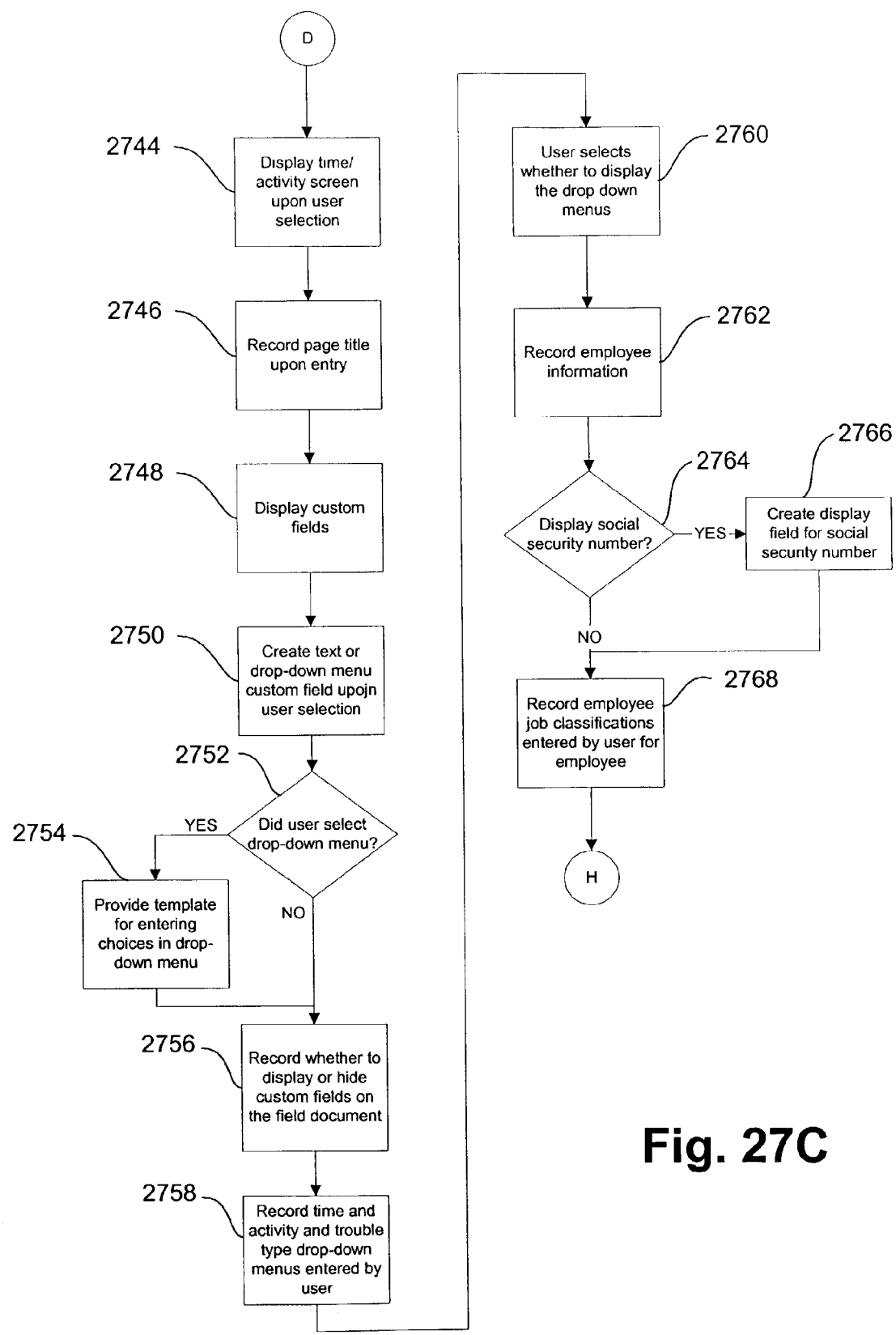
Figure 27D:
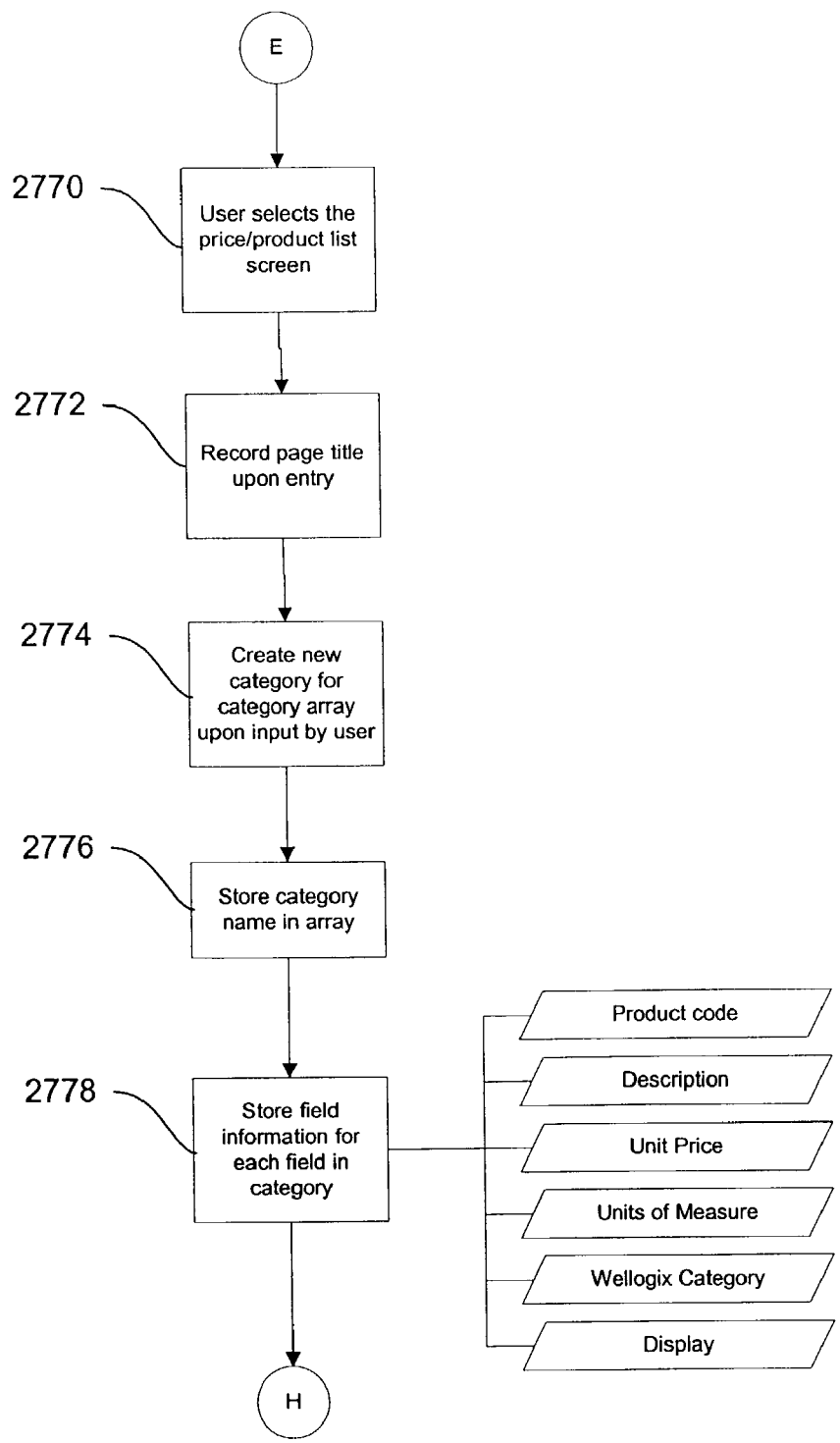

Referring now to FIG. 27C, the system may display the Job Time & Activity customization page if the operator so requests (operation 2744). Upon entry by the user, the system may then record the page title (operation 2746) and any user's selections as to whether various custom fields will be displayed (operation 2748). More specifically, the system may be configured to record text entered in the custom field by the user, text/entries selected via a drop down menu in a custom field and/or entries otherwise provided by the user (operation 2750). The system then determines whether the user has selected to use drop down menus in the custom fields (operation 2752). If the system determines that the user has selected to use drop down menus (operation 2752), a template may be provided for entering choices in the drop down menu (operation 2754).

Next, the system records the user's choices whether to display or hide custom fields on a Field Document (operation 2756). The system then records the time and activity and trouble type drop down menus entered by the user (operation 2758). The user then selects whether to display the drop down menus (operation 2760).

The system then records the employee information entered by the user (operation 2762). The system determines whether the user desires to display the employees' social security numbers (operation 2764). If so, the system creates a display field for the social security numbers (operation 2766).

Next, the system records the employee job classifications entered by the user (operation 2768). The system then proceeds with operations 2728–2742, as discussed previously hereinabove.

Referring again to operation 2720, on FIG. 27A, as mentioned above the service provider may choose between various pages to customize. When the service provider chooses to customize the product/price list screen for a service provider the process flow continues in FIG. 27D with operation 2770. Upon entry by the user, the system will record the page title (operation 2772). The system then creates a new category for a category array upon input by the user (operation 2774). A category name is then stored in the array (operation 2776) and field information for each field in a category (i.e. product code, description, unit price, units of measure, and display) is recorded in the array (operation 2778). Essentially, the array provides descriptors of characteristics for a given good or service. Once these descriptors have been entered, the system then proceeds with operations 2728–2742, as discussed previously hereinabove.

One embodiment of a user interface by which a system or device, providing the before mentioned customization features, may be accessed and/or utilized for at least one embodiment of the present invention is illustrated in FIGS. 28A to 28C. As shown in FIG. 28A, the before mentioned customization manager features may be accessed via a system providing web pages. It is to be appreciated, that such features may also be accessed in non-Web browser configured applications, such as an application providing a JavaScript or other customized applications. As shown for this particular embodiment, the customization manager enables a user to specify, for example, via a drop down menu, a unit type (e.g. SI or English) 2802, a company name 2804, and a company type 2806 (e.g. operator or service provider). When the user selects an operating company or service provider company from the drop down menu, a system or device implementing this embodiment of a customization manager then lists those pages, if any, which are available for customization and the status of each page. One example, of such a listing is provided in the text box 2808 shown in FIG. 28B. As mentioned previously, this page may be configured to present status information for any and/or all customizable pages, if any, in a status box 2810. For example, when the initial 30 customization is started for a company, the status box 2810 may be instructed to display ". . . " indicating that no customizations have been created for the company. The status may also indicate draft, final or other conditions. Also, operators and service providers may have different pages available for customization.

In one embodiment of the invention, the operator may create, edit and display custom fields on the Work Order page, Field Document Pricing Page, and the Invoice page. FIG. 28C depicts one embodiment of a user interface which enables a user to select various custom fields to be displayed for an operator. The screen/user interface may be pre-populated with the operator name 2812 from the operator name selected in the customization manager. The screen shown in FIG. 28C may also display other information such as the status of the page 2814 (i.e. final or draft), when it was last modified 2816, and who last modified it 2818. Customizable fields 2820 may also be listed. The user may also be provided with a selection as to whether to display a particular custom field on a work order, a Field Document, and/or an Invoice by checking the display on work order check box 2822, the display on Field Document check box 2824, or the display on invoice checkbox 2826, respectively. The user may also select whether a customizable field is to be read only, editable, or internal by clicking on the read only radio button 2828, the editable radio button 2830, or the internal radio button 2832, respectively. When a field is selected to be read only, ideally both operators and service providers may view the field, but only the operators can make changes to the field. However, when a field is selected to be editable, either the service provider or the operator may be permitted to view and/or make changes to the field. Alternatively, when a field is selected to be internal, the system is configured such that only an operator may view and make changes to the field. The user may also add new custom fields by clicking on the add new custom field button 2834. While and/or after the user has made any selections, the user may preview the custom fields on the work order page by clicking on the preview work order button 2836. Similarly, the user may preview the custom fields on the Field Document Pricing Page by clicking on the preview eFT pricing page button 2838. Similarly, the user may save the page as a draft by clicking the save draft button 2840, or the page may be saved as a final version by clicking the save final button 2842. Further, whenever the page is saved as a draft or a final version, the Last Modified Date field 2816 and the Last Modified By field 2818 may be automatically updated.

Figure 29A:
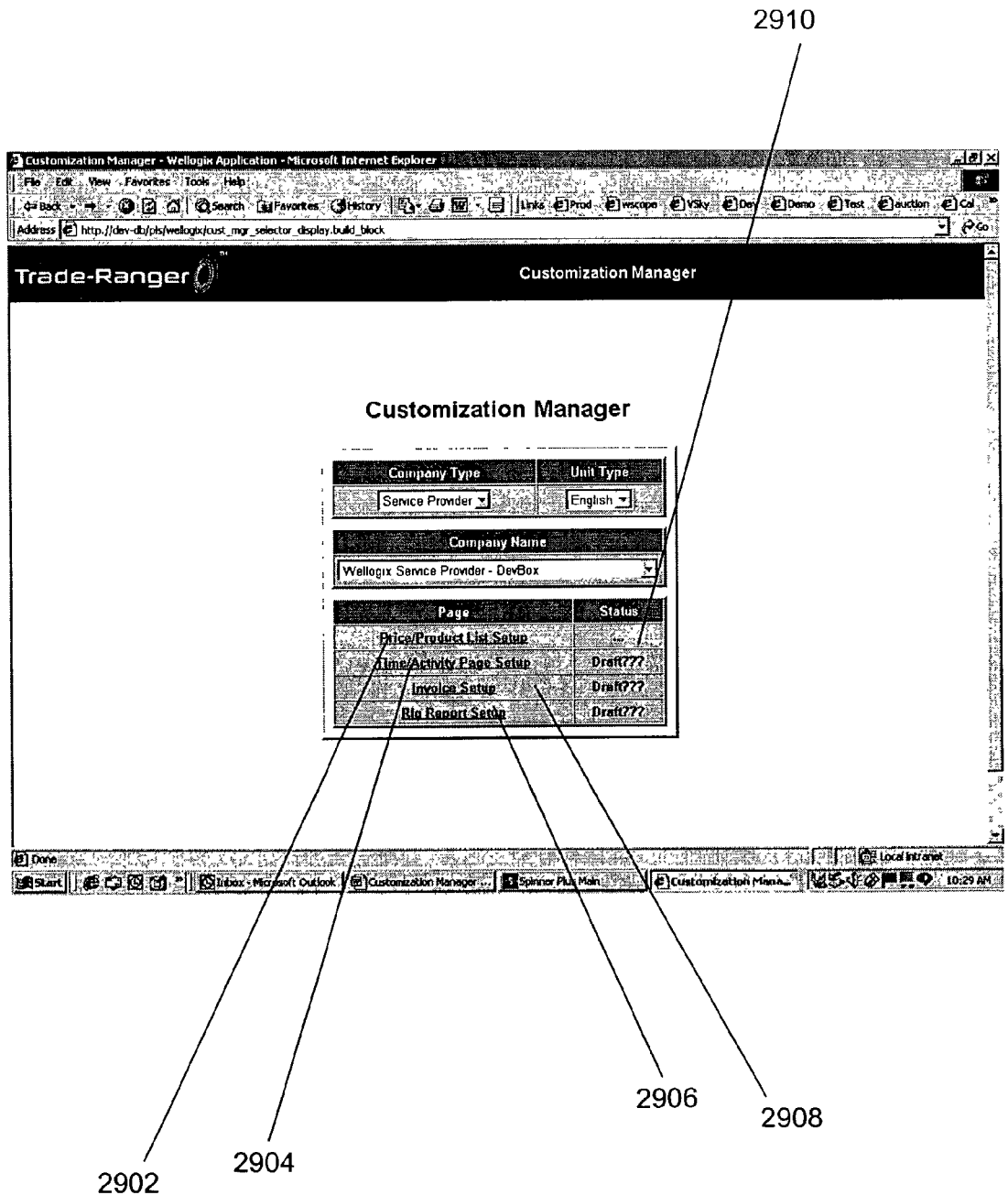

Referring now to FIG. 29A, as previously stated, when the user selects a service provider company from the drop down menu, the user interface/screen will refresh and list all the pages available for customization along with their respective statuses. For example, for the embodiment shown in FIG. 29A, the screens available for customization by the service provider include a price/product list setup page 2902, a time/activity page setup 2904, an invoice setup 2906, and a rig report setup 2908. The status 2910 of each page may also be displayed.

Figure 29B:
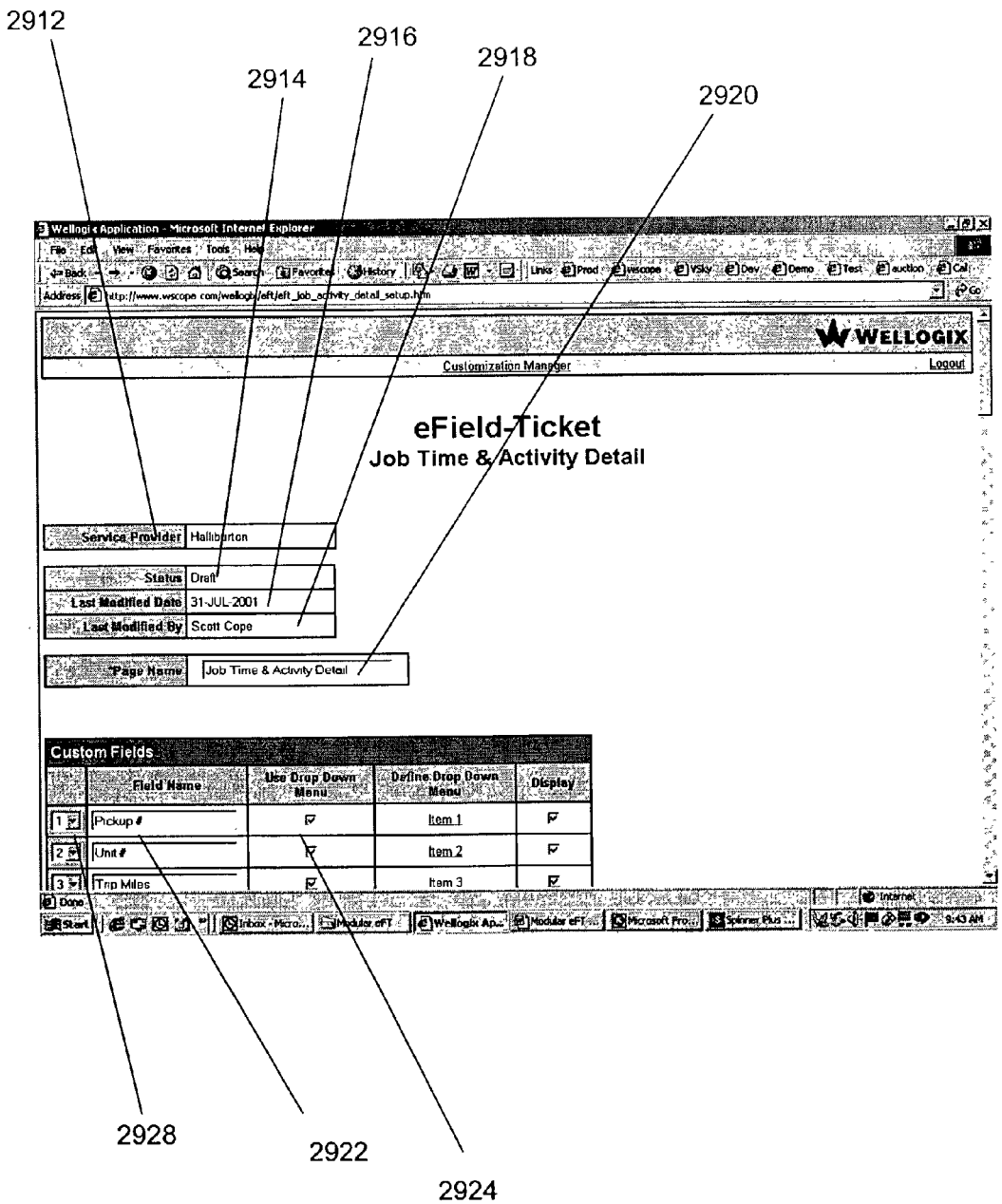

If the user selects to customize the time/activity page setup, an user interface/screen similar to those depicted in FIGS. 29B–29E may be displayed. The user interface/screen display may be pre-populated with the service provider name 2912 (as shown in FIG. 29B). The service provider name and other information may be pre-populated from earlier entries/information provided to and/or obtained by the customization manager. The screen shown in FIG. 29B may also display other information such as the status of the page 2914, when the page was last modified 2916, and who last modified the page 2918. The page name field 2920 preferably, by default, displays job time & activity detail, but may be changed by the user or may default to other information as desired for specific embodiments of the present invention. Further, the page name field 2920 generally will contain the name of the link listed on the Field Document Pricing Page and eFT Product List pages. It is to be appreciated that these pages may be provided within a modular Field Document or otherwise. Because the custom fields on the Job Time & Activity page generally pertain to service providers, the system may be configured so that operators may view the pages, but may not edit the pages. Additionally, in other embodiments, the service provider may also have other internally customized fields which an operator may not be able to view and/or edit.

Figure 29C:
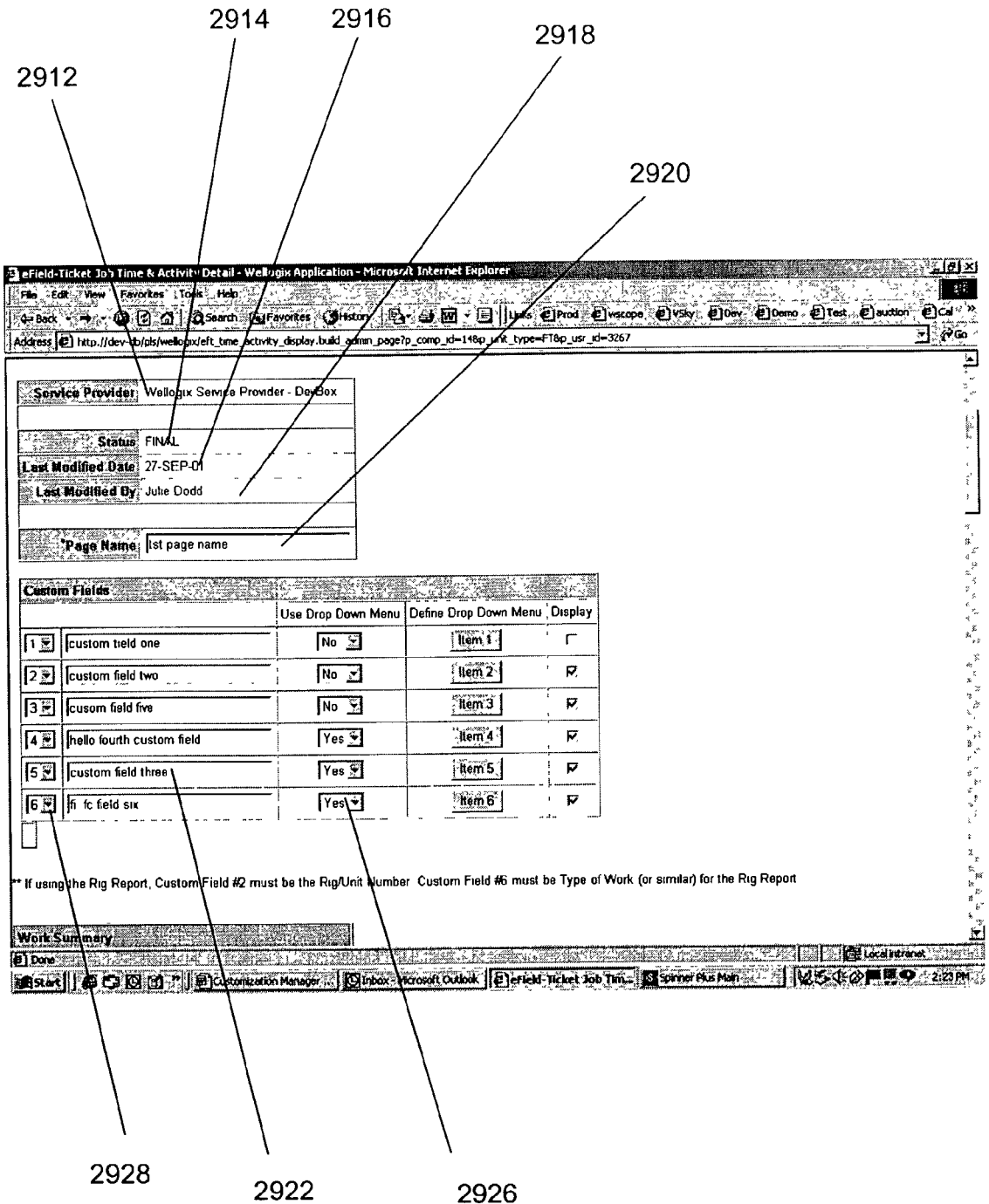

As shown in FIGS. 29B and 29C, various custom fields 2922 may be identified and listed, for example, on the left hand side of the user interface/screen. In the embodiments shown in FIGS. 29B and 29C, the service provider is allowed a maximum of six custom fields. However, in other embodiments, more or less fields may be customizable. The service provider may suitably select whether the custom field will be text boxes or drop down menus, for example, by selecting yes or no radio buttons, check boxes 2924 (as shown in FIG. 29B) or drop down menu options 2926 (as shown in FIG. 29C). In one embodiment, if the user selects to use a drop down menu, a maximum of twenty-five choices may be listed in the drop down menu. Similarly, the order of the custom fields may be altered by changing the rank order of each field (as identified by the numbers 2928 in the drop down menus on the left hand side of the screen). It is to be appreciated that other well known methods and techniques for ordering fields on a page may also be utilized. Additionally, text entry fields 2922 may also be provided in which a user may manually input or obtain from another listing a description for each custom field. As is provided for above with respect to the other options shown on FIG. 29C, the text entry fields may be pre-populated, populated via drop down menus, populated by manual text entry or otherwise populated, as necessary.

Figure 29D:
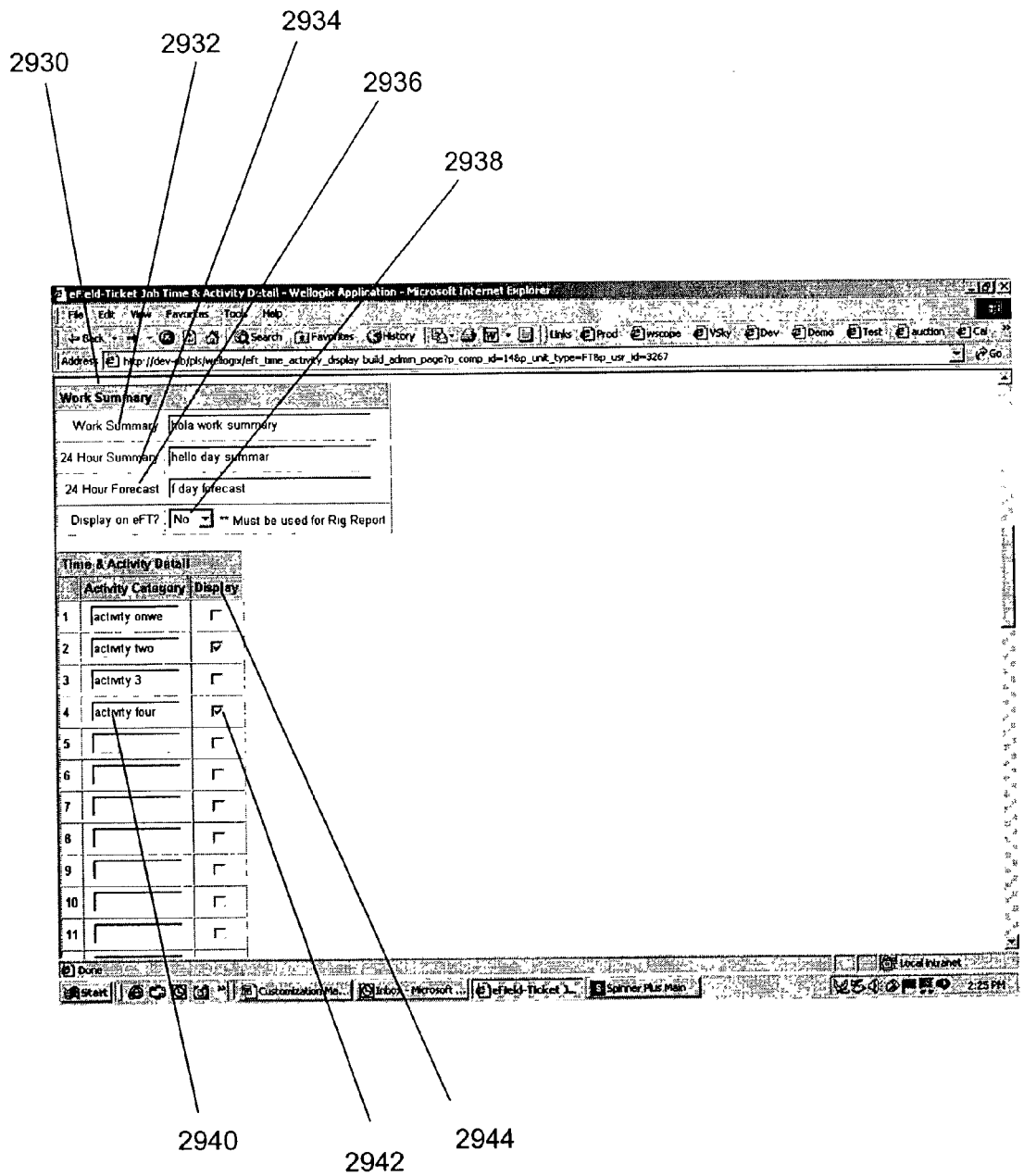

Referring now to FIG. 29D, the system may be configured to enable an user to also edit a work summary table 2930. For example, in this embodiment, the name of the work summary table may be changed, and the names of the row headers within the table may also be changed. The default name of the work summary table may be Work Summary, and the default row header names may be Work Summary 2932, 24 Hour Summary 2934, and 24 Hour Forecast 2936. Other header and/or row names may also be utilized as desired. The system may also be configured to enable the user to choose whether to display the work summary table on a Field Document. This choice may be made, for example, by selecting "yes" or "no" from a drop down menu 2938. The fields may be displayed if the service provider wants to allow the operator to run a rig report.

The system may also enable the user to define Time & Activity details. More specifically, a plurality of categories 2940 may be provided. In the present embodiment a maximum of 25 categories are permitted. Further, The system may allow the user to enter names in the text fields of the various Time & Activity categories. Further, the user may be provided the option of designating particular categories to display in the Time & Activity drop down menu, by suitably providing check boxes 2942, radio buttons, drop down menus or the like.

Figure 29E:
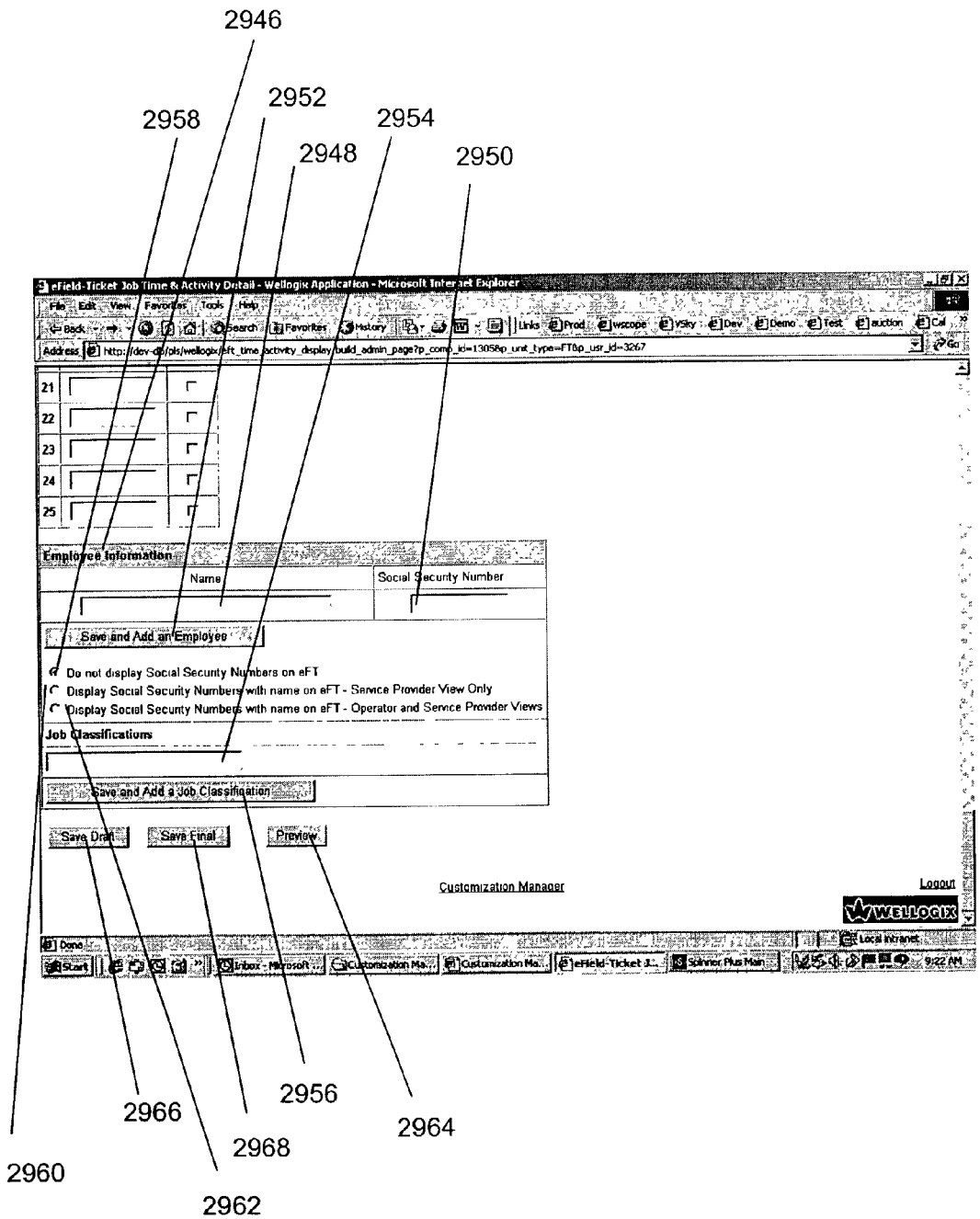

As shown in FIG. 29E, this embodiment of a system and user interface associated therewith may also enable a user may to enter employee information, for example, in an Employee Information table 2946. For example, the user may be able to enter an employee's name 2948 and/or social security number 2950 in the appropriate fields. Further, inputted employee information may be recorded in a database accessible by the system once the user "clicks" on a Save and Add Employee button 2952 or otherwise designates that an entry is to be saved.

In a similar manner, the user may define various job classifications by entering a particular job classification in the Job Classification field 2954. The system embodiment shown in FIG. 29E may be configured to record the entered job classification when the user clicks on the Save and Add a Job Classification button 2956. As shown in FIG. 29E, the user may be provided some choices relating to where employee social security numbers are displayed and who may view them. For example, the system enables a user to designate whether a social security number should be displayed on a Field Document by providing the "Do not display Social Security Numbers on EFT radio button 2958. However, the system also enables the user to choose to have social security numbers displayed on Field Documents, but on a restricted access basis, for example, so that only a service provider may view a social security number, by providing a "Display Social Security Numbers with name on eFT—Service Provider View Only" radio button 2960. The system may also be configured to enable a user to choose to have employee social security numbers displayed on Field Documents for both the operator and service provider views by providing the "Display Social Security Numbers with name on eFT—Operator and Service Provider Views" radio button 2962.

Further, the system enables a user to preview entries by providing a preview button 2964. When this button 2964 is selected or "clicked," the system displays a preview of the Job Time & Activity Detail page. The system also enables a user to choose whether to save the page as a draft version or a final version by providing the Save Draft 2966 or Save Final buttons 2968. The system may also be configured to record the user's work and update the status of the page to draft or final when the save draft button 2966 or the save final button 2968 is selected.

As previously stated, an embodiment of the present invention may also enable a user to customize the Price/Product List page for a service provider. As shown in FIG. 29A, when a user clicks on the Price/Product List Setup link 2902 to access the customization screen, a page similar to that depicted in FIGS. 29F–29H may be displayed.

Figure 29F:
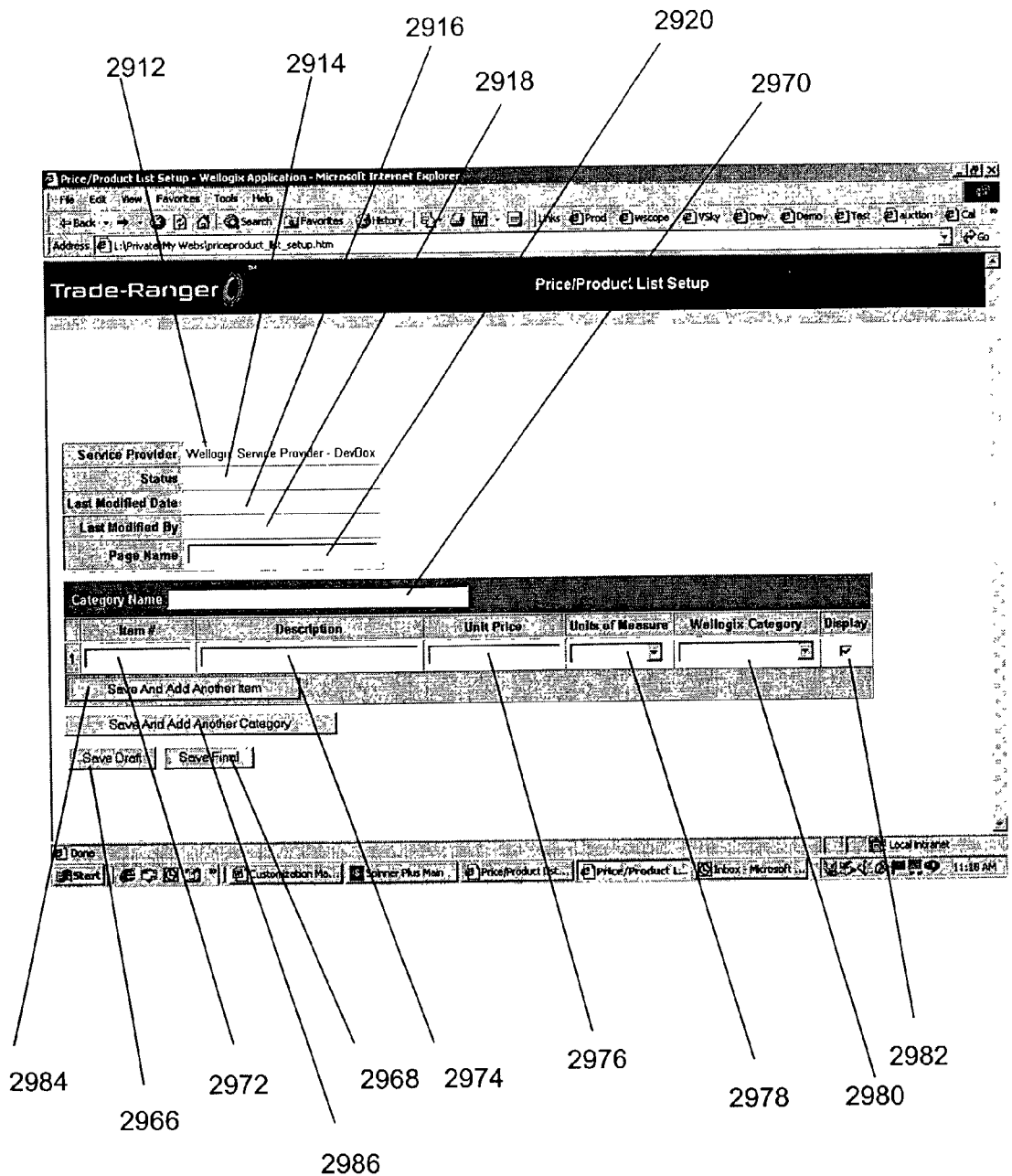
Figure 29G:
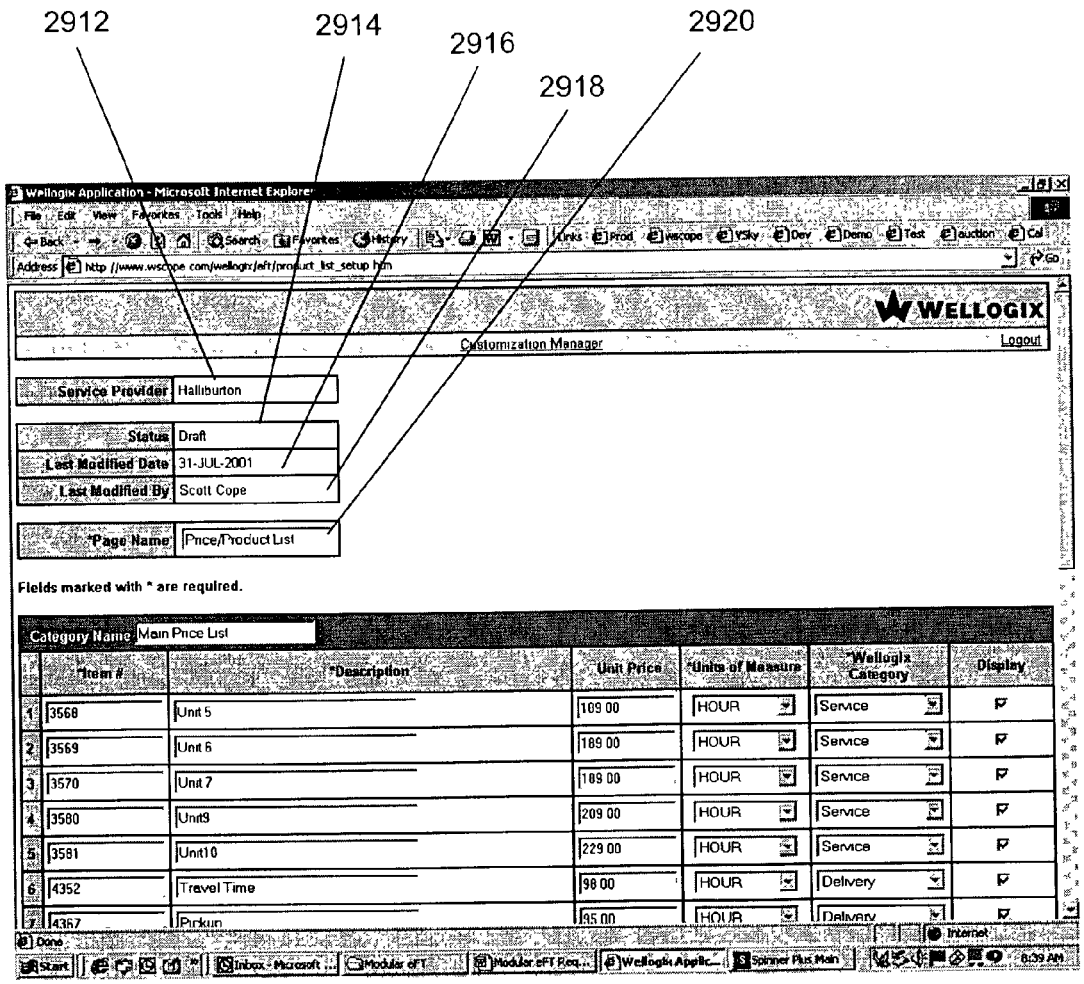
Figure 29H:
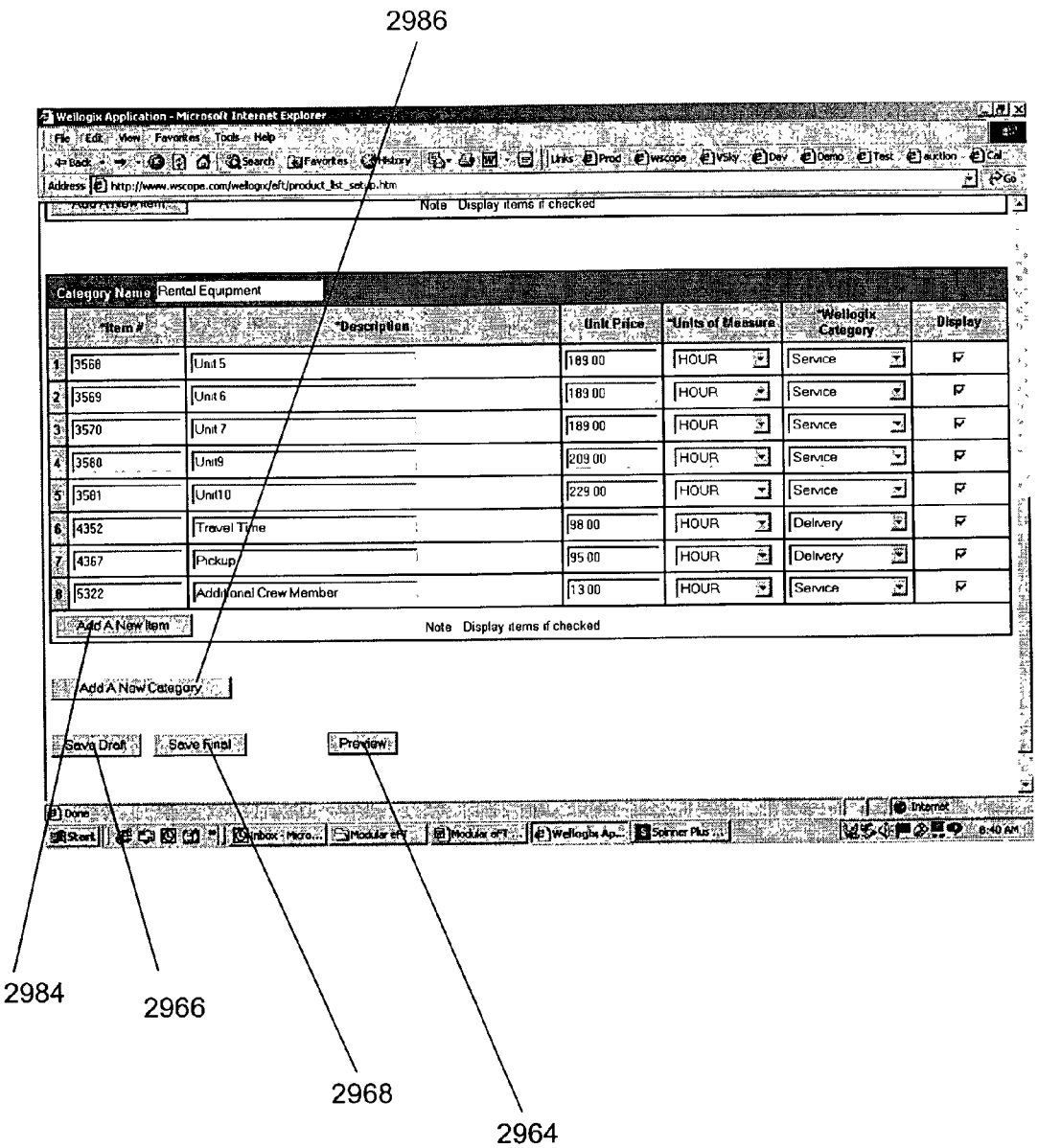

As shown in FIG. 29F, the user interface/screen may be pre-populated with the service provider name 2912 from the service provider name selected in the customization manager. Further, the screens shown in FIGS. 29F, 29G and/or 29H may also display other information such as the status of the page 2914 (i.e. final or draft), when it was last modified 2916, and who last modified it 2918. Further, the system/user interface may provide a page name field 2920 in which the name of the link listed on the Field Document Pricing Page and/or the Product List pages may be presented. Because the custom fields on the Price/Product List page pertain mainly to service providers, the system may be configured so that operators may be able to view these pages, but may not edit them. In another embodiment, the service provider may also be presented or have access to internal customized fields that an operator may not be able to view and/or edit.

The customization manager also enables a user to specify a category and enter various items within a particular category. For example, the system/user interface allows a user to specify a category name in the Category Name field 2970. In one embodiment, the category name may be limited to twenty-five characters. Also, the system allows an user to specify or provide data for each item in the fields below the Category Name 2970. One such field, is the Item # field 2972, which is commonly referred to as the product code. In certain embodiments, the Item # field 2972 may be limited to fifteen characters and may be a required field. Further, the system may be configured so that duplicate item numbers may not be entered, and to notify the user when a page is saved and duplicate numbers have been entered.

The system also allows a user to enter a description of an item in a Description field 2974. The Description field 2974 may be limited to fifty characters, and may be a required field for this and/or other embodiments. Similarly, the system allows a user to enter a unit of measure in the Unit Price 2976 and the Units of Measure field 2978, for example, using a drop down menu. The Units of Measure field 2978 may be a required field, and the choices in the drop down menu may be the same as those provided in a given Field Document, if so desired. Examples of choices that may appear in the Units of Measure drop down menu include the following: BBL, BBLS, CUFT, DAY, EACH, GAL/ SACKS, GALLONS, HOUR, JOB, LB, MILES, MONTH, SACKS, FT, and GAL.

The system/user interface may also be configured so that a user may choose a category from the drop down menu to insert into the WELLOGIX Category field 2980. The WELLOGIX Category field 2980 may be a required field, and the choices in the drop down menu may be the same as those provided on a given Field Document. Examples of choices that may appear in the WELLOGIX Category drop down menu include the following: Delivery Charges, Setup Charges, Service Charges, Product Charges, Equipment Charges, Third Party Charges, and Taxes and Fees. The system desirably also allows the user to choose whether to display an item on the Product List page of a modular Field Document by providing a display check box 2982 which corresponds to a given item. Likewise, if the display radio button 2982 is not checked, the item, preferably, will not be displayed.

The system/user interface also provides the option of having entries recorded by the customization manager by providing a Save and Add Another Item button 2984. When this button is selected, the customization manager desirably records the entries for the particular item and displays a new row of blank entry fields in which a next item, if any, may be entered by the user. Once the user has completed entry of all items pertaining to a particular category, the system enables the user to create a new category by providing an Add A New Category button 2986. When this button 2986 is selected or "clicked" the system records the user's entries in the previous category and displays blank entry fields for the new category to be entered. Further, once the user has completed any desired entries, the system enables to the user to preview the work/entries to date by providing a preview button 2964. When this button 2964 is selected, the system then displays a preview of the Price/Product List page. The user may also choose to save the page as a draft version or a final version by clicking on the Save Draft 2966 or Save Final buttons 2968 provided by the system on the user interface. The system will then record the user's work and update the status of the page to draft or final.

Versioning with the Customization Manager

Embodiments of the customization manager conforming to the present invention may also include a versioning feature. Versioning allows the user to change the operator and service provider custom fields and maintains a history of previously used custom fields. In one embodiment of the present invention, three types of customization manager versions may be provided: a working copy version, a current active version, and a previously created version. A version number may be assigned to each group of documents managed by the customization manager. The version numbers may start, for example, with the number one (1) for the oldest version and increment by one for each subsequently created version. Other numbering schemes may also be utilized. For example, a group of documents managed in the customization manager for use between a particular service provider and operator may have a working copy version number three, a current active version number two, and previously created version number one.

In one embodiment of the present invention, service providers may be provided access to four types of documents (time and activity, price/product list, invoice, and rig report). Each of these types of documents may be assigned unique version numbers. For example, the pages for service provider "A" and operator "B" within the customization manager with a version number six (6) may have the following version numbers:

| Customization Manger - SP-A & O-B Version 6 | |
|---|---|
| Time and Activity Version | 3 |
| Price and Product Version | 2 |
| Rig Report Version | 2 |
| Invoice Version | 3 |

Similarly, each custom page within the customization manager for operators (work order, Field Document and invoice) may have a unique version number. If changes are made to at least one page, the page may be assigned a new version number by a customization manager. Similarly, the particular document group may also be assigned version numbers. For example, if a service provider changes at least one of the four pages in a document, and the changes are saved with a new version number, the customization manager may be configured to also assign a new version number to the entire document. For instance, if the time and activity page from the previous example is saved with a new version number 4, the customization manager may be configured to assign a new version number 7 to the document group, as follows:

| Customization Manger - SP-A & O-B Version 7 | |
|---|---|
| Time and Activity Version | 4 |
| Price and Product Version | 2 |
| Rig Report Version | 2 |
| Invoice Version | 3 |

The process describing how one embodiment of the versioning feature may be provided is further described herein with reference to FIGS. 30A and 30B. As shown in FIG. 30A, when a user accesses or "enters" an embodiment of a customization manger (operation 3002), a system providing a versioning feature may be configured to display a present working copy of a given document with a version number (operation 3004). The system may also be configured to issue a query as to whether a request has been made by the user to display a current active version (operation 3006). If such a request has been made (either contemporaneously or prior) to display the current active version, the system retrieves and displays the current active version (operation 3008). At this point, the user may then decide to close the current active version (operation 3010).

If the system determines that no request has been made to display the current active version (operation 3006), the system then determines whether a request has been made to display a previous version (operation 3012). If a request has been made to display a previous version, the system retrieves and displays the previous version (operation 3014). Again, the user may then decide to close the previous version (operation 3010). If the system determines that no request has been made to display a previous version (operation 3012), the system then determines whether a request has been made to edit the working copy (operation 3016).

If a request has been made to edit the working copy (operation 3016), the system then displays the selected Field Document page to be edited along with the version number of the page (operation 3018). As the user edits the page, the system may be configured to automatically, periodically or upon user request store the user edits made to the desired custom fields within the page (operation 3020). The user may also choose to save the page as final (operation 3022), choose not to keep the changes made to the page (operation 3024), or save the page as a draft (operation 3026). If the user saves the page as a draft (operation 3026), the system closes the page and again determines whether a request has been made to display a current active version (operation 3006).

If the user chooses to save the page as final (operation 3022), the system automatically updates the version number of the page (operation 3028). Alternatively, if the user chooses not to keep the changes made to the page (operation 3024), the system retains the previous version number of the page (operation 3030). The user may then choose to make the working copy into the current version. At this point, the system then determines whether a request has been made to lock and change the working copy into the current version (operation 3032). If no such request has been made, the system closes the page and again determines whether a request has been made to display a current active version (operation 3006).

If the system determines that a request has been made to lock and change the working copy into the current version (operation 3032), the system determines whether all pages have been saved as final (operation 3034). If all pages have not been saved as final, the system informs the user that all pages must be saved as final before the working copy can be converted into the current active version (operation 3036). However, if all pages have been saved as final, the system queries the user to confirm or cancel the user's instruction to convert the working copy into the current active version (operation 3038). The system then determines whether the user has confirmed or cancelled his decision (operation 3040). If the decision was cancelled, the system does not update the working copy in the current active version (operation 3040). In contrast, if the decision was confirmed, the system converts the working copy into the current active version (operation 3044) and retires and saves the prior active version (operation 3046). The user may then choose to exit or remain in the customization manager. If the system determines that a request has been made to exit the customization manager (operation 3050), the system exits the user (operation 3052) from the customization manager. If the system determines that a request has not been made to exit the system (operation 3050), the system again attempts to display present working copy along with version number (operation 3004).

One embodiment of a user interface/screen prints which facilitates the above described versioning processes for a customization manager is shown in FIGS. 31A and 31B. As shown, these user interfaces/screen prints illustrate how various attributes of a user interface may relate to at least one embodiment of the previously described versioning process. Referring now to FIG. 31A, as with the previously described customization manager, upon entry into the customization manager and after the user has selected a company type (i.e. operator or service provider), a unit type 3104, and a company name 3106, the screen may be refreshed to display links to the various pages 3108 available for customization. However, when utilizing the versioning feature, a system implementing this feature may also include a version number to a working copy. Further, the system may be configured to o display by default a present working copy of a version upon entry into the customization manager. If no working copy exists, the current active version may be displayed along with its version number. Whatever page is displayed, the system may be configured to display the version number of the current active version 3110 on the screen. The system may also inform the user which page is currently being displayed 3112. For example, the screen depicted in FIG. 31A shows that the current active version is "2," and the current view is of "Version 3—Working Copy." The user may also be provided with the option of selecting a different page to display, for example, by selecting one from the drop down menu 3114.

As with the previously described customization manager, the system may be configured so that the user interface enables the user to select which available page to customize by clicking on its respective link 3108. After clicking on the link, the system preferably displays the selected page. Referring now to FIG. 31B, a price/product list page 3116 is displayed. The various attributes displayed on the page are not different from the previously described customization manager price/product list page with the exception that the version number 3118 of the page is displayed. Therefore, it is to be appreciated that any of the previously hereinabove described user interfaces/screen displays, web pages, documents or other information may be suitably identified by versioning.

One embodiment of a system which may be utilized in conjunction with and/or to implement any of the foregoing embodiments of the present invention is shown in FIG. 32. As shown, this system 3200 is illustrated in the context of an Internet embodiment wherein there is one service provider, one operator and a plurality of agents/users for each out in the field. As such, it is to be appreciated that non-Internet embodiments, hybrid Internet and non-Internet embodiments and/or embodiments with multiple service providers and/or operators may be provided.

More specifically, as shown for this illustrative embodiment, a plurality of user devices (preferably for use in the office and/or in the field) may be used. These user devices include: a workstation 3202, for example, a Intel processor or Apple processor based personal computer or the like that is utilized by a field operator #1; a laptop computer 3204, which may also be configured with an Intel processor, Macintosh processor or other processor, and may be suitably utilized, for example, a service provider's agent; and a personal data assistant (PDA) or the like 3206 which may also be suitably utilized, in this example by a field operator's agent. As shown, each of these user devices 3202, 3204, and/or 3206 may be suitably connected to the Internet 3210, via a communications medium 3222. It is to be appreciated that numerous mediums exist for establishing a communications link between a user device and the Internet, any of which may be utilized in particular embodiments of the present invention.

Further, the system 3200 also includes a server 3208. The server 3208 provides the processing systems for implementing the above mentioned features and functions of the present invention. One embodiment of such a server is the WELLOGIX server which may be suitably accessed over an Internet connection via the URL www.wellogix.com. Other servers, singularly or in a plurality, may be utilized in conjunction with the various embodiments of the present invention. The system 3200 also suitably includes at least one database 3220 which may be accessed over the Internet 3210 or otherwise. The database (which may be a distributed database) suitably provides those storage functions discussed hereinabove and other data storage functions. Again, numerous embodiments of data storage devices, systems, and applications exist, any of which may be suitably utilized in conjunction with the present invention.

Also, generally the system 3200 includes a services provider's processor 3213 which provides those service provider unique functions and features. The processor 3213 may also be connected directly or indirectly to back-end office systems 3214. Similarly, an operator processor 3216 may be included in the system 3200. Such processor 3216 may also be connected directly or indirectly to back-end office systems. Therefore, in general a system implementing/facilitating/providing the above mentioned features and functions of the present invention may utilize practically any compatible data processing systems, databases, user devices, back-end accounting systems and communications mediums.

While the systems and processes of the present invention have been described as encompassing numerous features, capabilities, architectures, and configurations, and depicted in detail for an Internet based embodiment, it is to be appreciated that the process of the present invention encompasses any and all combinations of these and comparable embodiments and is not to be construed as being limited to any preferred embodiment, or the Internet based embodiments specified in detail herein. Additionally, modifications may be made to the process flow, techniques, equipment used, or any other element, factor, or operation without departing from the scope of the present invention.

What is claimed is:

1. A process for capturing a state of a data input interface at a particular time, the data input interface providing an interface for entering actual data to populate a field document, wherein the data input interface is modified on a plurality of occasions to accept input of additional or alternate types of actual data, wherein each modification of the data input interface is a version of the data input interface, the process operating within a workflow process, the workflow process controlled by a processing system, the workflow process designed to facilitate the preparation for and performance of a complex project conducted between parties, wherein the parties are connected to the processing system via a communication network, the field document documenting the performance of at least one component of the complex project, the process comprising:
saving a first version of the data input interface, wherein a first set of actual data has been entered via the first version of the interface;
storing modifications to the first version of the data input interface to create a second version of the data input interface;
activating the second version of the data input interface, wherein a second set of data is entered via the second version of the data input interface;
deactivating the first version of the data input interface to prevent further input of the actual data via the first version of the data input interface.

2. The process of claim 1, wherein the step of deactivating further prevents display of the second set of data via the first version of the data input interface and potential confusion of the parties through possible presentation of the second set of data via the first version of the data input interface is alleviated.

3. The process of claim 1, further comprising displaying the second set of data via the second version of the data input interface when the second set of data is accessed.

4. The process of claim 1, further comprising displaying the first set of data via the first version of the data input interface when the first set of data is accessed after deactivation of the first version of the data input interface, wherein potential confusion of the parties through possible presentation of the first set of data via the second version of the data input interface is alleviated.

5. A process for capturing a state of a data array module at a particular time in a workflow process controlled by a processing system, the data array module providing instructions for storing actual data received via a field document in a data array in a memory portion of the processing system, wherein the data array module is modified on a plurality of occasions to provide instructions for storing additional or alternate types of actual data, wherein each modification of the data array module is a version of the data array module, the workflow process designed to facilitate the preparation for and performance of a complex project conducted between parties, wherein the parties are connected to the processing system via a communication network, and wherein the actual data is received via a field document that documents the performance of at least one component of the complex project, the process comprising:
saving a first version of the data array module providing instructions for storing actual data in a first data array configuration;
storing modifications to the first version of the data array module to create a second version of the data array module;
activating the second version of the data array module providing instructions for storing actual data in a second data array configuration;
deactivating the first version of the data array module to prevent further storing of actual data according to the instructions of the first version of the data array module.

6. The process of claim 5, wherein the step of activating further prevents actual data stored via instructions of the first version of the data array module from being accessed by instructions of the second version of the data array module.

7. The process of claim 5, wherein the step of deactivating further prevents actual data stored via instructions of the second version of the data array module from being accessed by instructions of the first version of the data array module.

8. The process of claim 5, wherein the step of deactivating provides for actual data stored in the first data array configuration to be accessed by the instructions of the first version of the data array module.

9. The process of claim 5, wherein the step of activating provides for actual data stored in the second data array configuration to be accessed by the instructions of the second version of the data array module.

10. The process of claim 1 or 5, wherein the actual data comprises an actual cost of goods, services, or both provided in the performance of the at least one component of the complex project.

11. The process of claim 1 or 5, wherein the actual data comprises an actual accounting of goods, services, or both provided in the performance of the at least one component of the complex project.

12. The process of claim 1 or 5, wherein the actual data comprises a measurement of a technical specification defining the complex project.

13. The process of claim 1 or 5, wherein the complex project is defined in terms of at least one parameter and the actual data comprises at least one measurement of the at least one parameter documenting the performance of the at least one component of the complex project.

14. The process of claim 13, wherein the at least one parameter is selected from a group comprising the following: physical, functional, temporal, financial, transactional, and geographical parameters.

15. The process of claim 1 or 5, wherein the communication network is selected from a group comprising the following: the Internet, an intranet, a cable network, a telephone network, a wireless network, a voice network, a frame-relay broadband network, a local area network, a wide area network, a public network, and a private network.

16. The process of claim 1 or 5, wherein the communication network operates over at least one of the transmission mediums selected from a group comprising the following: telephony, wireless telephony, digital subscriber line, two-way cable, fiber optic, radio, point-to-point microwave, and satellite.

17. The process of claim 1 or 5, wherein the complex project further comprises one of a type selected from a group comprising the following: oil and gas exploration and production, construction, manufacture of complex products, and provision of specialized services.

18. A system for capturing a state of a data array module in a workflow process at a particular time, wherein the data array module is modified on a plurality of occasions to provide instructions for storing additional or alternate types of actual data, wherein each modification of the data array module is a version of the data array module, the workflow process designed to facilitate the preparation for and performance of a complex project conducted between parties, wherein the parties are connected to the processing system via a communication network, and wherein the actual data is received via a field document that documents the performance of at least one component of the complex project, the system comprising:
 a memory that stores actual data received via a field document in a data array according to instructions provided by the data array module; and
 a processor that:
  saves to the memory a first version of the data array module providing instructions for storing actual data in a first data array configuration;
  modifies the first version of the data array module to create a second version of the data array module;
  saves to the memory the second version of the data array module;
  activates the second version of the data array module to provide instructions for storing actual data in a second data array configuration; and
  deactivates the first version of the data array module to prevent further storing of actual data according to the instructions of the first version of the data array module.

19. The system of claim 18, wherein the processor further prevents actual data stored via instructions of the first version of the data array module from being accessed by instructions of the second version of the data array module.

20. The system of claim 18, wherein the processor further prevents actual data stored via instructions of the second version of the data array module from being accessed by instructions of the first version of the data array module.

21. The system of claim 18, wherein the processor accesses actual data stored in the first data array configuration via instructions of the first version of the data array module.

22. The system of claim 18, wherein the processor access actual data stored in the second data array configuration via instructions of the second version of the data array module.

23. The system of claim 18, wherein the actual data comprises an actual cost of goods, services, or both provided in the performance of the at least one component of the complex project.

24. The system of claim 18, wherein the actual data comprises an actual accounting of goods, services, or both provided in the performance of the at least one component of the complex project.

25. The system of claim 18, wherein the actual data comprises a measurement of a technical specification defining the complex project.

26. The system of claim 18, wherein the complex project is defined in terms of at least one parameter and the actual data comprises at least one measurement of the at least one parameter documenting the performance of the at least one component of the complex project.

27. The system of claim 26, wherein the at least one parameter is selected from a group comprising the following: physical, functional, temporal, financial, transactional, and geographical parameters.

28. The system of claim 18, wherein the communication network is selected from a group comprising the following: the Internet, an intranet, a cable network, a telephone network, a wireless network, a voice network, a frame-relay broadband network, a local area network, a wide area network, a public network, and a private network.

29. The system of claim 18, wherein the communication network operates over at least one of the transmission mediums selected from a group comprising the following: telephony, wireless telephony, digital subscriber line, two-way cable, fiber optic, radio, point-to-point microwave, and satellite.

30. The system of claim 18, wherein the complex project further comprises one of a type selected from a group comprising the following: oil and gas exploration and production, construction, manufacture of complex products, and provision of specialized services.

* * * * *